US012545654B2

(12) United States Patent
Orton et al.

(10) Patent No.: US 12,545,654 B2
(45) Date of Patent: Feb. 10, 2026

(54) MYC INHIBITORS AND USES THEREOF

(71) Applicant: STEMSYNERGY THERAPEUTICS, INC., Miami, FL (US)

(72) Inventors: Darren Orton, Nashville, TN (US); Dennis Liang Fei, Miami, FL (US); Samir Saleh, Nashville, TN (US); Thomas Doundoulakis, Nashville, TN (US)

(73) Assignee: STEMSYNERGY THERAPEUTICS, INC., Miami, FL (US)

( * ) Notice: Subject to any disclaimer, the term of this patent is extended or adjusted under 35 U.S.C. 154(b) by 809 days.

(21) Appl. No.: 17/798,017

(22) PCT Filed: Feb. 10, 2021

(86) PCT No.: PCT/US2021/017456
§ 371 (c)(1),
(2) Date: Aug. 5, 2022

(87) PCT Pub. No.: WO2021/163192
PCT Pub. Date: Aug. 19, 2021

(65) Prior Publication Data

US 2023/0150956 A1 May 18, 2023

Related U.S. Application Data

(60) Provisional application No. 62/972,491, filed on Feb. 10, 2020.

(51) Int. Cl.
*C07D 277/46* (2006.01)

(52) U.S. Cl.
CPC .................................. *C07D 277/46* (2013.01)

(58) Field of Classification Search
CPC .................................................... C07D 277/46
See application file for complete search history.

(56) References Cited

U.S. PATENT DOCUMENTS

| | | | |
|---|---|---|---|
| 2007/0238726 A1 | 10/2007 | Blake et al. | |
| 2010/0120806 A1 | 5/2010 | Flynn et al. | |
| 2012/0123126 A1* | 5/2012 | Chen ....................... | A61P 29/00 546/153 |

FOREIGN PATENT DOCUMENTS

| | | | |
|---|---|---|---|
| CN | 106 349 158 A | 1/2017 |
| WO | WO-2010/051373 A1 | 5/2010 |
| WO | WO-2012/034055 A2 | 3/2012 |
| WO | WO-2012/034055 A3 | 3/2012 |
| WO | WO-2014/059429 A2 | 4/2014 |
| WO | WO-2014/059429 A3 | 4/2014 |
| WO | WO-2014/071247 A1 | 5/2014 |
| WO | WO-2014/190207 A1 | 11/2014 |
| WO | WO-2016/094688 A1 | 6/2016 |
| WO | WO-2016/196910 A1 | 12/2016 |
| WO | WO-2018/153293 A1 | 8/2018 |
| WO | WO-2019/148044 A1 | 8/2019 |

OTHER PUBLICATIONS

Extended European Search Report mailed on Mar. 13, 2024, for EP Patent Application No. 21754341.2, 15 pages.
Sumi, N.J. et al. (Sep. 19, 2019). "Divergent Polypharmacology-Driven Cellular Activity of Structurally Similar Multi-Kinase Inhibitors through Cumulative Effects on Individual Targets," *Cell Chemical Biology* 26(9):1240-1252.e11.
Wang, X.-N. et al. (May 2019). "MYC modulators in cancer: a patent review," *Expert Opin Ther Pat* 29(5):353-367.
Zhou, F. et al. (Apr. 15, 2018). "Discovery of N-aryl-N'-pyrimidin-4-yl ureas as irreversible L858R/T790M mutant selective epidermal growth factor receptor inhibitors," *Bioorg & Med Chem Lett* 28(7):1257-1261.
International Search Report mailed on Apr. 29, 2021 for PCT Application No. PCT/US2021/017456, filed Feb. 10, 2021, 2 pages.
Muller, et al. (May 23, 2014). "Targeting of the MYCN Protein with Small Molecule c-MYC Inhibitors," *PLOS One* 9(5):e97285.
Written Opinion mailed on Apr. 29, 2021 for PCT Application No. PCT/US2021/017456, filed Feb. 10, 2021, 3 pages.

* cited by examiner

*Primary Examiner* — Sarah Pihonak
*Assistant Examiner* — Mikhail O'donnel Robinson
(74) *Attorney, Agent, or Firm* — Mintz, Levin, Cohn, Ferris, Glovsky and Popeo, P.C.

(57) ABSTRACT

Disclosed herein, inter alia, are compounds for inhibiting N-MYC or Aurora A Kinase and uses thereof.

20 Claims, 5 Drawing Sheets

Specification includes a Sequence Listing.

FIG. 1A

| ID | Activity against N-MYC | ID | Activity against N-MYC |
|---|---|---|---|
| A1 ~ A31 | inactive | A50 | inactive |
| A31 | active | A51 | inactive |
| A32 | inactive | A52 | inactive |
| A33 | active | A53 | inactive |
| A34 | inactive | A54 | inactive |
| A35 | inactive | A55 | active |
| A36 | inactive | A56 | inactive |
| A37 | active | A57 | active |
| A38 | inactive | A58 | inactive |
| A39 | inactive | A59 | inactive |
| A41 | inactive | A60 | inactive |
| A42 | active | A61 | inactive |
| A43 | inactive | A62 | inactive |
| A44 | active | A63 | active |
| A45 | inactive | A64 | active |
| A46 | inactive | A65 | inactive |
| A47 | inactive | A66 | inactive |
| A48 | inactive | A67 | inactive |
| A49 | inactive | A68 | inactive |

FIG. 1B

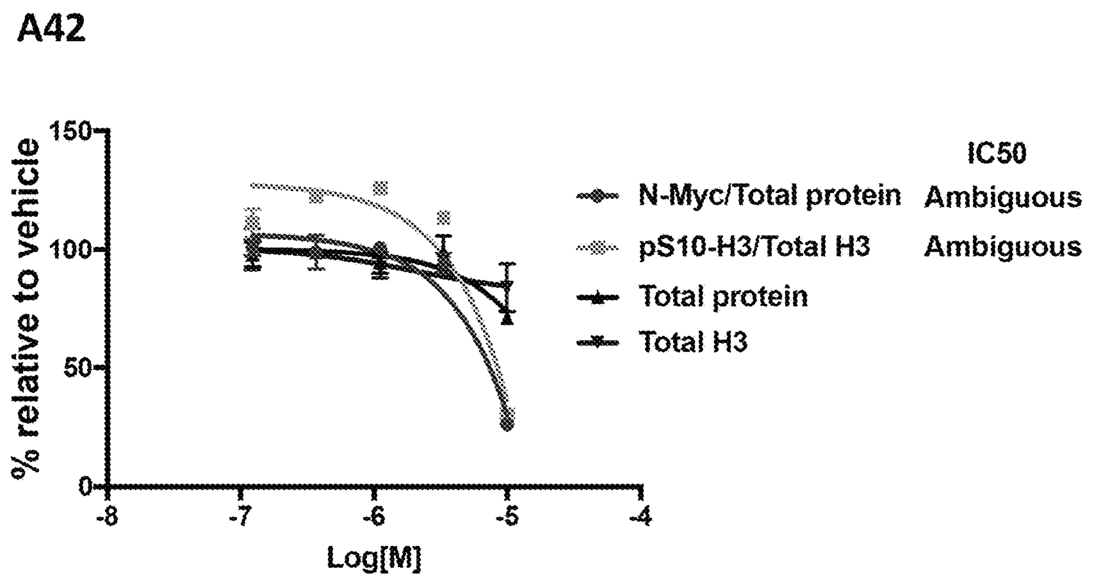

| ID | $IC_{50}$ for N-MYC inhibition |
|---|---|
| SSTA-101 | inactive |
| SSTA-102 | 6.0 μM |
| SSTA-103 ~ SSTA-143 | inactive |
| SSTA-144 | 5.7 μM |
| SSTA-145 | inactive |
| SSTA-146 | inactive |
| SSTA-147 | inactive |
| SSTA-148 | inactive |
| SSTA-149 | inactive |
| SSTA-150 | 6.7 μM |
| SSTA-151 | inactive |
| SSTA-152 | 0.30 μM |
| SSTA-153 | inactive |
| SSTA-154 | inactive |

SSTA-152

FIG. 2E
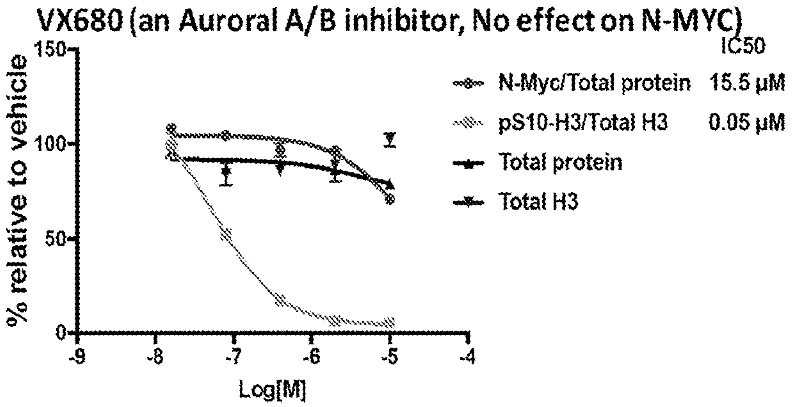
FIG. 3
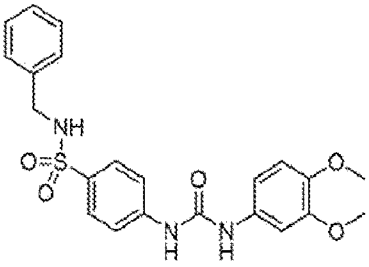
A-31
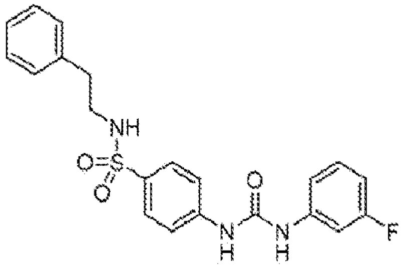
A-33
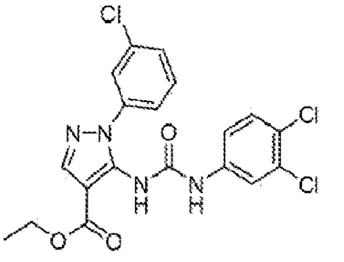
A-42
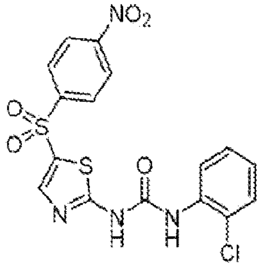
A44
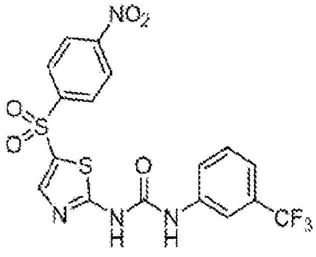
A63
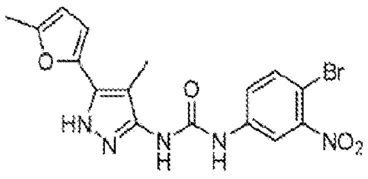
A-55
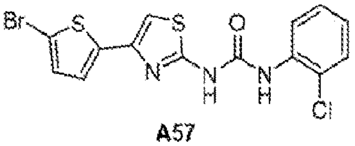
A57
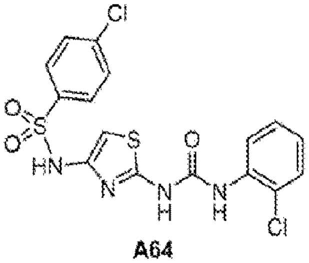
A64

SSTA-152

SSTA-264

SSTA-263

SSTA-260

SSTA-259

MYC INHIBITORS AND USES THEREOF

CROSS-REFERENCES TO RELATED APPLICATIONS

This application is the national stage filing under 35 U.S.C. § 371 of International Application No. PCT/US2021/017456 filed Feb. 10, 2021, which claims the benefit of U.S. Provisional Application No. 62/972,491, filed Feb. 10, 2020, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048509-502N01US_Sequence_Listing_ST25.txt, created Jul. 21, 2022, 7,997 bytes, machine format IBM-PC, MS Windows operating system, is hereby incorporated by reference.

BACKGROUND

N-MYC is a transcription factor with a basic helix-loop-helix domain. Excess N-MYC is associated with a variety of tumors. N-MYC associates with Aurora A kinase, which may protect N-MYC from degradation. Disclosed herein, inter alia, are solutions to these and other problems known in the art.

BRIEF SUMMARY OF THE INVENTION

In an aspect is provided a compound having the formula:

(I)

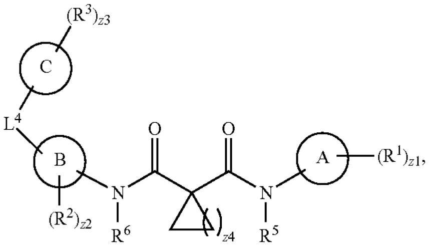

or a pharmaceutically acceptable salt thereof.

Ring A is phenyl or 5 to 6 membered heteroaryl.

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, and $R^{1D}$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl.

z1 is an integer from 0 to 5.

Ring B is 5 membered heteroaryl or phenyl.

$R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{2A}$, $R^{2B}$, $R^{2C}$, and $R^{2D}$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl.

z2 is an integer from 0 to 4.

Ring C is phenyl or 5 to 6 membered heteroaryl.

$R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NR^{3C}NR^{3A}R^{3B}$, $-ONR^{3A}R^{3B}$, $-NHC(O)NR^{3C}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroary; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{3A}$, $R^{3B}$, $R^{3C}$, and $R^{3D}$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl.

z3 is an integer from 0 to 5.

$L^4$ is a bond, —$N(R^4)$—, —O—, —S—, —$SO_2$—, —C(O)—, —C(O)$N(R^4)$—, —$N(R^4)$C(O)—, —$N(R^4)$C(O)NH—, —NHC(O)$N(R^4)$—, —C(O)O—, —OC(O)—, —$SO_2N(R^4)$—, —$N(R^4)SO_2$—, substituted or unsubstituted alkylene, or substituted or unsubstituted heteroalkylene.

z4 is an integer from 1 to 5.

$R^4$, $R^5$, and $R^6$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$X^1$, $X^2$, and $X^3$ are independently —F, —Cl, —Br, or —I.

n1, n2, and n3 are independently an integer from 0 to 4.

m1, m2, m3, v1, v2, and v3 are independently 1 or 2.

In an aspect is provided a pharmaceutical composition including a compound as described herein, including embodiments, and a pharmaceutically acceptable excipient.

In an aspect is provided a method of decreasing the level of Aurora A kinase protein activity in a subject, the method including administering a compound as described herein to the subject.

In an aspect is provided a method of decreasing the level of Aurora A kinase protein activity in a cell, the method including contacting the cell with a compound described herein.

In an aspect is provided a method of decreasing the level of N-MYC protein in a subject, the method including administering a compound as described herein to the subject.

In an aspect is provided a method of decreasing the level of N-MYC protein in a cell, the method including contacting the cell with a compound described herein.

In an aspect is provided a method of modulating the protein conformation of an Aurora A kinase protein, the method including contacting the Aurora A kinase protein with an effective amount of a compound described herein.

In an aspect is provided a method of changing the protein conformation of an Aurora A kinase protein to a conformation with reduced binding (e.g. in a cell or in a subject in need) to an N-MYC protein.

In an aspect is provided a method of inhibiting cancer cell growth, the method including contacting the cancer cell with an effective amount of a compound described herein.

In an aspect is provided a method of inhibiting cancer cell growth, the method including contacting the cancer cell with an effective amount of a compound described herein, wherein the compound modulates (e.g. reduces or inhibits) the N-MYC activity level, Aurora A kinase activity level, N-MYC protein level, or Aurora A kinase protein level in the cancer cell.

In an aspect is provided a method of treating a cancer in a subject in need thereof, the method including administering to the subject in need thereof an effective amount of a compound described herein.

In an aspect is provided a method of inhibiting cancer growth in a subject in need thereof, the method including administering to the subject in need thereof an effective amount of a compound described herein.

In an aspect is provided a method of inhibiting cancer growth in a subject in need thereof, the method including administering to the subject in need thereof an effective amount of a compound described herein, wherein the compound modulates (e.g. reduces or inhibits) the N-MYC activity level, Aurora A kinase activity level, N-MYC protein level, or Aurora A kinase protein level in the subject.

BRIEF DESCRIPTION OF THE DRAWINGS

FIG. 1A-1B. Inhibition of N-MYC protein at compound concentrations up to 30 μM, showing active or inactive under specific assay conditions; compound binding to Aurora A kinase compared to CD532.

FIG. 2A-2E. Compounds and IC50 N-MYC inhibition activity under specific assay conditions.

FIG. 3. Compounds showing N-MYC inhibition.

DETAILED DESCRIPTION

I. Definitions

Figure 2A:
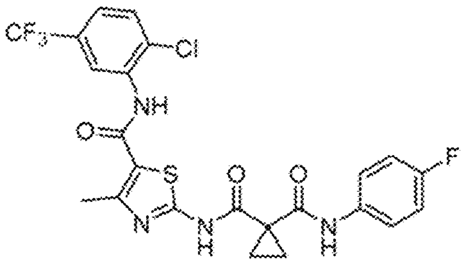
Figure 2B:
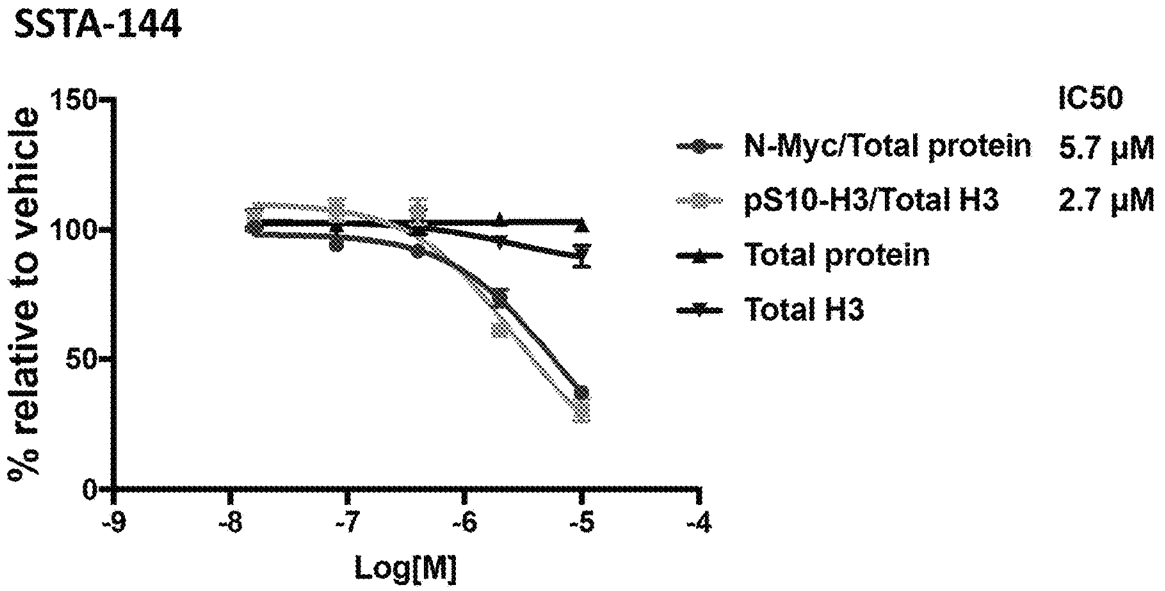
Figure 2C:
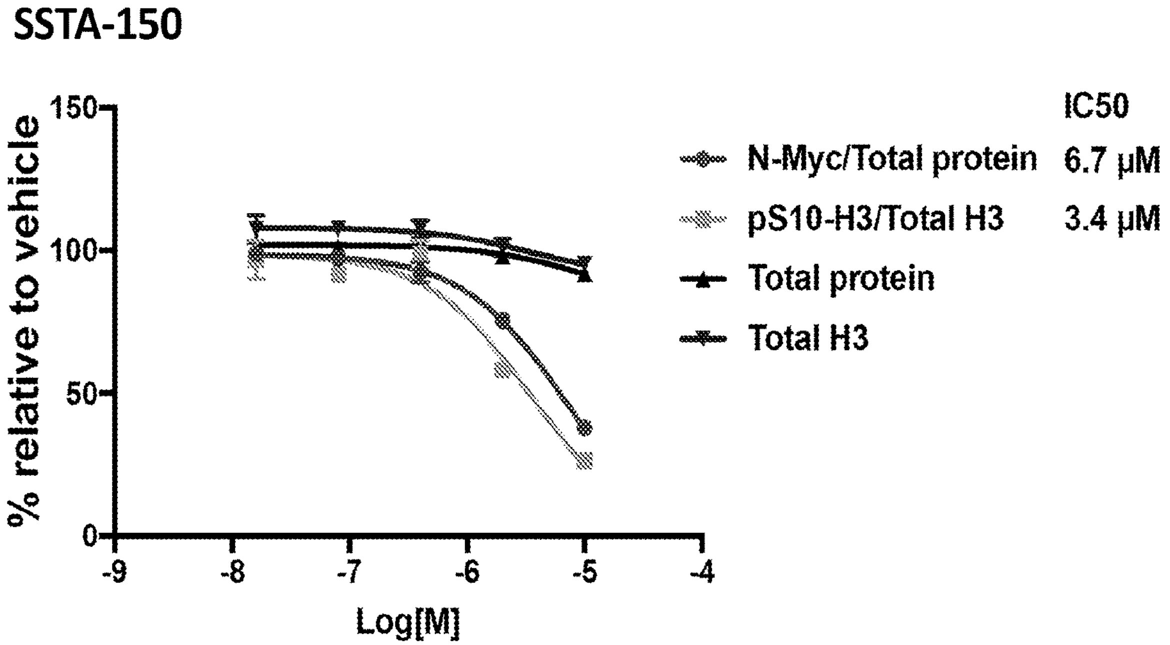
Figure 2D:
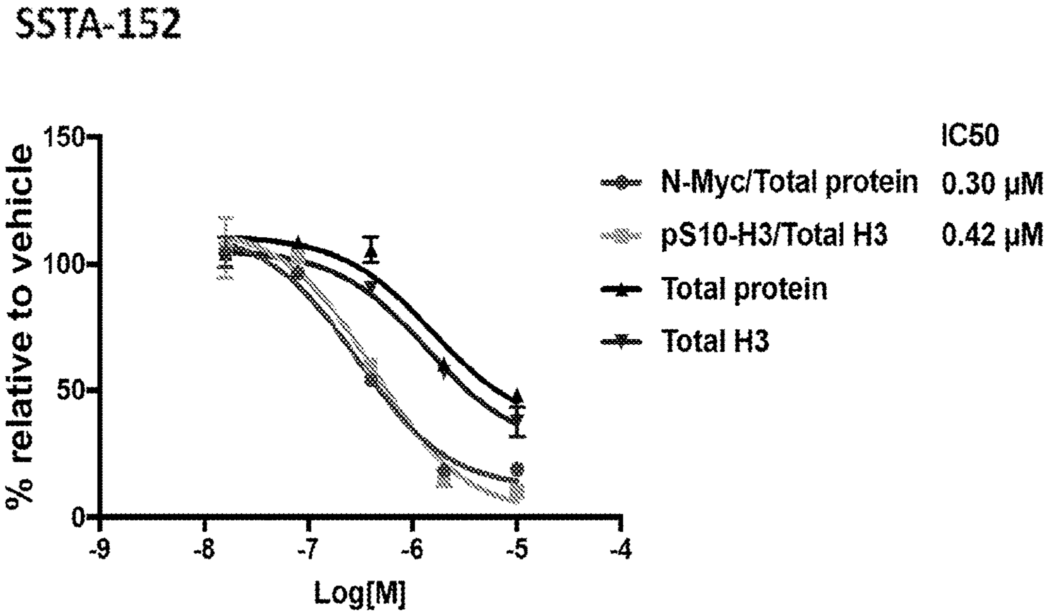
Figure 4:
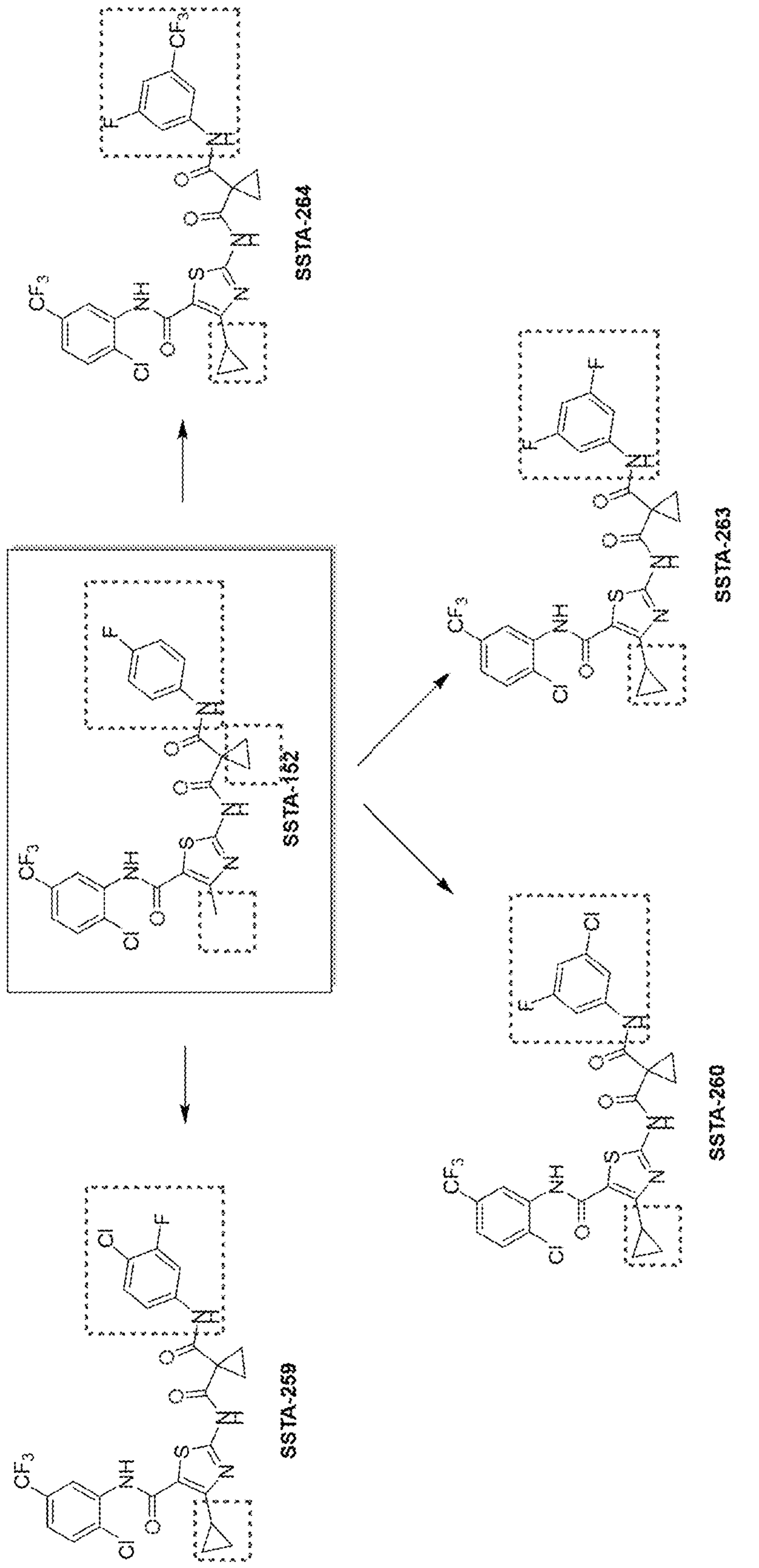
FIG. 4. Compounds showing N-MYC inhibition.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. In embodiments, an alkenyl includes one or more double bonds. An alkynyl may include more than one triple bond and/or one or more double bonds in addition to the one or more triple bonds. In embodiments, an alkynyl includes one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl. In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl, benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “~” denotes the point of attachment of a chemical moiety to the remainder of a molecule or chemical formula.

The term “oxo,” as used herein, means an oxygen that is double bonded to a carbon atom.

The term “alkylsulfonyl,” as used herein, means a moiety having the formula —$S(O_2)$—R', where R' is a substituted or unsubstituted alkyl group as defined above. R' may have a specified number of carbons (e.g., “$C_1$-$C_4$ alkylsulfonyl”).

The term “alkylarylene” as an arylene moiety covalently bonded to an alkylene moiety (also referred to herein as an alkylene linker). In embodiments, the alkylarylene group has the formula:

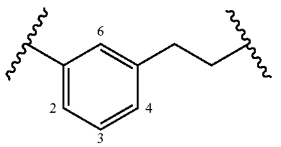

or

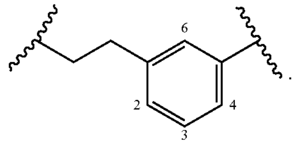

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$NHNH_2$, —$ONH_2$, —NHC(O)$NHNH_2$, substituted or unsubstituted $C_1$-$C_8$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X' is $-O-$, $-NR'-$, $-S-$, $-S(O)-$, $-S(O)_2-$, or $-S(O)_2NR'-$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_{20}$ alkyl, $C_1$-$C_{12}$ alkyl, $C_1$-$C_8$ alkyl, $C_1$-$C_6$ alkyl, $C_1$-$C_4$ alkyl, or $C_1$-$C_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., $C_3$-$C_{10}$ cycloalkyl, $C_3$-$C_8$ cycloalkyl, $C_3$-$C_6$ cycloalkyl, $C_4$-$C_6$ cycloalkyl, or $C_5$-$C_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., $C_6$-$C_{12}$ aryl, $C_6$-$C_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from:

(i) oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_{20}$ alkyl, $C_1$-$C_{12}$ alkyl, $C_1$-$C_8$ alkyl, $C_1$-$C_6$ alkyl, $C_1$-$C_4$ alkyl, or $C_1$-$C_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., $C_3$-$C_{10}$ cycloalkyl, $C_3$-$C_8$ cycloalkyl, $C_3$-$C_6$ cycloalkyl, $C_4$-$C_6$ cycloalkyl, or $C_5$-$C_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., $C_6$-$C_{12}$ aryl, $C_6$-$C_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$ alkyl, $C_1$-$C_{12}$ alkyl, $C_1$-$C_8$ alkyl, $C_1$-$C_6$ alkyl, $C_1$-$C_4$ alkyl, or $C_1$-$C_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., $C_3$-$C_{10}$ cycloalkyl, $C_3$-$C_8$ cycloalkyl, $C_3$-$C_6$ cycloalkyl, $C_4$-$C_6$ cycloalkyl, or $C_5$-$C_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., $C_6$-$C_{12}$ aryl, $C_6$-$C_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth herein, for example in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on a R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g. $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups (e.g. $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g. $R^{1.2}$, $R^{2.2}$, $R^{3.2}$, $R^{4.2}$, $R^{5.2}$ . . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g. $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g. when $R^{WW.1}$ is $R^{WW.2}$ substituted alkyl, examples of groups so formed include but are not limited to itself optionally substituted by 1 or more $R^{WW.2}$, which $R^{WW.2}$ is optionally substituted by one or more $R^{WW.3}$. By way of example when $R^{WW.1}$ is alkyl, groups that could be formed, include but are not limited to:

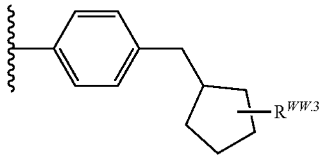

-continued

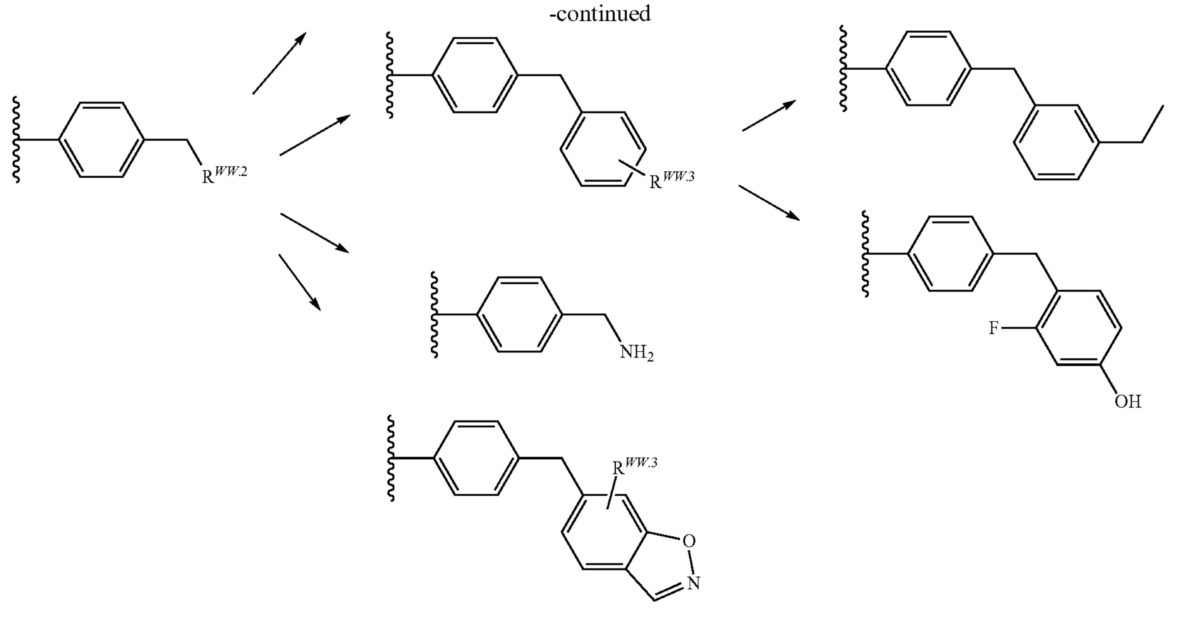

$R^{WW.1}$ is independently oxo, halogen, $—CX^{WW.1}_3$, $—CHX^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $—CX^{WW.1}_3$, $—CHX^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, —NHC═(O) $NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, $—CX^{WW.2}_3$, $—CHX^{WW.2}_2$, $—CH_2X^{WW.2}$, $—OCX^{WW.2}_3$, $—OCH_2X^{WW.2}$, $—OCHX^{WW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, —NHC═(O) $NH_2$, $—NHSO_2H$, —NHC═(O)H, —NHC(O)—OH, —NHOH, $—N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $—CX^{WW.2}_3$, $—CHX^{WW.2}_2$, $—CH_2X^{WW.2}$, $—OCX^{WW.2}_3$, $—OCH_2X^{WW.2}$, $—OCHX^{WW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, —NHC═(O) $NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, $—CX^{WW.3}_3$, $—CHX^{WW.3}_2$, $—CH_2X^{WW.3}$, $—OCX^{WW.3}_3$, $—OCH_2X^{WW.3}$, $—OCHX^{3}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O) $NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g. substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —N, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O)NH$_2$, $—NHSO_2H$, —NHC═(O)H, —NHC(O)—OH, —NHOH, $—N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O) NH$_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O) NH$_2$, $—NHSO_2H$, —NHC═(O)H, —NHC(O)—OH, —NHOH, $—N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O) NH$_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, $—CX^{LWW.3}_3$, $—CHX^{LWW.3}_2$, $—CH_2X^{LWW.3}$, $—OCX^{LWW.3}_3$, $—OCH_2X^{LWW.3}$, $—OCHX^{LWW.3}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O)NH$_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, $—CX^{WW}_3$, $—CHX^{WW}_2$, $—CH_2X^{WW}$, $—OCX^{WW}_3$, $—OCH_2X^{WW}$, $—OCHX^{WW}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC═(O)NHNH$_2$, —NHC═(O)$NH_2$, —$NHSO_2H$, —NHC═(O)H, —NHC(O)—OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g. 1, 2, 3, 1A, 2A, 3A, 1B, 2B, 3B, etc.). $R^{WW.1}$, $R^{WW.2}$, and $R^{WW.3}$, are as defined above.

In the event that any L linker group recited in a claim or chemical formula description set forth herein (i.e. an $L^{WW}$ substituent) is not explicitly defined, then that L group ($L^{WW}$ group) is herein defined as independently —O—, —NH—, —C(O)—, —C(O)NH—, —NHC(O)—, —NHC(O)NH—, —C(O)O—, —OC(O)—, —S—, —$SO_2$NH—, $R^{WW.1}$-substituted or unsubstituted alkylene (e.g., $C_1$-$C_8$, $C_1$-$C_6$, $C_1$-$C_4$, or $C_1$-$C_2$), $R^{WW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$, are as defined above. Alternatively, the L group is a bond.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein may be bound, for example, by covalent bond, linker (e.g. a first linker of second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like). For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g. phosphines) to form, for example, phosphate diester bonds;
(n) azides coupled to alkynes using copper catalyzed cycloaddition click chemistry; and
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

An "inhibitor" refers to a compound (e.g. compounds described herein) that reduces activity when compared to a control, such as absence of the compound or a compound with known inactivity.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

A "MYC inhibitor" or "N-MYC inhibitor" refers to a compound (e.g. a compound described herein) that decreases the activity of N-MYC or decreases the level of activity of N-MYC (e.g., in a cell or in a subject in need; by reducing the level of N-MYC protein in the cell or subject in need) when compared to a control, such as absence of the compound or a compound with known inactivity.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "N-MYC", "basic helix-loop-helix protein 37", "bHLHe37", "NMYC", or "MYCN" refers to the transcription factor N-MYC. The term includes any recombinant or naturally-occurring form of N-MYC, including variants thereof that maintain N-MYC function or activity (e.g., within at least 30%, 40%, 50%, 60%, 70%, 80%, 90%, 95%, or 100% function or activity compared to wildtype N-MYC). In embodiments, N-MYC is encoded by the MYCN gene. In embodiments, N-MYC has the amino acid sequence set forth in or corresponding to Entrez 4613, UniProt P04198, RefSeq (protein) NP_001280157, or RefSeq (protein) NP_005369. In embodiments, N-MYC has the amino acid sequence set forth in or corresponding to RefSeq (protein) NP_001280157.1. In embodiments, N-MYC has the amino acid sequence set forth in or corresponding to RefSeq (protein) NP_005369.2. In embodiments, N-MYC has the amino acid sequence (SEQ ID NO: 1)

MPSCSTSTMPGMICKNPDLEEDSLQPCFYPDEDDF

YFGGPDSTPPGEDIWKKFELLPTPPLSPSRGFAEH

SSEPPSWVTEMLLENELWGSPAEEDAFGLGGLGGL

TPNPVILQDCMWSGFSAREKLERAVSEKLQHGRGP

PTAGSTAQSPGAGAASPAGRGHGGAAGAGRAGAAL

PAELAHPAAECVDPAVVFPFPVNKREPAPVPAAPA

SAPAAGPAVASGAGIAAPAGAPGVAPPRPGGRQTS

GGDHKALSTSGEDTLSDSDDEDDEEEDEEEEIDVV

TVEKRRSSSNTKAVTTFTITVRPKNAALGPGRAQS

SELILKRCLPIHQQHNYAAPSPYVESEDAPPQKKI

KSEASPRPLKSVIPPKAKSLSPRNSDSEDSERRRN

HNILERQRRNDLRSSFLTLRDHVPELVKNEKAAKV

VILKKATEYVHSLQAEEHQLLLEKEKLQARQQQLL

KKIEHARTC.

The term "Aurora A kinase", "Aurora kinase A", "serine/threonine-protein kinase 6", or "AURKA" refers to the protein kinase Aurora A kinase. The term includes any recombinant or naturally-occurring form of Aurora A kinase, including variants thereof that maintain Aurora A kinase function or activity (e.g., within at least 30%, 40%, 50%, 60%, 70%, 80%, 90%, 95%, or 100% function or activity compared to wildtype Aurora A kinase). In embodiments, Aurora A kinase is encoded by the AURKA gene. In embodiments, Aurora A kinase has the amino acid sequence set forth in or corresponding to Entrez 6790, UniProt 014965, RefSeq (protein) NP_001310232, RefSeq (protein) NP_00940835, or RefSeq (protein) NP_003591. In embodiments, Aurora A kinase has the amino acid sequence set forth in or corresponding to RefSeq (protein) NP_001310232.1. In embodiments, Aurora A kinase has the amino acid sequence set forth in or corresponding to RefSeq (protein) NP_003591.2. In embodiments, Aurora A kinase has the amino acid sequence set forth in or corresponding to RefSeq (protein) NP_00940835.1. In embodiments, Aurora A kinase has the amino acid sequence

```
                                        (SEQ ID NO: 2)
MDRSKENCISGPVKATAPVGGPKRVLVTQQFPCQN

PLPVNSGQAQRVLCPSNSSQRIPLQAQKLVSSHKP

VQNQKQKQLQATSVPHPVSRPLNNTQKSKQPLPSA

PENNPEEELASKQKNEESKKRQWALEDFEIGRPLG

KGKFGNVYLAREKQSKFILALKVLFKAQLEKAGVE

HQLRREVEIQSHLRHPNILRLYGYFHDATRVYLIL

EYAPLGTVYRELQKLSKFDEQRTATYITELANALS

YCHSKRVIHRDIKPENLLLGSAGELKIADFGWSVH

APSSRRTTLCGTLDYLPPEMIEGRMHDEKVDLWSL

GVLCYEFLVGKPPFEANTYQETYKRISRVEFTFPD

FVTEGARDLISRLLKHNPSQRPMLREVLEHPWITA

NSSKPSNCQNKESASKQS
```

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. In some embodiments, an N-MYC associated disease modulator is a compound that reduces the severity of one or more symptoms of a disease associated with N-MYC (e.g. cancer). An N-MYC modulator is a compound that increases or decreases the activity or function or level of activity or level of function of N-MYC. In some embodiments, an N-MYC associated disease modulator is a compound that reduces the severity of one or more symptoms of a disease associated with N-MYC (e.g. cancer). An N-MYC modulator is a compound that increases or decreases the activity or function or level of activity or level of function of N-MYC.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with N-MYC activity, N-MYC associated cancer, N-MYC associated disease (e.g., cancer)) means that the disease (e.g. cancer) is caused by (in whole or in part), or a symptom of the disease is caused by (in whole or in part) the substance or substance activity or function. For example, a cancer associated with N-MYC activity or function may be a cancer that results (entirely or partially) from aberrant N-MYC function (e.g. enzyme activity, protein-protein interaction, signaling pathway) or a cancer wherein a particular symptom of the disease is caused (entirely or partially) by aberrant N-MYC activity or function. As used herein, what is described as being associated with a disease, if a causative agent, could be a target for treatment of the disease. For example, a cancer associated with N-MYC activity or function or a N-MYC associated disease (e.g., cancer), may be treated with a N-MYC modulator or N-MYC inhibitor, in the instance where increased N-MYC activity or function (e.g. signaling pathway activity) causes the disease (e.g., cancer). A cancer associated with N-MYC activity or function or a N-MYC associated disease (e.g., cancer), may be treated with a N-MYC modulator or N-MYC activator, in the instance where decreased N-MYC activity or function (e.g. signaling pathway activity) causes the disease (e.g., cancer). In embodiments, the term "associated" or "associated with" in the context of a substance or substance activity or function associated with a disease (e.g. a protein associated disease, a cancer associated with N-MYC activity, N-MYC associated cancer, N-MYC associated disease (e.g., cancer)) means that the disease (e.g. cancer) is caused by (in whole or in part), or a symptom of the disease is caused by (in whole or in part) the substance or substance activity or function. For example, a cancer associated with N-MYC activity or function may be a cancer that results (entirely or partially) from aberrant N-MYC function (e.g. enzyme activity, protein-protein interaction, signaling pathway) or a cancer wherein a particular symptom of the disease is caused (entirely or partially) by aberrant N-MYC activity or function. As used herein, what is described as being associated with a disease, if a causative agent, could be a target for treatment of the disease. For example, a cancer associated with N-MYC activity or function or a N-MYC associated disease (e.g., cancer), may be treated with an N-MYC modulator or N-MYC inhibitor, in the instance where increased N-MYC activity or function (e.g. signaling pathway activity) causes the disease (e.g., cancer). A cancer associated with N-MYC activity or function or a N-MYC associated disease (e.g., cancer), may be treated with a N-MYC modulator or N-MYC activator, in the instance where decreased N-MYC activity or function (e.g. signaling pathway activity) causes the disease (e.g., cancer).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term “signaling pathway” as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components. For example, binding of a N-MYC with a compound as described herein may reduce the level of a product of the N-MYC catalyzed reaction or the level of a downstream derivative of the product or binding may reduce the interactions between the N-MYC enzyme or a N-MYC reaction product and downstream effectors or signaling pathway components, resulting in changes in cell growth, proliferation, or survival. For example, binding of a N-MYC with a compound as described herein may reduce the level of a product of the N-MYC catalyzed reaction or the level of a downstream derivative of the product or binding may reduce the interactions between the N-MYC enzyme or a N-MYC reaction product and downstream effectors or signaling pathway components, resulting in changes in cell growth, proliferation, or survival. Alternatively, binding of a N-MYC with a compound as described herein may increase the level of a product of the N-MYC catalyzed reaction or the level of a downstream derivative of the product or binding may increase the interactions between the N-MYC enzyme or a N-MYC reaction product and downstream effectors or signaling pathway components, resulting in changes in cell growth, proliferation, or survival. Alternatively, binding of a N-MYC with a compound as described herein may increase the level of a product of the N-MYC catalyzed reaction or the level of a downstream derivative of the product or binding may increase the interactions between the N-MYC enzyme or a N-MYC reaction product and downstream effectors or signaling pathway components, resulting in changes in cell growth, proliferation, or survival.

In this disclosure, “comprises,” “comprising,” “containing” and “having” and the like can have the meaning ascribed to them in U.S. Patent law and can mean “includes,” “including,” and the like. “Consisting essentially of or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms “disease” or “condition” refer to a state of being or health status of a patient or subject capable of being treated with the compounds or methods provided herein. The disease may be a cancer. In some further instances, “cancer” refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin’s lymphomas (e.g., Burkitt’s, Small Cell, and Large Cell lymphomas), Hodgkin’s lymphoma, leukemia (including AML, ALL, and CML), or multiple myeloma.

As used herein, the term “cancer” refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin’s Disease, and Non-Hodgkin’s Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term “leukemia” refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, acute lymphoblastic leukemia (ALL), chronic lymphocytic leukemia (CLL), acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, acute myeloid leukemia (AML), chronic myeloid leukemia (CML), leukemia cutis, embryonal leukemia, eosinophilic leukemia, Gross’ leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myelodysplastic syndrome (MDS), myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling’s leukemia, stem cell leukemia, subleukemic leukemia, or undifferentiated cell leukemia.

As used herein, the term “lymphoma” refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin’s disease. Hodgkin’s disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma (MCL), follicular lymphoma, marginal zone B-cell lymphoma (MZL), mucosa-associated lymphatic tissue lymphoma (MALT), extranodal lymphoma, nodal (monocytoid B-cell) lymphoma, splenic lymphoma, diffuse large cell B-lymphoma (DLBCL), activated B-cell subtype diffuse large B-cell lymphoma (ABC-DBLCL), germinal center B-cell like diffuse large B-cell lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungocides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment (e.g., the patient has a disease, the patient suffers from a disease).

The term "prevent" refers to a decrease in the occurrence of N-MYC associated disease symptoms or N-MYC associated disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

In embodiments, an "anticancer agent" as used herein refers to a molecule (e.g. compound, peptide, protein, nucleic acid) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

In embodiments, "Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

II. Compounds

In an aspect is provided a compound having the formula:

(I)

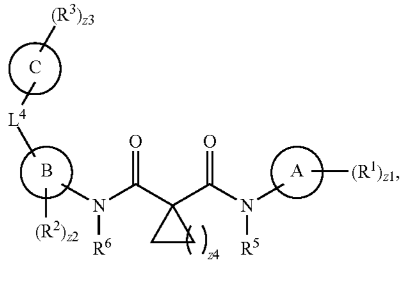

or a pharmaceutically acceptable salt thereof.

Ring A is phenyl or 5 to 6 membered heteroaryl.

$R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, and $R^{1D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl.

z1 is an integer from 0 to 5.

Ring B is 5 membered heteroaryl.

$R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)\ NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{2A}$, $R^{2B}$, $R^{2C}$, and $R^{2D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl.

z2 is an integer from 0 to 4.

Ring C is phenyl or 5 to 6 membered heteroaryl.

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)\ NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroary; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{3A}$, $R^{3B}$, $R^{3C}$, and $R^{3D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl.

z3 is an integer from 0 to 5.

$L^4$ is a bond, $—N(R^4)—$, —O—, —S—, $—SO_2—$, —C(O)—, $—C(O)N(R^4)—$, $—N(R^4)C(O)—$, $—N(R^4)C(O)NH—$, $—NHC(O)N(R^4)—$, —C(O)O—, —OC(O)—, $—SO_2N(R^4)—$, $—N(R^4)SO_2—$, substituted or unsubstituted alkylene, or substituted or unsubstituted heteroalkylene.

z4 is an integer from 1 to 5.

$R^4$, $R^5$, and $R^6$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$X^1$, $X^2$, and $X^3$ are independently —F, —Cl, —Br, or —I.

n1, n2, and n3 are independently an integer from 0 to 4.

m1, m2, m3, v1, v2, and v3 are independently 1 or 2.

In embodiments, the compound has the formula:

(II)

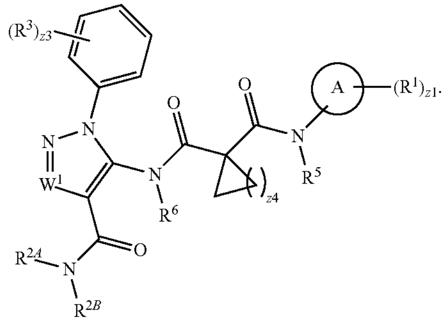

Ring A, $R^1$, $R^{2A}$, $R^{2B}$, $R^3$, $R^5$, $R^6$, z1, z3, and z4 are as described herein, including in embodiments.

$W^1$ is independently CH, N, or $C(R^2)$.

In embodiments, the compound has the formula:

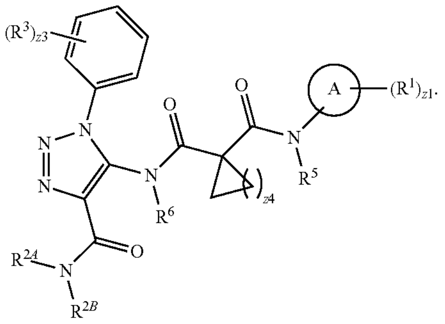

(IIa)

Ring A, $R^1$, $R^{2A}$, $R^{2B}$, $R^3$, $R^5$, $R^6$, z1, z3 and z4 are as described herein, including in embodiments.

In embodiments, the compound has the formula:

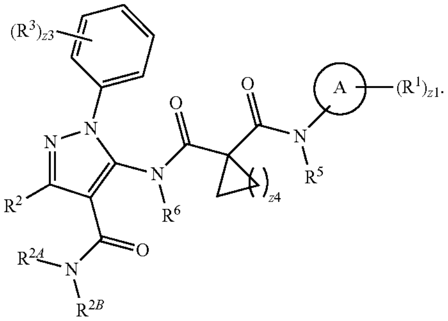

(IIb)

Ring A, $R^1$, $R^2$, $R^{2A}$, $R^{2B}$, $R^3$, $R^5$, $R^6$, z1, z3, and z4 are as described herein, including in embodiments.

In embodiments, the compound has the formula:

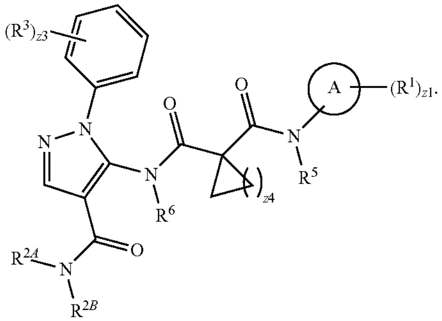

(IIc)

Ring A, $R^1$, $R^{2A}$, $R^{2B}$, $R^3$, $R^5$, $R^6$, z1, z3, and z4 are as described herein, including in embodiments.

In embodiments, the compound has the formula:

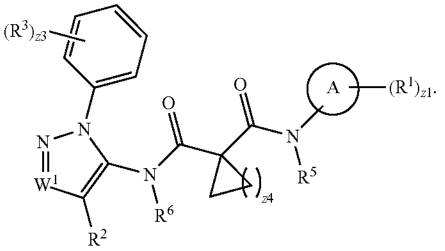

(IId)

Ring A, $W^1$, $R^1$, $R^2$, $R^3$, $R^5$, $R^6$, z1, z3, and z4 are as described herein, including in embodiments.

In embodiments, the compound has the formula:

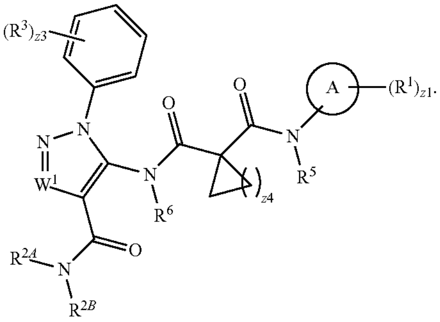

(II)

Ring A, $R^1$, $R^{2A}$, $R^{2B}$, $R^3$, $R^5$, $R^6$, z1, z3, and z4 are as described herein, including in embodiments.

$W^1$ is independently CH, N, or $C(R^2)$.

In embodiments, the compound has the formula:

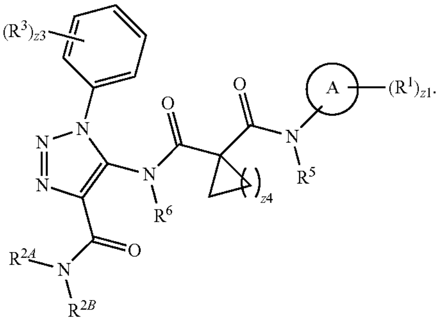

(IIa)

Ring A, $R^1$, $R^{2A}$, $R^{2B}$, $R^3$, $R^5$, $R^6$, z1, z3, and z4 are as described herein, including in embodiments.

In embodiments, the compound has the formula:

(IIb)

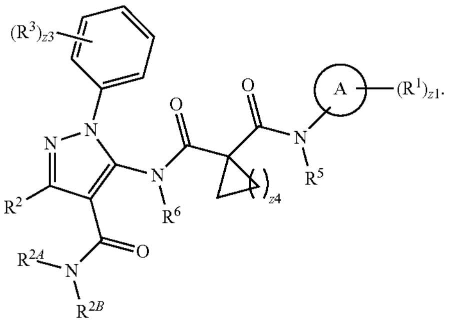

Ring A, $R^1$, $R^2$, $R^{2A}$, $R^{2B}$, $R^3$, $R^5$, $R^6$, z1, z3, and z4 are as described herein, including in embodiments.

In embodiments, the compound has the formula:

(IIc)

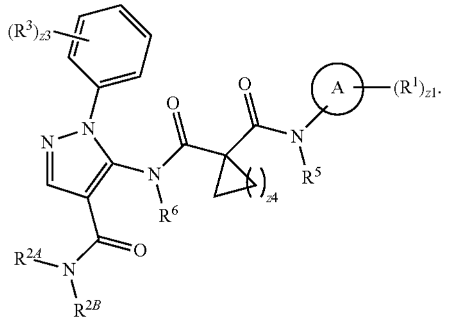

Ring A, $R^1$, $R^{2A}$, $R^{2B}$, $R^3$, $R^5$, $R^6$, z1, z3, and z4 are as described herein, including in embodiments.

In embodiments, the compound has the formula:

(IId)

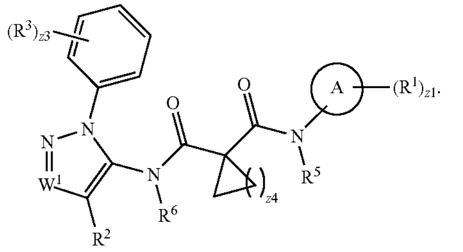

Ring A, $W^1$, $R^1$, $R^2$, $R^3$, $R^5$, $R^6$, z1, z3, and z4 are as described herein, including in embodiments.

In embodiments, $R^1$ is independently not —Cl. In embodiments, $R^1$ is independently not halogen. In embodiments, z1 is independently not 2. In embodiments, $R^5$ is independently not hydrogen. In embodiments, $R^6$ is independently not hydrogen. In embodiments, $R^2$ is independently not —C(O)OR$^{2C}$. In embodiments, $R^{2C}$ is independently not unsubstituted ethyl. In embodiments, $R^{2C}$ is independently not unsubstituted $C_1$-$C_3$ alkyl. In embodiments, $W^1$ is independently not CH. In embodiments, $R^3$ is independently not —Cl. In embodiments, $R^3$ is independently not halogen. In embodiments, z3 is independently not 1. In embodiments, Ring A is independently not phenyl. In embodiments, $L^4$ is not —O—.

In embodiments, the compound has the formula:

(IIe)

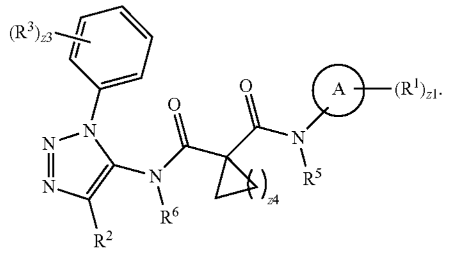

Ring A, $R^1$, $R^2$, $R^3$, $R^5$, $R^6$, z1, z3, and z4 are as described herein, including in embodiments.

In embodiments, the compound has the formula:

(IIf)

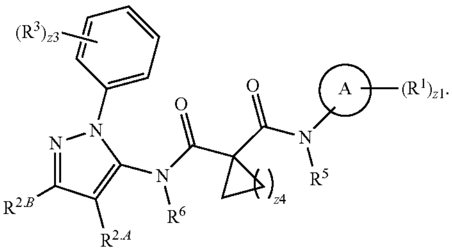

Ring A, $R^1$, $R^3$, $R^5$, $R^6$, $W^1$, z1, z3, and z4 are as described herein, including in embodiments. $R^{2.A}$ and $R^{2.B}$ are independently hydrogen or any value of $R^2$ as described herein, including embodiments.

In embodiments, $R^1$ is independently not —Cl. In embodiments, $R^1$ is independently not halogen. In embodiments, z1 is independently not 2. In embodiments, $R^5$ is independently not hydrogen. In embodiments, $R^6$ is independently not hydrogen. In embodiments, $R^2$ is independently not —C(O)OR$^{2C}$. In embodiments, $R^{2C}$ is independently not unsubstituted ethyl. In embodiments, $R^{2C}$ is independently not unsubstituted $C_1$-$C_3$ alkyl. In embodiments, $W^1$ is independently not CH. In embodiments, $R^3$ is independently not —Cl. In embodiments, $R^3$ is independently not halogen. In embodiments, z3 is independently not 1. In embodiments, Ring A is independently not phenyl. In embodiments, $L^4$ is not —O—.

In embodiments, the compound has the formula:

(IIe)

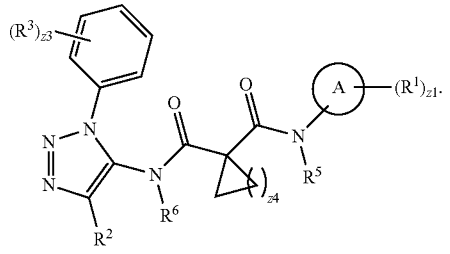

Ring A, $R^1$, $R^2$, $R^3$, $R^5$, $R^6$, z1, z3, and z4 are as described herein, including in embodiments.

In embodiments, the compound has the formula:

(IIf)

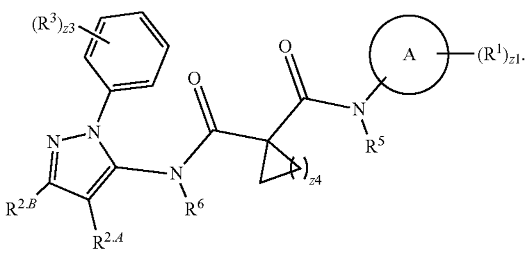

Ring A, $R^1$, $R^3$, $R^5$, $R^6$, $W^1$, z1, z3, and z4 are as described herein, including in embodiments. $R^{2.A}$ and $R^{2.B}$ are independently hydrogen or any value of $R^2$ as described herein, including embodiments.

In embodiments, $R^1$ is independently not —Cl. In embodiments, $R^1$ is independently not halogen. In embodiments, z1 is independently not 2. In embodiments, $R^5$ is independently not hydrogen. In embodiments, $R^6$ is independently not hydrogen. In embodiments, $R^{2.A}$ is independently not —C(O)OR$^{2C}$. In embodiments, $R^{2C}$ is independently not unsubstituted ethyl. In embodiments, $R^{2C}$ is independently not unsubstituted $C_1$-$C_3$ alkyl. In embodiments, $R^{2.B}$ is independently not hydrogen. In embodiments, $R^3$ is independently not —Cl. In embodiments, $R^3$ is independently not halogen. In embodiments, z3 is independently not 1. In embodiments, Ring A is independently not phenyl. In embodiments, $L^4$ is not —O—.

In embodiments, the compound has the formula:

(IIg)

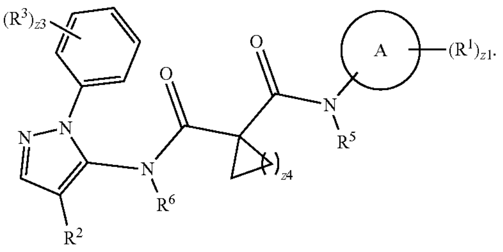

Ring A, $R^1$, $R^2$, $R^3$, $R^5$, $R^6$, $W^1$, z1, z3, and z4 are as described herein, including in embodiments.

In embodiments, $R^1$ is independently not —Cl. In embodiments, $R^1$ is independently not halogen. In embodiments, z1 is independently not 2. In embodiments, $R^5$ is independently not hydrogen. In embodiments, $R^6$ is independently not hydrogen. In embodiments, $R^2$ is independently not —C(O)OR$^{2C}$. In embodiments, $R^{2C}$ is independently not unsubstituted ethyl. In embodiments, $R^{2C}$ is independently not unsubstituted $C_1$-$C_3$ alkyl. In embodiments, $R^3$ is independently not —Cl. In embodiments, $R^3$ is independently not halogen. In embodiments, z3 is independently not 1. In embodiments, Ring A is independently not phenyl. In embodiments, $L^4$ is not —O—.

In embodiments, the compound has the formula:

(III)

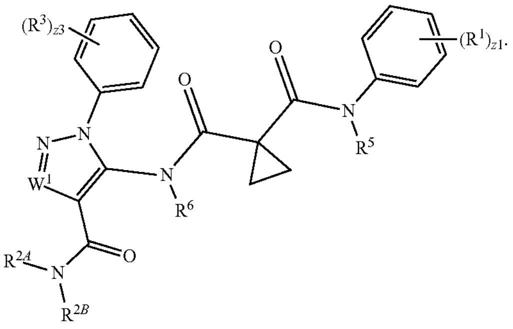

$R^1$, $R^{2A}$, $R^{2B}$, $R^3$, $R^5$, $R^6$, $W^1$, z1, and z3 are as described herein, including in embodiments.

In embodiments of the compound of formula III, $R^5$ and $R^6$ are independently hydrogen.

In embodiments, the compound has the formula:

(IIIa)

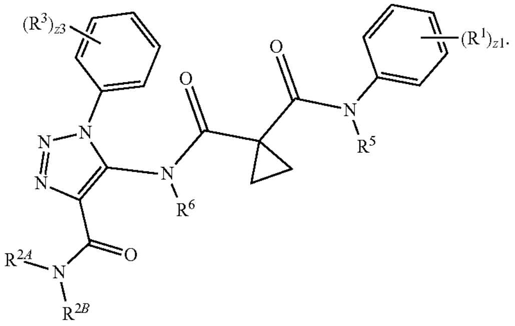

$R^1$, $R^{2A}$, $R^{2B}$, $R^3$, $R^5$, $R^6$, z1, and z3 are as described herein, including in embodiments.

In embodiments, the compound has the formula:

(IIIb)

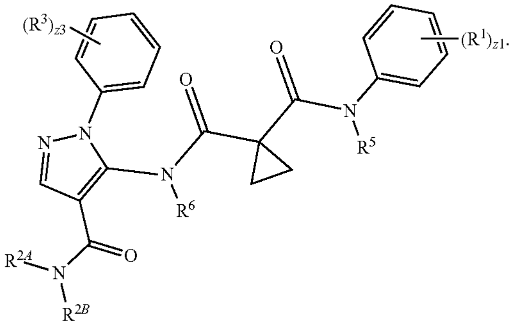

$R^1$, $R^{2A}$, $R^{2B}$, $R^3$, $R^5$, $R^6$, z1, and z3 are as described herein, including in embodiments.

In embodiments, the compound has the formula:

(IIIc)

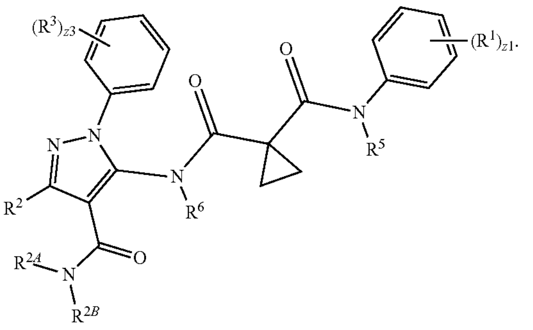

$R^1$, $R^2$, $R^{2A}$, $R^{2B}$, $R^3$, $R^5$, $R^6$, z1, and z3 are as described herein, including in embodiments.

In embodiments, the compound has the formula:

(IV)

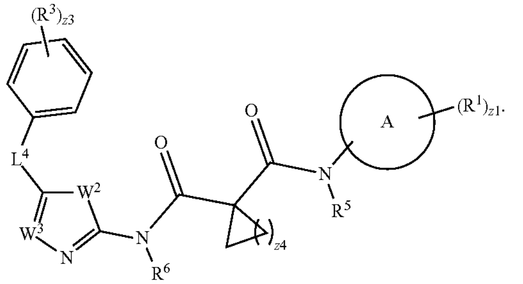

Ring A, $R^1$, $R^3$, $R^5$, $R^6$, $L^4$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $W^2$ is independently not S. In embodiments, $W^3$ is independently not CH. In embodiments, $R^3$ is independently not —Cl. In embodiments, $R^3$ is independently not halogen. In embodiments, $R^3$ is independently not —$NO_2$. In embodiments, z3 is independently not 1. In embodiments, $L^4$ is independently not —$SO_2$—. In embodiments, $L^4$ is independently not —$NHSO_2$—. In embodiments, $L^4$ is independently not —$SO_2NH$—. In embodiments, Ring A is independently not phenyl. In embodiments, $L^4$ is not —O—.

$W^2$ is independently S or O.

$W^3$ is independently CH or $C(R^2)$.

In embodiments of the compound of formula IV, $L^4$ is —$C(O)N(R^4)$—, —$N(R^4)C(O)$—, —$SO_2N(R^4)$—, or —$N(R^4)SO_2$—. In embodiments of the compound of formula IV, $L^4$ is —C(O)NH—, —NHC(O)—, —$SO_2NH$—, or —$NHSO_2$—.

In embodiments of the compound of formula IV, $R^5$ and $R^6$ are independently hydrogen.

In embodiments, the compound has the formula:

(IVa)

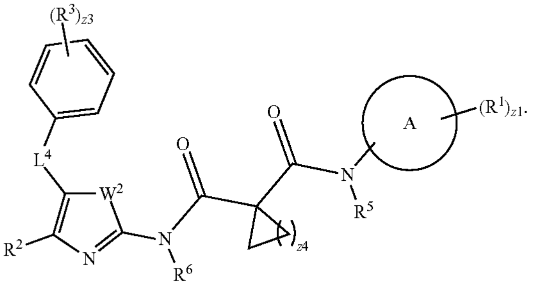

Ring A, $R^1$, $R^2$, $R^3$, $R^5$, $R^6$, $L^4$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^2$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $L^4$ is independently not —$SO_2$—. In embodiments, $L^4$ is independently not —$NHSO_2$—. In embodiments, $L^4$ is independently not —$SO_2NH$—. In embodiments, Ring A is independently not phenyl. In embodiments, $L^4$ is not —O—.

In embodiments, the compound has the formula:

(IVb)

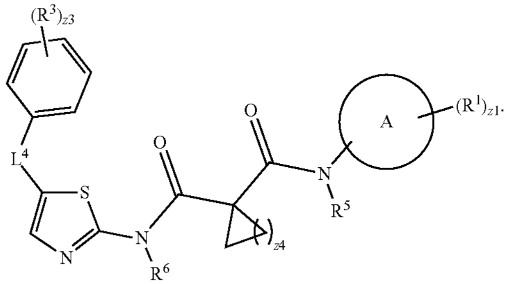

Ring A, $R^1$, $R^2$, $R^3$, $R^5$, $R^6$, $L^4$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $L^4$ is independently not —$SO_2$—. In embodiments, $L^4$ is independently not —$NHSO_2$—. In embodiments, $L^4$ is independently not —$SO_2NH$—. In embodiments, Ring A is independently not phenyl. In embodiments, $L^4$ is not —O—.

In embodiments, the compound has the formula:

(IVc)

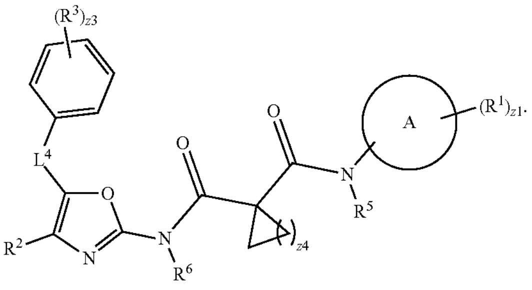

Ring A, $R^1$, $R^2$, $R^3$, $R^5$, $R^6$, $L^4$, z1, z3, and z4 are as described herein, including in embodiments.

In embodiments, the compound has the formula:

(IVd)

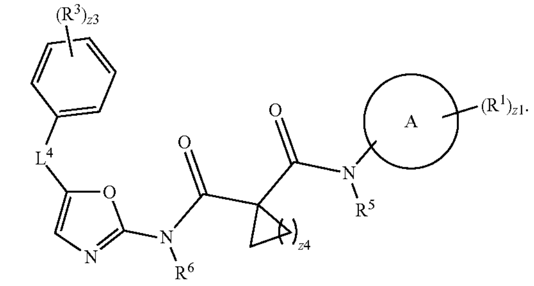

Ring A, $R^1$, $R^3$, $R^5$, $R^6$, $L^4$, z1, z3, and z4 are as described herein, including in embodiments.

In embodiments, the compound has the formula:

(IVe)

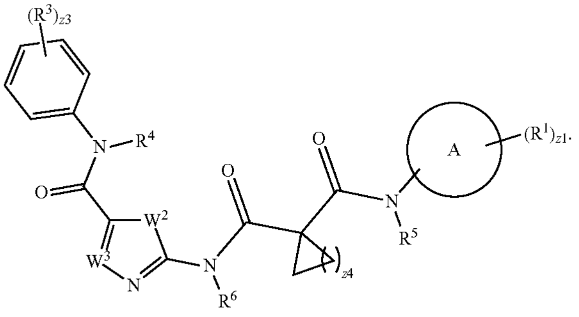

Ring A, $R^1$, $R^3$, $R^4$, $R^5$, $R^6$, $W^2$, $W^3$, z1, z3, and z4 are as described herein, including in embodiments.

In embodiments, the compound has the formula:

(IVf)

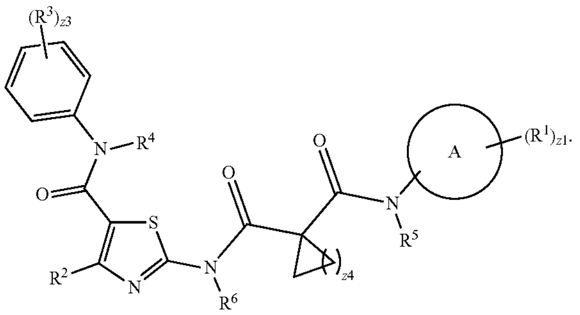

Ring A, $R^1$, $R^2$, $R^3$, $R^4$, $R^5$, $R^6$, z1, z3, and z4 are as described herein, including in embodiments.

In embodiments, the compound has the formula:

(IVg)

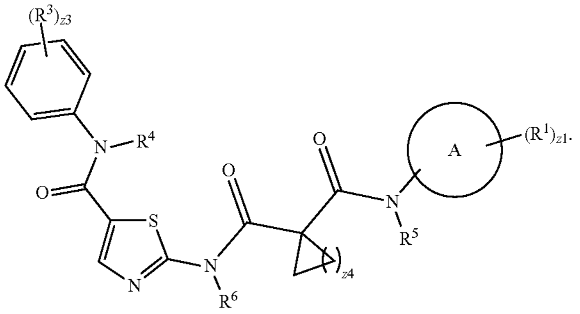

Ring A, $R^1$, $R^2$, $R^3$, $R^4$, $R^5$, $R^6$, z1, z3, and z4 are as described herein, including in embodiments.

In embodiments, the compound has the formula:

(IVh)

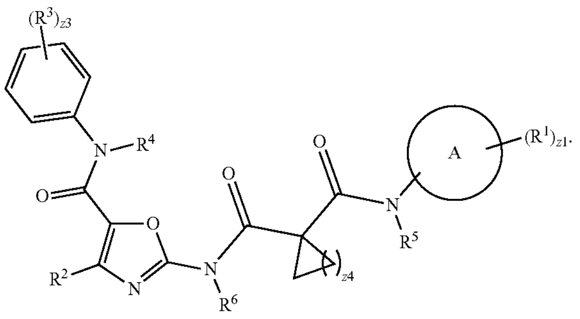

Ring A, $R^1$, $R^2$, $R^3$, $R^4$, $R^5$, $R^6$, z1 z3, and z4 are as described herein, including in embodiments.

In embodiments, the compound has the formula:

(IVi)

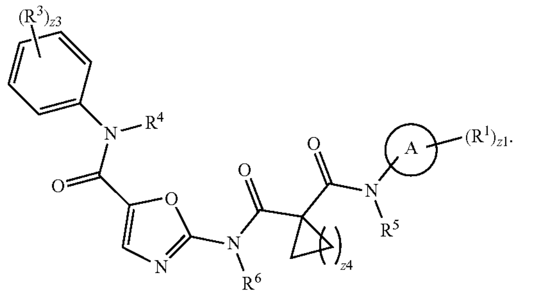

Ring A, $R^1$, $R^3$, $R^4$, $R^5$, $R^6$, z1, z3, and z4 are as described herein, including in embodiments.

In embodiments, the compound has the formula:

(IVj)

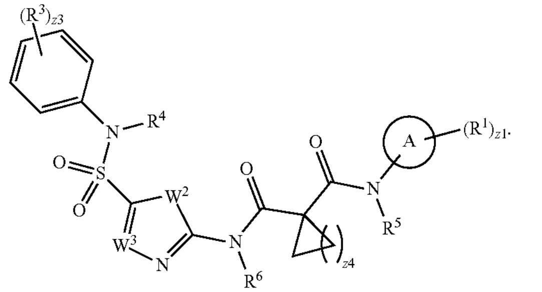

Ring A, $R^1$, $R^3$, $R^4$, $R^5$, $R^6$, $W^2$, $W^3$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $W^2$ is independently not S. In embodiments, $W^3$ is independently not CH. In embodiments, $R^3$ is independently not —Cl. In embodiments, $R^3$ is independently not halogen. In embodiments, $R^3$ is independently not —$NO_2$. In embodiments, z3 is independently not 1. In embodiments, $R^4$ is independently not hydrogen. In embodiments, Ring A is independently not phenyl. In embodiments, $L^4$ is not —O—.

In embodiments, the compound has the formula:

(IVk)

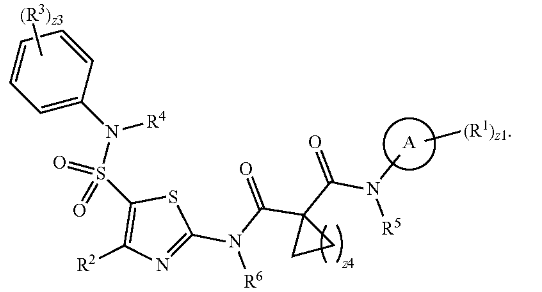

Ring A, $R^1$, $R^2$, $R^3$, $R^4$, $R^5$, $R^6$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^2$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $R^4$ is independently not hydrogen. In embodiments, Ring A is independently not phenyl. In embodiments, $L^4$ is not —O—.

In embodiments, the compound has the formula:

(Ivl)

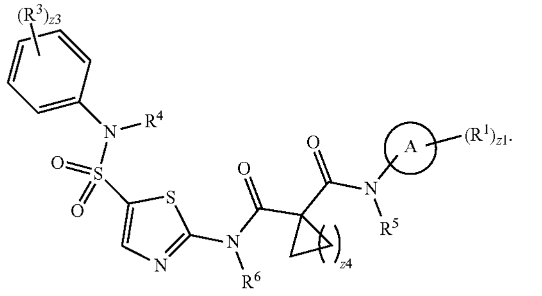

Ring A, $R^1$, $R^2$, $R^3$, $R^4$, $R^5$, $R^6$, z1 z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $R^4$ is independently not hydrogen. In embodiments, Ring A is independently not phenyl. In embodiments, $L^4$ is not —O—.

In embodiments, the compound has the formula:

(Ivm)

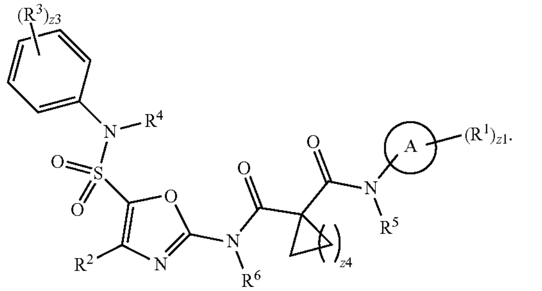

Ring A, $R^1$, $R^2$, $R^3$, $R^4$, $R^5$, $R^6$, z1, z3, and z4 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not $—CX^1_3$. In embodiments, z1 is independently not 1. In embodiments, $R^5$ is independently not hydrogen. In embodiments, $R^6$ is independently not hydrogen. In embodiments, $R^2$ is independently not hydrogen. In embodiments, $R^3$ is independently not —Cl. In embodiments, $R^3$ is independently not halogen. In embodiments, $R^3$ is independently not $—NO_2$. In embodiments, z3 is independently not 1. In embodiments, $R^4$ is independently not hydrogen. In embodiments, Ring A is independently not phenyl. In embodiments, $L^4$ is not —O—.

In embodiments, the compound has the formula:

(IVn)

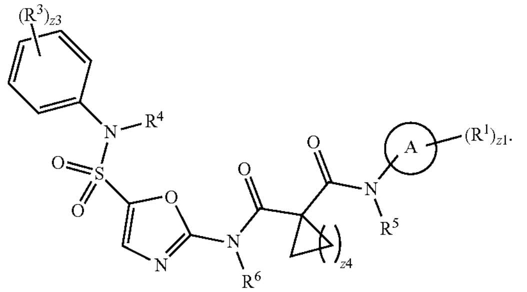

Ring A, $R^1$, $R^3$, $R^4$, $R^5$, $R^6$, z1, z3, and z4 are as described herein, including in embodiments.

In embodiments, $R^1$ is independently not $—CF_3$. In embodiments, $R^1$ is independently not —Cl. In embodiments, $R^1$ is independently not halogen. In embodiments, $R^1$ is independently not $—CX^1_3$. In embodiments, z1 is independently not 1. In embodiments, $R^5$ is independently not hydrogen. In embodiments, $R^6$ is independently not hydrogen. In embodiments, $R^3$ is independently not —Cl. In embodiments, $R^3$ is independently not halogen. In embodiments, $R^3$ is independently not $—NO_2$. In embodiments, z3 is independently not 1. In embodiments, $R^4$ is independently not hydrogen. In embodiments, Ring A is independently not phenyl. In embodiments, $L^4$ is not —O—.

In embodiments, the compound has the formula:

(V)

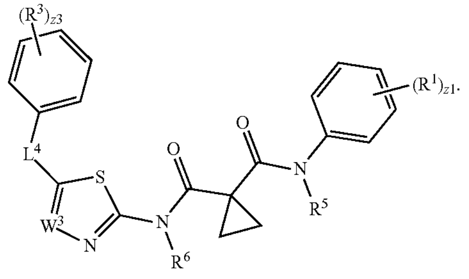

$R^1$, $R^3$, $R^5$, $R^6$, $L^4$, $W^3$, z1, and z3 are as described herein, including in embodiments.

In embodiments, $R^1$ is independently not $—CF_3$. In embodiments, $R^1$ is independently not —Cl. In embodiments, $R^1$ is independently not halogen. In embodiments, $R^1$ is independently not $—CX^1_3$. In embodiments, z1 is independently not 1. In embodiments, $R^5$ is independently not hydrogen. In embodiments, $R^6$ is independently not hydrogen. In embodiments, $R^3$ is independently not —Cl. In embodiments, $R^3$ is independently not halogen. In embodiments, $R^3$ is independently not $—NO_2$. In embodiments, z3 is independently not 1. In embodiments, $L^4$ is independently not $—SO_2NH—$. In embodiments, $L^4$ is independently not $—NHSO_2—$. In embodiments, $L^4$ is independently not $—SO_2—$. In embodiments, $W^3$ is independently not —CH—. In embodiments, $L^4$ is not —O—.

In embodiments of the compound of formula V, $L^4$ is $—C(O)N(R^4)—$, $—N(R^4)C(O)—$, $—SO_2N(R^4)—$, or $—N(R^4)SO_2—$. In embodiments of the compound of formula Ij, $L^4$ is —C(O)NH—, —NHC(O)—, $—SO_2NH—$, or $—NHSO_2—$.

In embodiments of the compound of formula V, $R^5$ and $R^6$ are independently hydrogen.

In embodiments, the compound has the formula:

(Va)

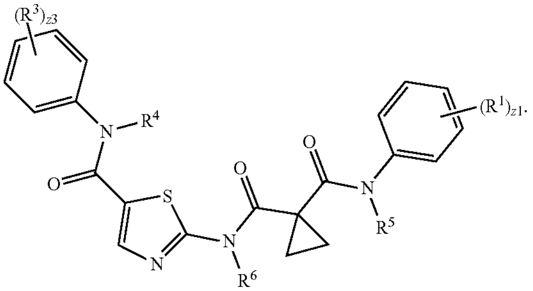

$R^1$, $R^3$, $R^4$, $R^5$, $R^6$, z1, and z3 are as described herein, including in embodiments.

In embodiments, the compound has the formula:

(Vb)

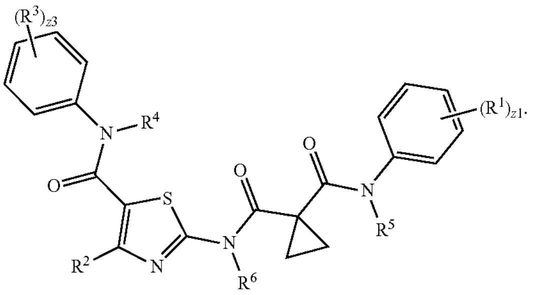

$R^1$, $R^2$, $R^3$, $R^4$, $R^5$, $R^6$, z1, and z3 are as described herein, including in embodiments.

In embodiments, the compound has the formula:

(Vc)

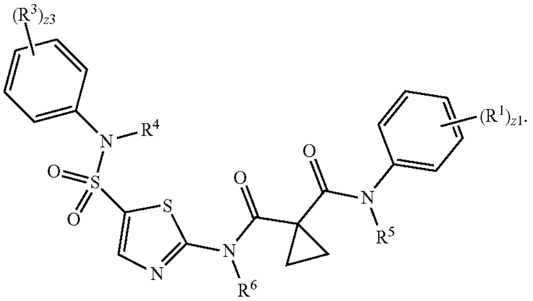

$R^1$, $R^3$, $R^4$, $R^5$, $R^6$, z1, and z3 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $R^4$ is independently not hydrogen. In embodiments, $L^4$ is not —O—.

In embodiments, the compound has the formula:

(Vd)

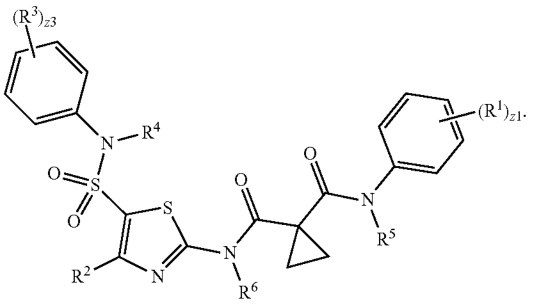

$R^1$, $R^2$, $R^3$, $R^4$, $R^5$, $R^6$, z1, and z3 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, $R^5$ is independently not hydrogen. In embodiments, $R^6$ is independently not hydrogen. In embodiments, $R^2$ is independently not hydrogen. In embodiments, $R^3$ is independently not —Cl. In embodiments, $R^3$ is independently not halogen. In embodiments, $R^3$ is independently not —$NO_2$. In embodiments, z3 is independently not 1. In embodiments, $R^4$ is independently not hydrogen. In embodiments, $L^4$ is not —O—.

In embodiments, the compound has the formula:

(Ia)

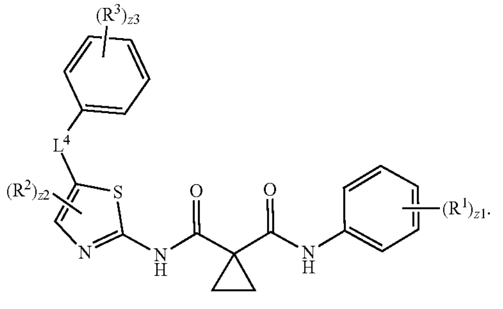

$R^1$, $R^2$, $R^3$, $L^4$, z1, z2, and z3 are as described herein, including in embodiments.

In embodiments, $R^1$ is independently not —$CF_3$. In embodiments, $R^1$ is independently not —Cl. In embodiments, $R^1$ is independently not halogen. In embodiments, $R^1$ is independently not —$CX^1_3$. In embodiments, z1 is independently not 1. In embodiments, z2 is independently not 0. In embodiments, $R^3$ is independently not —Cl. In embodiments, $R^3$ is independently not halogen. In embodiments, $R^3$ is independently not —$NO_2$. In embodiments, z3 is independently not 1. In embodiments, $L^4$ is independently not —$SO_2NH$—. In embodiments, $L^4$ is independently not —$NHSO_2$—. In embodiments, $L^4$ is independently not —$SO_2$—. In embodiments, $L^4$ is not —O—.

In embodiments of the compound of formula Ia, $L^4$ is a bond, —$SO_2$—, —C(O)NH—, —NHC(O)—, —$SO_2NH$—, or —$NHSO_2$—.

In embodiments, the compound has the formula:

(Ib)

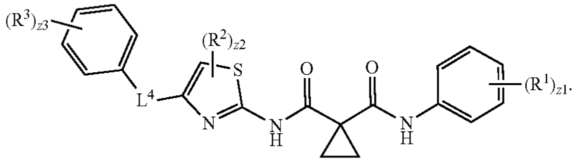

$R^1$, $R^2$, $R^3$, $L^4$, z1, z2, and z3 are as described herein, including in embodiments.

In embodiments, $R^1$ is independently not —Cl. In embodiments, $R^1$ is independently not halogen. In embodiments, z1 is independently not 1. In embodiments, $z^2$ is independently not 0. In embodiments, $R^3$ is independently not —Cl. In embodiments, $R^3$ is independently not halogen. In embodiments, $R^3$ is independently not —$NO_2$. In embodiments, z3 is independently not 1. In embodiments, $L^4$ is independently not —$SO_2NH$—. In embodiments, $L^4$ is independently not —$NHSO_2$—. In embodiments, $L^4$ is independently not —$SO_2$—. In embodiments, $L^4$ is not —O—.

In embodiments of the compound of formula Ib, $L^4$ is —$SO_2NH$— or —$NHSO_2$—.

In embodiments, the compound has the formula:

(Ic)

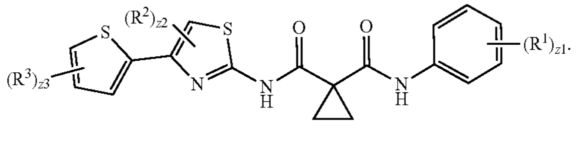

$R^1$, $R^2$, $R^3$, z1, z2, and z3 are as described herein, including in embodiments.

In embodiments, $R^1$ is independently not —Cl. In embodiments, $R^1$ is independently not halogen. In embodiments, z1 is independently not 1. In embodiments, z2 is independently not 0. In embodiments, $R^3$ is independently not —Br. In embodiments, $R^3$ is independently not halogen. In embodiments, $R^3$ is independently not —$NO_2$. In embodiments, z3 is independently not 1.

In embodiments, the compound has the formula:

(Ie)

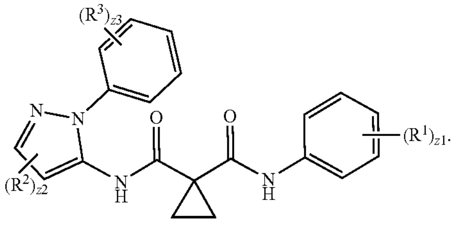

$R^1$, $R^2$, $R^3$, z1, z2, and z3 are as described herein, including in embodiments.

In embodiments, $R^1$ is independently not —Cl. In embodiments, $R^1$ is independently not halogen. In embodiments, z1 is independently not 2. In embodiments, $R^2$ is independently not $—C(O)OR^{2C}$. In embodiments, $R^{2C}$ is independently not unsubstituted ethyl. In embodiments, $R^{2C}$ is independently not unsubstituted $C_1$-$C_3$ alkyl. In embodiments, $R^3$ is independently not —Cl. In embodiments, $R^3$ is independently not halogen. In embodiments, z3 is independently not 1.

In embodiments, the compound has the formula:

(If)

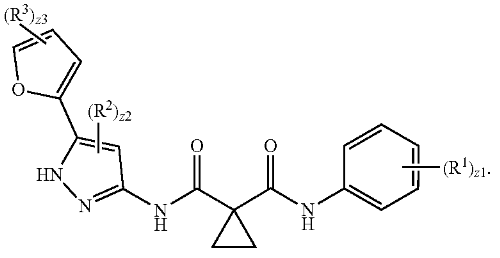

$R^1$, $R^2$, $R^3$, z1, z2, and z3 are as described herein, including in embodiments.

In embodiments, $R^1$ is independently not —Br. In embodiments, $R^1$ is independently not $—NO_2$. In embodiments, $R^1$ is independently not —Br or $—NO_2$. In embodiments, $R^1$ is independently not halogen. In embodiments, z1 is independently not 2. In embodiments, $R^2$ is independently not unsubstituted methyl. In embodiments, $R^2$ is independently not unsubstituted ethyl. In embodiments, $R^2$ is independently not unsubstituted $C_1$-$C_3$ alkyl. In embodiments, z2 is independently not 1. In embodiments, $R^3$ is independently not unsubstituted methyl. In embodiments, $R^3$ is independently not unsubstituted ethyl. In embodiments, $R^3$ is independently not unsubstituted $C_1$-$C_3$ alkyl. In embodiments, z3 is independently not 1.

In embodiments, Ring A is phenyl. In embodiments, Ring A is a 5 to 6 membered heteroaryl. In embodiments, Ring A is pyridyl. In embodiments, Ring A is 2-pyridyl. In embodiments, Ring A is 3-pyridyl. In embodiments, Ring A is 4-pyridyl. In embodiments, Ring A is pyrazinyl. In embodiments, Ring A is pyrimidinyl. In embodiments, Ring A is pyridazinyl. In embodiments, Ring A is triazinyl.

In embodiments, Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, or thiadiazolyl.

In embodiments, Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, or thiadiazolyl.

In embodiments, Ring B is pyrrolyl. In embodiments, Ring B is pyrazolyl. In embodiments, Ring B is imidazolyl. In embodiments, Ring B is triazolyl. In embodiments, Ring B is tetrazolyl. In embodiments, Ring B is furanyl. In embodiments, Ring B is thienyl. In embodiments, Ring B is oxazolyl. In embodiments, Ring B is isoxazolyl. In embodiments, Ring B is thiazolyl. In embodiments, Ring B is isothiazolyl. In embodiments, Ring B is oxadiazolyl. In embodiments, Ring B is thiadiazolyl.

In embodiments, Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

In embodiments, Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

In embodiments, Ring C is phenyl. In embodiments, Ring C is pyrrolyl. In embodiments, Ring C is pyrazolyl. In embodiments, Ring C is imidazolyl. In embodiments, Ring C is triazolyl. In embodiments, Ring C is tetrazolyl. In embodiments, Ring C is furanyl. In embodiments, Ring C is thienyl. In embodiments, Ring C is oxazolyl. In embodiments, Ring C is isoxazolyl. In embodiments, Ring C is thiazolyl. In embodiments, Ring C is isothiazolyl. In embodiments, Ring C is oxadiazolyl. In embodiments, Ring C is thiadiazolyl. In embodiments, Ring C is pyridyl. In embodiments, Ring C is pyrimidinyl. In embodiments, Ring C is pyridazinyl. In embodiments, Ring C is pyrazinyl. In embodiments, Ring C is triazinyl.

In embodiments, $R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $C(O)R^{1C}$, $—C(O)—OR^{1C}$, $—C(O)\ NR^{1A}R^{1B}$, $—OR^{1D}$, $—NR^{1A}SO_2R^{1D}$, $—NR^{1C}(O)R^{1C}$, $—NR^{1C}(O)OR^{1C}$, $—NR^{1A}OR^{1C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, two adjacent $R^1$ substituents are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^1$ is independently halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, $R^1$ is independently halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NO_2$, —SH, $—OCCl_3$, $—OCF_3$, $—OCBr_3$, $—OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_4$ alkyl, or substituted or unsubstituted 2 to 4 membered heteroalkyl. In embodiments, $R^1$ is independently halogen, —$CF_3$, —$NO_2$, or —$OCH_3$. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently —$CCl_3$. In embodiments, $R^1$ is independently —$CBr_3$. In embodiments, $R^1$ is independently —$CF_3$. In embodiments, $R^1$ is independently —$CI_3$. In embodiments, $R^1$ is independently —$CHCl_2$. In embodiments, $R^1$ is independently —$CHBr_2$. In embodiments, $R^1$ is independently —$CHF_2$. In embodiments, $R^1$ is independently —$CHI_2$. In embodiments, $R^1$ is independently —$CH_2Cl$. In embodiments, $R^1$ is independently —$CH_2Br$. In embodiments, $R^1$ is independently —$CH_2F$. In embodiments, $R^1$ is independently —$CH_2I$. In embodiments, $R^1$ is independently —CN. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$OCCl_3$. In embodiments, $R^1$ is independently —$OCF_3$. In embodiments, $R^1$ is independently —$OCBr_3$. In embodiments, $R^1$ is independently —$OCI_3$. In embodiments, $R^1$ is independently —$OCHCl_2$. In embodiments, $R^1$ is independently —$OCHBr_2$. In embodiments, $R^1$ is independently —$OCHI_2$. In embodiments, $R^1$ is independently —$OCHF_2$. In embodiments, $R^1$ is independently —$OCH_2Cl$. In embodiments, $R^1$ is independently —$OCH_2Br$. In embodiments, $R^1$ is independently —$OCH_2I$. In embodiments, $R^1$ is independently —$OCH_2F$. In embodiments, $R^1$ is independently halogen. In embodiments, $R^1$ is independently —$NO_2$. In embodiments, $R^1$ is independently —$OCH_3$. In embodiments, $R^1$ is independently —$OCH_2CH_3$. In embodiments, $R^1$ is independently —$OCH(CH_3)_2$. In embodiments, $R^1$ is independently —$OC(CH_3)_3$. In embodiments, $R^1$ is independently —$CH_3$. In embodiments, $R^1$ is independently —$CH_2CH_3$. In embodiments, $R^1$ is independently —$CH(CH_3)_2$. In embodiments, $R^1$ is independently —$C(CH_3)_3$.

In embodiments, $R^1$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, two adjacent $R^1$ substituents are joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently substituted or unsubstituted alkyl. In embodiments, $R^1$ is independently unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently substituted or unsubstituted heteroaryl.

In embodiments, $R^1$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, or substituted or unsubstituted 2 to 6 membered heteroalkyl. In embodiments, $R^1$ is independently —F, —Cl, —Br, —I, unsubstituted methyl, unsubstituted ethyl, or unsubstituted propyl.

In embodiments, $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, two adjacent $R^1$ substituents are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently substituted or unsubstituted $C_1$-$C_6$ alkyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted butyl. In embodiments, $R^1$ is independently substituted or unsubstituted 2 to 6 membered heteroalkyl. In embodiments, $R^1$ is independently substituted or unsubstituted $C_3$-$C_6$ cycloalkyl. In embodiments, $R^1$ is independently substituted or unsubstituted 3 to 6 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, two adjacent $R^1$ substituents are joined to form a substituted or unsubstituted $C_3$-$C_6$ cycloalkyl. In embodiments, two adjacent $R^1$ substituents are joined to form a substituted or unsubstituted 3 to 6 membered heterocycloalkyl. In embodiments, two adjacent $R^1$ substituents are joined to form a substituted or unsubstituted phenyl. In embodiments, two adjacent $R^1$ substituents are joined to form a substituted or unsubstituted 5 to 6 membered heteroaryl. In embodiments, $R^1$ is independently unsubstituted $C_1$-$C_6$ alkyl. In embodiments, $R^1$ is independently unsubstituted 2 to 6 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently unsubstituted phenyl. In embodiments, $R^1$ is independently unsubstituted 5 to 6 membered heteroaryl. In embodiments, two adjacent $R^1$ substituents are joined to form an unsubstituted $C_3$-$C_6$ cycloalkyl. In embodiments, two adjacent $R^1$ substituents are joined to form an unsubstituted 3 to 6 membered heterocycloalkyl. In embodiments, two adjacent $R^1$ substituents are joined to form an unsubstituted phenyl. In embodiments, two adjacent $R^1$ substituents are joined to form an unsubstituted 5 to 6 membered heteroaryl.

In embodiments, $R^1$ is independently substituted pyrrolyl. In embodiments, $R^1$ is independently substituted pyrazolyl. In embodiments, $R^1$ is independently substituted imidazolyl. In embodiments, $R^1$ is independently substituted triazolyl. In embodiments, $R^1$ is independently substituted tetrazolyl. In embodiments, $R^1$ is independently substituted furanyl. In embodiments, $R^1$ is independently substituted thienyl. In embodiments, $R^1$ is independently substituted oxazolyl. In embodiments, $R^1$ is independently substituted isoxazolyl. In embodiments, $R^1$ is independently substituted thiazolyl. In embodiments, $R^1$ is independently substituted isothiazolyl. In embodiments, $R^1$ is independently substituted oxadiazolyl. In embodiments, $R^1$ is independently substituted thiadiazolyl. In embodiments, $R^1$ is independently substituted phenyl. In embodiments, $R^1$ is independently methyl-substituted pyrrolyl. In embodiments, $R^1$ is independently methyl-substituted pyrazolyl. In embodiments, $R^1$ is independently methyl-substituted imidazolyl. In embodiments, $R^1$ is independently methyl-substituted triazolyl. In embodiments, $R^1$ is independently methyl-substituted tetrazolyl. In embodiments, $R^1$ is independently methyl-substituted furanyl. In embodiments, $R^1$ is independently methyl-substituted thienyl. In embodiments, $R^1$ is independently methyl-substituted oxazolyl. In embodiments, $R^1$ is independently methyl-substituted isoxazolyl. In embodiments, $R^1$ is independently methyl-substituted thiazolyl. In embodiments, $R^1$ is independently methyl-substituted isothiazolyl. In embodiments, $R^1$ is independently methyl-substituted oxadiazolyl. In embodiments, $R^1$ is independently methyl-substituted thiadiazolyl. In embodiments, $R^1$ is independently methyl-substituted phenyl. In embodiments, $R^1$ is independently unsubstituted pyrrolyl. In embodiments, $R^1$ is independently unsubstituted pyrazolyl. In embodiments, $R^1$ is independently unsubstituted imidazolyl. In embodiments, $R^1$ is independently unsubstituted triazolyl. In embodiments, $R^1$ is independently unsubstituted tetrazolyl. In embodiments, $R^1$ is independently unsubstituted furanyl. In embodiments, $R^1$ is independently unsubstituted thienyl. In embodiments, $R^1$ is independently unsubstituted oxazolyl. In embodiments, $R^1$ is independently unsubstituted isoxazolyl. In embodiments, $R^1$ is independently unsubstituted thiazolyl. In embodiments, $R^1$ is independently unsubstituted isothiazolyl. In embodiments, $R^1$ is independently unsubstituted oxadiazolyl. In embodiments, $R^1$ is independently unsubstituted thiadiazolyl. In embodiments, $R^1$ is independently unsubstituted phenyl.

In embodiments, z1 is an integer from 0 to 4. In embodiments, z1 is an integer from 1 to 5. In embodiments, z1 is 0. In embodiments, z1 is 1. In embodiments, z1 is 2. In embodiments, z1 is 3. In embodiments, z1 is 4. In embodiments, z1 is 5.

In embodiments, $R^{1A}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, substituted or unsubstituted $C_1$-$C_4$alkyl, or substituted or unsubstituted 2 to 4 membered heteroalkyl. In embodiments, $R^{1A}$ is independently hydrogen, substituted or unsubstituted $C_1$-$C_4$ alkyl, or substituted or unsubstituted 2 to 4 membered heteroalkyl. In embodiments, $R^{1A}$ is independently hydrogen. In embodiments, $R^{1A}$ is independently substituted or unsubstituted $C_1$-$C_4$ alkyl. In embodiments, $R^{1A}$ is independently substituted or unsubstituted 2 to 4 membered heteroalkyl. In embodiments, $R^{1A}$ is independently unsubstituted methyl. In embodiments, $R^{1A}$ is independently unsubstituted $C_1$-$C_4$ alkyl. In embodiments, $R^{1A}$ is independently unsubstituted 2 to 4 membered heteroalkyl.

In embodiments, $R^{1B}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, substituted or unsubstituted $C_1$-$C_4$ alkyl, or substituted or unsubstituted 2 to 4 membered heteroalkyl. In embodiments, $R^{1B}$ is independently hydrogen, substituted or unsubstituted $C_1$-$C_4$ alkyl, or substituted or unsubstituted 2 to 4 membered heteroalkyl. In embodiments, $R^{1B}$ is independently hydrogen. In embodiments, $R^{1B}$ is independently substituted or unsubstituted $C_1$-$C_4$ alkyl. In embodiments, $R^{1B}$ is independently substituted or unsubstituted 2 to 4 membered heteroalkyl. In embodiments, $R^{1B}$ is independently unsubstituted methyl. In embodiments, $R^{1B}$ is independently unsubstituted $C_1$-$C_4$ alkyl. In embodiments, $R^{1B}$ is independently unsubstituted 2 to 4 membered heteroalkyl.

In embodiments, $R^{1C}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, substituted or unsubstituted $C_1$-$C_4$ alkyl, or substituted or unsubstituted 2 to 4 membered heteroalkyl. In embodiments, $R^{1C}$ is independently hydrogen, substituted or unsubstituted $C_1$-$C_4$ alkyl, or substituted or unsubstituted 2 to 4 membered heteroalkyl. In embodiments, $R^{1C}$ is independently hydrogen. In embodiments, $R^{1C}$ is independently substituted or unsubstituted $C_1$-$C_4$ alkyl. In embodiments, $R^{1C}$ is independently substituted or unsubstituted 2 to 4 membered heteroalkyl. In embodiments, $R^{1C}$ is independently unsubstituted methyl. In embodiments, $R^{1C}$ is independently unsubstituted $C_1$-$C_4$ alkyl. In embodiments, $R^{1C}$ is independently unsubstituted 2 to 4 membered heteroalkyl.

In embodiments, $R^{1D}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, substituted or unsubstituted $C_1$-$C_4$ alkyl, or substituted or unsubstituted 2 to 4 membered heteroalkyl. In embodiments, $R^{1D}$ is independently hydrogen, substituted or unsubstituted $C_1$-$C_4$ alkyl, or substituted or unsubstituted 2 to 4 membered heteroalkyl. In embodiments, $R^{1D}$ is independently hydrogen. In embodiments, $R^{1D}$ is independently substituted or unsubstituted $C_1$-$C_4$ alkyl. In embodiments, $R^{1D}$ is independently substituted or unsubstituted 2 to 4 membered heteroalkyl. In embodiments, $R^{1D}$ is independently unsubstituted methyl. In embodiments, $R^{1D}$ is independently unsubstituted $C_1$-$C_4$ alkyl. In embodiments, $R^{1D}$ is independently unsubstituted 2 to 4 membered heteroalkyl.

In embodiments, $R^2$ is independently halogen, $—CX^2_3$, $—CHX^{22}$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)\ NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, two adjacent $R^2$ substituents are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^2$ is independently halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, $R^2$ is independently substituted or unsubstituted $C_1$-$C_6$ alkyl or substituted or unsubstituted 2 to 6 membered heteroalkyl. In embodiments, $R^2$ is independently $—CH_3$ or $—COOCH_2CH_3$. In embodiments, $R^2$ is independently —C(O)$R^{2C}$. In embodiments, $R^2$ is independently —C(O)—$OR^{2C}$. In embodiments, $R^2$ is independently —C(O)$NR^{2A}R^{2B}$. In embodiments, $R^2$ is independently oxo. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently —$CCl_3$. In embodiments, $R^2$ is independently —$CBr_3$. In embodiments, $R^2$ is independently —$CF_3$. In embodiments, $R^2$ is independently —$CI_3$. In embodiments, $R^2$ is independently —$CHCl_2$. In embodiments, $R^2$ is independently —$CHBr_2$. In embodiments, $R^2$ is independently —$CHF_2$. In embodiments, $R^2$ is independently —$CHI_2$. In embodiments, $R^2$ is independently —$CH_2Cl$. In embodiments, $R^2$ is independently —$CH_2Br$. In embodiments, $R^2$ is independently —$CH_2F$. In embodiments, $R^2$ is independently —$CH_2I$. In embodiments, $R^2$ is independently —CN. In embodiments, $R^2$ is independently —$SO_2Me$. In embodiments, $R^2$ is independently —$SO_2Et$. In embodiments, $R^2$ is independently —$SO_2NH_2$. In embodiments, $R^2$ is independently —OH. In embodiments, $R^2$ is independently —$OCH_3$. In embodiments, $R^2$ is independently —$NH_2$. In embodiments, $R^2$ is independently —COOH. In embodiments, $R^2$ is independently —$COCH_3$. In embodiments, $R^2$ is independently —$CONH_2$. In embodiments, $R^2$ is independently —$OCCl_3$. In embodiments, $R^2$ is independently —$OCF_3$. In embodiments, $R^2$ is independently —$OCBr_3$. In embodiments, $R^2$ is independently —$OCI_3$. In embodiments, $R^2$ is independently —$OCHCl_2$. In embodiments, $R^2$ is independently —$OCHBr_2$. In embodiments, $R^2$ is independently —$OCHI_2$. In embodiments, $R^2$ is independently —$OCHF_2$. In embodiments, $R^2$ is independently —$OCH_2Cl$. In embodiments, $R^2$ is independently —$OCH_2Br$. In embodiments, $R^2$ is independently —$OCH_2I$. In embodiments, $R^2$ is independently —$OCH_2F$.

In embodiments, $R^2$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, two adjacent $R^2$ substituents are joined to form a substituted or unsubstituted cycloalkyl, substituted or unsubstituted heterocycloalkyl, substituted or unsubstituted aryl, or substituted or unsubstituted heteroaryl. In embodiments, $R^2$ is independently substituted or unsubstituted alkyl. In embodiments, $R^2$ is independently unsubstituted alkyl. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently substituted or unsubstituted heteroalkyl. In embodiments, $R^2$ is independently unsubstituted heteroalkyl. In embodiments, $R^2$ is independently substituted or unsubstituted cycloalkyl. In embodiments, $R^2$ is independently substituted or unsubstituted heterocycloalkyl. In embodiments, $R^2$ is independently unsubstituted heterocycloalkyl. In embodiments, $R^2$ is independently substituted or unsubstituted aryl. In embodiments, $R^2$ is independently unsubstituted phenyl. In embodiments, $R^2$ is independently substituted or unsubstituted heteroaryl.

In embodiments, $R^{2A}$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, $R^{2A}$ is independently hydrogen.

In embodiments, $R^{2A}$ is independently substituted or unsubstituted $C_1$-$C_6$ alkyl or substituted or unsubstituted 2 to 6 membered heteroalkyl. In embodiments, $R^{2A}$ is independently —$CH_3$ or —$COOCH_2CH_3$. In embodiments, $R^{2A}$ is independently —C(O)$R^{2C}$. In embodiments, $R^{2A}$ is independently —C(O)—$OR^{2C}$. In embodiments, $R^{2A}$ is independently —C(O)$NR^{2A}R^{2B}$. In embodiments, $R^{2A}$ is independently oxo. In embodiments, $R^{2A}$ is independently —F. In embodiments, $R^{2A}$ is independently —Cl. In embodiments, $R^{2A}$ is independently —Br. In embodiments, $R^{2A}$ is independently —I. In embodiments, $R^{2A}$ is independently —$CCl_3$. In embodiments, $R^{2A}$ is independently —$CBr_3$. In embodiments, $R^{2A}$ is independently —$CF_3$. In embodiments, $R^{2A}$ is independently —$CI_3$. In embodiments, $R^{2A}$ is independently —$CHCl_2$. In embodiments, $R^{2A}$ is independently —$CHBr_2$. In embodiments, $R^{2A}$ is independently —$CHF_2$. In embodiments, $R^{2A}$ is independently —$CHI_2$. In embodiments, $R^{2A}$ is independently —$CH_2Cl$. In embodiments, $R^{2A}$ is independently —$CH_2Br$. In embodiments, $R^{2A}$ is independently —$CH_2F$. In embodiments, $R^{2A}$ is independently —$CH_2I$. In embodiments, $R^{2A}$ is independently —CN. In embodiments, $R^{2A}$ is independently —$SO_2Me$. In embodiments, $R^{2A}$ is independently —$SO_2Et$. In embodiments, $R^{2A}$ is independently —$SO_2NH_2$. In embodiments, $R^{2A}$ is independently —OH. In embodiments, $R^{2A}$ is independently —$OCH_3$. In embodiments, $R^{2A}$ is independently —$NH_2$. In embodiments, $R^{2A}$ is independently —COOH. In embodiments, $R^{2A}$ is independently —$COCH_3$. In embodiments, $R^{2A}$ is independently —$CONH_2$. In embodiments, $R^{2A}$ is independently —$OCCl_3$. In embodiments, $R^{2A}$ is independently —$OCF_3$. In embodiments, $R^{2A}$ is independently —$OCBr_3$. In embodiments, $R^{2A}$ is independently —$OCI_3$. In embodiments, $R^{2A}$ is independently —$OCHCl_2$. In embodiments, $R^{2A}$ is independently —$OCHBr_2$. In embodiments, $R^{2A}$ is independently —$OCHI_2$. In embodiments, $R^{2A}$ is independently —$OCHF_2$. In embodiments, $R^{2A}$ is independently —$OCH_2Cl$. In embodiments, $R^{2A}$ is independently —$OCH_2Br$. In embodiments, $R^{2A}$ is independently —$OCH_2I$. In embodiments, $R^{2A}$ is independently —$OCH_2F$.

In embodiments, $R^{2A}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, two adjacent $R^{2A}$ substituents are joined to form a substituted or unsubstituted cycloalkyl, substituted or unsubstituted heterocycloalkyl, substituted or unsubstituted aryl, or substituted or unsubstituted heteroaryl. In embodiments, $R^{2A}$ is independently substituted or unsubstituted alkyl. In embodiments, $R^{2A}$ is independently unsubstituted alkyl. In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently substituted or unsubstituted heteroalkyl. In embodiments, $R^{2A}$ is independently unsubstituted heteroalkyl. In embodiments, $R^{2A}$ is independently substituted or unsubstituted cycloalkyl. In embodiments, $R^{2A}$ is independently substituted or unsubstituted heterocycloalkyl. In embodiments, $R^{2.A}$ is independently unsubstituted heterocycloalkyl. In embodiments, $R^{2.A}$ is independently substituted or unsubstituted aryl. In embodiments, $R^{2.A}$ is independently unsubstituted phenyl. In embodiments, $R^{2.A}$ is independently substituted or unsubstituted heteroaryl.

In embodiments, $R^{2.B}$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, $R^{2.B}$ is independently hydrogen.

In embodiments, $R^{2.B}$ is independently substituted or unsubstituted $C_1$-$C_6$ alkyl or substituted or unsubstituted 2 to 6 membered heteroalkyl. In embodiments, $R^{2.B}$ is independently —$CH_3$ or —$COOCH_2CH_3$. In embodiments, $R^{2.B}$ is independently —C(O)$R^{2C}$. In embodiments, $R^{2.B}$ is independently —C(O)—$OR^{2C}$. In embodiments, $R^{2.B}$ is independently —C(O)$NR^{2B}R^{2B}$. In embodiments, $R^{2.B}$ is independently oxo. In embodiments, $R^{2.B}$ is independently —F. In embodiments, $R^{2.B}$ is independently —Cl. In embodiments, $R^{2.B}$ is independently —Br. In embodiments, $R^{2.B}$ is independently —I. In embodiments, $R^{2.B}$ is independently —$CCl_3$. In embodiments, $R^{2.B}$ is independently —$CBr_3$. In embodiments, $R^{2.B}$ is independently —$CF_3$. In embodiments, $R^{2.B}$ is independently —$CI_3$. In embodiments, $R^{2.B}$ is independently —$CHCl_2$. In embodiments, $R^{2.B}$ is independently —$CHBr_2$. In embodiments, $R^{2.B}$ is independently —$CHF_2$. In embodiments, $R^{2.B}$ is independently —$CHI_2$. In embodiments, $R^{2.B}$ is independently —$CH_2Cl$. In embodiments, $R^{2.B}$ is independently —$CH_2Br$. In embodiments, $R^{2.B}$ is independently —$CH_2F$. In embodiments, $R^{2.B}$ is independently —$CH_2I$. In embodiments, $R^{2.B}$ is independently —CN. In embodiments, $R^{2.B}$ is independently —$SO_2Me$. In embodiments, $R^{2.B}$ is independently —$SO_2Et$. In embodiments, $R^{2.B}$ is independently —$SO_2NH_2$. In embodiments, $R^{2.B}$ is independently —OH. In embodiments, $R^{2.B}$ is independently —$OCH_3$. In embodiments, $R^{2.B}$ is independently —$NH_2$. In embodiments, $R^{2.B}$ is independently —COOH. In embodiments, $R^{2.B}$ is independently —$COCH_3$. In embodiments, $R^{2.B}$ is independently —$CONH_2$. In embodiments, $R^{2.B}$ is independently —$OCCl_3$. In embodiments, $R^{2.B}$ is independently —$OCF_3$. In embodiments, $R^{2.B}$ is independently —$OCBr_3$. In embodiments, $R^{2.B}$ is independently —$OCI_3$. In embodiments, $R^{2.B}$ is independently —$OCHCl_2$. In embodiments, $R^{2.B}$ is independently —$OCHBr_2$. In embodiments, $R^{2.B}$ is independently —$OCHI_2$. In embodiments, $R^{2.B}$ is independently —$OCHF_2$. In embodiments, $R^{2.B}$ is independently —$OCH_2Cl$. In embodiments, $R^{2.B}$ is independently —$OCH_2Br$. In embodiments, $R^{2.B}$ is independently —$OCH_2I$. In embodiments, $R^{2.B}$ is independently —$OCH_2F$.

In embodiments, $R^{2.B}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, two adjacent $R^{2.B}$ substituents are joined to form a substituted or unsubstituted cycloalkyl, substituted or unsubstituted heterocycloalkyl, substituted or unsubstituted aryl, or substituted or unsubstituted heteroaryl. In embodiments, $R^{2.B}$ is independently substituted or unsubstituted alkyl. In embodiments, $R^{2.B}$ is independently unsubstituted alkyl. In embodiments, $R^{2.B}$ is independently unsubstituted methyl. In embodiments, $R^{2.B}$ is independently unsubstituted ethyl. In embodiments, $R^{2.B}$ is independently unsubstituted propyl. In embodiments, $R^{2.B}$ is independently substituted or unsubstituted heteroalkyl. In embodiments, $R^{2.B}$ is independently unsubstituted heteroalkyl. In embodiments, $R^{2.B}$ is independently substituted or unsubstituted cycloalkyl. In embodiments, $R^{2.B}$ is independently substituted or unsubstituted heterocycloalkyl. In embodiments, $R^{2.B}$ is independently unsubstituted heterocycloalkyl. In embodiments, $R^{2.B}$ is independently substituted or unsubstituted aryl. In embodiments, $R^{2.B}$ is independently unsubstituted phenyl. In embodiments, $R^{2.B}$ is independently substituted or unsubstituted heteroaryl.

In embodiments, z2 is an integer from 1 to 4. In embodiments, z2 is 0. In embodiments, z2 is 1. In embodiments, z2 is 2. In embodiments, z2 is 3. In embodiments, z2 is 4.

In embodiments, $R^{2A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2A}$ is independently hydrogen, substituted or unsubstituted $C_1$-$C_4$ alkyl, or substituted or unsubstituted 2 to 4 membered heteroalkyl. In embodiments, $R^{2A}$ is independently hydrogen. In embodiments, $R^{2A}$ is independently substituted or unsubstituted $C_1$-$C_4$ alkyl. In embodiments, $R^{2A}$ is independently substituted or unsubstituted 2 to 4 membered heteroalkyl. In embodiments, $R^{2A}$ is independently unsubstituted methyl. In embodiments, $R^{2A}$ is independently —$CCl_3$. In embodiments, $R^{2A}$ is independently —$CBr_3$. In embodiments, $R^{2A}$ is independently —$CF_3$. In embodiments, $R^{2A}$ is independently —$CI_3$. In embodiments, $R^{2A}$ is independently —$CHCl_2$. In embodiments, $R^{2A}$ is independently —$CHBr_2$. In embodiments, $R^{2A}$ is independently —$CHF_2$. In embodiments, $R^{2A}$ is independently —$CHI_2$. In embodiments, $R^{2A}$ is independently —$CH_2Cl$. In embodiments, $R^{2A}$ is independently —$CH_2Br$. In embodiments, $R^{2A}$ is independently —$CH_2F$. In embodiments, $R^{2A}$ is independently —$CH_2I$. In embodiments, $R^{2A}$ is independently —CN. In embodiments, $R^{2A}$ is independently —OH. In embodiments, $R^{2A}$ is independently —COOH. In embodiments, $R^{2A}$ is independently —$CONH_2$. In embodiments, $R^{2A}$ is independently —$OCCl_3$. In embodiments, $R^{2A}$ is independently —$OCF_3$. In embodiments, $R^{2A}$ is independently —$OCBr_3$. In embodiments, $R^{2A}$ is independently —$OCI_3$. In embodiments, $R^{2A}$ is independently —$OCHCl_2$. In embodiments, $R^{2A}$ is independently —$OCHBr_2$. In embodiments, $R^{2A}$ is independently —$OCHI_2$. In embodiments, $R^{2A}$ is independently —$OCHF_2$. In embodiments, $R^{2A}$ is independently —$OCH_2Cl$. In embodiments, $R^{2A}$ is independently —$OCH_2Br$. In embodiments, $R^{2A}$ is independently —$OCH_2I$. In embodiments, $R^{2A}$ is independently —$OCH_2F$. In embodiments, $R^{2A}$ is independently —$OCH_3$. In embodiments, $R^{2A}$ is independently —$OCH_2CH_3$. In embodiments, $R^{2A}$ is independently —$OCH(CH_3)_2$. In embodiments, $R^{2A}$ is independently —$OC(CH_3)_3$. In embodiments, $R^{2A}$ is independently —$CH_3$. In embodiments, $R^{2A}$ is independently —$CH_2CH_3$. In embodiments, $R^{2A}$ is independently —$CH(CH_3)_2$. In embodiments, $R^{2A}$ is independently —$C(CH_3)_3$. In embodiments, $R^{2A}$ is independently unsubstituted $C_1$-$C_4$ alkyl. In embodiments, $R^{2A}$ is independently unsubstituted 2 to 4 membered heteroalkyl.

In embodiments, $R^{2B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2B}$ is independently hydrogen, substituted or unsubstituted $C_1$-$C_4$ alkyl, or substituted or unsubstituted 2 to 4 membered heteroalkyl. In embodiments, $R^{2B}$ is independently hydrogen. In embodiments, $R^{2B}$ is independently substituted or unsubstituted $C_1$-$C_4$ alkyl. In embodiments, $R^{2B}$ is independently substituted or unsubstituted 2 to 4 membered heteroalkyl. In embodiments, $R^{2B}$ is independently unsubstituted methyl. In embodiments, $R^{2B}$ is independently —$CCl_3$. In embodiments, $R^{2B}$ is independently —$CBr_3$. In embodiments, $R^{2B}$ is independently —$CF_3$. In embodiments, $R^{2B}$ is independently —$CI_3$. In embodiments, $R^{2B}$ is independently —$CHCl_2$. In embodiments, $R^{2B}$ is independently —$CHBr_2$. In embodiments, $R^{2B}$ is independently —$CHF_2$. In embodiments, $R^{2B}$ is independently —$CHI_2$. In embodiments, $R^{2B}$ is independently —$CH_2Cl$. In embodiments, $R^{2B}$ is independently —$CH_2Br$. In embodiments, $R^{2B}$ is independently —$CH_2F$. In embodiments, $R^{2B}$ is independently —$CH_2I$. In embodiments, $R^{2B}$ is independently —CN. In embodiments, $R^{2B}$ is independently —OH. In embodiments, $R^{2B}$ is independently —COOH. In embodiments, $R^{2B}$ is independently —$CONH_2$. In embodiments, $R^{2B}$ is independently —$OCCl_3$. In embodiments, $R^{2B}$ is independently —$OCF_3$. In embodiments, $R^{2B}$ is independently —$OCBr_3$. In embodiments, $R^{2B}$ is independently —$OCI_3$. In embodiments, $R^{2B}$ is independently —$OCHCl_2$. In embodiments, $R^{2B}$ is independently —$OCHBr_2$. In embodiments, $R^{2B}$ is independently —$OCHI_2$. In embodiments, $R^{2B}$ is independently —$OCHF_2$. In embodiments, $R^{2B}$ is independently —$OCH_2Cl$. In embodiments, $R^{2B}$ is independently —$OCH_2Br$. In embodiments, $R^{2B}$ is independently —$OCH_2I$. In embodiments, $R^{2B}$ is independently —$OCH_2F$. In embodiments, $R^{2B}$ is independently —$OCH_3$. In embodiments, $R^{2B}$ is independently —$OCH_2CH_3$. In embodiments, $R^{2B}$ is independently —$OCH(CH_3)_2$. In embodiments, $R^{2B}$ is independently —$OC(CH_3)_3$. In embodiments, $R^{2B}$ is independently —$CH_3$. In embodiments, $R^{2B}$ is independently —$CH_2CH_3$. In embodiments, $R^{2B}$ is independently —$CH(CH_3)_2$. In embodiments, $R^{2B}$ is independently —$C(CH_3)_3$. In embodiments, $R^{2B}$ is independently unsubstituted $C_1$-$C_4$ alkyl. In embodiments, $R^{2B}$ is independently unsubstituted 2 to 4 membered heteroalkyl.

In embodiments, $R^{2C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2C}$ is independently hydrogen, substituted or unsubstituted $C_1$-$C_4$ alkyl, or substituted or unsubstituted 2 to 4 membered heteroalkyl. In embodiments, $R^{2C}$ is independently hydrogen. In embodiments, $R^{2C}$ is independently substituted or unsubstituted $C_1$-$C_4$ alkyl. In embodiments, $R^{2C}$ is independently substituted or unsubstituted 2 to 4 membered heteroalkyl. In embodiments, $R^{2C}$ is independently unsubstituted methyl. In embodiments, $R^{2C}$ is independently —$CCl_3$. In embodiments, $R^{2C}$ is independently —$CBr_3$. In embodiments, $R^{2C}$ is independently —$CF_3$. In embodiments, $R^{2C}$ is independently —$CI_3$. In embodiments, $R^{2C}$ is independently —$CHCl_2$. In embodiments, $R^{2C}$ is independently —$CHBr_2$. In embodiments, $R^{2C}$ is independently —$CHF_2$. In embodiments, $R^{2C}$ is independently —$CHI_2$. In embodiments, $R^{2C}$ is independently —$CH_2Cl$. In embodiments, $R^{2C}$ is independently —$CH_2Br$. In embodiments, $R^{2C}$ is independently —$CH_2F$. In embodiments, $R^{2C}$ is independently —$CH_2I$. In embodiments, $R^{2C}$ is independently —CN. In embodiments, $R^{2C}$ is independently —OH. In embodiments, $R^{2C}$ is independently —COOH. In embodiments, $R^{2C}$ is independently —$CONH_2$. In embodiments, $R^{2C}$ is independently —$OCCl_3$. In embodiments, $R^{2C}$ is independently —$OCF_3$. In embodiments, $R^{2C}$ is independently —$OCBr_3$. In embodiments, $R^{2C}$ is independently —$OCI_3$. In embodiments, $R^{2C}$ is independently —$OCHCl_2$. In embodiments, $R^{2C}$ is independently —$OCHBr_2$. In embodiments, $R^{2C}$ is independently —$OCHI_2$. In embodiments, $R^{2C}$ is independently —$OCHF_2$. In embodiments, $R^{2C}$ is independently —$OCH_2Cl$. In embodiments, $R^{2C}$ is independently —$OCH_2Br$. In embodiments, $R^{2C}$ is independently —$OCH_2I$. In embodiments, $R^{2C}$ is independently —$OCH_2F$. In embodiments, $R^{2C}$ is independently —$OCH_3$. In embodiments, $R^{2C}$ is independently —$OCH_2CH_3$. In embodiments, $R^{2C}$ is independently —$OCH(CH_3)_2$. In embodiments, $R^{2C}$ is independently —$OC(CH_3)_3$. In embodiments, $R^{2C}$ is independently —$CH_3$. In embodiments, $R^{2C}$ is independently —$CH_2CH_3$. In embodiments, $R^{2C}$ is independently —$CH(CH_3)_2$. In embodiments, $R^{2C}$ is independently —$C(CH_3)_3$. In embodiments, $R^{2C}$ is independently unsubstituted $C_1$-$C_4$ alkyl. In embodiments, $R^{2C}$ is independently unsubstituted 2 to 4 membered heteroalkyl.

In embodiments, $R^{2D}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$alkyl, or substituted or unsubstituted 2 to 4 membered heteroalkyl. In embodiments, $R^{2D}$ is independently hydrogen, substituted or unsubstituted $C_1$-$C_4$ alkyl, or substituted or unsubstituted 2 to 4 membered heteroalkyl. In embodiments, $R^{2D}$ is independently hydrogen. In embodiments, $R^{2D}$ is independently substituted or unsubstituted $C_1$-$C_4$ alkyl. In embodiments, $R^{2D}$ is independently substituted or unsubstituted 2 to 4 membered heteroalkyl. In embodiments, $R^{2D}$ is independently unsubstituted methyl. In embodiments, $R^{2D}$ is independently —$CCl_3$. In embodiments, $R^{2D}$ is independently —$CBr_3$. In embodiments, $R^{2D}$ is independently —$CF_3$. In embodiments, $R^{2D}$ is independently —$CI_3$. In embodiments, $R^{2D}$ is independently —$CHCl_2$. In embodiments, $R^{2D}$ is independently —$CHBr_2$. In embodiments, $R^{2D}$ is independently —$CHF_2$. In embodiments, $R^{2D}$ is independently —$CHI_2$. In embodiments, $R^{2D}$ is independently —$CH_2Cl$. In embodiments, $R^{2D}$ is independently —$CH_2Br$. In embodiments, $R^{2D}$ is independently —$CH_2F$. In embodiments, $R^{2D}$ is independently —$CH_2I$. In embodiments, $R^{2D}$ is independently —CN. In embodiments, $R^{2D}$ is independently —OH. In embodiments, $R^{2D}$ is independently —COOH. In embodiments, $R^{2D}$ is independently —$CONH_2$. In embodiments, $R^{2D}$ is independently —$OCCl_3$. In embodiments, $R^{2D}$ is independently —$OCF_3$. In embodiments, $R^{2D}$ is independently —$OCBr_3$. In embodiments, $R^{2D}$ is independently —$OCI_3$. In embodiments, $R^{2D}$ is independently —$OCHCl_2$. In embodiments, $R^{2D}$ is independently —$OCHBr_2$. In embodiments, $R^{2D}$ is independently —$OCHI_2$. In embodiments, $R^{2D}$ is independently —$OCHF_2$. In embodiments, $R^{2D}$ is independently —$OCH_2Cl$. In embodiments, $R^{2D}$ is independently —$OCH_2Br$. In embodiments, $R^{2D}$ is independently —$OCH_2I$. In embodiments, $R^{2D}$ is independently —$OCH_2F$. In embodiments, $R^{2D}$ is independently —$OCH_3$. In embodiments, $R^{2D}$ is independently —$OCH_2CH_3$. In embodiments, $R^{2D}$ is independently —$OCH(CH_3)_2$. In embodiments, $R^{2D}$ is independently —$OC(CH_3)_3$. In embodiments, $R^{2D}$ is independently —$CH_3$. In embodiments, $R^{2D}$ is independently —$CH_2CH_3$. In embodiments, $R^{2D}$ is independently —$CH(CH_3)_2$. In embodiments, $R^{2D}$ is independently —$C(CH_3)_3$. In embodiments, $R^{2D}$ is independently unsubstituted $C_1$-$C_4$ alkyl. In embodiments, $R^{2D}$ is independently unsubstituted 2 to 4 membered heteroalkyl.

In embodiments, $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —NHC(O) $NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, two adjacent $R^3$ substituents are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

In embodiments, $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$NO_2$, or substituted or unsubstituted $C_1$-$C_6$ alkyl. In embodiments, $R^3$ is independently halogen, —$CF_3$, —$NO_2$, or —$CH_3$. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently —$CCl_3$. In embodiments, $R^3$ is independently —$CBr_3$. In embodiments, $R^3$ is independently —$CF_3$. In embodiments, $R^3$ is independently —$CI_3$. In embodiments, $R^3$ is independently —$CHCl_2$. In embodiments, $R^3$ is independently —$CHBr_2$. In embodiments, $R^3$ is independently —$CHF_2$. In embodiments, $R^3$ is independently —$CHI_2$. In embodiments, $R^3$ is independently —$CH_2Cl$. In embodiments, $R^3$ is independently —$CH_2Br$. In embodiments, $R^3$ is independently —$CH_2F$. In embodiments, $R^3$ is independently —$CH_2I$. In embodiments, $R^3$ is independently —CN. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —)$CCl_3$. In embodiments, $R^3$ is independently —$OCF_3$. In embodiments, $R^3$ is independently —$OCBr_3$. In embodiments, $R^3$ is independently —$OCI_3$. In embodiments, $R^3$ is independently —$OCHCl_2$. In embodiments, $R^3$ is independently —$OCHBr_2$. In embodiments, $R^3$ is independently —$OCHI_2$. In embodiments, $R^3$ is independently —$OCHF_2$. In embodiments, $R^3$ is independently —$OCH_2Cl$. In embodiments, $R^3$ is independently —$OCH_2Br$. In embodiments, $R^3$ is independently —$OCH_2I$. In embodiments, $R^3$ is independently —$OCH_2F$. In embodiments, $R^3$ is independently halogen. In embodiments, $R^3$ is independently —$NO_2$. In embodiments, $R^3$ is independently —$OCH_3$. In embodiments, $R^3$ is independently —$OCH_2CH_3$. In embodiments, $R^3$ is independently —$OCH(CH_3)_2$. In embodiments, $R^3$ is independently —$OC(CH_3)_3$. In embodiments, $R^3$ is independently —$CH_3$. In embodiments, $R^3$ is independently —$CH_2CH_3$. In embodiments, $R^3$ is independently —$CH(CH_3)_2$. In embodiments, $R^3$ is independently —$C(CH_3)_3$.

In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, two adjacent $R^3$ substituents are joined to form a substituted or unsubstituted cycloalkyl, substituted or unsubstituted heterocycloalkyl, substituted or unsubstituted aryl, or substituted or unsubstituted heteroaryl. In embodiments, $R^3$ is independently substituted or unsubstituted alkyl. In embodiments, $R^3$ is independently unsubstituted alkyl. In embodiments, $R^3$ is independently substituted or unsubstituted heteroalkyl. In embodiments, $R^3$ is independently substituted or unsubstituted cycloalkyl. In embodiments, $R^3$ is independently substituted or unsubstituted heterocycloalkyl. In embodiments, $R^3$ is independently substituted or unsubstituted aryl. In embodiments, $R^3$ is independently substituted or unsubstituted heteroaryl.

In embodiments, $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, or substituted or unsubstituted 2 to 6 membered heteroalkyl. In embodiments, $R^3$ is independently —F, —Cl, —Br, —I, unsubstituted methyl, unsubstituted ethyl, or unsubstituted propyl.

In embodiments, $R^3$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, two adjacent $R^3$ substituents are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently substituted or unsubstituted $C_1$-$C_6$ alkyl. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted butyl. In embodiments, $R^3$ is independently substituted or unsubstituted 2 to 6 membered heteroalkyl. In embodiments, $R^3$ is independently substituted or unsubstituted $C_3$-$C_6$ cycloalkyl. In embodiments, $R^3$ is independently substituted or unsubstituted 3 to 6 membered heterocycloalkyl. In embodiments, $R^3$ is independently substituted or unsubstituted $C_6$-$C_{10}$ aryl. In embodiments, $R^3$ is independently substituted or unsubstituted 5 to 10 membered heteroaryl. In embodiments, two adjacent $R^3$ substituents are joined to form a substituted or unsubstituted $C_3$-$C_6$ cycloalkyl. In embodiments, two adjacent $R^3$ substituents are joined to form a substituted or unsubstituted 3 to 6 membered heterocycloalkyl. In embodiments, two adjacent $R^3$ substituents are joined to form a substituted or unsubstituted phenyl. In embodiments, two adjacent $R^3$ substituents are joined to form a substituted or unsubstituted 5 to 6 membered heteroaryl. In embodiments, $R^3$ is independently unsubstituted $C_1$-$C_6$ alkyl. In embodiments, $R^3$ is independently unsubstituted 2 to 6 membered heteroalkyl. In embodiments, $R^3$ is independently unsubstituted $C_3$-$C_6$ cycloalkyl. In embodiments, $R^3$ is independently unsubstituted 3 to 6 membered heterocycloalkyl. In embodiments, $R^3$ is independently unsubstituted $C_6$-$C_{10}$ aryl. In embodiments, $R^3$ is independently unsubstituted 5 to 10 membered heteroaryl. In embodiments, $R^3$ is independently unsubstituted phenyl. In embodiments, $R^3$ is independently unsubstituted 5 to 6 membered heteroaryl. In embodiments, two adjacent $R^3$ substituents are joined to form an unsubstituted $C_3$-$C_6$ cycloalkyl. In embodiments, two adjacent $R^3$ substituents are joined to form an unsubstituted 3 to 6 membered heterocycloalkyl. In embodiments, two adjacent $R^3$ substituents are joined to form an unsubstituted phenyl. In embodiments, two adjacent $R^3$ substituents are joined to form an unsubstituted 5 to 6 membered heteroaryl.

In embodiments, z3 is an integer from 0 to 4. In embodiments, z3 is an integer from 1 to 5. In embodiments, z3 is 0. In embodiments, z3 is 1. In embodiments, z3 is 2. In embodiments, z3 is 3. In embodiments, z3 is 4. In embodiments, z3 is 5.

In embodiments, $R^{3A}$ is independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, substituted or unsubstituted $C_1$-$C_4$alkyl, or substituted or unsubstituted 2 to 4 membered heteroalkyl. In embodiments, $R^{3A}$ is independently hydrogen, substituted or unsubstituted $C_1$-$C_4$ alkyl, or substituted or unsubstituted 2 to 4 membered heteroalkyl. In embodiments, $R^{3A}$ is independently hydrogen. In embodiments, $R^{3A}$ is independently substituted or unsubstituted $C_1$-$C_4$ alkyl. In embodiments, $R^{3A}$ is independently substituted or unsubstituted 2 to 4 membered heteroalkyl. In embodiments, $R^{3A}$ is independently unsubstituted methyl. In embodiments, $R^{3A}$ is independently unsubstituted $C_1$-$C_4$ alkyl. In embodiments, $R^{3A}$ is independently unsubstituted 2 to 4 membered heteroalkyl.

In embodiments, $R^{3B}$ is independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, substituted or unsubstituted $C_1$-$C_4$ alkyl, or substituted or unsubstituted 2 to 4 membered heteroalkyl. In embodiments, $R^{3B}$ is independently hydrogen, substituted or unsubstituted $C_1$-$C_4$ alkyl, or substituted or unsubstituted 2 to 4 membered heteroalkyl. In embodiments, $R^{3B}$ is independently hydrogen. In embodiments, $R^{3B}$ is independently substituted or unsubstituted $C_1$-$C_4$ alkyl. In embodiments, $R^{3B}$ is independently substituted or unsubstituted 2 to 4 membered heteroalkyl. In embodiments, $R^{3B}$ is independently unsubstituted methyl. In embodiments, $R^{3B}$ is independently unsubstituted $C_1$-$C_4$ alkyl. In embodiments, $R^{3B}$ is independently unsubstituted 2 to 4 membered heteroalkyl.

In embodiments, $R^{3C}$ is independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, substituted or unsubstituted $C_1$-$C_4$ alkyl, or substituted or unsubstituted 2 to 4 membered heteroalkyl. In embodiments, $R^{3C}$ is independently hydrogen, substituted or unsubstituted $C_1$-$C_4$ alkyl, or substituted or unsubstituted 2 to 4 membered heteroalkyl. In embodiments, $R^{3C}$ is independently hydrogen. In embodiments, $R^{3C}$ is independently substituted or unsubstituted $C_1$-$C_4$ alkyl. In embodiments, $R^{3C}$ is independently substituted or unsubstituted 2 to 4 membered heteroalkyl. In embodiments, $R^{3C}$ is independently unsubstituted methyl. In embodiments, $R^{3C}$ is independently unsubstituted $C_1$-$C_4$ alkyl. In embodiments, $R^{3C}$ is independently unsubstituted 2 to 4 membered heteroalkyl.

In embodiments, $R^{3D}$ is independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, substituted or unsubstituted $C_1$-$C_4$ alkyl, or substituted or unsubstituted 2 to 4 membered heteroalkyl. In embodiments, $R^{3D}$ is independently hydrogen, substituted or unsubstituted $C_1$-$C_4$ alkyl, or substituted or unsubstituted 2 to 4 membered heteroalkyl. In embodiments, $R^{3D}$ is independently hydrogen. In embodiments, $R^{3D}$ is independently substituted or unsubstituted $C_1$-$C_4$ alkyl. In embodiments, $R^{3D}$ is independently substituted or unsubstituted 2 to 4 membered heteroalkyl. In embodiments, $R^{3D}$ is independently unsubstituted methyl. In embodiments, $R^{3D}$ is independently unsubstituted $C_1$-$C_4$ alkyl. In embodiments, $R^{3D}$ is independently unsubstituted 2 to 4 membered heteroalkyl.

In embodiments, $L^4$ is a bond, $-NH-$, $-O-$, $-S-$, $-SO_2-$, $-C(O)-$, $-C(O)NH-$, $-NHC(O)-$, $-NHC(O)NH-$, $-C(O)O-$, $-OC(O)-$, $-SO_2NH-$, $-NHSO_2-$, substituted or unsubstituted $C_1$-$C_6$ alkylene, or substituted or unsubstituted 2 to 6 membered heteroalkylene. In embodiments, $L^4$ is a bond, $-SO_2-$, $-C(O)NH-$, $-NHC(O)-$, $-SO_2NH-$, $-NHSO_2-$, substituted or unsubstituted $C_1$-$C_4$ alkylene, or substituted or unsubstituted 2 to 4 membered heteroalkylene. In embodiments, $L^4$ is a bond, $-SO_2-$, $-C(O)NH-$, $-NHC(O)-$, $-SO_2NH-$, or $-NHSO_2-$. In embodiments, $L^4$ is $-C(O)NH-$, $-NHC(O)-$, $-SO_2NH-$, or $-NHSO_2-$. In embodiments, $L^4$ is $-SO_2NH-$ or $-NHSO_2-$. In embodiments, $L^4$ is $-SO_2NHCH_2-$ or $-SO_2NHCH_2CH_2-$. In embodiments, $L^4$ is $-C(O)N(R^4)-$, $-N(R^4)C(O)-$, $-SO_2N(R^4)-$, or $-N(R^4)SO_2-$. In embodiments, $L^4$ is a bond. In embodiments, $L^4$ is $-NH-$. In embodiments, $L^4$ is $-O-$. In embodiments, $L^4$ is $-S-$. In embodiments, $L^4$ is $-SO_2-$. In embodiments, $L^4$ is $-C(O)-$. In embodiments, $L^4$ is $-C(O)NH-$. In embodiments, $L^4$ is $-NHC(O)-$. In embodiments, $L^4$ is $-NHC(O)NH-$. In embodiments, $L^4$ is $-C(O)O-$. In embodiments, $L^4$ is $-OC(O)-$. In embodiments, $L^4$ is $-SO_2NH-$. In embodiments, $L^4$ is $-NHSO_2-$. In embodiments, $L^4$ is substituted or unsubstituted $C_1$-$C_6$ alkylene. In embodiments, $L^4$ is substituted or unsubstituted 2 to 6 membered heteroalkylene. In embodiments, $L^4$ is $-SO_2NHCH_2-$. In embodiments, $L^4$ is $-SO_2NHCH_2CH_2-$. In embodiments, $L^4$ is $-C(O)NHCH_2-$. In embodiments, $L^4$ is $-C(O)NHCH_2CH_2-$. In embodiments, $L^4$ is $-C(O)N(R^4)-$. In embodiments, $L^4$ is $-N(R^4)C(O)-$. In embodiments, $L^4$ is $-SO_2N(R^4)-$. In embodiments, $L^4$ is $-N(R^4)SO_2-$. In embodiments, $L^4$ is not $-O-$.

In embodiments, $R^4$ is independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^4$ is independently hydrogen, —$CCl_3$, —$CBr_3$, —$CF_3$, —$CI_3$, $CHCl_2$, —$CHBr_2$, —$CHF_2$, —$CHI_2$, —$CH_2C_1$, —$CH_2Br$, —$CH_2F$, —$CH_2I$, or substituted or unsubstituted $C_1$-$C_6$ alkyl. In embodiments, $R^4$ is independently hydrogen. In embodiments, $R^4$ is independently —$CCl_3$. In embodiments, $R^4$ is independently —$CBr_3$. In embodiments, $R^4$ is independently —$CF_3$. In embodiments, $R^4$ is independently —$CI_3$. In embodiments, $R^4$ is independently —$CHCl_2$. In embodiments, $R^4$ is independently —$CHBr_2$. In embodiments, $R^4$ is independently —$CHF_2$. In embodiments, $R^4$ is independently —$CHI_2$. In embodiments, $R^4$ is independently —$CH_2C_1$. In embodiments, $R^4$ is independently —$CH_2Br$. In embodiments, $R^4$ is independently —$CH_2F$. In embodiments, $R^4$ is independently —$CH_2I$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$OCCl_3$. In embodiments, $R^4$ is independently —$OCF_3$. In embodiments, $R^4$ is independently —$OCBr_3$. In embodiments, $R^4$ is independently —$OCI_3$. In embodiments, $R^4$ is independently —$OCHCl_2$. In embodiments, $R^4$ is independently —$OCHBr_2$. In embodiments, $R^4$ is independently —$OCHI_2$. In embodiments, $R^4$ is independently —$OCHF_2$. In embodiments, $R^4$ is independently —$OCH_2Cl$. In embodiments, $R^4$ is independently —$OCH_2Br$. In embodiments, $R^4$ is independently —$OCH_2I$. In embodiments, $R^4$ is independently —$OCH_2F$. In embodiments, $R^4$ is independently —$OCH_3$. In embodiments, $R^4$ is independently —$OCH_2CH_3$. In embodiments, $R^4$ is independently —$OCH(CH_3)_2$. In embodiments, $R^4$ is independently —$OC(CH_3)_3$. In embodiments, $R^4$ is independently —$CH_3$. In embodiments, $R^4$ is independently —$CH_2CH_3$. In embodiments, $R^4$ is independently —$CH(CH_3)_2$. In embodiments, $R^4$ is independently —$C(CH_3)_3$.

In embodiments, $R^4$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently substituted or unsubstituted alkyl. In embodiments, $R^4$ is independently unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently substituted or unsubstituted heterocycloalkyl. In embodiments, $R^4$ is independently substituted or unsubstituted aryl. In embodiments, $R^4$ is independently substituted or unsubstituted heteroaryl.

In embodiments, $R^4$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, or substituted or unsubstituted 2 to 6 membered heteroalkyl. In embodiments, $R^4$ is independently unsubstituted methyl, unsubstituted ethyl, or unsubstituted propyl.

In embodiments, $R^4$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently substituted or unsubstituted $C_1$-$C_6$ alkyl. In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently unsubstituted butyl. In embodiments, $R^4$ is independently substituted or unsubstituted 2 to 6 membered heteroalkyl. In embodiments, $R^4$ is independently substituted or unsubstituted $C_3$-$C_6$ cycloalkyl. In embodiments, $R^4$ is independently substituted or unsubstituted 3 to 6 membered heterocycloalkyl. In embodiments, $R^4$ is independently substituted or unsubstituted phenyl. In embodiments, $R^4$ is independently substituted or unsubstituted 5 to 6 membered heteroaryl. In embodiments, $R^4$ is independently unsubstituted $C_1$-$C_6$ alkyl. In embodiments, $R^4$ is independently unsubstituted 2 to 6 membered heteroalkyl. In embodiments, $R^4$ is independently unsubstituted $C_3$-$C_6$ cycloalkyl. In embodiments, $R^4$ is independently unsubstituted 3 to 6 membered heterocycloalkyl. In embodiments, $R^4$ is independently unsubstituted phenyl. In embodiments, $R^4$ is independently unsubstituted 5 to 6 membered heteroaryl.

In embodiments, z4 is an integer from 1 to 4. In embodiments, z4 is 1 or 2. In embodiments, z4 is 1. In embodiments, z4 is 2. In embodiments, z4 is 3. In embodiments, z4 is 4. In embodiments, z4 is 5.

In embodiments, $R^5$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^5$ is independently hydrogen, —$CCl_3$, —$CBr_3$, —$CF_3$, —$CI_3$, $CHCl_2$, —$CHBr_2$, —$CHF_2$, —$CHI_2$, —$CH_2C_1$, —$CH_2Br$, —$CH_2F$, —$CH_2I$, or substituted or unsubstituted $C_1$-$C_6$ alkyl. In embodiments, $R^5$ is independently hydrogen. In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2C_1$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —CN. In embodiments, $R^5$ is independently —OH. In embodiments, $R^5$ is independently —$NH_2$. In embodiments, $R^5$ is independently —COOH. In embodiments, $R^5$ is independently —$CONH_2$. In embodiments, $R^5$ is independently —$OCCl_3$. In embodiments, $R^5$ is independently —$OCF_3$. In embodiments, $R^5$ is independently —$OCBr_3$. In embodiments, $R^5$ is independently —$OCI_3$. In embodiments, $R^5$ is independently —$OCHCl_2$. In embodiments, $R^5$ is independently —$OCHBr_2$. In embodiments, $R^5$ is independently —$OCHI_2$. In embodiments, $R^5$ is independently —$OCHF_2$. In embodiments, $R^5$ is independently —$OCH_2Cl$. In embodiments, $R^5$ is independently —$OCH_2Br$. In embodiments, $R^5$ is independently —$OCH_2I$. In embodiments, $R^5$ is independently —$OCH_2F$. In embodiments, $R^5$ is independently —$OCH_3$. In embodiments, $R^5$ is independently —$OCH_2CH_3$. In embodiments, $R^5$ is independently —$OCH(CH_3)_2$. In embodiments, $R^5$ is independently —$OC(CH_3)_3$. In embodiments, $R^5$ is independently —$CH_3$. In embodiments, $R^5$ is independently —$CH_2CH_3$. In embodiments, $R^5$ is independently —$CH(CH_3)_2$. In embodiments, $R^5$ is independently —$C(CH_3)_3$.

In embodiments, $R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently substituted or unsubstituted alkyl. In embodiments, $R^5$ is independently unsubstituted alkyl. In embodiments, $R^5$ is independently substituted or unsubstituted heteroalkyl. In embodiments, $R^5$ is independently substituted or unsubstituted cycloalkyl. In embodiments, $R^5$ is independently substituted or unsubstituted heterocycloalkyl. In embodiments, $R^5$ is independently substituted or unsubstituted aryl. In embodiments, $R^5$ is independently substituted or unsubstituted heteroaryl.

In embodiments, $R^5$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, or substituted or unsubstituted 2 to 6 membered heteroalkyl. In embodiments, $R^5$ is independently unsubstituted methyl, unsubstituted ethyl, or unsubstituted propyl.

In embodiments, $R^5$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently substituted or unsubstituted $C_1$-$C_6$ alkyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently unsubstituted butyl. In embodiments, $R^5$ is independently substituted or unsubstituted 2 to 6 membered heteroalkyl. In embodiments, $R^5$ is independently substituted or unsubstituted $C_3$-$C_6$ cycloalkyl. In embodiments, $R^5$ is independently substituted or unsubstituted 3 to 6 membered heterocycloalkyl. In embodiments, $R^5$ is independently substituted or unsubstituted phenyl. In embodiments, $R^5$ is independently substituted or unsubstituted 5 to 6 membered heteroaryl. In embodiments, $R^5$ is independently unsubstituted $C_1$-$C_6$ alkyl. In embodiments, $R^5$ is independently unsubstituted 2 to 6 membered heteroalkyl. In embodiments, $R^5$ is independently unsubstituted $C_3$-$C_6$ cycloalkyl. In embodiments, $R^5$ is independently unsubstituted 3 to 6 membered heterocycloalkyl. In embodiments, $R^5$ is independently unsubstituted phenyl. In embodiments, $R^5$ is independently unsubstituted 5 to 6 membered heteroaryl.

In embodiments, $R^6$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^6$ is independently hydrogen, —$CCl_3$, —$CBr_3$, —$CF_3$, —$CI_3$, $CHCl_2$, —$CHBr_2$, —$CHF_2$, —$CHI_2$, —$CH_2C_1$, —$CH_2Br$, —$CH_2F$, —$CH_2I$, or substituted or unsubstituted $C_1$-$C_6$ alkyl. In embodiments, $R^6$ is independently hydrogen. In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —$CH_2C_1$. In embodiments, $R^6$ is independently —$CH_2Br$. In embodiments, $R^6$ is independently —$CH_2F$. In embodiments, $R^6$ is independently —$CH_2I$. In embodiments, $R^6$ is independently —CN. In embodiments, $R^6$ is independently —OH. In embodiments, $R^6$ is independently —$NH_2$. In embodiments, $R^6$ is independently —COOH. In embodiments, $R^6$ is independently —$CONH_2$. In embodiments, $R^6$ is independently —$OCCl_3$. In embodiments, $R^6$ is independently —$OCF_3$. In embodiments, $R^6$ is independently —$OCBr_3$. In embodiments, $R^6$ is independently —$OCI_3$. In embodiments, $R^6$ is independently —$OCHCl_2$. In embodiments, $R^6$ is independently —$OCHBr_2$. In embodiments, $R^6$ is independently —$OCHI_2$. In embodiments, $R^6$ is independently —$OCHF_2$. In embodiments, $R^6$ is independently —$OCH_2Cl$. In embodiments, $R^6$ is independently —$OCH_2Br$. In embodiments, $R^6$ is independently —$OCH_2I$. In embodiments, $R^6$ is independently —$OCH_2F$. In embodiments, $R^6$ is independently —$OCH_3$. In embodiments, $R^6$ is independently —$OCH_2CH_3$. In embodiments, $R^6$ is independently —$OCH(CH_3)_2$. In embodiments, $R^6$ is independently —$OC(CH_3)_3$. In embodiments, $R^6$ is independently —$CH_3$. In embodiments, $R^6$ is independently —$CH_2CH_3$. In embodiments, $R^6$ is independently —$CH(CH_3)_2$. In embodiments, $R^6$ is independently —$C(CH_3)_3$.

In embodiments, $R^6$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is independently substituted or unsubstituted alkyl. In embodiments, $R^6$ is independently unsubstituted alkyl. In embodiments, $R^6$ is independently substituted or unsubstituted heteroalkyl. In embodiments, $R^6$ is independently substituted or unsubstituted cycloalkyl. In embodiments, $R^6$ is independently substituted or unsubstituted heterocycloalkyl. In embodiments, $R^6$ is independently substituted or unsubstituted aryl. In embodiments, $R^6$ is independently substituted or unsubstituted heteroaryl.

In embodiments, $R^6$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_6$ alkyl, or substituted or unsubstituted 2 to 6 membered heteroalkyl. In embodiments, $R^6$ is independently unsubstituted methyl, unsubstituted ethyl, or unsubstituted propyl.

In embodiments, $R^6$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^6$ is independently substituted or unsubstituted $C_1$-$C_6$ alkyl. In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently unsubstituted butyl. In embodiments, $R^6$ is independently substituted or unsubstituted 2 to 6 membered heteroalkyl. In embodiments, $R^6$ is independently substituted or unsubstituted $C_3$-$C_6$ cycloalkyl. In embodiments, $R^6$ is independently substituted or unsubstituted 3 to 6 membered heterocycloalkyl. In embodiments, $R^6$ is independently substituted or unsubstituted phenyl. In embodiments, $R^6$ is independently substituted or unsubstituted 5 to 6 membered heteroaryl. In embodiments, $R^6$ is independently unsubstituted $C_1$-$C_6$ alkyl. In embodiments, $R^6$ is independently unsubstituted 2 to 6 membered heteroalkyl. In embodiments, $R^6$ is independently unsubstituted $C_3$-$C_6$ cycloalkyl. In embodiments, $R^6$ is independently unsubstituted 3 to 6 membered heterocycloalkyl. In embodiments, $R^6$ is independently unsubstituted phenyl. In embodiments, $R^6$ is independently unsubstituted 5 to 6 membered heteroaryl.

In embodiments, $R^5$ and $R^6$ are independently hydrogen.

In embodiments, n1, n2, and n3 are independently an integer from 0 to 4. In embodiments, n1 is independently an integer from 0 to 4. In embodiments, n1 is independently 0. In embodiments, n1 is independently 1. In embodiments, n1 is independently 2. In embodiments, n1 is independently 3. In embodiments, n1 is independently 4. In embodiments, n2 is independently an integer from 0 to 4. In embodiments, n2 is independently 0. In embodiments, n2 is independently 1. In embodiments, n2 is independently 2. In embodiments, n2 is independently 3. In embodiments, n2 is independently 4. In embodiments, n3 is independently an integer from 0 to 4. In embodiments, n3 is independently 0. In embodiments, n3 is independently 1. In embodiments, n3 is independently 2. In embodiments, n3 is independently 3. In embodiments, n3 is independently 4. In embodiments, m1, m2, m3, v1, v2, and v3 are independently 1 or 2. In embodiments, m1 is independently 1. In embodiments, m1 is independently 2. In embodiments, m2 is independently 1. In embodiments, m2 is independently 2. In embodiments, v1 is independently 1. In embodiments, v1 is independently 2. In embodiments, v2 is independently 1. In embodiments, v2 is independently 2. In embodiments, m3 is independently 1. In embodiments, m3 is independently 2. In embodiments, v3 is independently 1. In embodiments, v3 is independently 2.

In embodiments, $X^1$, $X^2$, and $X^3$ are independently —F, —Cl, —Br, or —I. In embodiments, $X^1$ is independently —F, —Cl, —Br, or —I. In embodiments, $X^1$ is independently —F. In embodiments, $X^1$ is independently —Cl. In embodiments, $X^1$ is independently —Br. In embodiments, $X^1$ is independently —I. In embodiments, $X^2$ is independently —F, —Cl, —Br, or —I. In embodiments, $X^2$ is independently —F. In embodiments, $X^2$ is independently —Cl. In embodiments, $X^2$ is independently —Br. In embodiments, $X^2$ is independently —I. In embodiments, $X^3$ is independently —F, —Cl, —Br, or —I. In embodiments, $X^3$ is independently —F. In embodiments, $X^3$ is independently —Cl. In embodiments, $X^3$ is independently —Br. In embodiments, $X^3$ is independently —I.

In embodiments, the compound has the formula:

(VIa)

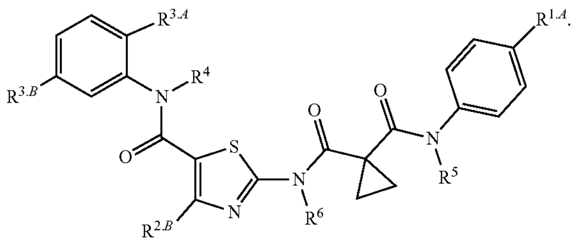

$R^4$, $R^5$, and $R^6$ are as described herein, including in embodiments. $R^{1.A}$ is independently hydrogen or any value of $R^1$ as described herein, including embodiments. $R^{2.B}$ is independently hydrogen or any value of $R^2$ as described herein, including embodiments. $R^{3.A}$ and $R^{3.B}$ are independently hydrogen or any value of $R^3$ as described herein, including embodiments.

In embodiments, the compound has the formula:

(VIb)

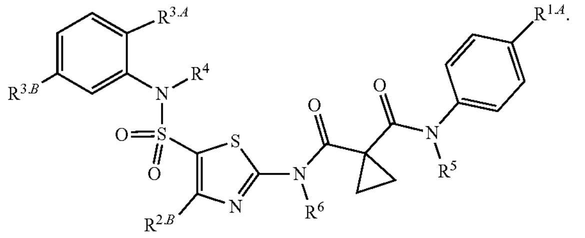

$R^4$, $R^5$, and $R^6$ are as described herein, including in embodiments. $R^{1.A}$ is independently hydrogen or any value of $R^1$ as described herein, including embodiments. $R^{2.B}$ is independently hydrogen or any value of $R^2$ as described herein, including embodiments. $R^{3.A}$ and $R^{3.B}$ are independently hydrogen or any value of $R^3$ as described herein, including embodiments.

In embodiments, $R^{1.A}$ is independently not —$CF_3$. In embodiments, $R^{1.A}$ is independently not —Cl. In embodiments, $R^{1.A}$ is independently not —F. In embodiments, $R^{1.A}$ is independently not halogen. In embodiments, $R^{1.A}$ is independently not —$CX^1_3$. In embodiments, z1 is independently not 1. In embodiments, $R^5$ is independently not hydrogen. In embodiments, $R^6$ is independently not hydrogen. In embodiments, $R^{2.B}$ is independently not hydrogen. In embodiments, $R^4$ is independently not hydrogen.

In embodiments, the compound has the formula:

(VIc)

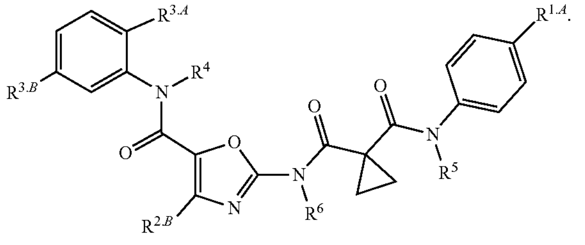

$R^4$, $R^5$, and $R^6$ are as described herein, including in embodiments. $R^{1.A}$ is independently hydrogen or any value of $R^1$ as described herein, including embodiments. $R^{2.B}$ is independently hydrogen or any value of $R^2$ as described herein, including embodiments. $R^{3.A}$ and $R^{3.B}$ are independently hydrogen or any value of $R^3$ as described herein, including embodiments.

In embodiments, $R^{1.A}$ is independently not —$CF_3$. In embodiments, $R^{1.A}$ is independently not —Cl. In embodiments, $R^{1.A}$ is independently not —F. In embodiments, $R^{1.A}$ is independently not halogen. In embodiments, $R^{1.A}$ is independently not —$CX^1_3$. In embodiments, z1 is independently not 1. In embodiments, $R^5$ is independently not hydrogen. In embodiments, $R^6$ is independently not hydrogen. In embodiments, $R^{2.B}$ is independently not hydrogen. In embodiments, $R^4$ is independently not hydrogen.

In embodiments, the compound has the formula:

(VId)

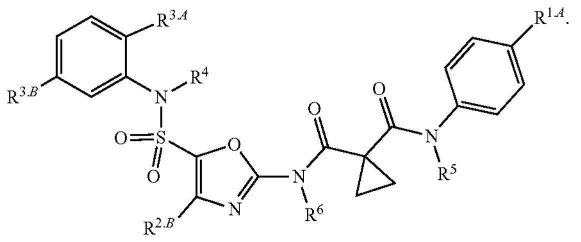

$R^4$, $R^5$, and $R^6$ are as described herein, including in embodiments. $R^{1.A}$ is independently hydrogen or any value of $R^1$ as described herein, including embodiments. $R^{2.B}$ is independently hydrogen or any value of $R^2$ as described herein, including embodiments. $R^{3.A}$ and $R^{3.B}$ are independently hydrogen or any value of $R^3$ as described herein, including embodiments.

In embodiments, $R^{1.A}$ is independently not —$CF_3$. In embodiments, $R^{1.A}$ is independently not —Cl. In embodiments, $R^{1.A}$ is independently not —F. In embodiments, $R^{1.A}$ is independently not halogen. In embodiments, $R^{1.A}$ is independently not —$CX^1_3$. In embodiments, z1 is independently not 1. In embodiments, $R^5$ is independently not hydrogen. In embodiments, $R^6$ is independently not hydrogen. In embodiments, $R^{2.B}$ is independently not hydrogen. In embodiments, $R^4$ is independently not hydrogen.

In embodiments, the compound has the formula:

(VIe)

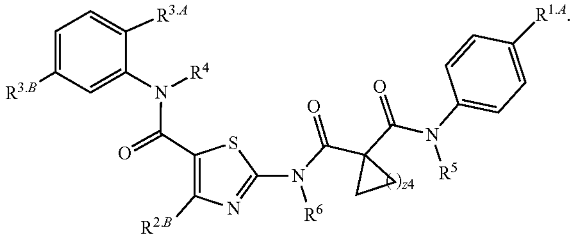

$R^4$, $R^5$, $R^6$, and z4 are as described herein, including in embodiments. $R^{1.A}$ is independently hydrogen or any value of $R^1$ as described herein, including embodiments. $R^{2.B}$ is independently hydrogen or any value of $R^2$ as described herein, including embodiments. $R^{3.A}$ and $R^{3.B}$ are independently hydrogen or any value of $R^3$ as described herein, including embodiments.

In embodiments, $R^{1.A}$ is independently not —$CF_3$. In embodiments, $R^{1.A}$ is independently not —Cl. In embodiments, $R^{1.A}$ is independently not —F. In embodiments, $R^{1.A}$ is independently not halogen. In embodiments, $R^{1.A}$ is independently not —$CX^1_3$. In embodiments, z1 is independently not 1. In embodiments, $R^5$ is independently not hydrogen. In embodiments, $R^6$ is independently not hydrogen. In embodiments, $R^{2.B}$ is independently not hydrogen. In embodiments, $R^4$ is independently not hydrogen.

In embodiments, $R^{1.A}$ is independently halogen. In embodiments, $R^{1.A}$ is independently —F. In embodiments, $R^{1.A}$ is independently —Cl. In embodiments, $R^{1.A}$ is independently —Br. In embodiments, $R^{1.A}$ is independently —I. In embodiments, $R^{1.A}$ is independently hydrogen.

In embodiments, $R^{2.B}$ is independently —$CCl_3$. In embodiments, $R^{2.B}$ is independently —$CBr_3$. In embodiments, $R^{2.B}$ is independently —$CF_3$. In embodiments, $R^{2.B}$ is independently —$CI_3$. In embodiments, $R^{2.B}$ is independently —$CHCl_2$. In embodiments, $R^{2.B}$ is independently —$CHBr_2$. In embodiments, $R^{2.B}$ is independently —$CHF_2$. In embodiments, $R^{2.B}$ is independently —$CHI_2$. In embodiments, $R^{2.B}$ is independently —$CH_2C_1$. In embodiments, $R^{2.B}$ is independently —$CH_2Br$. In embodiments, $R^{2.B}$ is independently —$CH_2F$. In embodiments, $R^{2.B}$ is independently —$CH_2I$. In embodiments, $R^{2.B}$ is independently —$CH_3$. In embodiments, $R^{2.B}$ is independently —$CH_2CH_3$. In embodiments, $R^{2.B}$ is independently —$CH(CH_3)_2$. In embodiments, $R^{2.B}$ is independently —$C(CH_3)_3$. In embodiments, $R^{2.B}$ is independently unsubstituted $C_1$-$C_4$ alkyl. In embodiments, $R^{2.B}$ is independently hydrogen.

In embodiments, $R^{3.A}$ is independently halogen. In embodiments, $R^{3.A}$ is independently —F. In embodiments, $R^{3.A}$ is independently —Cl. In embodiments, $R^{3.A}$ is independently —Br. In embodiments, $R^{3.A}$ is independently —I. In embodiments, $R^{3.A}$ is independently hydrogen.

In embodiments, $R^{3.B}$ is independently —$CCl_3$. In embodiments, $R^{3.B}$ is independently —$CBr_3$. In embodiments, $R^{3.B}$ is independently —$CF_3$. In embodiments, $R^{3.B}$ is independently —$CI_3$. In embodiments, $R^{3.B}$ is independently —$CHCl_2$. In embodiments, $R^{3.B}$ is independently —$CHBr_2$. In embodiments, $R^{3.B}$ is independently —$CHF_2$. In embodiments, $R^{3.B}$ is independently —$CHI_2$. In embodiments, $R^{3.B}$ is independently —$CH_2Cl$. In embodiments, $R^{3.B}$ is independently —$CH_2Br$. In embodiments, $R^{3.B}$ is independently —$CH_2F$. In embodiments, $R^{3.B}$ is independently —$CH_2I$. In embodiments, $R^{3.B}$ is independently —$CH_3$. In embodiments, $R^{3.B}$ is independently —$CH_2CH_3$. In embodiments, $R^{3.B}$ is independently —$CH(CH_3)_2$. In embodiments, $R^{3.B}$ is independently —$C(CH_3)_3$. In embodiments, $R^{3.B}$ is independently unsubstituted $C_1$-$C_4$ alkyl. In embodiments, $R^{3.B}$ is independently hydrogen.

In embodiments, $R^4$ is independently —$CCl_3$. In embodiments, $R^4$ is independently —$CBr_3$. In embodiments, $R^4$ is independently —$CF_3$. In embodiments, $R^4$ is independently —$CI_3$. In embodiments, $R^4$ is independently —$CHCl_2$. In embodiments, $R^4$ is independently —$CHBr_2$. In embodiments, $R^4$ is independently —$CHF_2$. In embodiments, $R^4$ is independently —$CHI_2$. In embodiments, $R^4$ is independently —$CH_2Cl$. In embodiments, $R^4$ is independently —$CH_2Br$. In embodiments, $R^4$ is independently —$CH_2F$. In embodiments, $R^4$ is independently —$CH_2I$. In embodiments, $R^4$ is independently —$CH_3$. In embodiments, $R^4$ is independently —$CH_2CH_3$. In embodiments, $R^4$ is independently —$CH(CH_3)_2$. In embodiments, $R^4$ is independently —$C(CH_3)_3$. In embodiments, $R^4$ is independently unsubstituted $C_1$-$C_4$ alkyl. In embodiments, $R^4$ is independently hydrogen.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —$CH_3$. In embodiments, $R^5$ is independently —$CH_2CH_3$. In embodiments, $R^5$ is independently —$CH(CH_3)_2$. In embodiments, $R^5$ is independently —$C(CH_3)_3$. In embodiments, $R^5$ is independently unsubstituted $C_1$-$C_4$ alkyl. In embodiments, $R^5$ is independently hydrogen.

In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —$CH_2Cl$. In embodiments, $R^6$ is independently —$CH_2Br$. In embodiments, $R^6$ is independently —$CH_2F$. In embodiments, $R^6$ is independently —$CH_2I$. In embodiments, $R^6$ is independently —$CH_3$. In embodiments, $R^6$ is independently —$CH_2CH_3$. In embodiments, $R^6$ is independently —$CH(CH_3)_2$. In embodiments, $R^6$ is independently —$C(CH_3)_3$. In embodiments, $R^6$ is independently unsubstituted $C_1$-$C_4$ alkyl. In embodiments, $R^6$ is independently hydrogen.

In embodiments, the compound has the formula:

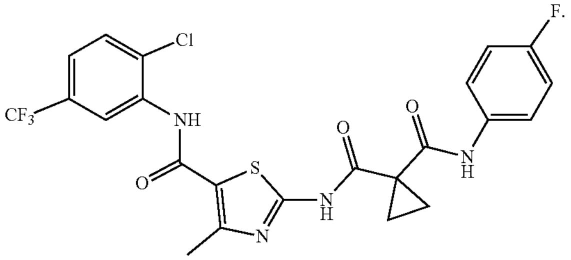 [SMILES: Cc1nc(NC(=O)C2(C(=O)Nc3ccc(F)cc3)CC2)sc1C(=O)Nc1cc(C(F)(F)F)ccc1Cl]

In embodiments, the compound has the formula:

(VIII)

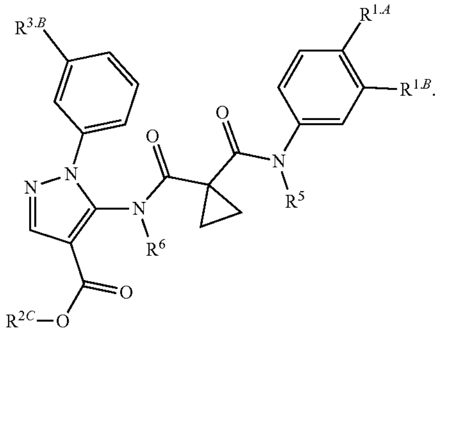

$R^{2C}$, $R^5$, and $R^6$ are as described herein, including in embodiments. $R^{1.A}$ and $R^{1.B}$ are independently hydrogen or any value of $R^1$ as described herein, including embodiments. $R^{3.B}$ is independently hydrogen or any value of $R^3$ as described herein, including embodiments.

In embodiments, $R^{1.A}$ is independently not —$CF_3$. In embodiments, $R^{1.A}$ is independently not —Cl. In embodiments, $R^{1.A}$ is independently not halogen. In embodiments, $R^{1.A}$ is independently not —$CX^1_3$. In embodiments, $R^{1.B}$ is independently not —$CF_3$. In embodiments, $R^{1.B}$ is independently not —Cl. In embodiments, $R^{1.B}$ is independently not halogen. In embodiments, $R^{1.B}$ is independently not —$CX^1_3$. In embodiments, $R^5$ is independently not hydrogen. In embodiments, $R^6$ is independently not hydrogen. In embodiments, $R^{2C}$ is independently not unsubstituted ethyl. In embodiments, $R^{2C}$ is independently not unsubstituted $C_1$-$C_3$ alkyl. In embodiments, $R^{3.B}$ is independently not —$CF_3$. In embodiments, $R^{3.B}$ is independently not —Cl. In embodiments, $R^{3.B}$ is independently not halogen. In embodiments, $R^{3.B}$ is independently not —$CX^1_3$.

In embodiments, $R^{1.A}$ is independently halogen. In embodiments, $R^{1.A}$ is independently —F. In embodiments, $R^{1.A}$ is independently —Cl. In embodiments, $R^{1.A}$ is independently —Br. In embodiments, $R^{1.A}$ is independently —I. In embodiments, $R^{1.A}$ is independently hydrogen.

In embodiments, $R^{1.B}$ is independently halogen. In embodiments, $R^{1.B}$ is independently —F. In embodiments, $R^{1.B}$ is independently —Cl. In embodiments, $R^{1.B}$ is independently —Br. In embodiments, $R^{1.B}$ is independently —I. In embodiments, $R^{1.B}$ is independently hydrogen.

In embodiments, $R^{2C}$ is independently —$CCl_3$. In embodiments, $R^{2C}$ is independently —$CBr_3$. In embodiments, $R^{2C}$ is independently —$CF_3$. In embodiments, $R^{2C}$ is independently —$CI_3$. In embodiments, $R^{2C}$ is independently —$CHCl_2$. In embodiments, $R^{2C}$ is independently —$CHBr_2$. In embodiments, $R^{2C}$ is independently —$CHF_2$. In embodiments, $R^{2C}$ is independently —$CHI_2$. In embodiments, $R^{2C}$ is independently —$CH_2Cl$. In embodiments, $R^{2C}$ is independently —$CH_2Br$. In embodiments, $R^{2C}$ is independently —$CH_2F$. In embodiments, $R^{2C}$ is independently —$CH_2I$. In embodiments, $R^{2C}$ is independently —$CH_3$. In embodiments, $R^{2C}$ is independently —$CH_2CH_3$. In embodiments, $R^{2C}$ is independently —$CH(CH_3)_2$. In embodiments, $R^{2C}$ is independently —$C(CH_3)_3$. In embodiments, $R^{2C}$ is independently unsubstituted $C_1$-$C_4$ alkyl. In embodiments, $R^{2C}$ is independently hydrogen.

In embodiments, $R^{3.B}$ is independently halogen. In embodiments, $R^{3.B}$ is independently —F. In embodiments, $R^{3.B}$ is independently —Cl. In embodiments, $R^{3.B}$ is independently —Br. In embodiments, $R^{3.B}$ is independently —I. In embodiments, $R^{3.B}$ is independently hydrogen.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —$CH_3$. In embodiments, $R^5$ is independently —$CH_2CH_3$. In embodiments, $R^5$ is independently —$CH(CH_3)_2$. In embodiments, $R^5$ is independently —$C(CH_3)_3$. In embodiments, $R^5$ is independently unsubstituted $C_1$-$C_4$ alkyl. In embodiments, $R^5$ is independently hydrogen.

In embodiments, $R^6$ is independently $-CCl_3$. In embodiments, $R^6$ is independently $-CBr_3$. In embodiments, $R^6$ is independently $-CF_3$. In embodiments, $R^6$ is independently $-CI_3$. In embodiments, $R^6$ is independently $-CHCl_2$. In embodiments, $R^6$ is independently $-CHBr_2$. In embodiments, $R^6$ is independently $-CHF_2$. In embodiments, $R^6$ is independently $-CHI_2$. In embodiments, $R^6$ is independently $-CH_2Cl$. In embodiments, $R^6$ is independently $-CH_2Br$. In embodiments, $R^6$ is independently $-CH_2F$. In embodiments, $R^6$ is independently $-CH_2I$. In embodiments, $R^6$ is independently $-CH_3$. In embodiments, $R^6$ is independently $-CH_2CH_3$. In embodiments, $R^6$ is independently $-CH(CH_3)_2$. In embodiments, $R^6$ is independently $-C(CH_3)_3$. In embodiments, $R^6$ is independently unsubstituted $C_1$-$C_4$ alkyl. In embodiments, $R^6$ is independently hydrogen.

In embodiments, the compound has the formula:

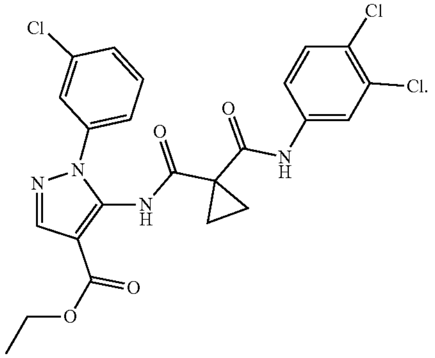 [SMILES: CCOC(=O)c1cnn(-c2cccc(Cl)c2)c1NC(=O)C1(C(=O)Nc2ccc(Cl)c(Cl)c2)CC1]

In embodiments, the compound does not have the formula:

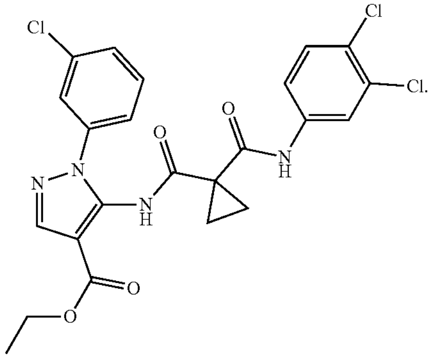 [SMILES: CCOC(=O)c1cnn(-c2cccc(Cl)c2)c1NC(=O)C1(C(=O)Nc2ccc(Cl)c(Cl)c2)CC1]

In embodiments, the compound has the formula:

(IX)

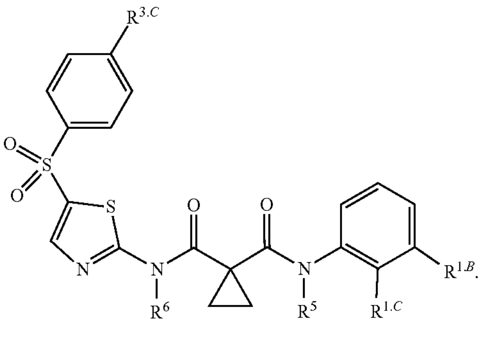

$R^5$ and $R^6$ are as described herein, including in embodiments. $R^{1.B}$ and $R^{1.C}$ are independently hydrogen or any value of $R^1$ as described herein, including embodiments. $R^{3.C}$ is independently hydrogen or any value of $R^3$ as described herein, including embodiments.

In embodiments, $R^{1.C}$ is independently not $-CF_3$. In embodiments, $R^{1.C}$ is independently not $-Cl$. In embodiments, $R^{1.C}$ is independently not halogen. In embodiments, $R^{1.C}$ is independently not $-CX^1_3$. In embodiments, $R^{1.B}$ is independently not $-CF_3$. In embodiments, $R^{1.B}$ is independently not $-Cl$. In embodiments, $R^{1.B}$ is independently not halogen. In embodiments, $R^{1.B}$ is independently not $-CX^1_3$. In embodiments, $R^{1.B}$ is independently not $-CH_3$. In embodiments, $R^{1.B}$ is independently not $-CH_2CH_3$. In embodiments, $R^5$ is independently not hydrogen. In embodiments, $R^6$ is independently not hydrogen. In embodiments, $R^{3.C}$ is independently not $-NO_2$. In embodiments, $R^{3.C}$ is independently not $-Cl$. In embodiments, $R^{3.C}$ is independently not halogen.

In embodiments, $R^{1.B}$ is independently $-CCl_3$. In embodiments, $R^{1.B}$ is independently $-CBr_3$. In embodiments, $R^{1.B}$ is independently $-CF_3$. In embodiments, $R^{1.B}$ is independently $-CI_3$. In embodiments, $R^{1.B}$ is independently $-CHCl_2$. In embodiments, $R^{1.B}$ is independently $-CHBr_2$. In embodiments, $R^{1.B}$ is independently $-CHF_2$. In embodiments, $R^{1.B}$ is independently $-CHI_2$. In embodiments, $R^{1.B}$ is independently $-CH_2Cl$. In embodiments, $R^{1.B}$ is independently $-CH_2Br$. In embodiments, $R^{1.B}$ is independently $-CH_2F$. In embodiments, $R^{1.B}$ is independently $-CH_2I$. In embodiments, $R^{1.B}$ is independently $-CH_3$. In embodiments, $R^{1.B}$ is independently $-CH_2CH_3$. In embodiments, $R^{1.B}$ is independently $-CH(CH_3)_2$. In embodiments, $R^{1.B}$ is independently $-C(CH_3)_3$. In embodiments, $R^{1.B}$ is independently unsubstituted $C_1$-$C_4$ alkyl. In embodiments, $R^{1.B}$ is independently hydrogen.

In embodiments, $R^{1.C}$ is independently halogen. In embodiments, $R^{1.C}$ is independently $-F$. In embodiments, $R^{1.C}$ is independently $-Cl$. In embodiments, $R^{1.C}$ is independently $-Br$. In embodiments, $R^{1.C}$ is independently $-I$. In embodiments, $R^{1.C}$ is independently hydrogen.

In embodiments, $R^{3.C}$ is independently halogen. In embodiments, $R^{3.C}$ is independently $-F$. In embodiments, $R^{3.C}$ is independently $-Cl$. In embodiments, $R^{3.C}$ is independently $-Br$. In embodiments, $R^{3.C}$ is independently $-I$. In embodiments, $R^{3.C}$ is independently hydrogen. In embodiments, $R^{3.C}$ is independently $-OH$. In embodiments, $R^{3.C}$ is independently $-OCCl_3$. In embodiments, $R^{3.C}$ is independently $-OCF_3$. In embodiments, $R^{3.C}$ is independently $-OCBr_3$. In embodiments, $R^{3.C}$ is independently $-OCI_3$. In embodiments, $R^{3.C}$ is independently $-OCHCl_2$. In embodiments, $R^{3.C}$ is independently $-OCHBr_2$. In embodiments, $R^{3.C}$ is independently $-OCHI_2$. In embodiments, $R^{3.C}$ is independently $-OCHF_2$. In embodiments, $R^{3.C}$ is independently $-OCH_2Cl$. In embodiments, $R^{3.C}$ is independently $-OCH_2Br$. In embodiments, $R^{3.C}$ is independently $-OCH_2I$. In embodiments, $R^{3.C}$ is independently $-OCH_2F$. In embodiments, $R^{3.C}$ is independently $-CCl_3$. In embodiments, $R^{3.C}$ is independently $-CBr_3$. In embodiments, $R^{3.C}$ is independently $-CF_3$. In embodiments, $R^{3.C}$ is independently $-CI_3$. In embodiments, $R^{3.C}$ is independently $-CHCl_2$. In embodiments, $R^{3.C}$ is independently $-CHBr_2$. In embodiments, $R^{3.C}$ is independently $-CHF_2$. In embodiments, $R^{3.C}$ is independently $-CHI_2$. In embodiments, $R^{3.C}$ is independently $-CH_2Cl$. In embodiments, $R^{3.C}$ is independently $-CH_2Br$. In embodiments, $R^{3.C}$ is independently —$CH_2F$. In embodiments, $R^{3.C}$ is independently —$CH_2I$. In embodiments, $R^{3.C}$ is independently —$NO_2$.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —$CH_3$. In embodiments, $R^5$ is independently —$CH_2CH_3$. In embodiments, $R^5$ is independently —$CH(CH_3)_2$. In embodiments, $R^5$ is independently —$C(CH_3)_3$. In embodiments, $R^5$ is independently unsubstituted $C_1$-$C_4$ alkyl. In embodiments, $R^5$ is independently hydrogen.

In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —$CH_2Cl$. In embodiments, $R^6$ is independently —$CH_2Br$. In embodiments, $R^6$ is independently —$CH_2F$. In embodiments, $R^6$ is independently —$CH_2I$. In embodiments, $R^6$ is independently —$CH_3$. In embodiments, $R^6$ is independently —$CH_2CH_3$. In embodiments, $R^6$ is independently —$CH(CH_3)_2$. In embodiments, $R^6$ is independently —$C(CH_3)_3$. In embodiments, $R^6$ is independently unsubstituted $C_1$-$C_4$ alkyl. In embodiments, $R^6$ is independently hydrogen.

In embodiments, the compound has the formula:

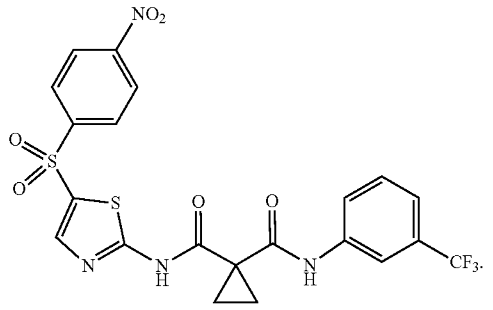 [SMILES: O=C(Nc1cccc(C(F)(F)F)c1)C1(C(=O)Nc2ncc(S(=O)(=O)c3ccc([N+](=O)[O-])cc3)s2)CC1]

In embodiments, the compound does not have the formula:

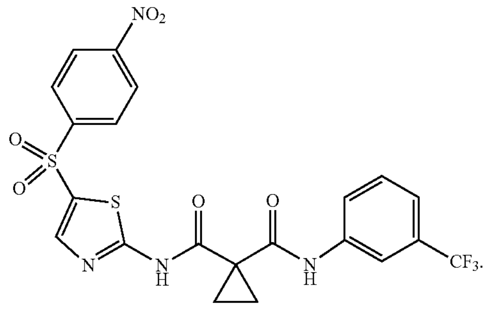 [SMILES: O=C(Nc1cccc(C(F)(F)F)c1)C1(C(=O)Nc2ncc(S(=O)(=O)c3ccc([N+](=O)[O-])cc3)s2)CC1]

In embodiments, the compound has the formula:

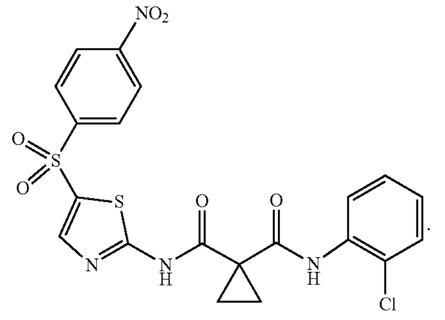 [SMILES: O=C(Nc1ncc(S(=O)(=O)c2ccc([N+](=O)[O-])cc2)s1)C1(C(=O)Nc2ccccc2Cl)CC1]

In embodiments, the compound does not have the formula:

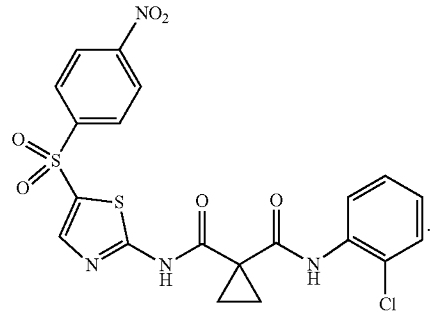 [SMILES: O=C(Nc1ncc(S(=O)(=O)c2ccc([N+](=O)[O-])cc2)s1)C1(C(=O)Nc2ccccc2Cl)CC1]

In embodiments, the compound has the formula:

(X)

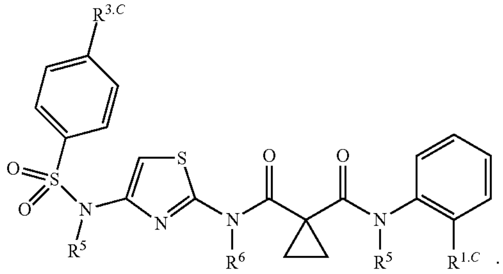

$R^4$, $R^5$, and $R^6$ are as described herein, including in embodiments. $R^{1.C}$ is independently hydrogen or any value of $R^1$ as described herein, including embodiments. $R^{3.C}$ is independently hydrogen or any value of $R^3$ as described herein, including embodiments.

In embodiments, $R^{1.C}$ is independently not —$CF_3$. In embodiments, $R^{1.C}$ is independently not —Cl. In embodiments, $R^{1.C}$ is independently not halogen. In embodiments, $R^{1.C}$ is independently not —$CX^1{}_3$. In embodiments, $R^{1.B}$ is independently not —$CF_3$. In embodiments, $R^5$ is independently not hydrogen. In embodiments, $R^6$ is independently not hydrogen. In embodiments, $R^4$ is independently not hydrogen. In embodiments, $R^{3.C}$ is independently not —Cl. In embodiments, $R^{3.C}$ is independently not halogen.

In embodiments, $R^{1.C}$ is independently halogen. In embodiments, $R^{1.C}$ is independently —F. In embodiments, $R^{1.C}$ is independently —Cl. In embodiments, $R^{1.C}$ is independently —Br. In embodiments, $R^{1.C}$ is independently —I. In embodiments, $R^{1.C}$ is independently hydrogen.

In embodiments, $R^{3.C}$ is independently halogen. In embodiments, $R^{3.C}$ is independently —F. In embodiments, $R^{3.C}$ is independently —Cl. In embodiments, $R^{3.C}$ is independently —Br. In embodiments, $R^{3.C}$ is independently —I. In embodiments, $R^{3.C}$ is independently hydrogen.

In embodiments, $R^5$ is independently $-CCl_3$. In embodiments, $R^5$ is independently $-CBr_3$. In embodiments, $R^5$ is independently $-CF_3$. In embodiments, $R^5$ is independently $-CI_3$. In embodiments, $R^5$ is independently $-CHCl_2$. In embodiments, $R^5$ is independently $-CHBr_2$. In embodiments, $R^5$ is independently $-CHF_2$. In embodiments, $R^5$ is independently $-CHI_2$. In embodiments, $R^5$ is independently $-CH_2Cl$. In embodiments, $R^5$ is independently $-CH_2Br$. In embodiments, $R^5$ is independently $-CH_2F$. In embodiments, $R^5$ is independently $-CH_2I$. In embodiments, $R^5$ is independently $-CH_3$. In embodiments, $R^5$ is independently $-CH_2CH_3$. In embodiments, $R^5$ is independently $-CH(CH_3)_2$. In embodiments, $R^5$ is independently $-C(CH_3)_3$. In embodiments, $R^5$ is independently unsubstituted $C_1$-$C_4$ alkyl. In embodiments, $R^5$ is independently hydrogen.

In embodiments, $R^6$ is independently $-CCl_3$. In embodiments, $R^6$ is independently $-CBr_3$. In embodiments, $R^6$ is independently $-CF_3$. In embodiments, $R^6$ is independently $-CI_3$. In embodiments, $R^6$ is independently $-CHCl_2$. In embodiments, $R^6$ is independently $-CHBr_2$. In embodiments, $R^6$ is independently $-CHF_2$. In embodiments, $R^6$ is independently $-CHI_2$. In embodiments, $R^6$ is independently $-CH_2Cl$. In embodiments, $R^6$ is independently $-CH_2Br$. In embodiments, $R^6$ is independently $-CH_2F$. In embodiments, $R^6$ is independently $-CH_2I$. In embodiments, $R^6$ is independently $-CH_3$. In embodiments, $R^6$ is independently $-CH_2CH_3$. In embodiments, $R^6$ is independently $-CH(CH_3)_2$. In embodiments, $R^6$ is independently $-C(CH_3)_3$. In embodiments, $R^6$ is independently unsubstituted $C_1$-$C_4$ alkyl. In embodiments, $R^6$ is independently hydrogen.

In embodiments, the compound has the formula:

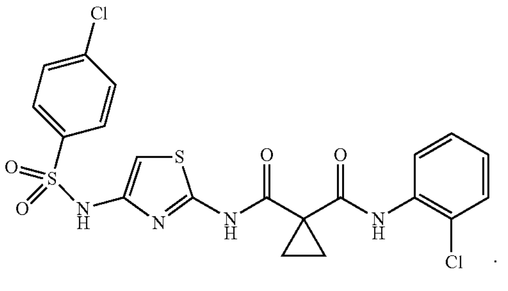 [SMILES: O=C(Nc1nc(NS(=O)(=O)c2ccc(Cl)cc2)cs1)C1(C(=O)Nc2ccccc2Cl)CC1]

In embodiments, the compound does not have the formula:

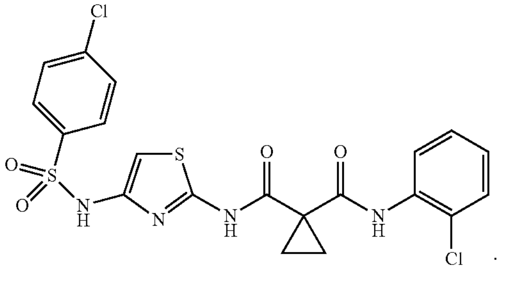 [SMILES: O=C(Nc1nc(NS(=O)(=O)c2ccc(Cl)cc2)cs1)C1(C(=O)Nc2ccccc2Cl)CC1]

In embodiments, the compound has the formula:

(XI)

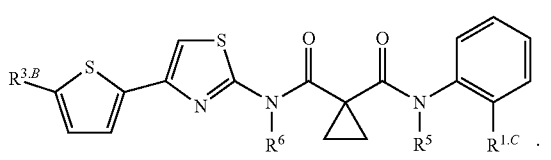

$R^5$ and $R^6$ are as described herein, including in embodiments. $R^{1.C}$ is independently hydrogen or any value of $R^1$ as described herein, including embodiments. $R^{3.B}$ is independently hydrogen or any value of $R^3$ as described herein, including embodiments.

In embodiments, $R^{1.C}$ is independently not $-CF_3$. In embodiments, $R^{1.C}$ is independently not —Cl. In embodiments, $R^{1.C}$ is independently not halogen. In embodiments, $R^{1.C}$ is independently not $-CX^1_3$. In embodiments, $R^{1.B}$ is independently not $-CF_3$. In embodiments, $R^5$ is independently not hydrogen. In embodiments, $R^6$ is independently not hydrogen. In embodiments, $R^{3.B}$ is independently not —Br. In embodiments, $R^{3.B}$ is independently not halogen.

In embodiments, $R^{1.C}$ is independently halogen. In embodiments, $R^{1.C}$ is independently —F. In embodiments, $R^{1.C}$ is independently —Cl. In embodiments, $R^{1.C}$ is independently —Br. In embodiments, $R^{1.C}$ is independently —I. In embodiments, $R^{1.C}$ is independently hydrogen.

In embodiments, $R^{3.B}$ is independently halogen. In embodiments, $R^{3.B}$ is independently —F. In embodiments, $R^{3.B}$ is independently —Cl. In embodiments, $R^{3.B}$ is independently —Br. In embodiments, $R^{3.B}$ is independently —I. In embodiments, $R^{3.B}$ is independently hydrogen.

In embodiments, $R^5$ is independently $-CCl_3$. In embodiments, $R^5$ is independently $-CBr_3$. In embodiments, $R^5$ is independently $-CF_3$. In embodiments, $R^5$ is independently $-CI_3$. In embodiments, $R^5$ is independently $-CHCl_2$. In embodiments, $R^5$ is independently $-CHBr_2$. In embodiments, $R^5$ is independently $-CHF_2$. In embodiments, $R^5$ is independently $-CHI_2$. In embodiments, $R^5$ is independently $-CH_2Cl$. In embodiments, $R^5$ is independently $-CH_2Br$. In embodiments, $R^5$ is independently $-CH_2F$. In embodiments, $R^5$ is independently $-CH_2I$. In embodiments, $R^5$ is independently $-CH_3$. In embodiments, $R^5$ is independently $-CH_2CH_3$. In embodiments, $R^5$ is independently $-CH(CH_3)_2$. In embodiments, $R^5$ is independently $-C(CH_3)_3$. In embodiments, $R^5$ is independently unsubstituted $C_1$-$C_4$ alkyl. In embodiments, $R^5$ is independently hydrogen.

In embodiments, $R^6$ is independently $-CCl_3$. In embodiments, $R^6$ is independently $-CBr_3$. In embodiments, $R^6$ is independently $-CF_3$. In embodiments, $R^6$ is independently $-CI_3$. In embodiments, $R^6$ is independently $-CHCl_2$. In embodiments, $R^6$ is independently $-CHBr_2$. In embodiments, $R^6$ is independently $-CHF_2$. In embodiments, $R^6$ is independently $-CHI_2$. In embodiments, $R^6$ is independently $-CH_2Cl$. In embodiments, $R^6$ is independently $-CH_2Br$. In embodiments, $R^6$ is independently $-CH_2F$. In embodiments, $R^6$ is independently $-CH_2I$. In embodiments, $R^6$ is independently $-CH_3$. In embodiments, $R^6$ is independently $-CH_2CH_3$. In embodiments, $R^6$ is independently $-CH(CH_3)_2$. In embodiments, $R^6$ is independently $-C(CH_3)_3$. In embodiments, $R^6$ is independently unsubstituted $C_1$-$C_4$ alkyl. In embodiments, $R^6$ is independently hydrogen.

In embodiments, the compound has the formula:

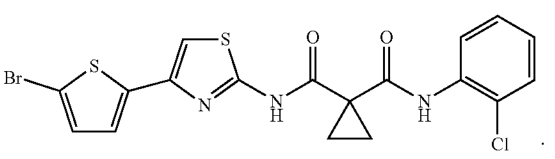 [SMILES: O=C(Nc1nc(-c2ccc(Br)s2)cs1)C1(C(=O)Nc2ccccc2Cl)CC1]

In embodiments, the compound does not have the formula:

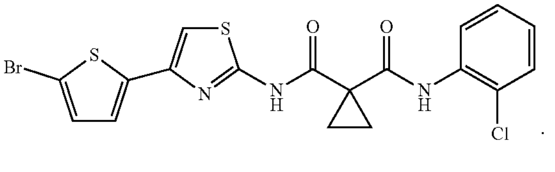 [SMILES: O=C(Nc1nc(-c2ccc(Br)s2)cs1)C1(C(=O)Nc2ccccc2Cl)CC1]

In embodiments, the compound has the formula:

(XII)

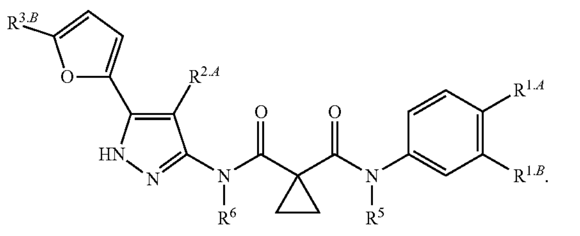

$R^5$ and $R^6$ are as described herein, including in embodiments. $R^{1.A}$ and $R^{1.B}$ are independently hydrogen or any value of $R^1$ as described herein, including embodiments. $R^{2.A}$ is independently hydrogen or any value of $R^2$ as described herein, including embodiments. $R^{3.B}$ is independently hydrogen or any value of $R^3$ as described herein, including embodiments.

In embodiments, $R^{1.A}$ is independently not —Br. In embodiments, $R^{1.B}$ is independently not —$NO_2$. In embodiments, $R^{1.A}$ is independently not halogen. In embodiments, $R^{2.A}$ is independently not unsubstituted methyl. In embodiments, $R^{2.A}$ is independently not unsubstituted ethyl. In embodiments, $R^{2.A}$ is independently not unsubstituted $C_1$-$C_3$ alkyl. In embodiments, $R^6$ is independently not hydrogen. In embodiments, $R^5$ is independently not hydrogen. In embodiments, $R^{3.B}$ is independently not unsubstituted methyl. In embodiments, $R^{3.B}$ is independently not unsubstituted ethyl. In embodiments, $R^{3.B}$ is independently not unsubstituted $C_1$-$C_3$ alkyl.

In embodiments, $R^{1.A}$ is independently halogen. In embodiments, $R^{1.A}$ is independently —F. In embodiments, $R^{1.A}$ is independently —Cl. In embodiments, $R^{1.A}$ is independently —Br. In embodiments, $R^{1.A}$ is independently —I. In embodiments, $R^{1.A}$ is independently hydrogen.

In embodiments, $R^{1.B}$ is independently halogen. In embodiments, $R^{1.B}$ is independently —F. In embodiments, $R^{1.B}$ is independently —Cl. In embodiments, $R^{1.B}$ is independently —Br. In embodiments, $R^{1.B}$ is independently —I. In embodiments, $R^{1.B}$ is independently hydrogen. In embodiments, $R^{1.B}$ is independently —OH. In embodiments, $R^{1.B}$ is independently —$OCCl_3$. In embodiments, $R^{1.B}$ is independently —$OCF_3$. In embodiments, $R^{1.B}$ is independently —$OCBr_3$. In embodiments, $R^{1.B}$ is independently —$OCI_3$. In embodiments, $R^{1.B}$ is independently —$OCHCl_2$. In embodiments, $R^{1.B}$ is independently —$OCHBr_2$. In embodiments, $R^{1.B}$ is independently —$OCHI_2$. In embodiments, $R^{1.B}$ is independently —$OCHF_2$. In embodiments, $R^{1.B}$ is independently —$OCH_2Cl$. In embodiments, $R^{1.B}$ is independently —$OCH_2Br$. In embodiments, $R^{1.B}$ is independently —$OCH_2I$. In embodiments, $R^{1.B}$ is independently —$OCH_2F$. In embodiments, $R^{1.B}$ is independently —$CCl_3$. In embodiments, $R^{1.B}$ is independently —$CBr_3$. In embodiments, $R^{1.B}$ is independently —$CF_3$. In embodiments, $R^{1.B}$ is independently —$CI_3$. In embodiments, $R^{1.B}$ is independently —$CHCl_2$. In embodiments, $R^{1.B}$ is independently —$CHBr_2$. In embodiments, $R^{1.B}$ is independently —$CHF_2$. In embodiments, $R^{1.B}$ is independently —$CHI_2$. In embodiments, $R^{1.B}$ is independently —$CH_2Cl$. In embodiments, $R^{1.B}$ is independently —$CH_2Br$. In embodiments, $R^{1.B}$ is independently —$CH_2F$. In embodiments, $R^{1.B}$ is independently —$CH_2I$. In embodiments, $R^{1.B}$ is independently —$NO_2$.

In embodiments, $R^{2.A}$ is independently —$CCl_3$. In embodiments, $R^{2.A}$ is independently —$CBr_3$. In embodiments, $R^{2.A}$ is independently —$CF_3$. In embodiments, $R^{2.A}$ is independently —$CI_3$. In embodiments, $R^{2.A}$ is independently —$CHCl_2$. In embodiments, $R^{2.A}$ is independently —$CHBr_2$. In embodiments, $R^{2.A}$ is independently —$CHF_2$. In embodiments, $R^{2.A}$ is independently —$CHI_2$. In embodiments, $R^{2.A}$ is independently —$CH_2Cl$. In embodiments, $R^{2.A}$ is independently —$CH_2Br$. In embodiments, $R^{2.A}$ is independently —$CH_2F$. In embodiments, $R^{2.A}$ is independently —$CH_2I$. In embodiments, $R^{2.A}$ is independently —$CH_3$. In embodiments, $R^{2.A}$ is independently —$CH_2CH_3$. In embodiments, $R^{2.A}$ is independently —$CH(CH_3)_2$. In embodiments, $R^{2.A}$ is independently —$C(CH_3)_3$. In embodiments, $R^{2.A}$ is independently unsubstituted $C_1$-$C_4$ alkyl. In embodiments, $R^{2.A}$ is independently hydrogen.

In embodiments, $R^{3.B}$ is independently —$CCl_3$. In embodiments, $R^{3.B}$ is independently —$CBr_3$. In embodiments, $R^{3.B}$ is independently —$CF_3$. In embodiments, $R^{3.B}$ is independently —$CI_3$. In embodiments, $R^{3.B}$ is independently —$CHCl_2$. In embodiments, $R^{3.B}$ is independently —$CHBr_2$. In embodiments, $R^{3.B}$ is independently —$CHF_2$. In embodiments, $R^{3.B}$ is independently —$CHI_2$. In embodiments, $R^{3.B}$ is independently —$CH_2C_1$. In embodiments, $R^{3.B}$ is independently —$CH_2Br$. In embodiments, $R^{3.B}$ is independently —$CH_2F$. In embodiments, $R^{3.B}$ is independently —$CH_2I$. In embodiments, $R^{3.B}$ is independently —$CH_3$. In embodiments, $R^{3.B}$ is independently —$CH_2CH_3$. In embodiments, $R^{3.B}$ is independently —$CH(CH_3)_2$. In embodiments, $R^{3.B}$ is independently —$C(CH_3)_3$. In embodiments, $R^{3.B}$ is independently unsubstituted $C_1$-$C_4$ alkyl. In embodiments, $R^{3.B}$ is independently hydrogen.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —$CH_3$. In embodiments, $R^5$ is independently —$CH_2CH_3$. In embodiments, $R^5$ is independently —$CH(CH_3)_2$. In embodiments, $R^5$ is independently —$C(CH_3)_3$. In embodiments, $R^5$ is independently unsubstituted $C_1$-$C_4$ alkyl. In embodiments, $R^5$ is independently hydrogen.

In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —$CH_2Cl$. In embodiments, $R^6$ is independently —$CH_2Br$. In embodiments, $R^6$ is independently —$CH_2F$. In embodiments, $R^6$ is independently —$CH_2I$. In embodiments, $R^6$ is independently —$CH_3$. In embodiments, $R^6$ is independently —$CH_2CH_3$. In embodiments, $R^6$ is independently —$CH(CH_3)_2$. In embodiments, $R^6$ is independently —$C(CH_3)_3$. In embodiments, $R^6$ is independently unsubstituted $C_1$-$C_4$ alkyl. In embodiments, $R^6$ is independently hydrogen.

In embodiments, the compound has the formula:

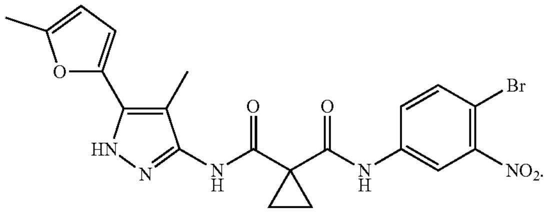 [SMILES: Cc1ccc(-c2[nH]nc(NC(=O)C3(C(=O)Nc4ccc(Br)c([N+](=O)[O-])c4)CC3)c2C)o1]

In embodiments, the compound does not have the formula:

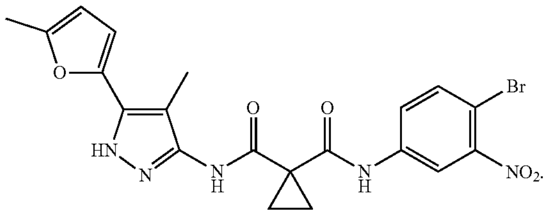 [SMILES: Cc1ccc(-c2[nH]nc(NC(=O)C3(C(=O)Nc4ccc(Br)c([N+](=O)[O-])c4)CC3)c2C)o1]

In an aspect is provided a compound having the formula:

(Id)

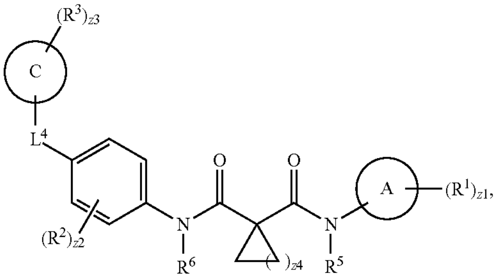

or a pharmaceutically acceptable salt thereof, wherein $L^4$ is —$SO_2N(R^4)CH_2CH_2$—, —$CH_2CH_2N(R^4)SO_2$—, —$SO_2N(R^4)CH_2$—, or —$CH_2N(R^4)SO_2$—; and Ring A, Ring C, $R^1$, $R^2$, $R^3$, $R^4$, $R^3$, $R^6$, z1, z2, z3, and z4 are as described herein, including in embodiments.

In embodiments, $R^1$ is independently not —F. In embodiments, $R^1$ is independently not unsubstituted methoxy. In embodiments, $R^1$ is independently not halogen. In embodiments, $R^1$ is independently not unsubstituted $C_1$-$C_3$ alkoxy. In embodiments, z1 is independently not 2. In embodiments, z1 is independently not 1. In embodiments, z2 is independently not 0. In embodiments, $R^6$ is independently not hydrogen. In embodiments, $R^5$ is independently not hydrogen. In embodiments, z3 is independently not 0. In embodiments, $L^4$ is independently not —$SO_2NHCH_2CH_2$—. In embodiments, $L^4$ is independently not —$CH_2CH_2NHSO_2$—. In embodiments, $L^4$ is independently not —$SO_2NHCH_2$—. In embodiments, $L^4$ is independently not —$CH_2NHSO_2$—. In embodiments, Ring C is independently not phenyl. In embodiments, Ring A is independently not phenyl.

In embodiments of the compound of formula Id, Ring A is phenyl. In embodiments of the compound of formula Id, Ring A is a 5 to 6 membered heteroaryl. In embodiments of the compound of formula Id, Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl. In embodiments of the compound of formula Id, $R^5$ and $R^6$ are independently hydrogen.

In embodiments of the compound of formula Id, the compound has the formula:

(Ida)

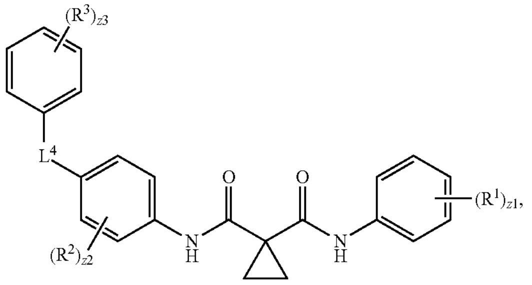

wherein $L^4$ is —$SO_2N(R^4)CH_2CH_2$—, —$CH_2CH_2N(R^4)SO_2$—, —$SO_2N(R^4)CH_2$—, or —$CH_2N(R^4)SO_2$—; $R^1$, $R^2$, $R^3$, $R^4$, z1, z2, and z3 are as described herein, including in embodiments.

In embodiments, $R^1$ is independently not —F. In embodiments, $R^1$ is independently not unsubstituted methoxy. In embodiments, $R^1$ is independently not halogen. In embodiments, $R^1$ is independently not unsubstituted $C_1$-$C_3$ alkoxy. In embodiments, z1 is independently not 2. In embodiments, z1 is independently not 1. In embodiments, z2 is independently not 0. In embodiments, z3 is independently not 0. In embodiments, $L^4$ is independently not —$SO_2NHCH_2CH_2$—. In embodiments, $L^4$ is independently not —$CH_2CH_2NHSO_2$—. In embodiments, $L^4$ is independently not —$SO_2NHCH_2$—. In embodiments, $L^4$ is independently not —$CH_2NHSO_2$—.

In embodiments of the compound of formula Id, the compound has the formula:

(VIIa)

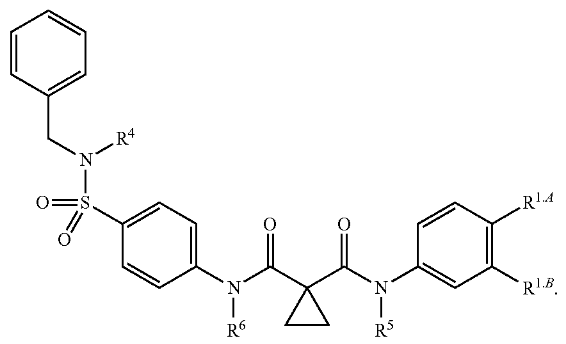

$R^4$, $R^5$, and $R^6$ are as described herein, including in embodiments. $R^{1.A}$ and $R^{1.B}$ are independently hydrogen or any value of R as described herein, including embodiments.

In embodiments, $R^{1.B}$ is independently not —F. In embodiments, $R^{1.B}$ is independently not halogen. In embodiments, $R^{1.A}$ is independently not unsubstituted methoxy. In embodiments, $R^{1.A}$ is independently not unsubstituted $C_1$-$C_3$ alkoxy. In embodiments, $R^{1.A}$ is independently not hydrogen. In embodiments, $R^{1.B}$ is independently not unsubstituted methoxy. In embodiments, $R^{1.B}$ is independently not unsubstituted $C_1$-$C_3$ alkoxy. In embodiments, $R^6$ is independently not hydrogen. In embodiments, $R^5$ is independently not hydrogen. In embodiments, $R^4$ is independently not hydrogen.

In embodiments of the compound of formula Id, the compound has the formula:

(VIIb)

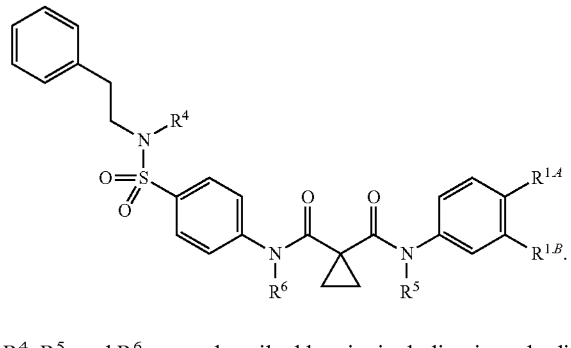

$R^4$, $R^5$, and $R^6$ are as described herein, including in embodiments. $R^{1.A}$ and $R^{1.B}$ are independently hydrogen or any value of R as described herein, including embodiments.

In embodiments, $R^{1.B}$ is independently not —F. In embodiments, $R^{1.B}$ is independently not halogen. In embodiments, $R^{1.A}$ is independently not unsubstituted methoxy. In embodiments, $R^{1.A}$ is independently not unsubstituted $C_1$-$C_3$ alkoxy. In embodiments, $R^{1.A}$ is independently not hydrogen. In embodiments, $R^{1.B}$ is independently not unsubstituted methoxy. In embodiments, $R^{1.B}$ is independently not unsubstituted $C_1$-$C_3$ alkoxy. In embodiments, $R^6$ is independently not hydrogen. In embodiments, $R^5$ is independently not hydrogen. In embodiments, $R^4$ is independently not hydrogen.

In embodiments, $R^{1.A}$ is independently —OH. In embodiments, $R^{1.A}$ is independently —$OCCl_3$. In embodiments, $R^{1.A}$ is independently —$OCF_3$. In embodiments, $R^{1.A}$ is independently —$OCBr_3$. In embodiments, $R^{1.A}$ is independently —$OCI_3$. In embodiments, $R^{1.A}$ is independently —$OCHCl_2$. In embodiments, $R^{1.A}$ is independently —$OCHBr_2$. In embodiments, $R^{1.A}$ is independently —$OCHI_2$. In embodiments, $R^{1.A}$ is independently —$OCHF_2$. In embodiments, $R^{1.A}$ is independently —$OCH_2Cl$. In embodiments, $R^{1.A}$ is independently —$OCH_2Br$. In embodiments, $R^{1.A}$ is independently —$OCH_2I$. In embodiments, $R^{1.A}$ is independently —$OCH_2F$. In embodiments, $R^{1.A}$ is independently —$OCH_3$. In embodiments, $R^{1.A}$ is independently —$OCH_2CH_3$. In embodiments, $R^{1.A}$ is independently —$OCH(CH_3)_2$. In embodiments, $R^{1.A}$ is independently —$OC(CH_3)_3$. In embodiments, $R^{1.A}$ is independently unsubstituted 2 to 4 membered heteroalkyl. In embodiments, $R^{1.A}$ is independently —F. In embodiments, $R^{1.A}$ is independently —Cl. In embodiments, $R^{1.A}$ is independently —Br. In embodiments, $R^{1.A}$ is independently —I. In embodiments, $R^{1.A}$ is independently halogen. In embodiments, $R^{1.A}$ is independently hydrogen.

In embodiments, $R^{1.B}$ is independently —OH. In embodiments, $R^{1.B}$ is independently —$OCCl_3$. In embodiments, $R^{1.B}$ is independently —$OCF_3$. In embodiments, $R^{1.B}$ is independently —$OCBr_3$. In embodiments, $R^{1.B}$ is independently —$OCI_3$. In embodiments, $R^{1.B}$ is independently —$OCHCl_2$. In embodiments, $R^{1.B}$ is independently —$OCHBr_2$. In embodiments, $R^{1.B}$ is independently —$OCHI_2$. In embodiments, $R^{1.B}$ is independently —$OCHF_2$. In embodiments, $R^{1.B}$ is independently —$OCH_2Cl$. In embodiments, $R^{1.B}$ is independently —$OCH_2Br$. In embodiments, $R^{1.B}$ is independently —$OCH_2I$. In embodiments, $R^{1.B}$ is independently —$OCH_2F$. In embodiments, $R^{1.B}$ is independently —$OCH_3$. In embodiments, $R^{1.B}$ is independently —$OCH_2CH_3$. In embodiments, $R^{1.B}$ is independently —$OCH(CH_3)_2$. In embodiments, $R^{1.B}$ is independently —$OC(CH_3)_3$. In embodiments, $R^{1.B}$ is independently unsubstituted 2 to 4 membered heteroalkyl. In embodiments, $R^{1.B}$ is independently —F. In embodiments, $R^{1.B}$ is independently —Cl. In embodiments, $R^{1.B}$ is independently —Br. In embodiments, $R^{1.B}$ is independently —I. In embodiments, $R^{1.B}$ is independently halogen. In embodiments, $R^{1.B}$ is independently hydrogen.

In embodiments, $R^4$ is independently —$CCl_3$. In embodiments, $R^4$ is independently —$CBr_3$. In embodiments, $R^4$ is independently —$CF_3$. In embodiments, $R^4$ is independently —$CI_3$. In embodiments, $R^4$ is independently —$CHCl_2$. In embodiments, $R^4$ is independently —$CHBr_2$. In embodiments, $R^4$ is independently —$CHF_2$. In embodiments, $R^4$ is independently —$CHI_2$. In embodiments, $R^4$ is independently —$CH_2Cl$. In embodiments, $R^4$ is independently —$CH_2Br$. In embodiments, $R^4$ is independently —$CH_2F$. In embodiments, $R^4$ is independently —$CH_2I$. In embodiments, $R^4$ is independently —$CH_3$. In embodiments, $R^4$ is independently —$CH_2CH_3$. In embodiments, $R^4$ is independently —$CH(CH_3)_2$. In embodiments, $R^4$ is independently —$C(CH_3)_3$. In embodiments, $R^4$ is independently unsubstituted $C_1$-$C_4$ alkyl. In embodiments, $R^4$ is independently hydrogen.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —$CH_3$. In embodiments, $R^5$ is independently $-CH_2CH_3$. In embodiments, $R^5$ is independently $-CH(CH_3)_2$. In embodiments, $R^5$ is independently $-C(CH_3)_3$. In embodiments, $R^5$ is independently unsubstituted $C_1$-$C_4$ alkyl. In embodiments, $R^5$ is independently hydrogen.

In embodiments, $R^6$ is independently $-CCl_3$. In embodiments, $R^6$ is independently $-CBr_3$. In embodiments, $R^6$ is independently $-CF_3$. In embodiments, $R^6$ is independently $-CI_3$. In embodiments, $R^6$ is independently $-CHCl_2$. In embodiments, $R^6$ is independently $-CHBr_2$. In embodiments, $R^6$ is independently $-CHF_2$. In embodiments, $R^6$ is independently $-CHI_2$. In embodiments, $R^6$ is independently $-CH_2Cl$. In embodiments, $R^6$ is independently $-CH_2Br$. In embodiments, $R^6$ is independently $-CH_2F$. In embodiments, $R^6$ is independently $-CH_2I$. In embodiments, $R^6$ is independently $-CH_3$. In embodiments, $R^6$ is independently $-CH_2CH_3$. In embodiments, $R^6$ is independently $-CH(CH_3)_2$. In embodiments, $R^6$ is independently $-C(CH_3)_3$. In embodiments, $R^6$ is independently unsubstituted $C_1$-$C_4$ alkyl. In embodiments, $R^6$ is independently hydrogen.

In embodiments, the compound has the formula:

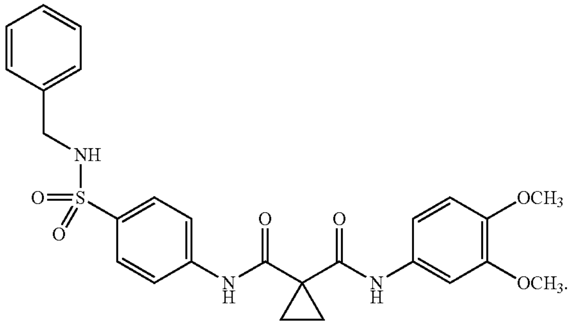 [SMILES: COc1ccc(NC(=O)C2(C(=O)Nc3ccc(S(=O)(=O)NCc4ccccc4)cc3)CC2)cc1OC]

In embodiments, the compound does not have the formula:

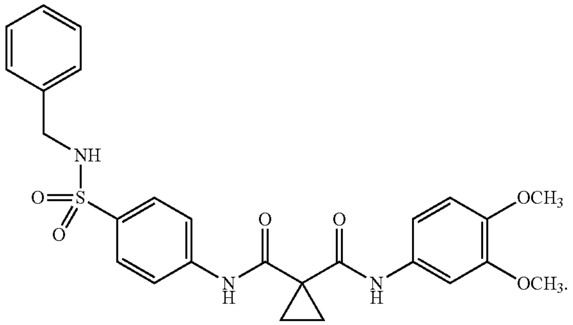 [SMILES: COc1ccc(NC(=O)C2(C(=O)Nc3ccc(S(=O)(=O)NCc4ccccc4)cc3)CC2)cc1OC]

In embodiments, the compound has the formula:

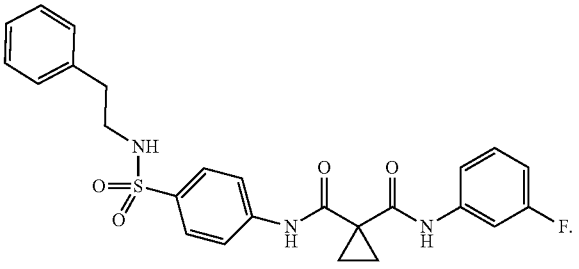 [SMILES: O=C(Nc1ccc(S(=O)(=O)NCCc2ccccc2)cc1)C1(C(=O)Nc2cccc(F)c2)CC1]

In embodiments, the compound does not have the formula:

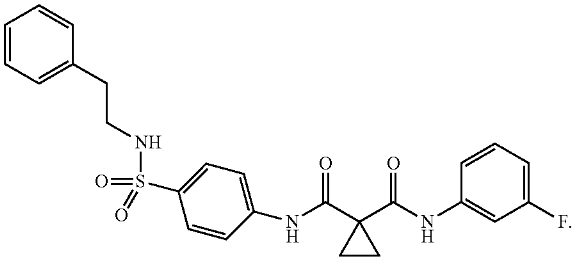 [SMILES: O=C(Nc1ccc(S(=O)(=O)NCCc2ccccc2)cc1)C1(C(=O)Nc2cccc(F)c2)CC1]

In embodiments, the compound reduces the level of phosphorylation of histone H3. In embodiments, the compound reduces the level of phosphorylation of the amino acid corresponding to serine 10 of human histone H3.

In embodiments, $R^1$ is independently not $-Cl$. In embodiments, $R^1$ is independently not halogen. In embodiments, $R^1$ is independently not $-CF_3$. In embodiments, $R^1$ is independently not $-CX^1_3$. In embodiments, $R^1$ is independently not $-Br$. In embodiments, $R^1$ is independently not $-NO_2$. In embodiments, $R^1$ is independently not $-Br$ or $-NO_2$. In embodiments, $R^1$ is independently not $-F$. In embodiments, $R^1$ is independently not unsubstituted methoxy. In embodiments, $R^1$ is independently not unsubstituted $C_1$-$C_3$ alkoxy. In embodiments, $R^1$ is independently not $-CH_3$. In embodiments, $R^1$ is independently not $-CH_2CH_3$. In embodiments, $R^{1.A}$ is independently not $-CF_3$. In embodiments, $R^{1.A}$ is independently not $-Cl$. In embodiments, $R^{1.A}$ is independently not $-F$. In embodiments, $R^{1.A}$ is independently not halogen. In embodiments, $R^{1.A}$ is independently not $-CX^1_3$. In embodiments, $R^{1.A}$ is independently not $-Br$. In embodiments, $R^{1.A}$ is independently not unsubstituted methoxy. In embodiments, $R^{1.A}$ is independently not unsubstituted $C_1$-$C_3$ alkoxy. In embodiments, $R^{1.A}$ is independently not hydrogen. In embodiments, $R^{1.B}$ is independently not $-CF_3$. In embodiments, $R^{1.B}$ is independently not $-Cl$. In embodiments, $R^{1.B}$ is independently not halogen. In embodiments, $R^{1.B}$ is independently not $-CX^1_3$. In embodiments, $R^{1.B}$ is independently not $-CH_3$. In embodiments, $R^{1.B}$ is independently not $-CH_2CH_3$. In embodiments, $R^{1.B}$ is independently not $-NO_2$. In embodiments, $R^{1.B}$ is independently not $-F$. In embodiments, $R^{1.B}$ is independently not unsubstituted methoxy. In embodiments, $R^{1.B}$ is independently not unsubstituted $C_1$-$C_3$ alkoxy. In embodiments, $R^{1.C}$ is independently not $-CF_3$. In embodiments, $R^{1.C}$ is independently not $-Cl$. In embodiments, $R^{1.C}$ is independently not halogen. In embodiments, $R^{1.C}$ is independently not $-CX^1_3$. In embodiments, $R^2$ is independently not $-C(O)OR^{2C}$. In embodiments, $R^2$ is independently not hydrogen. In embodiments, $R^2$ is independently not unsubstituted methyl. In embodiments, $R^2$ is independently not unsubstituted ethyl. In embodiments, $R^2$ is independently not unsubstituted $C_1$-$C_3$ alkyl. In embodiments, $R^{2.A}$ is independently not $-C(O)OR^{2C}$. In embodiments, $R^{2.A}$ is independently not unsubstituted methyl. In embodiments, $R^{2.A}$ is independently not unsubstituted ethyl. In embodiments, $R^{2.A}$ is independently not unsubstituted $C_1$-$C_3$ alkyl. In embodiments, $R^{2.B}$ is independently not hydrogen. In embodiments, $R^{2C}$ is independently not unsubstituted ethyl. In embodiments, $R^{2C}$ is independently not unsubstituted $C_1$-$C_3$ alkyl. In embodiments, $R^3$ is independently not $-Cl$. In embodiments, $R^3$ is independently not halogen. In embodiments, $R^3$ is independently not $-NO_2$. In embodiments, $R^3$ is independently not $-Br$. In embodiments, $R^3$ is independently not unsubstituted methyl. In embodiments, $R^3$ is independently not unsubstituted ethyl. In embodiments, $R^3$ is independently not unsubstituted $C_1$-$C_3$ alkyl. In embodiments, $R^3$ is independently not —$CF_3$. In embodiments, $R^3$ is independently not —$CX^1_3$. In embodiments, $R^{3.B}$ is independently not —$CF_3$. In embodiments, $R^{3.B}$ is independently not —Cl. In embodiments, $R^{3.B}$ is independently not halogen. In embodiments, $R^{3.B}$ is independently not —$CX^1_3$. In embodiments, $R^{3.B}$ is independently not —Br. In embodiments, $R^{3.B}$ is independently not unsubstituted methyl. In embodiments, $R^{3.B}$ is independently not unsubstituted ethyl. In embodiments, $R^{3.B}$ is independently not unsubstituted $C_1$-$C_3$ alkyl. In embodiments, $R^{3.C}$ is independently not —$NO_2$. In embodiments, $R^{3.C}$ is independently not —Cl. In embodiments, $R^{3.C}$ is independently not halogen. In embodiments, $L^4$ is independently not —$SO_2$—. In embodiments, $L^4$ is independently not —$NHSO_2$—. In embodiments, $L^4$ is independently not —$SO_2NH$—. In embodiments, $L^4$ is independently not —$SO_2NHCH_2CH_2$—. In embodiments, $L^4$ is independently not —$CH_2CH_2NHSO_2$—. In embodiments, $L^4$ is independently not —$CH_2CH_2NHSO_2$—. In embodiments, $L^4$ is independently not —$CH_2NHSO_2$—. In embodiments, $L^4$ is independently not —$SO_2NHCH_2$—. In embodiments, $R^4$ is independently not hydrogen. In embodiments, $R^5$ is independently not hydrogen. In embodiments, $R^6$ is independently not hydrogen. In embodiments, $W^1$ is independently not CH. In embodiments, $W^2$ is independently not S. In embodiments, $W^3$ is independently not CH. In embodiments, z1 is independently not 2. In embodiments, z1 is independently not 1. In embodiments, z2 is independently not 0. In embodiments, z2 is independently not 1. In embodiments, z3 is independently not 1. In embodiments, z3 is independently not 0. In embodiments, Ring A is independently not phenyl. In embodiments, Ring C is independently not phenyl. In embodiments, $L^4$ is not —O—.

In embodiments, the compound has the formula:

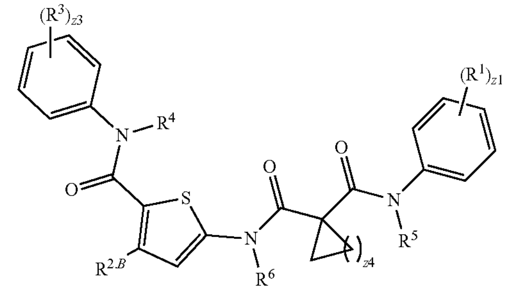

and $R^1$, $R^{2B}$, $R^3$, $R^4$, $R^5$, $R^6$, z1, z3, and z4 are as described herein, including in embodiments.

In embodiments, the compound has the formula:

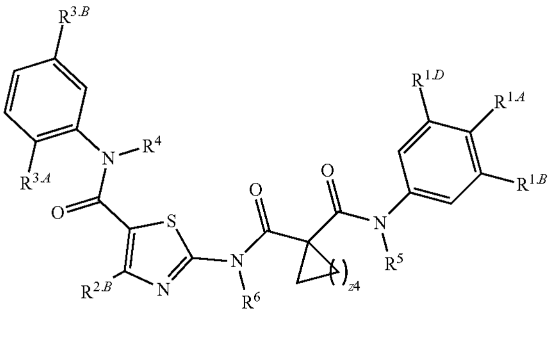

and $R^{1.A}$, $R^{1.B}$, $R^{2.B}$, $R^{3.A}$, $R^{3.B}$, $R^4$, $R^5$, $R^6$, and z4 are as described herein, including in embodiments. $R^{1.D}$ is independently hydrogen or any value of $R^1$ as described herein, including embodiments.

In embodiments, the compound has the formula:

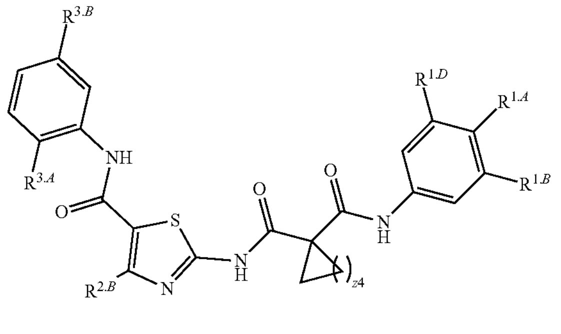

and $R^{1.A}$, $R^{1.B}$, $R^{1.D}$, $R^{2.B}$, $R^{3.A}$, $R^{3.B}$, and z4 are as described herein, including in embodiments.

In embodiments, the compound has the formula:

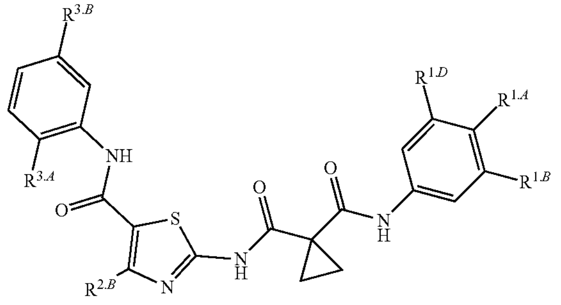

and $R^{1.A}$, $R^{1.B}$, $R^{1.D}$, $R^{2.B}$, $R^{3.A}$, and $R^{3.B}$ are as described herein, including in embodiments.

In embodiments, the compound has the formula:

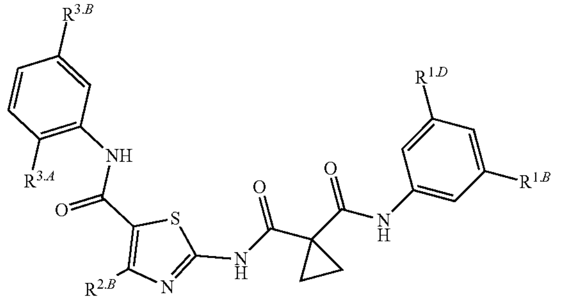

and $R^{1.B}$, $R^{1.D}$, $R^{2.B}$, $R^{3.A}$, and $R^{3.B}$ are as described herein, including in embodiments.

In embodiments, the compound has the formula:

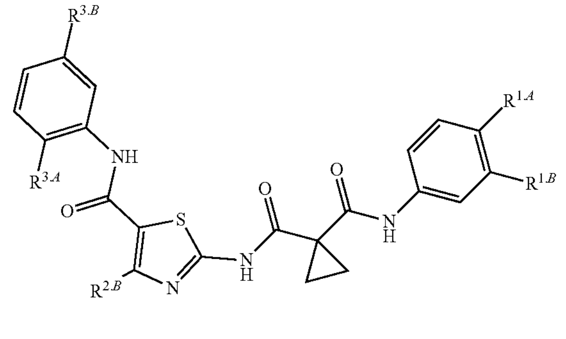

and $R^{1.A}$, $R^{1.B}$, $R^{1.B}$, $R^{3.A}$, and $R^{3.B}$ are as described herein, including in embodiments.

In embodiments, the compound has the formula:

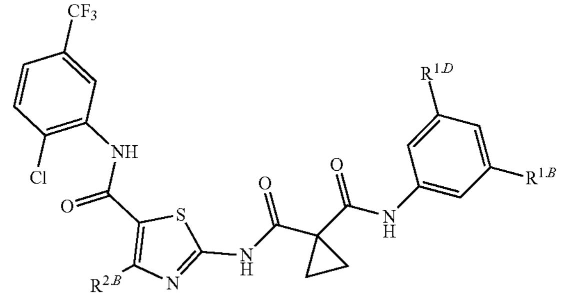

and $R^{1.B}$, $R^{1.D}$, and $R^{2.B}$ are as described herein, including in embodiments.

In embodiments, the compound has the formula:

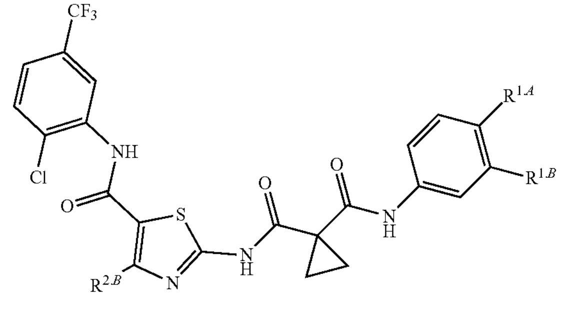

and $R^{1.A}$, $R^{1.B}$, and $R^{2.B}$ are as described herein, including in embodiments.

In embodiments, the compound has the formula:

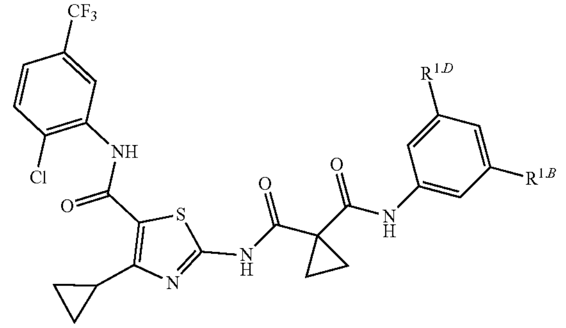

and $R^{1.B}$ and $R^{1.D}$ are as described herein, including in embodiments.

In embodiments, the compound has the formula:

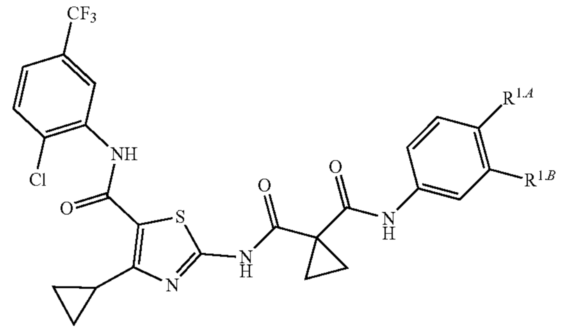

and $R^{1.A}$ and $R^{1.B}$ are as described herein, including in embodiments.

In embodiments, the compound has the formula:

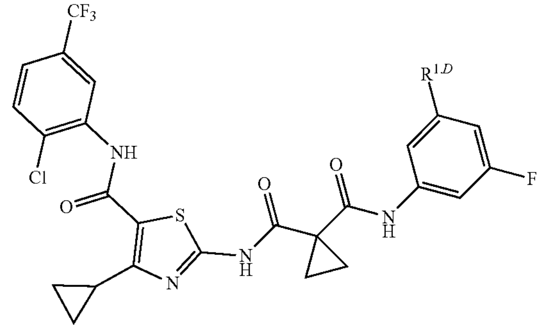

and $R^{1.D}$ is as described herein, including in embodiments.

In embodiments, the compound has the formula:

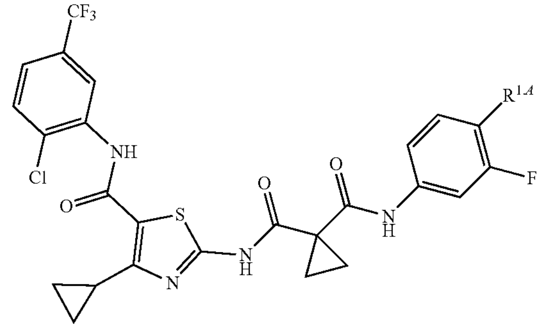

and $R^{1.A}$ is as described herein, including in embodiments.

In embodiments, $R^{1.A}$ is independently $-CCl_3$. In embodiments, $R^{1.A}$ is independently $-CF_3$. In embodiments, $R^{1.A}$ is independently $-CBr_3$. In embodiments, $R^{1.A}$ is independently $-CI_3$. In embodiments, $R^{1.A}$ is independently $-CHCl_2$. In embodiments, $R^{1.A}$ is independently $-CHBr_2$. In embodiments, $R^{1.A}$ is independently $-CHI_2$. In embodiments, $R^{1.A}$ is independently $-CHF_2$. In embodiments, $R^{1.A}$ is independently $-CH_2Cl$. In embodiments, $R^{1.A}$ is independently $-CH_2Br$. In embodiments, $R^{1.A}$ is independently $-CH_2I$. In embodiments, $R^{1.A}$ is independently $-CH_2F$. In embodiments, $R^{1.A}$ is independently $-CH_3$. In embodiments, $R^{1.A}$ is independently $-CH_2CH_3$. In embodiments, $R^{1.A}$ is independently $-CH(CH_3)_2$. In embodiments, $R^{1.A}$ is independently $-C(CH_3)_3$. In embodiments, $R^{1.A}$ is independently unsubstituted 2 to 4 membered heteroalkyl. In embodiments, $R^{1.A}$ is independently —F. In embodiments, $R^{1.A}$ is independently —Cl. In embodiments, $R^{1.A}$ is independently —Br. In embodiments, $R^{1.A}$ is independently —I. In embodiments, $R^{1.A}$ is independently halogen. In embodiments, $R^{1.A}$ is independently hydrogen. In embodiments, $R^{1.A}$ is independently halogen, $-CX^1_3$, $-CHX^1_2$, or $-CH_2X^1$. In embodiments, $R^{1.A}$ is independently halogen or $-CX^1_3$. In embodiments, $R^{1.A}$ is independently $-CX^1_3$. In embodiments, $R^{1.A}$ is independently $-CHX^1_2$. In embodiments, $R^{1.A}$ is independently $-CH_2X^1$. In embodiments, $R^{1.A}$ is independently substituted or unsubstituted alkyl. In embodiments, $R^{1.A}$ is independently substituted alkyl. In embodiments, $R^{1.A}$ is independently unsubstituted alkyl. In embodiments, $R^{1.A}$ is independently halo-substituted or unsubstituted alkyl. In embodiments, $R^{1.A}$ is independently halo-substituted alkyl. In embodiments, $R^{1.A}$ is independently substituted or unsubstituted $C_1$-$C_4$ alkyl. In embodiments, $R^{1.A}$ is independently substituted $C_1$-$C_4$ alkyl. In embodiments, $R^{1.A}$ is independently unsubstituted $C_1$-$C_4$ alkyl. In embodiments, $R^{1.A}$ is independently halo-substituted or unsubstituted $C_1$-$C_4$ alkyl. In embodiments, $R^{1.A}$ is independently halo-substituted $C_1$-$C_4$ alkyl. In embodiments, $R^{1.A}$ is independently substituted or unsubstituted $C_1$-$C_3$ alkyl. In embodiments, $R^{1.A}$ is independently substituted $C_1$-$C_3$ alkyl. In embodiments, $R^{1.A}$ is independently unsubstituted $C_1$-$C_3$ alkyl. In embodiments, $R^{1.A}$ is independently halo-substituted or unsubstituted $C_1$-$C_3$ alkyl. In embodiments, $R^{1.A}$ is independently halo-substituted $C_1$-$C_3$ alkyl. In embodiments, $R^{1.A}$ is independently hydrogen. In embodiments, $R^{1.A}$ is independently $-OCCl_3$. In embodiments, $R^{1.A}$ is independently $-OCF_3$. In embodiments, $R^{1.A}$ is independently $-OCBr_3$. In embodiments, $R^{1.A}$ is independently $-OCI_3$. In embodiments, $R^{1.A}$ is independently $-OCHCl_2$. In embodiments, $R^{1.A}$ is independently $-OCHBr_2$. In embodiments, $R^{1.A}$ is independently $-OCHI_2$. In embodiments, $R^{1.A}$ is independently $-OCHF_2$. In embodiments, $R^{1.A}$ is independently $-OCH_2Cl$. In embodiments, $R^{1.A}$ is independently $-OCH_2Br$. In embodiments, $R^{1.A}$ is independently $-OCH_2I$. In embodiments, $R^{1.A}$ is independently $-OCH_2F$. In embodiments, $R^{1.A}$ is independently $-OCH_3$. In embodiments, $R^{1.A}$ is independently $-OCH_2CH_3$. In embodiments, $R^{1.A}$ is independently $-OCH(CH_3)_2$. In embodiments, $R^{1.A}$ is independently $-OC(CH_3)_3$. In embodiments, $R^{1.A}$ is independently unsubstituted 2 to 4 membered heteroalkyl. In embodiments, $R^{1.A}$ is independently hydrogen. In embodiments, $R^{1.A}$ is independently halogen or $-OCX^1_3$. In embodiments, $R^{1.A}$ is independently $-OCX^1_3$. In embodiments, $R^{1.A}$ is independently $-OCHX^1_2$. In embodiments, $R^{1.A}$ is independently $-OCH_2X^1$.

In embodiments, $R^{1.A}$ is independently substituted pyrrolyl. In embodiments, $R^{1.A}$ is independently substituted pyrazolyl. In embodiments, $R^{1.A}$ is independently substituted imidazolyl. In embodiments, $R^{1.A}$ is independently substituted triazolyl. In embodiments, $R^{1.A}$ is independently substituted tetrazolyl. In embodiments, $R^{1.A}$ is independently substituted furanyl. In embodiments, $R^{1.A}$ is independently substituted thienyl. In embodiments, $R^{1.A}$ is independently substituted oxazolyl. In embodiments, $R^{1.A}$ is independently substituted isoxazolyl. In embodiments, $R^{1.A}$ is independently substituted thiazolyl. In embodiments, $R^{1.A}$ is independently substituted isothiazolyl. In embodiments, $R^{1.A}$ is independently substituted oxadiazolyl. In embodiments, $R^{1.A}$ is independently substituted thiadiazolyl. In embodiments, $R^{1.A}$ is independently substituted phenyl. In embodiments, $R^{1.A}$ is independently methyl-substituted pyrrolyl. In embodiments, $R^{1.A}$ is independently methyl-substituted pyrazolyl. In embodiments, $R^{1.A}$ is independently methyl-substituted imidazolyl. In embodiments, $R^{1.A}$ is independently methyl-substituted triazolyl. In embodiments, $R^{1.A}$ is independently methyl-substituted tetrazolyl. In embodiments, $R^{1.A}$ is independently methyl-substituted furanyl. In embodiments, $R^{1.A}$ is independently methyl-substituted thienyl. In embodiments, $R^{1.A}$ is independently methyl-substituted oxazolyl. In embodiments, $R^{1.A}$ is independently methyl-substituted isoxazolyl. In embodiments, $R^{1.A}$ is independently methyl-substituted thiazolyl. In embodiments, $R^{1.A}$ is independently methyl-substituted isothiazolyl. In embodiments, $R^{1.A}$ is independently methyl-substituted oxadiazolyl. In embodiments, $R^{1.A}$ is independently methyl-substituted thiadiazolyl. In embodiments, $R^{1.A}$ is independently methyl-substituted phenyl. In embodiments, $R^{1.A}$ is independently unsubstituted pyrrolyl. In embodiments, $R^{1.A}$ is independently unsubstituted pyrazolyl. In embodiments, $R^{1.A}$ is independently unsubstituted imidazolyl. In embodiments, $R^{1.A}$ is independently unsubstituted triazolyl. In embodiments, $R^{1.A}$ is independently unsubstituted tetrazolyl. In embodiments, $R^{1.A}$ is independently unsubstituted furanyl. In embodiments, $R^{1.A}$ is independently unsubstituted thienyl. In embodiments, $R^{1.A}$ is independently unsubstituted oxazolyl. In embodiments, $R^{1.A}$ is independently unsubstituted isoxazolyl. In embodiments, $R^{1.A}$ is independently unsubstituted thiazolyl. In embodiments, $R^{1.A}$ is independently unsubstituted isothiazolyl. In embodiments, $R^{1.A}$ is independently unsubstituted oxadiazolyl. In embodiments, $R^{1.A}$ is independently unsubstituted thiadiazolyl. In embodiments, $R^{1.A}$ is independently unsubstituted phenyl.

In embodiments, $R^{1.B}$ is independently $-CCl_3$. In embodiments, $R^{1.B}$ is independently $-CF_3$. In embodiments, $R^{1.B}$ is independently $-CBr_3$. In embodiments, $R^{1.B}$ is independently $-CI_3$. In embodiments, $R^{1.B}$ is independently $-CHCl_2$. In embodiments, $R^{1.B}$ is independently $-CHBr_2$. In embodiments, $R^{1.B}$ is independently $-CHI_2$. In embodiments, $R^{1.B}$ is independently $-CHF_2$. In embodiments, $R^{1.B}$ is independently $-CH_2Cl$. In embodiments, $R^{1.B}$ is independently $-CH_2Br$. In embodiments, $R^{1.B}$ is independently $-CH_2I$. In embodiments, $R^{1.B}$ is independently $-CH_2F$. In embodiments, $R^{1.B}$ is independently $-CH_3$. In embodiments, $R^{1.B}$ is independently $-CH_2CH_3$. In embodiments, $R^{1.B}$ is independently $-CH(CH_3)_2$. In embodiments, $R^{1.B}$ is independently $-C(CH_3)_3$. In embodiments, $R^{1.B}$ is independently unsubstituted 2 to 4 membered heteroalkyl. In embodiments, $R^{1.B}$ is independently —F. In embodiments, $R^{1.B}$ is independently —Cl. In embodiments, $R^{1.B}$ is independently —Br. In embodiments, $R^{1B}$ is independently —I. In embodiments, $R^{1.B}$ is independently halogen. In embodiments, $R^{1.B}$ is independently hydrogen. In embodiments, $R^{1.B}$ is independently halogen, $-CX^1_3$, $-CHX^1_2$, or $-CH_2X^1$. In embodiments, $R^{1.B}$ is independently halogen or $-CX^1_3$. In embodiments, $R^{1.B}$ is independently $-CX^1_3$. In embodiments, $R^{1.B}$ is independently $-CHX^1_2$. In embodiments, $R^{1.B}$ is independently $-CH_2X^1$. In embodiments, $R^{1.B}$ is independently substituted or unsubstituted alkyl. In embodiments, $R^{1.B}$ is independently substituted alkyl. In embodiments, $R^{1.B}$ is independently unsubstituted alkyl. In embodiments, $R^{1.B}$ is independently halo-substituted or unsubstituted alkyl. In embodiments, $R^{1.B}$ is independently halo-substituted alkyl. In embodiments, $R^{1.B}$ is independently substituted or unsubstituted $C_1$-$C_4$ alkyl. In embodiments, $R^{1.B}$ is independently substituted $C_1$-$C_4$ alkyl. In embodiments, $R^{1.B}$ is independently unsubstituted $C_1$-$C_4$ alkyl. In embodiments, $R^{1.B}$ is independently halo-substituted or unsubstituted $C_1$-$C_4$ alkyl. In embodiments, $R^{1.B}$ is independently halo-substituted $C_1$-$C_4$ alkyl. In embodiments, $R^{1.B}$ is independently substituted or unsubstituted $C_1$-$C_3$ alkyl. In embodiments, $R^{1.B}$ is independently substituted $C_1$-$C_3$ alkyl. In embodiments, $R^{1.B}$ is independently unsubstituted $C_1$-$C_3$ alkyl. In embodiments, $R^{1.B}$ is independently halo-substituted or unsubstituted $C_1$-$C_3$ alkyl. In embodiments, $R^{1.B}$ is independently halo-substituted $C_1$-$C_3$ alkyl. In embodiments, $R^{1.B}$ is independently hydrogen. In embodiments, $R^{1.B}$ is independently $-OCCl_3$. In embodiments, $R^{1.B}$ is independently $-OCF_3$. In embodiments, $R^{1.B}$ is independently $-OCBr_3$. In embodiments, $R^{1.B}$ is independently $-OCI_3$. In embodiments, $R^{1.B}$ is independently $-OCHCl_2$. In embodiments, $R^{1.B}$ is independently $-OCHBr_2$. In embodiments, $R^{1.B}$ is independently $-OCHI_2$. In embodiments, $R^{1.B}$ is independently $-OCHF_2$. In embodiments, $R^{1.B}$ is independently $-OCH_2Cl$. In embodiments, $R^{1.B}$ is independently $-OCH_2Br$. In embodiments, $R^{1.B}$ is independently $-OCH_2I$. In embodiments, $R^{1.B}$ is independently $-OCH_2F$. In embodiments, $R^{1.B}$ is independently $-OCH_3$. In embodiments, $R^{1.B}$ is independently $-OCH_2CH_3$. In embodiments, $R^{1.B}$ is independently $-OCH(CH_3)_2$. In embodiments, $R^{1.B}$ is independently $-OC(CH_3)_3$. In embodiments, $R^{1.B}$ is independently unsubstituted 2 to 4 membered heteroalkyl. In embodiments, $R^{1.B}$ is independently hydrogen. In embodiments, $R^{1.B}$ is independently halogen or $-OCX^1_3$. In embodiments, $R^{1.B}$ is independently $-OCX^1_3$. In embodiments, $R^{1.B}$ is independently $-OCHX^1_2$. In embodiments, $R^{1.B}$ is independently $-OCH_2X^1$.

In embodiments, $R^{1.B}$ is independently substituted pyrrolyl. In embodiments, $R^{1.B}$ is independently substituted pyrazolyl. In embodiments, $R^{1.B}$ is independently substituted imidazolyl. In embodiments, $R^{1.B}$ is independently substituted triazolyl. In embodiments, $R^{1.B}$ is independently substituted tetrazolyl. In embodiments, $R^{1.B}$ is independently substituted furanyl. In embodiments, $R^{1.B}$ is independently substituted thienyl. In embodiments, $R^{1.B}$ is independently substituted oxazolyl. In embodiments, $R^{1.B}$ is independently substituted isoxazolyl. In embodiments, $R^{1.B}$ is independently substituted thiazolyl. In embodiments, $R^{1.B}$ is independently substituted isothiazolyl. In embodiments, $R^{1.B}$ is independently substituted oxadiazolyl. In embodiments, $R^{1.B}$ is independently substituted thiadiazolyl. In embodiments, $R^{1.B}$ is independently substituted phenyl. In embodiments, $R^{1.B}$ is independently methyl-substituted pyrrolyl. In embodiments, $R^{1.B}$ is independently methyl-substituted pyrazolyl. In embodiments, $R^{1.B}$ is independently methyl-substituted imidazolyl. In embodiments, $R^{1.B}$ is independently methyl-substituted triazolyl. In embodiments, $R^{1.B}$ is independently methyl-substituted tetrazolyl. In embodiments, $R^{1.B}$ is independently methyl-substituted furanyl. In embodiments, $R^{1.B}$ is independently methyl-substituted thienyl. In embodiments, $R^{1.B}$ is independently methyl-substituted oxazolyl. In embodiments, $R^{1.B}$ is independently methyl-substituted isoxazolyl. In embodiments, $R^{1.B}$ is independently methyl-substituted thiazolyl. In embodiments, $R^{1.B}$ is independently methyl-substituted isothiazolyl. In embodiments, $R^{1.B}$ is independently methyl-substituted oxadiazolyl. In embodiments, $R^{1.B}$ is independently methyl-substituted thiadiazolyl. In embodiments, $R^{1.B}$ is independently methyl-substituted phenyl. In embodiments, $R^{1.B}$ is independently unsubstituted pyrrolyl. In embodiments, $R^{1.B}$ is independently unsubstituted pyrazolyl. In embodiments, $R^{1.B}$ is independently unsubstituted imidazolyl. In embodiments, $R^{1.B}$ is independently unsubstituted triazolyl. In embodiments, $R^{1.B}$ is independently unsubstituted tetrazolyl. In embodiments, $R^{1.B}$ is independently unsubstituted furanyl. In embodiments, $R^{1.B}$ is independently unsubstituted thienyl. In embodiments, $R^{1.B}$ is independently unsubstituted oxazolyl. In embodiments, $R^{1.B}$ is independently unsubstituted isoxazolyl. In embodiments, $R^{1.B}$ is independently unsubstituted thiazolyl. In embodiments, $R^{1.B}$ is independently unsubstituted isothiazolyl. In embodiments, $R^{1.B}$ is independently unsubstituted oxadiazolyl. In embodiments, $R^{1.B}$ is independently unsubstituted thiadiazolyl. In embodiments, $R^{1.B}$ is independently unsubstituted phenyl.

In embodiments, $R^{1.C}$ is independently $-CCl_3$. In embodiments, $R^{1.C}$ is independently $-CF_3$. In embodiments, $R^{1.C}$ is independently $-CBr_3$. In embodiments, $R^{1.C}$ is independently $-CI_3$. In embodiments, $R^{1.C}$ is independently $-CHCl_2$. In embodiments, $R^{1.C}$ is independently $-CHBr_2$. In embodiments, $R^{1.C}$ is independently $-CHI_2$. In embodiments, $R^{1.C}$ is independently $-CHF_2$. In embodiments, $R^{1.C}$ is independently $-CH_2Cl$. In embodiments, $R^{1.C}$ is independently $-CH_2Br$. In embodiments, $R^{1.C}$ is independently $-CH_2I$. In embodiments, $R^{1.C}$ is independently $-CH_2F$. In embodiments, $R^{1.C}$ is independently $-CH_3$. In embodiments, $R^{1.C}$ is independently $-CH_2CH_3$. In embodiments, $R^{1.C}$ is independently $-CH(CH_3)_2$. In embodiments, $R^{1.C}$ is independently $-C(CH_3)_3$. In embodiments, $R^{1.C}$ is independently unsubstituted 2 to 4 membered heteroalkyl. In embodiments, $R^{1.C}$ is independently $-F$. In embodiments, $R^{1.C}$ is independently $-Cl$. In embodiments, $R^{1.C}$ is independently $-Br$. In embodiments, $R^{1.C}$ is independently $-I$. In embodiments, $R^{1.C}$ is independently halogen. In embodiments, $R^{1.C}$ is independently hydrogen. In embodiments, $R^{1.C}$ is independently halogen, $-CX^1_3$, $-CHX^1_2$, or $-CH_2X^1$. In embodiments, $R^{1.C}$ is independently halogen or $-CX^1_3$. In embodiments, $R^{1.C}$ is independently $-CX^1_3$. In embodiments, $R^{1.C}$ is independently $-CHX^1_2$. In embodiments, $R^{1.C}$ is independently $-CH_2X^1$. In embodiments, $R^{1.C}$ is independently substituted or unsubstituted alkyl. In embodiments, $R^{1.C}$ is independently substituted alkyl. In embodiments, $R^{1.C}$ is independently unsubstituted alkyl. In embodiments, $R^{1.C}$ is independently halo-substituted or unsubstituted alkyl. In embodiments, $R^{1.C}$ is independently halo-substituted alkyl. In embodiments, $R^{1.C}$ is independently substituted or unsubstituted $C_1$-$C_4$ alkyl. In embodiments, $R^{1.C}$ is independently substituted $C_1$-$C_4$ alkyl. In embodiments, $R^{1.C}$ is independently unsubstituted $C_1$-$C_4$ alkyl. In embodiments, $R^{1.C}$ is independently halo-substituted or unsubstituted $C_1$-$C_4$ alkyl. In embodiments, $R^{1.C}$ is independently halo-substituted $C_1$-$C_4$ alkyl. In embodiments, $R^{1.C}$ is independently substituted or unsubstituted $C_1$-$C_3$ alkyl. In embodiments, $R^{1.C}$ is independently substituted $C_1$-$C_3$ alkyl. In embodiments, $R^{1.C}$ is independently unsubstituted $C_1$-$C_3$ alkyl. In embodiments, $R^{1.C}$ is independently halo-substituted or unsubstituted $C_1$-$C_3$ alkyl. In embodiments, $R^{1.C}$ is independently halo-substituted $C_1$-$C_3$ alkyl. In embodiments, $R^{1.C}$ is independently hydrogen. In embodiments, $R^{1.C}$ is independently $-OCCl_3$. In embodiments, $R^{1.C}$ is independently $-OCF_3$. In embodiments, $R^{1.C}$ is independently $-OCBr_3$. In embodiments, $R^{1.C}$ is independently $-OCI_3$. In embodiments, $R^{1.C}$ is independently $-OCHCl_2$. In embodiments, $R^{1.C}$ is independently $-OCHBr_2$. In embodiments, $R^{1.C}$ is independently $-OCHI_2$. In embodiments, $R^{1.C}$ is independently $-OCHF_2$. In embodiments, $R^{1.C}$ is independently $-OCH_2Cl$. In embodiments, $R^{1.C}$ is independently $-OCH_2Br$. In embodiments, $R^{1.C}$ is independently —$OCH_2I$. In embodiments, $R^{1.C}$ is independently —$OCH_2F$. In embodiments, $R^{1.C}$ is independently —$OCH_3$. In embodiments, $R^{1.C}$ is independently —$OCH_2CH_3$. In embodiments, $R^{1.C}$ is independently —$OCH(CH_3)_2$. In embodiments, $R^{1.C}$ is independently —$OC(CH_3)_3$. In embodiments, $R^{1.C}$ is independently unsubstituted 2 to 4 membered heteroalkyl. In embodiments, $R^{1.C}$ is independently hydrogen. In embodiments, $R^{1.C}$ is independently halogen or —$OCX^1_3$. In embodiments, $R^{1.C}$ is independently —$OCX^1_3$. In embodiments, $R^{1.C}$ is independently —$OCHX^1_2$. In embodiments, $R^{1.C}$ is independently —$OCH_2X^1$.

In embodiments, $R^{1.C}$ is independently substituted pyrrolyl. In embodiments, $R^{1.C}$ is independently substituted pyrazolyl. In embodiments, $R^{1.C}$ is independently substituted imidazolyl. In embodiments, $R^{1.C}$ is independently substituted triazolyl. In embodiments, $R^{1.C}$ is independently substituted tetrazolyl. In embodiments, $R^{1.C}$ is independently substituted furanyl. In embodiments, $R^{1.C}$ is independently substituted thienyl. In embodiments, $R^{1.C}$ is independently substituted oxazolyl. In embodiments, $R^{1.C}$ is independently substituted isoxazolyl. In embodiments, $R^{1.C}$ is independently substituted thiazolyl. In embodiments, $R^{1.C}$ is independently substituted isothiazolyl. In embodiments, $R^{1.C}$ is independently substituted oxadiazolyl. In embodiments, $R^{1.C}$ is independently substituted thiadiazolyl. In embodiments, $R^{1.C}$ is independently substituted phenyl. In embodiments, $R^{1.C}$ is independently methyl-substituted pyrrolyl. In embodiments, $R^{1.C}$ is independently methyl-substituted pyrazolyl. In embodiments, $R^{1.C}$ is independently methyl-substituted imidazolyl. In embodiments, $R^{1.C}$ is independently methyl-substituted triazolyl. In embodiments, $R^{1.C}$ is independently methyl-substituted tetrazolyl. In embodiments, $R^{1.C}$ is independently methyl-substituted furanyl. In embodiments, $R^{1.C}$ is independently methyl-substituted thienyl. In embodiments, $R^{1.C}$ is independently methyl-substituted oxazolyl. In embodiments, $R^{1.C}$ is independently methyl-substituted isoxazolyl. In embodiments, $R^{1.C}$ is independently methyl-substituted thiazolyl. In embodiments, $R^{1.C}$ is independently methyl-substituted isothiazolyl. In embodiments, $R^{1.C}$ is independently methyl-substituted oxadiazolyl. In embodiments, $R^{1.C}$ is independently methyl-substituted thiadiazolyl. In embodiments, $R^{1.C}$ is independently methyl-substituted phenyl. In embodiments, $R^{1.C}$ is independently unsubstituted pyrrolyl. In embodiments, $R^{1.C}$ is independently unsubstituted pyrazolyl. In embodiments, $R^{1.C}$ is independently unsubstituted imidazolyl. In embodiments, $R^{1.C}$ is independently unsubstituted triazolyl. In embodiments, $R^{1.C}$ is independently unsubstituted tetrazolyl. In embodiments, $R^{1.C}$ is independently unsubstituted furanyl. In embodiments, $R^{1.C}$ is independently unsubstituted thienyl. In embodiments, $R^{1.C}$ is independently unsubstituted oxazolyl. In embodiments, $R^{1.C}$ is independently unsubstituted isoxazolyl. In embodiments, $R^{1.C}$ is independently unsubstituted thiazolyl. In embodiments, $R^{1.C}$ is independently unsubstituted isothiazolyl. In embodiments, $R^{1.C}$ is independently unsubstituted oxadiazolyl. In embodiments, $R^{1.C}$ is independently unsubstituted thiadiazolyl. In embodiments, $R^{1.C}$ is independently unsubstituted phenyl.

In embodiments, $R^{1.D}$ is independently —$CCl_3$. In embodiments, $R^{1.D}$ is independently —$CF_3$. In embodiments, $R^{1.D}$ is independently —$CBr_3$. In embodiments, $R^{1.D}$ is independently —$CI_3$. In embodiments, $R^{1.D}$ is independently —$CHCl_2$. In embodiments, $R^{1.D}$ is independently —$CHBr_2$. In embodiments, $R^{1.D}$ is independently —$CHI_2$. In embodiments, $R^{1.D}$ is independently —$CHF_2$. In embodiments, $R^{1.D}$ is independently —$CH_2Cl$. In embodiments, $R^{1.D}$ is independently —$CH_2Br$. In embodiments, $R^{1.D}$ is independently —$CH_2I$. In embodiments, $R^{1.D}$ is independently —$CH_2F$. In embodiments, $R^{1.D}$ is independently —$CH_3$. In embodiments, $R^{1.D}$ is independently —$CH_2CH_3$. In embodiments, $R^{1.D}$ is independently —$CH(CH_3)_2$. In embodiments, $R^{1.D}$ is independently —$C(CH_3)_3$. In embodiments, $R^{1.D}$ is independently unsubstituted 2 to 4 membered heteroalkyl. In embodiments, $R^{1.D}$ is independently —F. In embodiments, $R^{1.D}$ is independently —Cl. In embodiments, $R^{1.D}$ is independently —Br. In embodiments, $R^{1.D}$ is independently —I. In embodiments, $R^{1.D}$ is independently halogen. In embodiments, $R^{1.D}$ is independently hydrogen. In embodiments, $R^{1.D}$ is independently halogen, —$CX^1_3$, —$CHX^1_2$, or —$CH_2X^1$. In embodiments, $R^{1.D}$ is independently halogen or —$CX^1_3$. In embodiments, $R^{1.D}$ is independently —$CX^1_3$. In embodiments, $R^{1.D}$ is independently —$CHX^1_2$. In embodiments, $R^{1.D}$ is independently —$CH_2X^1$. In embodiments, $R^{1.D}$ is independently substituted or unsubstituted alkyl. In embodiments, $R^{1.D}$ is independently substituted alkyl. In embodiments, $R^{1.D}$ is independently unsubstituted alkyl. In embodiments, $R^{1.D}$ is independently halo-substituted or unsubstituted alkyl. In embodiments, $R^{1.D}$ is independently halo-substituted alkyl. In embodiments, $R^{1.D}$ is independently substituted or unsubstituted $C_1$-$C_4$ alkyl. In embodiments, $R^{1.D}$ is independently substituted $C_1$-$C_4$ alkyl. In embodiments, $R^{1.D}$ is independently unsubstituted $C_1$-$C_4$ alkyl. In embodiments, $R^{1.D}$ is independently halo-substituted or unsubstituted $C_1$-$C_4$ alkyl. In embodiments, $R^{1.D}$ is independently halo-substituted $C_1$-$C_4$ alkyl. In embodiments, $R^{1.D}$ is independently substituted or unsubstituted $C_1$-$C_3$ alkyl. In embodiments, $R^{1.D}$ is independently substituted $C_1$-$C_3$ alkyl. In embodiments, $R^{1.D}$ is independently unsubstituted $C_1$-$C_3$ alkyl. In embodiments, $R^{1.D}$ is independently halo-substituted or unsubstituted $C_1$-$C_3$ alkyl. In embodiments, $R^{1.D}$ is independently halo-substituted $C_1$-$C_3$ alkyl. In embodiments, $R^{1.D}$ is independently hydrogen. In embodiments, $R^{1.D}$ is independently —$OCCl_3$. In embodiments, $R^{1.D}$ is independently —$OCF_3$. In embodiments, $R^{1.D}$ is independently —$OCBr_3$. In embodiments, $R^{1.D}$ is independently —$OCI_3$. In embodiments, $R^{1.D}$ is independently —$OCHCl_2$. In embodiments, $R^{1.D}$ is independently —$OCHBr_2$. In embodiments, $R^{1.D}$ is independently —$OCHI_2$. In embodiments, $R^{1.D}$ is independently —$OCHF_2$. In embodiments, $R^{1.D}$ is independently —$OCH_2Cl$. In embodiments, $R^{1.D}$ is independently —$OCH_2Br$. In embodiments, $R^{1.D}$ is independently —$OCH_2I$. In embodiments, $R^{1.D}$ is independently —$OCH_2F$. In embodiments, $R^{1.D}$ is independently —$OCH_3$. In embodiments, $R^{1.D}$ is independently —$OCH_2CH_3$. In embodiments, $R^{1.D}$ is independently —$OCH(CH_3)_2$. In embodiments, $R^{1.D}$ is independently —$OC(CH_3)_3$. In embodiments, $R^{1.D}$ is independently unsubstituted 2 to 4 membered heteroalkyl. In embodiments, $R^{1.D}$ is independently hydrogen. In embodiments, $R^{1.D}$ is independently halogen or —$OCX^1_3$. In embodiments, $R^{1.D}$ is independently —$OCX^1_3$. In embodiments, $R^{1.D}$ is independently —$OCHX^1_2$. In embodiments, $R^{1.D}$ is independently —$OCH_2X^1$.

In embodiments, $R^{1.D}$ is independently substituted pyrrolyl. In embodiments, $R^{1.D}$ is independently substituted pyrazolyl. In embodiments, $R^{1.D}$ is independently substituted imidazolyl. In embodiments, $R^{1.D}$ is independently substituted triazolyl. In embodiments, $R^{1.D}$ is independently substituted tetrazolyl. In embodiments, $R^{1.D}$ is independently substituted furanyl. In embodiments, $R^{1.D}$ is independently substituted thienyl. In embodiments, $R^{1.D}$ is independently substituted oxazolyl. In embodiments, $R^{1.D}$ is independently substituted isoxazolyl. In embodiments, $R^{1.D}$ is independently substituted thiazolyl. In embodiments, $R^{1.D}$ is independently substituted isothiazolyl. In embodiments, $R^{1.D}$ is independently substituted oxadiazolyl. In embodiments, $R^{1.D}$ is independently substituted thiadiazolyl. In embodiments, $R^{1.D}$ is independently substituted phenyl. In embodiments, $R^{1.D}$ is independently methyl-substituted pyrrolyl. In embodiments, $R^{1.D}$ is independently methyl-substituted pyrazolyl. In embodiments, $R^{1.D}$ is independently methyl-substituted imidazolyl. In embodiments, $R^{1.D}$ is independently methyl-substituted triazolyl. In embodiments, $R^{1.D}$ is independently methyl-substituted tetrazolyl. In embodiments, $R^{1.D}$ is independently methyl-substituted furanyl. In embodiments, $R^{1.D}$ is independently methyl-substituted thienyl. In embodiments, $R^{1.D}$ is independently methyl-substituted oxazolyl. In embodiments, $R^{1.D}$ is independently methyl-substituted isoxazolyl. In embodiments, $R^{1.D}$ is independently methyl-substituted thiazolyl. In embodiments, $R^{1.D}$ is independently methyl-substituted isothiazolyl. In embodiments, $R^{1.D}$ is independently methyl-substituted oxadiazolyl. In embodiments, $R^{1.D}$ is independently methyl-substituted thiadiazolyl. In embodiments, $R^{1.D}$ is independently methyl-substituted phenyl. In embodiments, $R^{1.D}$ is independently unsubstituted pyrrolyl. In embodiments, $R^{1.D}$ is independently unsubstituted pyrazolyl. In embodiments, $R^{1.D}$ is independently unsubstituted imidazolyl. In embodiments, $R^{1.D}$ is independently unsubstituted triazolyl. In embodiments, $R^{1.D}$ is independently unsubstituted tetrazolyl. In embodiments, $R^{1.D}$ is independently unsubstituted furanyl. In embodiments, $R^{1.D}$ is independently unsubstituted thienyl. In embodiments, $R^{1.D}$ is independently unsubstituted oxazolyl. In embodiments, $R^{1.D}$ is independently unsubstituted isoxazolyl. In embodiments, $R^{1.D}$ is independently unsubstituted thiazolyl. In embodiments, $R^{1.D}$ is independently unsubstituted isothiazolyl. In embodiments, $R^{1.D}$ is independently unsubstituted oxadiazolyl. In embodiments, $R^{1.D}$ is independently unsubstituted thiadiazolyl. In embodiments, $R^{1.D}$ is independently unsubstituted phenyl.

In embodiments, $R^{1.B}$ is independently —$CF_3$ and $R^{1.D}$ is independently —F. In embodiments, $R^{1.B}$ is independently —F and $R^{1.D}$ is independently —F. In embodiments, $R^{1B}$ is independently —Cl and $R^{1.D}$ is independently —F. In embodiments, $R^{1.D}$ is independently —$CF_3$ and $R^{1.B}$ is independently —F. In embodiments, $R^{1.D}$ is independently —F and $R^{1B}$ is independently —F. In embodiments, $R^{1.D}$ is independently —Cl and $R^{1B}$ is independently —F. In embodiments, $R^{1.B}$ is independently —$CF_3$ and $R^{1.A}$ is independently —F. In embodiments, $R^{1.B}$ is independently —F and $R^{1.A}$ is independently —F. In embodiments, $R^{1.B}$ is independently —Cl and $R^{1.A}$ is independently —F. In embodiments, $R^{1.A}$ is independently —$CF_3$ and $R^{1.B}$ is independently —F. In embodiments, $R^{1.A}$ is independently —F and $R^{1.B}$ is independently —F. In embodiments, $R^{1.A}$ is independently —Cl and $R^{1.B}$ is independently —F. In embodiments, $R^{1.D}$ is independently —$CF_3$ and $R^{1.A}$ is independently —F. In embodiments, $R^{1.D}$ is independently —F and $R^{1.A}$ is independently —F. In embodiments, $R^{1.D}$ is independently —Cl and $R^{1.A}$ is independently —F. In embodiments, $R^{1.A}$ is independently —$CF_3$ and $R^{1.D}$ is independently —F. In embodiments, $R^{1.A}$ is independently —F and $R^{1.D}$ is independently —F. In embodiments, $R^{1.A}$ is independently —Cl and $R^{1.D}$ is independently —F.

In embodiments, $R^{2.B}$ is independently —$CCl_3$. In embodiments, $R^{2.B}$ is independently —$CF_3$. In embodiments, $R^{2.B}$ is independently —$CBr_3$. In embodiments, $R^{2.B}$ is independently —$CI_3$. In embodiments, $R^{2.B}$ is independently —$CHCl_2$. In embodiments, $R^{2.B}$ is independently —$CHBr_2$. In embodiments, $R^{2.B}$ is independently —$CHI_2$. In embodiments, $R^{2.B}$ is independently —$CHF_2$. In embodiments, $R^{2.B}$ is independently —$CH_2Cl$. In embodiments, $R^{2.B}$ is independently —$CH_2Br$. In embodiments, $R^{2.B}$ is independently —$CH_2I$. In embodiments, $R^{2.B}$ is independently —$CH_2F$. In embodiments, $R^{2.B}$ is independently —$CH_3$. In embodiments, $R^{2.B}$ is independently —$CH_2CH_3$. In embodiments, $R^{2.B}$ is independently —$CH(CH_3)_2$. In embodiments, $R^{2.B}$ is independently —$C(CH_3)_3$. In embodiments, $R^{2.B}$ is independently unsubstituted 2 to 4 membered heteroalkyl. In embodiments, $R^{2.B}$ is independently —F. In embodiments, $R^{2.B}$ is independently —Cl. In embodiments, $R^{2.B}$ is independently —Br. In embodiments, $R^{2.B}$ is independently —I. In embodiments, $R^{2.B}$ is independently halogen. In embodiments, $R^{2.B}$ is independently hydrogen. In embodiments, $R^{2.B}$ is independently halogen, —$CX^2_3$, —$CHX^2_2$, or —$CH_2X^2$. In embodiments, $R^{2.B}$ is independently halogen or —$CX^2_3$. In embodiments, $R^{2.B}$ is independently —$CX^2_3$. In embodiments, $R^{2.B}$ is independently —$CHX^{22}$ In embodiments, $R^{2.B}$ is independently —$CH_2X^2$. In embodiments, $R^{2.B}$ is independently substituted or unsubstituted alkyl. In embodiments, $R^{2.B}$ is independently substituted alkyl. In embodiments, $R^{2.B}$ is independently unsubstituted alkyl. In embodiments, $R^{2.B}$ is independently halo-substituted or unsubstituted alkyl. In embodiments, $R^{2.B}$ is independently halo-substituted alkyl. In embodiments, $R^{2.B}$ is independently substituted or unsubstituted $C_1$-$C_4$ alkyl. In embodiments, $R^{2.B}$ is independently substituted $C_1$-$C_4$ alkyl. In embodiments, $R^{2.B}$ is independently unsubstituted $C_1$-$C_4$ alkyl. In embodiments, $R^{2.B}$ is independently halo-substituted or unsubstituted $C_1$-$C_4$ alkyl. In embodiments, $R^{2.B}$ is independently halo-substituted $C_1$-$C_4$ alkyl. In embodiments, $R^{2.B}$ is independently substituted or unsubstituted $C_1$-$C_3$ alkyl. In embodiments, $R^{2.B}$ is independently substituted $C_1$-$C_3$ alkyl. In embodiments, $R^{2.B}$ is independently unsubstituted $C_1$-$C_3$ alkyl. In embodiments, $R^{2.B}$ is independently halo-substituted or unsubstituted $C_1$-$C_3$ alkyl. In embodiments, $R^{2.B}$ is independently halo-substituted $C_1$-$C_3$ alkyl. In embodiments, $R^{2.B}$ is independently substituted or unsubstituted cycloalkyl. In embodiments, $R^{2.B}$ is independently substituted cycloalkyl. In embodiments, $R^{2.B}$ is independently unsubstituted cycloalkyl. In embodiments, $R^{2.B}$ is independently halo-substituted or unsubstituted cycloalkyl. In embodiments, $R^{2.B}$ is independently halo-substituted cycloalkyl. In embodiments, $R^{2.B}$ is independently substituted or unsubstituted $C_3$-$C_6$ cycloalkyl. In embodiments, $R^{2.B}$ is independently substituted $C_3$-$C_6$ cycloalkyl. In embodiments, $R^{2.B}$ is independently unsubstituted $C_3$-$C_6$ cycloalkyl. In embodiments, $R^{2.B}$ is independently halo-substituted or unsubstituted $C_3$-$C_6$ cycloalkyl. In embodiments, $R^{2.B}$ is independently halo-substituted $C_3$-$C_6$ cycloalkyl. In embodiments, $R^{2.B}$ is independently substituted or unsubstituted $C_3$-$C_4$ cycloalkyl. In embodiments, $R^{2.B}$ is independently substituted $C_3$-$C_4$ cycloalkyl. In embodiments, $R^{2.B}$ is independently unsubstituted $C_3$-$C_4$ cycloalkyl. In embodiments, $R^{2.B}$ is independently halo-substituted or unsubstituted $C_3$-$C_4$ cycloalkyl. In embodiments, $R^{2.B}$ is independently halo-substituted $C_3$-$C_4$ cycloalkyl. In embodiments, $R^{2.B}$ is independently substituted or unsubstituted cyclopropyl. In embodiments, $R^{2.B}$ is independently substituted cyclopropyl. In embodiments, $R^{2.B}$ is independently unsubstituted cyclopropyl. In embodiments, $R^{2.B}$ is independently halo-substituted or unsubstituted cyclopropyl. In embodiments, $R^{2.B}$ is independently halo-substituted cyclopropyl. In embodiments, $R^{2.B}$ is independently hydrogen. In embodiments, $R^{2.B}$ is independently -(unsubstituted $C_1$-$C_4$ alkyl)O (unsubstituted $C_1$-$C_4$ alkyl). In embodiments, $R^{2.B}$ is independently -(unsubstituted $C_1$-$C_2$ alkyl)O (unsubstituted $C_1$-$C_2$ alkyl). In embodiments, $R^{2.B}$ is independently —$CH_2OCH_3$. In embodiments, $R^{2.B}$ is independently unsubstituted phenyl. In embodiments, $R^{2.B}$ is independently unsubstituted 5 to 6 membered heteroaryl.

In embodiments, $R^{3.A}$ is independently —$CCl_3$. In embodiments, $R^{3.A}$ is independently —$CF_3$. In embodiments, $R^{3.A}$ is independently —$CBr_3$. In embodiments, $R^{3.A}$ is independently —$CI_3$. In embodiments, $R^{3.A}$ is independently —$CHCl_2$. In embodiments, $R^{3.A}$ is independently —$CHBr_2$. In embodiments, $R^{3.A}$ is independently —$CHI_2$. In embodiments, $R^{3.A}$ is independently —$CHF_2$. In embodiments, $R^{3.A}$ is independently —$CH_2Cl$. In embodiments, $R^{3.A}$ is independently —$CH_2Br$. In embodiments, $R^{3.A}$ is independently —$CH_2I$. In embodiments, $R^{3.A}$ is independently —$CH_2F$. In embodiments, $R^{3.A}$ is independently —$CH_3$. In embodiments, $R^{3.A}$ is independently —$CH_2CH_3$. In embodiments, $R^{3.A}$ is independently —$CH(CH_3)_2$. In embodiments, $R^{3.A}$ is independently —$C(CH_3)_3$. In embodiments, $R^{3.A}$ is independently unsubstituted 2 to 4 membered heteroalkyl. In embodiments, $R^{3.A}$ is independently —F. In embodiments, $R^{3.A}$ is independently —Cl. In embodiments, $R^{3.A}$ is independently —Br. In embodiments, $R^{3.A}$ is independently —I. In embodiments, $R^{3.A}$ is independently halogen. In embodiments, $R^{3.A}$ is independently hydrogen. In embodiments, $R^{3.A}$ is independently halogen, —$CX^3_3$, —$CHX^3_2$, or —$CH_2X^3$. In embodiments, $R^{3.A}$ is independently halogen or $CX^3_3$. In embodiments, $R^{3.A}$ is independently —$CX^3_3$. In embodiments, $R^{3.A}$ is independently —$CHX^3_2$. In embodiments, $R^{3.A}$ is independently —$CH_2X^3$. In embodiments, $R^{3.A}$ is independently substituted or unsubstituted alkyl. In embodiments, $R^{3.A}$ is independently substituted alkyl. In embodiments, $R^{3.A}$ is independently unsubstituted alkyl. In embodiments, $R^{3.A}$ is independently halo-substituted or unsubstituted alkyl. In embodiments, $R^{3.A}$ is independently halo-substituted alkyl. In embodiments, $R^{3.A}$ is independently substituted or unsubstituted $C_1$-$C_4$ alkyl. In embodiments, $R^{3.A}$ is independently substituted $C_1$-$C_4$ alkyl. In embodiments, $R^{3.A}$ is independently unsubstituted $C_1$-$C_4$ alkyl. In embodiments, $R^{3.A}$ is independently halo-substituted or unsubstituted $C_1$-$C_4$ alkyl. In embodiments, $R^{3.A}$ is independently halo-substituted $C_1$-$C_4$ alkyl. In embodiments, $R^{3.A}$ is independently substituted or unsubstituted $C_1$-$C_3$ alkyl. In embodiments, $R^{3.A}$ is independently substituted $C_1$-$C_3$ alkyl. In embodiments, $R^{3.A}$ is independently unsubstituted $C_1$-$C_3$ alkyl. In embodiments, $R^{3.A}$ is independently halo-substituted or unsubstituted $C_1$-$C_3$ alkyl. In embodiments, $R^{3.A}$ is independently halo-substituted $C_1$-$C_3$ alkyl. In embodiments, $R^{3.A}$ is independently hydrogen.

In embodiments, $R^{3.B}$ is independently —$CCl_3$. In embodiments, $R^{3.B}$ is independently —$CF_3$. In embodiments, $R^{3.B}$ is independently —$CBr_3$. In embodiments, $R^{3.B}$ is independently —$CI_3$. In embodiments, $R^{3.B}$ is independently —$CHCl_2$. In embodiments, $R^{3.B}$ is independently —$CHBr_2$. In embodiments, $R^{3.B}$ is independently —$CHI_2$. In embodiments, $R^{3.B}$ is independently —$CHF_2$. In embodiments, $R^{3.B}$ is independently —$CH_2Cl$. In embodiments, $R^{3.B}$ is independently —$CH_2Br$. In embodiments, $R^{3.B}$ is independently —$CH_2I$. In embodiments, $R^{3.B}$ is independently —$CH_2F$. In embodiments, $R^{3.B}$ is independently —$CH_3$. In embodiments, $R^{3.B}$ is independently —$CH_2CH_3$. In embodiments, $R^{3.B}$ is independently —$CH(CH_3)_2$. In embodiments, $R^{3.B}$ is independently —$C(CH_3)_3$. In embodiments, $R^{3.B}$ is independently unsubstituted 2 to 4 membered heteroalkyl. In embodiments, $R^{3.B}$ is independently —F. In embodiments, $R^{3.B}$ is independently —Cl. In embodiments, $R^{3.B}$ is independently —Br. In embodiments, $R^{3.B}$ is independently —I. In embodiments, $R^{3.B}$ is independently halogen. In embodiments, $R^{3.B}$ is independently hydrogen. In embodiments, $R^{3.B}$ is independently halogen, —$CX^3_3$, —$CHX^3_2$, or —$CH_2X^3$. In embodiments, $R^{3.B}$ is independently halogen or —$CX^3_3$. In embodiments, $R^{3.B}$ is independently —$CX^3_3$. In embodiments, $R^{3.B}$ is independently —$CHX^3_2$. In embodiments, $R^{3.B}$ is independently —$CH_2X^3$. In embodiments, $R^{3.B}$ is independently substituted or unsubstituted alkyl. In embodiments, $R^{3.B}$ is independently substituted alkyl. In embodiments, $R^{3.B}$ is independently unsubstituted alkyl. In embodiments, $R^{3.B}$ is independently halo-substituted or unsubstituted alkyl. In embodiments, $R^{3.B}$ is independently halo-substituted alkyl. In embodiments, $R^{3.B}$ is independently substituted or unsubstituted $C_1$-$C_4$ alkyl. In embodiments, $R^{3.B}$ is independently substituted $C_1$-$C_4$ alkyl. In embodiments, $R^{3.B}$ is independently unsubstituted $C_1$-$C_4$ alkyl. In embodiments, $R^{3.B}$ is independently halo-substituted or unsubstituted $C_1$-$C_4$ alkyl. In embodiments, $R^{3.B}$ is independently halo-substituted $C_1$-$C_4$ alkyl. In embodiments, $R^{3.B}$ is independently substituted or unsubstituted $C_1$-$C_3$ alkyl. In embodiments, $R^{3.B}$ is independently substituted $C_1$-$C_3$ alkyl. In embodiments, $R^{3.B}$ is independently unsubstituted $C_1$-$C_3$ alkyl. In embodiments, $R^{3.B}$ is independently halo-substituted or unsubstituted $C_1$-$C_3$ alkyl. In embodiments, $R^{3.B}$ is independently halo-substituted $C_1$-$C_3$ alkyl. In embodiments, $R^{3.B}$ is independently hydrogen. In embodiments, $R^{3.A}$ is independently —$CF_3$ and $R^{3.B}$ is independently —F. In embodiments, $R^{3.A}$ is independently —F and $R^{3.B}$ is independently —F. In embodiments, $R^{3.A}$ is independently —Cl and $R^{3.B}$ is independently —F. In embodiments, $R^{3.B}$ is independently —$CF_3$ and $R^{3.A}$ is independently —F. In embodiments, $R^{3.B}$ is independently —$CF_3$ and $R^{3.A}$ is independently —Cl. In embodiments, $R^{3.B}$ is independently —Cl and $R^{3.A}$ is independently —$CF_3$. In embodiments, $R^{3.B}$ is independently —F and $R^{3.A}$ is independently —$CF_3$.

In embodiments, $X^1$ is independently —F. In embodiments, $X^1$ is independently —Cl. In embodiments, $X^1$ is independently —Br. In embodiments, $X^1$ is independently —I. In embodiments, $X^2$ is independently —F. In embodiments, $X^2$ is independently —Cl. In embodiments, $X^2$ is independently —Br. In embodiments, $X^2$ is independently —I. In embodiments, $X^3$ is independently —F. In embodiments, $X^3$ is independently —Cl. In embodiments, $X^3$ is independently —Br. In embodiments, $X^3$ is independently —I.

In embodiments, z4 is independently 1. In embodiments, z4 is independently 2. In embodiments, z4 is independently 3. In embodiments, z4 is independently 4.

In embodiments, $R^4$ is independently —$CCl_3$. In embodiments, $R^4$ is independently —$CF_3$. In embodiments, $R^4$ is independently —$CBr_3$. In embodiments, $R^4$ is independently —$CI_3$. In embodiments, $R^4$ is independently —$CHCl_2$. In embodiments, $R^4$ is independently —$CHBr_2$. In embodiments, $R^4$ is independently —$CHI_2$. In embodiments, $R^4$ is independently —$CHF_2$. In embodiments, $R^4$ is independently —$CH_2Cl$. In embodiments, $R^4$ is independently —$CH_2Br$. In embodiments, $R^4$ is independently —$CH_2I$. In embodiments, $R^4$ is independently —$CH_2F$. In embodiments, $R^4$ is independently —$CH_3$. In embodiments, $R^4$ is independently —$CH_2CH_3$. In embodiments, $R^4$ is independently —$CH(CH_3)_2$. In embodiments, $R^4$ is independently —$C(CH_3)_3$. In embodiments, $R^4$ is independently unsubstituted 2 to 4 membered heteroalkyl. In embodiments, $R^4$ is independently substituted or unsubstituted alkyl. In embodiments, $R^4$ is independently substituted alkyl. In embodiments, $R^4$ is independently unsubstituted alkyl. In embodiments, $R^4$ is independently halo-substituted or unsubstituted alkyl. In embodiments, $R^4$ is independently halo-substituted alkyl. In embodiments, $R^4$ is independently substituted or unsubstituted $C_1$-$C_4$ alkyl. In embodiments, $R^4$ is independently substituted $C_1$-$C_4$ alkyl. In embodiments, $R^4$ is independently unsubstituted $C_1$-$C_4$ alkyl. In embodiments, $R^4$ is independently halo-substituted or unsubstituted $C_1$-$C_4$ alkyl. In embodiments, $R^4$ is independently halo-substituted $C_1$-$C_4$ alkyl. In embodiments, $R^4$ is independently substituted or unsubstituted $C_1$-$C_3$ alkyl. In embodiments, $R^4$ is independently substituted $C_1$-$C_3$ alkyl. In embodiments, $R^4$ is independently unsubstituted $C_1$-$C_3$ alkyl. In embodiments, $R^4$ is independently halo-substituted or unsubstituted $C_1$-$C_3$ alkyl. In embodiments, $R^4$ is independently halo-substituted $C_1$-$C_3$ alkyl. In embodiments, $R^4$ is independently substituted or unsubstituted cycloalkyl. In embodiments, $R^4$ is independently substituted cycloalkyl. In embodiments, $R^4$ is independently unsubstituted cycloalkyl. In embodiments, $R^4$ is independently halo-substituted or unsubstituted cycloalkyl. In embodiments, $R^4$ is independently halo-substituted cycloalkyl. In embodiments, $R^4$ is independently substituted or unsubstituted $C_3$-$C_6$ cycloalkyl. In embodiments, $R^4$ is independently substituted $C_3$-$C_6$ cycloalkyl. In embodiments, $R^4$ is independently unsubstituted $C_3$-$C_6$ cycloalkyl. In embodiments, $R^4$ is independently halo-substituted or unsubstituted $C_3$-$C_6$ cycloalkyl. In embodiments, $R^4$ is independently halo-substituted $C_3$-$C_6$ cycloalkyl. In embodiments, $R^4$ is independently substituted or unsubstituted $C_3$-$C_4$ cycloalkyl. In embodiments, $R^4$ is independently substituted $C_3$-$C_4$ cycloalkyl. In embodiments, $R^4$ is independently unsubstituted $C_3$-$C_4$ cycloalkyl. In embodiments, $R^4$ is independently halo-substituted or unsubstituted $C_3$-$C_4$ cycloalkyl. In embodiments, $R^4$ is independently halo-substituted $C_3$-$C_4$ cycloalkyl. In embodiments, $R^4$ is independently substituted or unsubstituted cyclopropyl. In embodiments, $R^4$ is independently substituted cyclopropyl. In embodiments, $R^4$ is independently unsubstituted cyclopropyl. In embodiments, $R^4$ is independently halo-substituted or unsubstituted cyclopropyl. In embodiments, $R^4$ is independently halo-substituted cyclopropyl. In embodiments, $R^4$ is independently hydrogen.

In embodiments, $R^5$ is independently $-CCl_3$. In embodiments, $R^5$ is independently $-CF_3$. In embodiments, $R^5$ is independently $-CBr_3$. In embodiments, $R^5$ is independently $-CI_3$. In embodiments, $R^5$ is independently $-CHCl_2$. In embodiments, $R^5$ is independently $-CHBr_2$. In embodiments, $R^5$ is independently $-CHI_2$. In embodiments, $R^5$ is independently $-CHF_2$. In embodiments, $R^5$ is independently $-CH_2Cl$. In embodiments, $R^5$ is independently $-CH_2Br$. In embodiments, $R^5$ is independently $-CH_2I$. In embodiments, $R^5$ is independently $-CH_2F$. In embodiments, $R^5$ is independently $-CH_3$. In embodiments, $R^5$ is independently $-CH_2CH_3$. In embodiments, $R^5$ is independently $-CH(CH_3)_2$. In embodiments, $R^5$ is independently $-C(CH_3)_3$. In embodiments, $R^5$ is independently unsubstituted 2 to 4 membered heteroalkyl. In embodiments, $R^5$ is independently substituted or unsubstituted alkyl. In embodiments, $R^5$ is independently substituted alkyl. In embodiments, $R^5$ is independently unsubstituted alkyl. In embodiments, $R^5$ is independently halo-substituted or unsubstituted alkyl. In embodiments, $R^5$ is independently halo-substituted alkyl. In embodiments, $R^5$ is independently substituted or unsubstituted $C_1$-$C_4$ alkyl. In embodiments, $R^5$ is independently substituted $C_1$-$C_4$ alkyl. In embodiments, $R^5$ is independently unsubstituted $C_1$-$C_4$ alkyl. In embodiments, $R^5$ is independently halo-substituted or unsubstituted $C_1$-$C_4$ alkyl. In embodiments, $R^5$ is independently halo-substituted $C_1$-$C_4$ alkyl. In embodiments, $R^5$ is independently substituted or unsubstituted $C_1$-$C_3$ alkyl. In embodiments, $R^5$ is independently substituted $C_1$-$C_3$ alkyl. In embodiments, $R^5$ is independently unsubstituted $C_1$-$C_3$ alkyl. In embodiments, $R^5$ is independently halo-substituted or unsubstituted $C_1$-$C_3$ alkyl. In embodiments, $R^5$ is independently halo-substituted $C_1$-$C_3$ alkyl. In embodiments, $R^5$ is independently substituted or unsubstituted cycloalkyl. In embodiments, $R^5$ is independently substituted cycloalkyl. In embodiments, $R^5$ is independently unsubstituted cycloalkyl. In embodiments, $R^5$ is independently halo-substituted or unsubstituted cycloalkyl. In embodiments, $R^5$ is independently halo-substituted cycloalkyl. In embodiments, $R^5$ is independently substituted or unsubstituted $C_3$-$C_6$ cycloalkyl. In embodiments, $R^5$ is independently substituted $C_3$-$C_6$ cycloalkyl. In embodiments, $R^5$ is independently unsubstituted $C_3$-$C_6$ cycloalkyl. In embodiments, $R^5$ is independently halo-substituted or unsubstituted $C_3$-$C_6$ cycloalkyl. In embodiments, $R^5$ is independently halo-substituted $C_3$-$C_6$ cycloalkyl. In embodiments, $R^5$ is independently substituted or unsubstituted $C_3$-$C_4$ cycloalkyl. In embodiments, $R^5$ is independently substituted $C_3$-$C_4$ cycloalkyl. In embodiments, $R^5$ is independently unsubstituted $C_3$-$C_4$ cycloalkyl. In embodiments, $R^5$ is independently halo-substituted or unsubstituted $C_3$-$C_4$ cycloalkyl. In embodiments, $R^5$ is independently halo-substituted $C_3$-$C_4$ cycloalkyl. In embodiments, $R^5$ is independently substituted or unsubstituted cyclopropyl. In embodiments, $R^5$ is independently substituted cyclopropyl. In embodiments, $R^5$ is independently unsubstituted cyclopropyl. In embodiments, $R^5$ is independently halo-substituted or unsubstituted cyclopropyl. In embodiments, $R^5$ is independently halo-substituted cyclopropyl. In embodiments, $R^5$ is independently hydrogen.

In embodiments, $R^6$ is independently $-CCl_3$. In embodiments, $R^6$ is independently $-CF_3$. In embodiments, $R^6$ is independently $-CBr_3$. In embodiments, $R^6$ is independently $-CI_3$. In embodiments, $R^6$ is independently $-CHCl_2$. In embodiments, $R^6$ is independently $-CHBr_2$. In embodiments, $R^6$ is independently $-CHI_2$. In embodiments, $R^6$ is independently $-CHF_2$. In embodiments, $R^6$ is independently $-CH_2Cl$. In embodiments, $R^6$ is independently $-CH_2Br$. In embodiments, $R^6$ is independently $-CH_2I$. In embodiments, $R^6$ is independently $-CH_2F$. In embodiments, $R^6$ is independently $-CH_3$. In embodiments, $R^6$ is independently $-CH_2CH_3$. In embodiments, $R^6$ is independently $-CH(CH_3)_2$. In embodiments, $R^6$ is independently $-C(CH_3)_3$. In embodiments, $R^6$ is independently unsubstituted 2 to 4 membered heteroalkyl. In embodiments, $R^6$ is independently substituted or unsubstituted alkyl. In embodiments, $R^6$ is independently substituted alkyl. In embodiments, $R^6$ is independently unsubstituted alkyl. In embodiments, $R^6$ is independently halo-substituted or unsubstituted alkyl. In embodiments, $R^6$ is independently halo-substituted alkyl. In embodiments, $R^6$ is independently substituted or unsubstituted $C_1$-$C_4$ alkyl. In embodiments, $R^6$ is independently substituted $C_1$-$C_4$ alkyl. In embodiments, $R^6$ is independently unsubstituted $C_1$-$C_4$ alkyl. In embodiments, $R^6$ is independently halo-substituted or unsubstituted $C_1$-$C_4$ alkyl. In embodiments, $R^6$ is independently halo-substituted $C_1$-$C_4$ alkyl. In embodiments, $R^6$ is independently substituted or unsubstituted $C_1$-$C_3$ alkyl. In embodiments, $R^6$ is independently substituted $C_1$-$C_3$ alkyl. In embodiments, $R^6$ is independently unsubstituted $C_1$-$C_3$ alkyl. In embodiments, $R^6$ is independently halo-substituted or unsubstituted $C_1$-$C_3$ alkyl. In embodiments, $R^6$ is independently halo-substituted $C_1$-$C_3$ alkyl. In embodiments, $R^6$ is independently substituted or unsubstituted cycloalkyl. In embodiments, $R^6$ is independently substituted cycloalkyl. In embodiments, $R^6$ is independently unsubstituted cycloalkyl. In embodiments, $R^6$ is independently halo-substituted or unsubstituted cycloalkyl. In embodiments, $R^6$ is independently halo-substituted cycloalkyl. In embodiments, $R^6$ is independently substituted or unsubstituted $C_3$-$C_6$ cycloalkyl. In embodiments, $R^6$ is independently substituted $C_3$-$C_6$ cycloalkyl. In embodiments, $R^6$ is independently unsubstituted $C_3$-$C_6$ cycloalkyl. In embodiments, $R^6$ is independently halo-substituted or unsubstituted $C_3$-$C_6$ cycloalkyl. In embodiments, $R^6$ is independently halo-substituted $C_3$-$C_6$ cycloalkyl. In embodiments, $R^6$ is independently substituted or unsubstituted $C_3$-$C_4$ cycloalkyl. In embodiments, $R^6$ is independently substituted $C_3$-$C_4$ cycloalkyl. In embodiments, $R^6$ is independently unsubstituted $C_3$-$C_4$ cycloalkyl. In embodiments, $R^6$ is independently halo-substituted or unsubstituted $C_3$-$C_4$ cycloalkyl. In embodiments, $R^6$ is independently halo-substituted $C_3$-$C_4$ cycloalkyl. In embodiments, $R^6$ is independently substituted or unsubstituted cyclopropyl. In embodiments, $R^6$ is independently substituted cyclopropyl. In embodiments, $R^6$ is independently unsubstituted cyclopropyl. In embodiments, $R^6$ is independently halo-substituted or unsubstituted cyclopropyl. In embodiments, $R^6$ is independently halo-substituted cyclopropyl. In embodiments, $R^6$ is independently hydrogen.

In embodiments, the compound has the formula:

(SSTA-152)

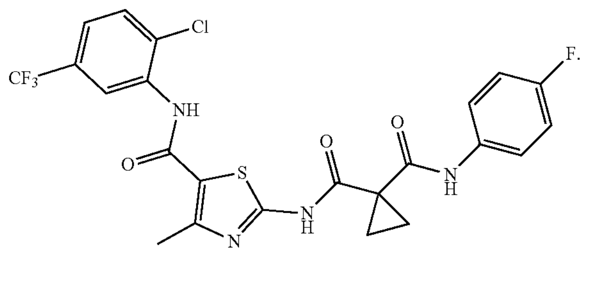

In embodiments, the compound has the formula:

(SSTA-259)

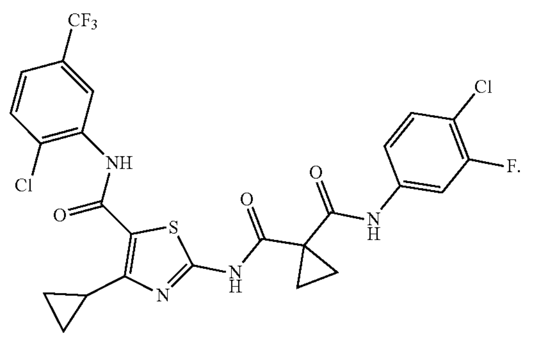

In embodiments, the compound has the formula:

(SSTA-260)

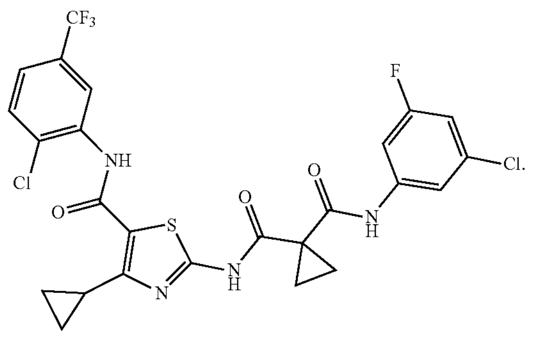

In embodiments, the compound has the formula:

(SSTA-263)

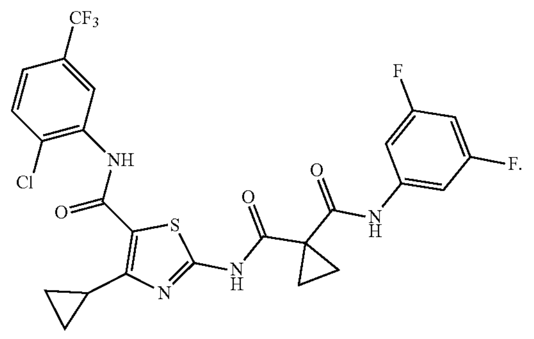

In embodiments, the compound has the formula:

(SSTA-264)

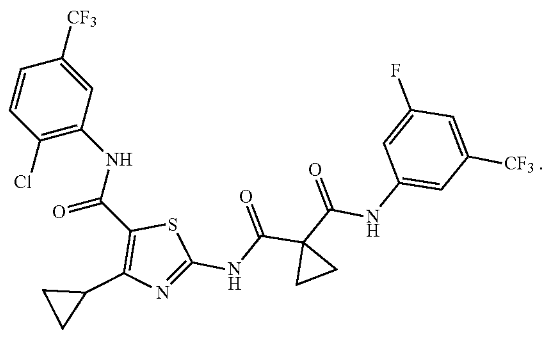

In embodiments, when $R^1$ is substituted, $R^1$ is substituted with one or more first substituent groups denoted by $R^{1.1}$ as explained in the definitions section above in the description of “first substituent group(s)”. In embodiments, when an $R^{1.1}$ substituent group is substituted, the $R^{1.1}$ substituent group is substituted with one or more second substituent groups denoted by $R^{1.2}$ as explained in the definitions section above in the description of “first substituent group(s)”. In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when two adjacent $R^1$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1.A}$ is substituted, $R^{1.A}$ is substituted with one or more first substituent groups denoted by $R^{1.A.1}$ as explained in the definitions section above in the description of "first substituent group(s)". In embodiments, when an $R^{1.A.1}$ substituent group is substituted, the $R^{1.A.1}$ substituent group is substituted with one or more second substituent groups denoted by $R^{1.A.2}$ as explained in the definitions section above in the description of "first substituent group(s)". In embodiments, when an $R^{1.A.2}$ substituent group is substituted, the $R^{1.A.2}$ substituent group is substituted with one or more third substituent groups denoted by $R^{1.A.3}$ as explained in the definitions section above in the description of "first substituent group(s)". In the above embodiments, $R^{1.A}$, $R^{1.A.1}$, $R^{1.A.2}$, and $R^{1.A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1.A}$, $R^{1.A.1}$, $R^{1.A.2}$, and $R^{1.A.3}$, respectively.

In embodiments, when $R^{1.B}$ is substituted, $R^{1.B}$ is substituted with one or more first substituent groups denoted by $R^{1.B.1}$ as explained in the definitions section above in the description of "first substituent group(s)". In embodiments, when an $R^{1.B.1}$ substituent group is substituted, the $R^{1.B.1}$ substituent group is substituted with one or more second substituent groups denoted by $R^{1.B.2}$ as explained in the definitions section above in the description of "first substituent group(s)". In embodiments, when an $R^{1.B.2}$ substituent group is substituted, the $R^{1.B.2}$ substituent group is substituted with one or more third substituent groups denoted by $R^{1.B.3}$ as explained in the definitions section above in the description of "first substituent group(s)". In the above embodiments, $R^{1.B}$, $R^{1.B.1}$, $R^{1.B.2}$, and $R^{1.B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1.B}$, $R^{1.B.1}$, $R^{1.B.2}$, and $R^{1.B.3}$, respectively.

In embodiments, when $R^{1.C}$ is substituted, $R^{1.C}$ is substituted with one or more first substituent groups denoted by $R^{1.C.1}$ as explained in the definitions section above in the description of "first substituent group(s)". In embodiments, when an $R^{1.C.1}$ substituent group is substituted, the $R^{1.C.1}$ substituent group is substituted with one or more second substituent groups denoted by $R^{1.C.2}$ as explained in the definitions section above in the description of "first substituent group(s)". In embodiments, when an $R^{1.C.2}$ substituent group is substituted, the $R^{1.C.2}$ substituent group is substituted with one or more third substituent groups denoted by $R^{1.C.3}$ as explained in the definitions section above in the description of "first substituent group(s)". In the above embodiments, $R^{1.C}$, $R^{1.C.1}$, $R^{1.C.2}$, and $R^{1.C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1.C}$, $R^{1.C.1}$, $R^{1.C.2}$, and $R^{1.C.3}$, respectively.

In embodiments, when $R^{1.D}$ is substituted, $R^{1.D}$ is substituted with one or more first substituent groups denoted by $R^{1.D.1}$ as explained in the definitions section above in the description of "first substituent group(s)". In embodiments, when an $R^{1.D.1}$ substituent group is substituted, the $R^{1.D.1}$ substituent group is substituted with one or more second substituent groups denoted by $R^{1.D.2}$ as explained in the definitions section above in the description of "first substituent group(s)". In embodiments, when an $R^{1.D.2}$ substituent group is substituted, the $R^{1.D.2}$ substituent group is substituted with one or more third substituent groups denoted by $R^{1.D.3}$ as explained in the definitions section above in the description of "first substituent group(s)". In the above embodiments, $R^{1.D}$, $R^{1.D.1}$, $R^{1.D.2}$, and $R^{1.D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1.D}$, $R^{1.D.1}$, $R^{1.D.2}$, and $R^{1.D.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1B}$ is substituted, $R^{1B}$ is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1A}$ and $R^{1B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1A}$ and $R^{1B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1C}$ is substituted, $R^{1C}$ is substituted with one or more first substituent groups denoted by $R^{1C.1}$ as explained in the definitions section above in the description of "first substituent group(s)". In embodiments, when an $R^{1C.1}$ substituent group is substituted, the $R^{1C.1}$ substituent group is substituted with one or more second substituent groups denoted by $R^{1C.2}$ as explained in the definitions section above in the description of "first substituent group(s)". In embodiments, when an $R^{1C.2}$ substituent group is substituted, the $R^{1C.2}$ substituent group is substituted with one or more third substituent groups denoted by $R^{1C.3}$ as explained in the definitions section above in the description of "first substituent group(s)". In the above embodiments, $R^{1C}$, $R^{1C.1}$, $R^{1C.2}$, and $R^{1C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1C}$, $R^{1C.1}$, $R^{1C.2}$, and $R^{1C.3}$, respectively.

In embodiments, when $R^{1D}$ is substituted, $R^{1D}$ is substituted with one or more first substituent groups denoted by $R^{1D.1}$ as explained in the definitions section above in the description of "first substituent group(s)". In embodiments, when an $R^{1D.1}$ substituent group is substituted, the $R^{1D.1}$ substituent group is substituted with one or more second substituent groups denoted by $R^{1D.2}$ as explained in the definitions section above in the description of "first substituent group(s)". In embodiments, when an $R^{1D.2}$ substituent group is substituted, the $R^{1D.2}$ substituent group is substituted with one or more third substituent groups denoted by $R^{1D.3}$ as explained in the definitions section above in the description of "first substituent group(s)". In the above embodiments, $R^{1D}$, $R^{1D.1}$, $R^{1D.2}$, and $R^{1D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1D}$, $R^{1D.1}$, $R^{1D.2}$, and $R^{1D.3}$, respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2.A}$ is substituted, $R^{2.A}$ is substituted with one or more first substituent groups denoted by $R^{2.A.1}$ as explained in the definitions section above in the description of "first substituent group(s)". In embodiments, when an $R^{2.A.1}$ substituent group is substituted, the $R^{2.A.1}$ substituent group is substituted with one or more second substituent groups denoted by $R^{2.A.2}$ as explained in the definitions section above in the description of "first substituent group(s)". In embodiments, when an $R^{2.A.2}$ substituent group is substituted, the $R^{2.A.2}$ substituent group is substituted with one or more third substituent groups denoted by $R^{2.A.3}$ as explained in the definitions section above in the description of "first substituent group(s)". In the above embodiments, $R^{2.A}$, $R^{2.A.1}$, $R^{2.A.2}$, and $R^{2.A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2.A}$, $R^{2A.1}$, $R^{2.A.2}$, and $R^{2.A.3}$, respectively.

In embodiments, when $R^{2.B}$ is substituted, $R^{2.B}$ is substituted with one or more first substituent groups denoted by $R^{2.B.1}$ as explained in the definitions section above in the description of "first substituent group(s)". In embodiments, when an $R^{2.B.1}$ substituent group is substituted, the $R^{2.B.1}$ substituent group is substituted with one or more second substituent groups denoted by $R^{2.B.2}$ as explained in the definitions section above in the description of "first substituent group(s)". In embodiments, when an $R^{2.B.2}$ substituent group is substituted, the $R^{2.B.2}$ substituent group is substituted with one or more third substituent groups denoted by $R^{2.B.3}$ as explained in the definitions section above in the description of "first substituent group(s)". In the above embodiments, $R^{2.B}$, $R^{2.B.1}$, $R^{2.B.2}$, and $R^{2.B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2.B}$, $R^{2.B.1}$, $R^{2.B.2}$, and $R^{2.B.3}$, respectively.

In embodiments, when two adjacent $R^2$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2B}$ is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2A}$ and $R^{2B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$, respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{1D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.1}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when two adjacent $R^3$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.1}$ substituent group is substituted, the $R^{3.1}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when $R^{3.A}$ is substituted, $R^{3.A}$ is substituted with one or more first substituent groups denoted by $R^{3.A.1}$ as explained in the definitions section above in the description of "first substituent group(s)". In embodiments, when an $R^{3.A.1}$ substituent group is substituted, the $R^{3.A.1}$ substituent group is substituted with one or more second substituent groups denoted by $R^{3.A.2}$ as explained in the definitions section above in the description of "first substituent group(s)". In embodiments, when an $R^{3.A.2}$ substituent group is substituted, the $R^{3.A.2}$ substituent group is substituted with one or more third substituent groups denoted by $R^{3.A.3}$ as explained in the definitions section above in the description of "first substituent group(s)". In the above embodiments, $R^{3.A}$, $R^{3.A.1}$, $R^{3.A.2}$, and $R^{3.A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3.A}$, $R^{3.A.1}$, $R^{3.A.2}$, and $R^{3.A.3}$, respectively.

In embodiments, when $R^{3.B}$ is substituted, $R^{3.B}$ is substituted with one or more first substituent groups denoted by $R^{3.B.1}$ as explained in the definitions section above in the description of "first substituent group(s)". In embodiments, when an $R^{3.B.1}$ substituent group is substituted, the $R^{3.B.1}$ substituent group is substituted with one or more second substituent groups denoted by $R^{3.B.2}$ as explained in the definitions section above in the description of "first substituent group(s)". In embodiments, when an $R^{3.B.2}$ substituent group is substituted, the $R^{3.B.2}$ substituent group is substituted with one or more third substituent groups denoted by $R^{3.B.3}$ as explained in the definitions section above in the description of "first substituent group(s)". In the above embodiments, $R^{3.B}$, $R^{3.B.1}$, $R^{3.B.2}$, and $R^{3.B.3}$ have values corresponding to the values of $R^{WW}$, $R^{WW.1}$, $R^{WW.2}$, and $R^{W}$ 3, respectively, as explained in the definitions section above in the description of "first substituent group(s)", wherein $R^{WW}$, $R^{WW.1}$, $R^{WW.2}$, and $R^{WW.3}$ correspond to $R^{3.B}$, $R^{3.B.1}$, $R^{3.B.2}$, and $R^{3.B.3}$, respectively.

In embodiments, when $R^{3.C}$ is substituted, $R^{3.C}$ is substituted with one or more first substituent groups denoted by $R^{3.C.1}$ as explained in the definitions section above in the description of "first substituent group(s)". In embodiments, when an $R^{3.C.1}$ substituent group is substituted, the $R^{3.C.1}$ substituent group is substituted with one or more second substituent groups denoted by $R^{3.C.2}$ as explained in the definitions section above in the description of "first substituent group(s)". In embodiments, when an $R^{3.C.2}$ substituent group is substituted, the $R^{3.C.2}$ substituent group is substituted with one or more third substituent groups denoted by $R^{3.C.3}$ as explained in the definitions section above in the description of "first substituent group(s)". In the above embodiments, $R^{3.C}$, $R^{3.C.1}$, $R^{3.C.2}$, and $R^{3.C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3.C}$, $R^{3.C.1}$, $R^{3.C.2}$, and $R^{3.C.3}$, respectively.

In embodiments, when $R^{3A}$ is substituted, $R^{3A}$ is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3B}$ is substituted, $R^{3B}$ is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3A}$ and $R^{3B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3A}$ and $R^{3B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3C}$ is substituted, $R^{3C}$ is substituted with one or more first substituent groups denoted by $R^{3C.1}$ as explained in the definitions section above in the description of "first substituent group(s)". In embodiments, when an $R^{3C.1}$ substituent group is substituted, the $R^{3C.1}$ substituent group is substituted with one or more second substituent groups denoted by $R^{3C.2}$ as explained in the definitions section above in the description of "first substituent group(s)". In embodiments, when an $R^{3C.2}$ substituent group is substituted, the $R^{3C.2}$ substituent group is substituted with one or more third substituent groups denoted by $R^{3C.3}$ as explained in the definitions section above in the description of "first substituent group(s)". In the above embodiments, $R^{3C}$, $R^{3C.1}$, $R^{3C.2}$, and $R^{3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3C}$, $R^{3C.1}$, $R^{3C.2}$, and $R^{3C.3}$, respectively.

In embodiments, when $R^{3D}$ is substituted, $R^{3D}$ is substituted with one or more first substituent groups denoted by $R^{3D.1}$ as explained in the definitions section above in the description of "first substituent group(s)". In embodiments, when an $R^{3D.1}$ substituent group is substituted, the $R^{3D.1}$ substituent group is substituted with one or more second substituent groups denoted by $R^{3D.2}$ as explained in the definitions section above in the description of "first substituent group(s)". In embodiments, when an $R^{3D.2}$ substituent group is substituted, the $R^{3D.2}$ substituent group is substituted with one or more third substituent groups denoted by $R^{3D.3}$ as explained in the definitions section above in the description of "first substituent group(s)". In the above embodiments, $R^{3D}$, $R^{3D.1}$, $R^{3D.2}$, and $R^{3D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3D}$, $R^{3D.1}$, $R^{3D.2}$, and $R^{3D.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{52}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.1}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^6$ is substituted, $R^6$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when $L^4$ is substituted, $L^4$ is substituted with one or more first substituent groups denoted by $R^{L4.1}$ as explained in the definitions section above in the description of "first substituent group(s)". In embodiments, when an $R^{L4.1}$ substituent group is substituted, the $R^{L4.1}$ substituent group is substituted with one or more second substituent groups denoted by $R^{L4.2}$ as explained in the definitions section above in the description of "first substituent group(s)". In embodiments, when an $R^{L4.2}$ substituent group is substituted, the $R^{L4.2}$ substituent group is substituted with one or more third substituent groups denoted by $R^{L4.3}$ as explained in the definitions section above in the description of "first substituent group(s)". In the above embodiments, $L^4$, $R^{L4.1}$, $R^{L4.2}$, and $R^{L4.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^4$, $R^{L4.1}$, $R^{L4.2}$, and $R^{L4.3}$, respectively.

In embodiments, $R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)OR^{1C}$, $—C(O)\ NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, two adjacent $R^1$ substituents may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted ring that is formed when two adjacent $R^1$ substituents join (e.g., substituted cycloalkyl, substituted heterocycloalkyl, substituted aryl, or substituted heteroaryl) is substituted with at least one substituent group, size-limited substituent group, or lower substituent group; wherein if the substituted ring is substituted with a plurality of groups selected from substituent groups, size-limited substituent groups, and lower substituent groups; each substituent group, size-limited substituent group, and/or lower substituent group may optionally be different. In embodiments, when a substituted ring that is formed when two adjacent $R^1$ substituents join is substituted, it is substituted with at least one substituent group. In embodiments, when a substituted ring that is formed when two adjacent $R^1$ substituents join is substituted, it is substituted with at least one size-limited substituent group. In embodiments, when a substituted ring that is formed when two adjacent $R^1$ substituents join is substituted, it is substituted with at least one lower substituent group.

In embodiments, $R^{1A}$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1.A}$ is substituted with a plurality of groups selected from substituent groups, size-limited substituent groups, and lower substituent groups; each substituent group, size-limited substituent group, and/or lower substituent group may optionally be different. In embodiments, when $R^{1.A}$ is substituted, it is substituted with at least one substituent group. In embodiments, when $R^{1.A}$ is substituted, it is substituted with at least one size-limited substituent group. In embodiments, when $R^{1.A}$ is substituted, it is substituted with at least one lower substituent group.

In embodiments, $R^{1.B}$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1.B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1.B}$ is substituted with a plurality of groups selected from substituent groups, size-limited substituent groups, and lower substituent groups; each substituent group, size-limited substituent group, and/or lower substituent group may optionally be different. In embodiments, when $R^{1.B}$ is substituted, it is substituted with at least one substituent group. In embodiments, when $R^{1.B}$ is substituted, it is substituted with at least one size-limited substituent group. In embodiments, when $R^{1.B}$ is substituted, it is substituted with at least one lower substituent group.

In embodiments, $R^{1.C}$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1.C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1.C}$ is substituted with a plurality of groups selected from substituent groups, size-limited substituent groups, and lower substituent groups; each substituent group, size-limited substituent group, and/or lower substituent group may optionally be different. In embodiments, when $R^{1.C}$ is substituted, it is substituted with at least one substituent group. In embodiments, when $R^{1.C}$ is substituted, it is substituted with at least one size-limited substituent group. In embodiments, when $R^{1.C}$ is substituted, it is substituted with at least one lower substituent group.

In embodiments, $R^{1.D}$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, —N3, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1.D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1.D}$ is substituted with a plurality of groups selected from substituent groups, size-limited substituent groups, and lower substituent groups; each substituent group, size-limited substituent group, and/or lower substituent group may optionally be different. In embodiments, when $R^{1.D}$ is substituted, it is substituted with at least one substituent group. In embodiments, when $R^{1.D}$ is substituted, it is substituted with at least one size-limited substituent group. In embodiments, when $R^{1.D}$ is substituted, it is substituted with at least one lower substituent group.

In embodiments, $R^{1A}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1B}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, $R^{1A}$ and $R^{1B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring that is formed when $R^{1A}$ and $R^{1B}$ substituents bonded to the same nitrogen atom join (e.g., substituted heterocycloalkyl or substituted heteroaryl) is substituted with at least one substituent group, size-limited substituent group, or lower substituent group; wherein if the substituted ring is substituted with a plurality of groups selected from substituent groups, size-limited substituent groups, and lower substituent groups; each substituent group, size-limited substituent group, and/or lower substituent group may optionally be different. In embodiments, when a substituted ring that is formed when $R^{1A}$ and $R^{1B}$ substituents bonded to the same nitrogen atom join is substituted, it is substituted with at least one substituent group. In embodiments, when a substituted ring that is formed when $R^{1A}$ and $R^{1B}$ substituents bonded to the same nitrogen atom join is substituted, it is substituted with at least one size-limited substituent group. In embodiments, when a substituted ring that is formed when $R^{1A}$ and $R^{1B}$ substituents bonded to the same nitrogen atom join is substituted, it is substituted with at least one lower substituent group.

In embodiments, $R^{1C}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, $R^{1D}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1D}$ is substituted with a plurality of groups selected from substituent groups, size-limited substituent groups, and lower substituent groups; each substituent group, size-limited substituent group, and/or lower substituent group may optionally be different. In embodiments, when $R^{1D}$ is substituted, it is substituted with at least one substituent group. In embodiments, when $R^{1D}$ is substituted, it is substituted with at least one size-limited substituent group. In embodiments, when $R^{1D}$ is substituted, it is substituted with at least one lower substituent group.

In embodiments, $R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^2R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O) NR^{2A}R^{2B}$, $—OR^{2D}$, $—NR^{2A}SO_2R^{1D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^{2.A}$ is independently hydrogen, halogen, $—CX^2_3$, $—CHX^2_2$, $—CH_2X^2$, $—OCX^2_3$, $—OCH_2X^2$, $—OCHX^{22}$, —CN, $—SO_{n2}R^{2D}$, $—SO_{v2}NR^{2A}R^{2B}$, $NR^{2C}NR^{2A}R^2$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O) NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2.A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.A}$ is substituted with a plurality of groups selected from substituent groups, size-limited substituent groups, and lower substituent groups; each substituent group, size-limited substituent group, and/or lower substituent group may optionally be different. In embodiments, when $R^{2.A}$ is substituted, it is substituted with at least one substituent group. In embodiments, when $R^{2.A}$ is substituted, it is substituted with at least one size-limited substituent group. In embodiments, when $R^{2.A}$ is substituted, it is substituted with at least one lower substituent group.

In embodiments, $R^{2.B}$ is independently hydrogen, halogen, $—CX^2_3$, $—CHX^2_2$, $—CH_2X^2$, $—OCX^2_3$, $—OCH_2X^2$, $—OCHX^{22}$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2.B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.B}$ is substituted with a plurality of groups selected from substituent groups, size-limited substituent groups, and lower substituent groups; each substituent group, size-limited substituent group, and/or lower substituent group may optionally be different. In embodiments, when $R^{2.B}$ is substituted, it is substituted with at least one substituent group. In embodiments, when $R^{2.B}$ is substituted, it is substituted with at least one size-limited substituent group. In embodiments, when $R^{2.B}$ is substituted, it is substituted with at least one lower substituent group.

In embodiments, $R^{2A}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, $R^{2B}$ is independently hydrogen, $—CCl_3$, $—CBr_3$, $—CF_3$, $—CI_3$, $CHCl_2$, $—CHBr_2$, $—CHF_2$, $—CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, $R^{2A}$ and $R^{2B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring that is formed when $R^{2A}$ and $R^{2B}$ substituents bonded to the same nitrogen atom join (e.g., substituted heterocycloalkyl or substituted heteroaryl) is substituted with at least one substituent group, size-limited substituent group, or lower substituent group; wherein if the substituted ring is substituted with a plurality of groups selected from substituent groups, size-limited substituent groups, and lower substituent groups; each substituent group, size-limited substituent group, and/or lower substituent group may optionally be different. In embodiments, when a substituted ring that is formed when $R^{2A}$ and $R^{2B}$ substituents bonded to the same nitrogen atom join is substituted, it is substituted with at least one substituent group. In embodiments, when a substituted ring that is formed when $R^{2A}$ and $R^{2B}$ substituents bonded to the same nitrogen atom join is substituted, it is substituted with at least one size-limited substituent group. In embodiments, when a substituted ring that is formed when $R^{2A}$ and $R^{2B}$ substituents bonded to the same nitrogen atom join is substituted, it is substituted with at least one lower substituent group.

In embodiments, $R^{2C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, $R^{2D}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, two adjacent $R^3$ substituents may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted ring that is formed when two adjacent $R^3$ substituents join (e.g., substituted cycloalkyl, substituted heterocycloalkyl, substituted aryl, or substituted heteroaryl) is substituted with at least one substituent group, size-limited substituent group, or lower substituent group; wherein if the substituted ring is substituted with a plurality of groups selected from substituent groups, size-limited substituent groups, and lower substituent groups; each substituent group, size-limited substituent group, and/or lower substituent group may optionally be different. In embodiments, when a substituted ring that is formed when two adjacent $R^3$ substituents join is substituted, it is substituted with at least one substituent group. In embodiments, when a substituted ring that is formed when two adjacent $R^3$ substituents join is substituted, it is substituted with at least one size-limited substituent group. In embodiments, when a substituted ring that is formed when two adjacent $R^3$ substituents join is substituted, it is substituted with at least one lower substituent group.

In embodiments, $R^{3.A}$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3.A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3.A}$ is substituted with a plurality of groups selected from substituent groups, size-limited substituent groups, and lower substituent groups; each substituent group, size-limited substituent group, and/or lower substituent group may optionally be different. In embodiments, when $R^{3.A}$ is substituted, it is substituted with at least one substituent group. In embodiments, when $R^{3.A}$ is substituted, it is substituted with at least one size-limited substituent group. In embodiments, when $R^{3.A}$ is substituted, it is substituted with at least one lower substituent group.

In embodiments, $R^{3.B}$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3.B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3.B}$ is substituted with a plurality of groups selected from substituent groups, size-limited substituent groups, and lower substituent groups; each substituent group, size-limited substituent group, and/or lower substituent group may optionally be different. In embodiments, when $R^{3.B}$ is substituted, it is substituted with at least one substituent group. In embodiments, when $R^{3.B}$ is substituted, it is substituted with at least one size-limited substituent group. In embodiments, when $R^{3.B}$ is substituted, it is substituted with at least one lower substituent group.

In embodiments, $R^{3.C}$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3.C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3.C}$ is substituted with a plurality of groups selected from substituent groups, size-limited substituent groups, and lower substituent groups; each substituent group, size-limited substituent group, and/or lower substituent group may optionally be different. In embodiments, when $R^{3.C}$ is substituted, it is substituted with at least one substituent group. In embodiments, when $R^{3.C}$ is substituted, it is substituted with at least one size-limited substituent group. In embodiments, when $R^{3.C}$ is substituted, it is substituted with at least one lower substituent group.

In embodiments, $R^{3A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^{3A}$ and $R^{3B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring that is formed when $R^{3A}$ and $R^{3B}$ substituents bonded to the same nitrogen atom join (e.g., substituted heterocycloalkyl or substituted heteroaryl) is substituted with at least one substituent group, size-limited substituent group, or lower substituent group; wherein if the substituted ring is substituted with a plurality of groups selected from substituent groups, size-limited substituent groups, and lower substituent groups; each substituent group, size-limited substituent group, and/or lower substituent group may optionally be different. In embodiments, when a substituted ring that is formed when $R^{3A}$ and $R^{3B}$ substituents bonded to the same nitrogen atom join is substituted, it is substituted with at least one substituent group. In embodiments, when a substituted ring that is formed when $R^{3A}$ and $R^{3B}$ substituents bonded to the same nitrogen atom join is substituted, it is substituted with at least one size-limited substituent group. In embodiments, when a substituted ring that is formed when $R^{3A}$ and $R^{3B}$ substituents bonded to the same nitrogen atom join is substituted, it is substituted with at least one lower substituent group.

In embodiments, $R^{3C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, $R^{3D}$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3D}$ is substituted with a plurality of groups selected from substituent groups, size-limited substituent groups, and lower substituent groups; each substituent group, size-limited substituent group, and/or lower substituent group may optionally be different. In embodiments, when $R^{3D}$ is substituted, it is substituted with at least one substituent group. In embodiments, when $R^{3D}$ is substituted, it is substituted with at least one size-limited substituent group. In embodiments, when $R^{3D}$ is substituted, it is substituted with at least one lower substituent group.

In embodiments, $R^4$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^6$ is independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $L^4$ is a bond, —$N(R^4)$—, —O—, —S—, —$SO_2$—, —C(O)—, —C(O)$N(R^4)$—, —$N(R^4)$C(O)—, —$N(R^4)$C(O)NH—, —NHC(O)$N(R^4)$—, —C(O)O—, —OC(O)—, —$SO_2N(R^4)$—, —$N(R^4)SO_2$—, substituted or unsubstituted alkylene (e.g., $C_1$-$C_{10}$, $C_1$-$C_8$, $C_1$-$C_6$, $C_1$-$C_4$, $C_1$-$C_2$, $C_2$-$C_{10}$, $C_2$-$C_8$, $C_2$-$C_6$, or $C_2$-$C_4$), or substituted or unsubstituted heteroalkylene (e.g., 2 to 8 membered, 2 to 6 membered, 4 to 6 membered, 2 to 3 membered, or 4 to 5 membered).

In embodiments, a substituted $L^4$ (e.g., substituted alkylene or substituted heteroalkylene) is substituted with at least one substituent group, size-limited substituent group, or lower substituent group; wherein if the substituted $L^4$ is substituted with a plurality of groups selected from substituent groups, size-limited substituent groups, and lower substituent groups; each substituent group, size-limited substituent group, and/or lower substituent group may optionally be different. In embodiments, when $L^4$ is substituted, it is substituted with at least one substituent group. In embodiments, when $L^4$ is substituted, it is substituted with at least one size-limited substituent group. In embodiments, when $L^4$ is substituted, it is substituted with at least one lower substituent group.

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein. In embodiments, the compound is a compound described herein (e.g., in an aspect, embodiment, example, table, figure, or claim). In embodiments, the compound, or a pharmaceutically acceptable salt thereof, is the compound. In embodiments, the compound, or a pharmaceutically acceptable salt thereof, is the pharmaceutically acceptable salt of the compound.

III. Pharmaceutical Compositions

In an aspect is provided a pharmaceutical composition including a compound as described herein, including embodiments, and a pharmaceutically acceptable excipient. In embodiments, the compound as described herein is included in a therapeutically effective amount.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the administering does not include administration of any active agent other than the recited active agent (e.g., a compound described herein).

IV. Methods of Use

In an aspect is provided a method of decreasing the level of Aurora A kinase protein activity in a subject, the method including administering a compound as described herein to the subject. In embodiments, the compound is administered in an effective amount. In embodiments, the compound is administered in a therapeutically effective amount.

In an aspect is provided a method of decreasing the level of Aurora A kinase protein activity in a cell, the method including contacting the cell with a compound described herein. In embodiments, the compound is administered in an effective amount.

In an aspect is provided a method of decreasing the level of N-MYC protein in a subject, the method including administering a compound as described herein to the subject. In embodiments, the compound is administered in an effective amount. In embodiments, the compound is administered in a therapeutically effective amount.

In an aspect is provided a method of decreasing the level of N-MYC protein in a cell, the method including contacting the cell with a compound described herein. In embodiments, the compound is administered in an effective amount.

In embodiments, the compound contacts an N-MYC protein or Aurora A kinase protein. In embodiments, the compound contacts an N-MYC protein. In embodiments, the compound contacts an Aurora A kinase protein. In embodiments, the compound contacts an N-MYC protein and an Aurora A kinase protein.

In embodiments, the compound reduces the level of N-MYC activity (e.g., in a cell, in a subject, compared to a control such as absence of the compound under otherwise identical conditions). In embodiments, the compound reduces the level of N-MYC protein (e.g., in a cell, in a subject, compared to a control such as absence of the compound under otherwise identical conditions).

In embodiments, the compound modulates the protein conformation of the Aurora A kinase protein. In embodiments the compound reduces the level of N-MYC protein contacting Aurora A kinase protein.

In embodiments, the compound reduces the level of N-MYC protein contacting an Aurora A kinase protein (e.g., in a cell, in a subject, compared to a control such as absence of the compound under otherwise identical conditions).

In an aspect is provided a method of modulating the protein conformation of an Aurora A kinase protein, the method including contacting the Aurora A kinase protein with an effective amount of a compound described herein. In embodiments, the modulated Aurora A kinase protein conformation reduces the level of Aurora A kinase protein contacting N-MYC protein (e.g. in a cell or in a subject in need).

In an aspect is provided a method of changing the protein conformation of an Aurora A kinase protein to a conformation with reduced binding (e.g. in a cell or in a subject in need) to an N-MYC protein. In embodiments, the method includes contacting the Aurora A kinase protein with an effective amount of a compound described herein.

In an aspect is provided a method of inhibiting cancer cell growth, the method including contacting the cancer cell with an effective amount of a compound described herein. In embodiments, the compound modulates (e.g. reduces or inhibits) N-MYC activity level, Aurora A kinase activity level, N-MYC protein level, or Aurora A kinase protein level in the cancer cell. In embodiments, the compound modulates (e.g. reduces or inhibits) the N-MYC activity (e.g. transcriptional activation) level in the cancer cell (e.g., compared to a control such as absence of the compound under otherwise identical conditions). In embodiments, the compound modulates (e.g. reduces or inhibits) the Aurora A kinase activity level in the cancer cell (e.g., compared to a control such as absence of the compound under otherwise identical conditions). In embodiments, the compound modulates (e.g. reduces or inhibits) the N-MYC protein level in the cancer cell (e.g., compared to a control such as absence of the compound under otherwise identical conditions). In embodiments, the compound modulates (e.g. reduces or inhibits) the Aurora A kinase protein level in the cancer cell (e.g., compared to a control such as absence of the compound under otherwise identical conditions). In embodiments, the compound reduces the interaction between N-MYC protein and Aurora A kinase protein (e.g., in a cell, in a subject, compared to a control such as absence of the compound under otherwise identical conditions). In embodiments, the compound increases the level of degradation of N-MYC protein (e.g., in a cell, in a subject, compared to a control such as absence of the compound under otherwise identical conditions).

In an aspect is provided a method of inhibiting cancer cell growth, the method including contacting the cancer cell with an effective amount of a compound described herein, wherein the compound modulates (e.g. reduces or inhibits) the N-MYC activity level, Aurora A kinase activity level, N-MYC protein level, or Aurora A kinase protein level in the cancer cell.

In an aspect is provided a method of treating a cancer in a subject in need thereof, the method including administering to the subject in need thereof an effective amount of a compound described herein. In embodiments, the compound is administered in a therapeutically effective amount.

In embodiments, the cancer is lung cancer, prostate cancer, ovarian cancer, lymphoma, acute lymphoblastic leukemia, acute myeloid leukemia, Ewing Sarcoma, multiple myeloma, Non-Hodgkin lymphoma, medulloblastoma, retinoblastoma, glioma, glioblastoma, pancreatic cancer, neuroblastoma, rhabdomyosarcoma, osteosarcoma, Wilms Tumour, or breast cancer. In embodiments, the cancer is lung cancer, prostate cancer, ovarian cancer, lymphoma, acute lymphoblastic leukemia, acute myeloid leukemia, Ewing Sarcoma, multiple myeloma, Non-Hodgkin lymphoma, medulloblastoma, retinoblastoma, glioma, glioblastoma, pancreatic cancer, or neuroblastoma. In embodiments, the cancer is lung cancer. In embodiments, the cancer is prostate cancer. In embodiments, the cancer is ovarian cancer. In embodiments, the cancer is lymphoma. In embodiments, the cancer is acute lymphoblastic leukemia. In embodiments, the cancer is acute myeloid leukemia. In embodiments, the cancer is Ewing Sarcoma. In embodiments, the cancer is multiple myeloma. In embodiments, the cancer is Non-Hodgkin lymphoma. In embodiments, the cancer is medulloblastoma. In embodiments, the cancer is retinoblastoma. In embodiments, the cancer is glioma. In embodiments, the cancer is glioblastoma. In embodiments, the cancer is pancreatic cancer. In embodiments, the cancer is neuroblastoma. In embodiments, the cancer is rhabdomyosarcoma. In embodiments, the cancer is osteosarcoma. In embodiments, the cancer is Wilms Tumour. In embodiments, the cancer is breast cancer.

In an aspect is provided a method of inhibiting cancer growth in a subject in need thereof, the method including administering to the subject in need thereof an effective amount of a compound described herein. In embodiments, the compound modulates (e.g. reduces or inhibits) the N-MYC activity level, Aurora A kinase activity level, N-MYC protein level, or Aurora A kinase protein level in the subject. In embodiments, the compound modulates (e.g. reduces or inhibits) the N-MYC activity level in the subject (e.g., compared to a control such as absence of the compound under otherwise identical conditions). In embodiments, the compound modulates (e.g. reduces or inhibits) the Aurora A kinase activity level in the subject (e.g., compared to a control such as absence of the compound under otherwise identical conditions). In embodiments, the compound modulates (e.g. reduces or inhibits) the N-MYC protein level in the subject (e.g., compared to a control such as absence of the compound under otherwise identical conditions). In embodiments, the compound modulates (e.g. reduces or inhibits) the Aurora A kinase protein level in the subject (e.g., compared to a control such as absence of the compound under otherwise identical conditions). In embodiments, the compound is administered in a therapeutically effective amount.

In an aspect is provided a method of inhibiting cancer growth in a subject in need thereof, the method including administering to the subject in need thereof an effective amount of a compound described herein, wherein the compound modulates (e.g. reduces or inhibits) the N-MYC activity level, Aurora A kinase activity level, N-MYC protein level, or Aurora A kinase protein level in the subject. In embodiments, the compound is administered in a therapeutically effective amount.

In embodiments, the method further includes co-administering an anti-cancer agent to the subject in need. In embodiments, the method reduces the level of phosphorylation of histone H3. In embodiments, the method reduces the level of phosphorylation of the amino acid corresponding to serine 10 of human histone H3. In embodiments, the method includes cell cycle arrest (e.g., of cancer cell). In embodiments, the method includes cell death (e.g., of cancer cell). In embodiments, the method increases the level of cell cycle arrest (e.g., relative to control such as absence of the compound) (e.g., of cancer cell). In embodiments, the method increases the level of cell death (e.g., relative to control such as absence of the compound) (e.g., of cancer cell).

V. Embodiments

Embodiment P1. A compound having the formula:

(I)

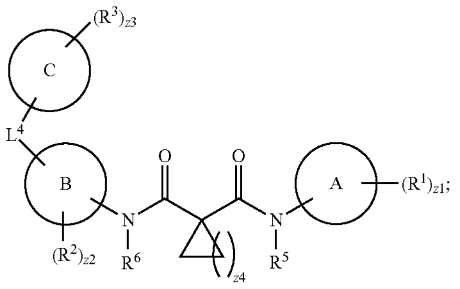

wherein,

Ring A is phenyl or 5 to 6 membered heteroaryl;

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1C}(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

Ring B is 5 membered heteroaryl;

$R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl z2 is an integer from 0 to 4;

Ring C is phenyl or 5 to 6 membered heteroaryl;

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl z3 is an integer from 0 to 5;

$L^4$ is a bond, $—N(R^4)—$, —O—, —S—, $—SO_2—$, —C(O)—, $—C(O)N(R^4)—$, $—N(R^4)C(O)—$, $—N(R^4)C(O)NH—$, $—NHC(O)N(R^4)—$, —C(O)O—, —OC(O)—, $—SO_2N(R^4)—$, $—N(R^4)SO_2—$, substituted or unsubstituted alkylene, or, substituted or unsubstituted heteroalkylene;

z4 is an integer from 1 to 5;

$R^4$, $R^5$, and $R^6$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2;

or a pharmaceutically acceptable salt thereof.

Embodiment P2. The compound of embodiment P1, wherein Ring A is phenyl.

Embodiment P3. The compound of embodiment P1, wherein Ring A is a 5 to 6 membered heteroaryl.

Embodiment P4. The compound of one of embodiments P1 to P3, wherein Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl.

Embodiment P5. The compound of one of embodiments P1 to P4, wherein Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

Embodiment P6. The compound of one of embodiments P1 to P5, wherein $R^5$ and $R^6$ are independently hydrogen.

Embodiment P7. The compound of one of embodiments P1 to P6, wherein $L^4$ is a bond, —NH—, —O—, —S—, $—SO_2—$, —C(O)—, —C(O)NH—, —NHC(O)—, —NHC(O)NH—, —C(O)O—, —OC(O)—, $—SO_2NH—$, $—NHSO_2—$, substituted or unsubstituted $C_1$-$C_6$ alkylene, or, substituted or unsubstituted 2 to 6 membered heteroalkylene.

Embodiment P8. The compound of one of embodiments P1 to P6, wherein $L^4$ is a bond, $—SO_2—$, —C(O)NH—, —NHC(O)—, $—SO_2NH—$, $—NHSO_2—$, substituted or unsubstituted $C_1$-$C_4$ alkylene, or, substituted or unsubstituted 2 to 4 membered heteroalkylene.

Embodiment P9. The compound of one of embodiments P1 to P8, wherein z4 is 1.

Embodiment P10. The compound of one of embodiments P1 to P9, having the formula:

(Ia)

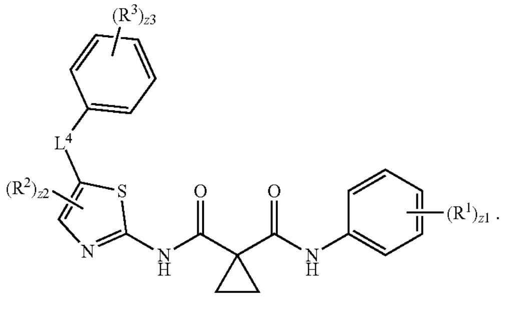

Embodiment P11. The compound of embodiment 10, wherein $L^4$ is a bond, —$SO_2$—, —C(O)NH—, —NHC(O)—, —$SO_2NH$—, or —$NHSO_2$—.

Embodiment P12. The compound of one of embodiments P1 to P9, having the formula:

(Ib)

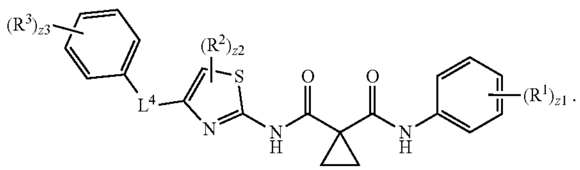

Embodiment P13. The compound of embodiment P12, wherein $L^4$ is —$SO_2NH$— or —$NHSO_2$—.

Embodiment P14. The compound of one of embodiments P1 to P9 having the formula:

(Ic)

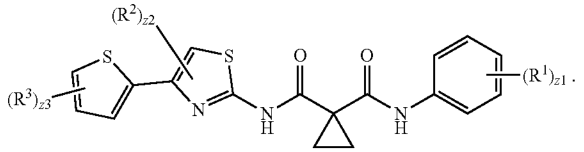

Embodiment P15. The compound of one of embodiments P1 to P9, having the formula:

(Ie)

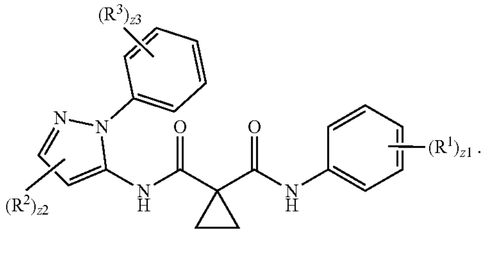

Embodiment P16. The compound of one of embodiments P1 to P9, having the formula:

(If)

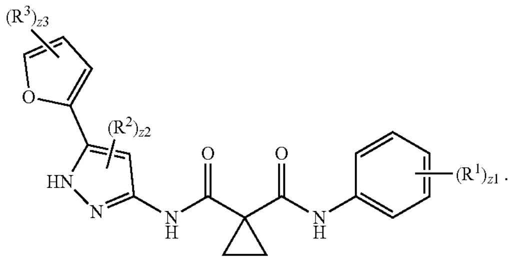

Embodiment P17. The compound of one of embodiments P1 to P3, having the formula:

(II)

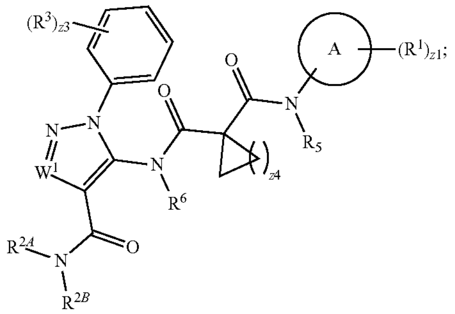

wherein $W^1$ is independently CH, N, or $C(R^2)$.

Embodiment P18. The compound of embodiment 17, having the formula:

(III)

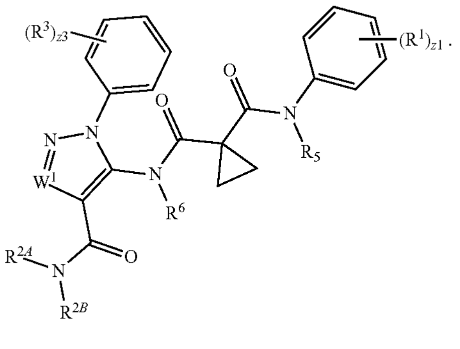

Embodiment P19. The compound of one of embodiments P17 to P18, wherein $R^5$ and $R^6$ are independently hydrogen.

Embodiment P20. The compound of one of embodiments P1 to P3, having the formula:

(IV)

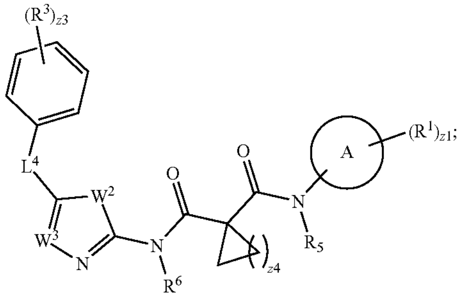

wherein $W^2$ is independently S or O; and $W^3$ is independently CH or $C(R^2)$.

Embodiment P21. The compound of embodiment P20, having the formula:

(V)

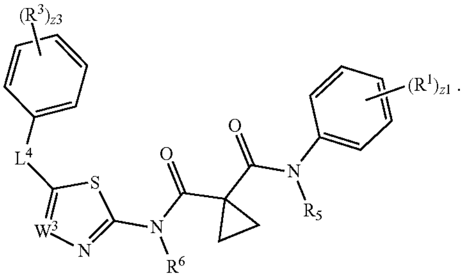

Embodiment P22. The compound of one of embodiments P20 to P21, wherein $L^4$ is $—C(O)N(R^4)—$, $—N(R^4)C(O)—$, $—SO_2N(R^4)—$, or $—N(R^4)SO_2—$.

Embodiment P23. The compound of one of embodiments P20 to P21, wherein $L^4$ is —C(O)NH—, —NHC(O)—, $—SO_2NH—$, or $—NHSO_2—$.

Embodiment P24. The compound of one of embodiments P20 to P23, wherein $R^5$ and $R^6$ are independently hydrogen.

Embodiment P25. A compound having the formula:

(Id)

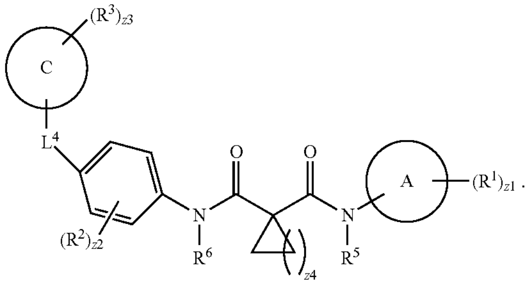

wherein,

Ring A is phenyl or 5 to 6 membered heteroaryl;

$R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1C}(O)R^{1C}$, $—NR^{1C}(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

$R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl z2 is an integer from 0 to 4;

Ring C is phenyl or 5 to 6 membered heteroaryl;

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl z3 is an integer from 0 to 5;

$L^4$ is $—SO_2N(R^4)CH_2CH_2—$, $—CH_2CH_2N(R^4)SO_2—$, $—SO_2N(R^4)CH_2—$, or $—CH_2N(R^4)SO_2—$;

z4 is an integer from 1 to 5;

$R^4$, $R^5$, and $R^6$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2;

or a pharmaceutically acceptable salt thereof.

Embodiment P26. The compound of embodiment P25, wherein Ring A is phenyl.

Embodiment P27. The compound of embodiment P25, wherein Ring A is a 5 to 6 membered heteroaryl.

Embodiment P28. The compound of one of embodiments P25 to P27, wherein Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, or thiadiazolyl.

Embodiment P29. The compound of one of embodiments P25 to P28, wherein Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

Embodiment P30. The compound of one of embodiments P25 to P29, wherein $R^5$ and $R^6$ are independently hydrogen.

Embodiment P31. The compound of one of embodiments P1 to P30, wherein $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —NHC(O) $NR^{1A}R^{1B}$, —$N(O)_{m1}$, —$NR^{1A}R^{1B}$, $C(O)R^{1C}$, —C(O)—$OR^{1C}$, —C(O) $NR^{1A}R^{1B}$, —$OR^{1D}$, —$NR^{1A}SO_2R^{1D}$, —$NR^{1A}C(O)R^{1C}$, —$NR^{1C}(O)OR^{1C}$, —$NR^{1A}OR^{1C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P32. The compound of one of embodiments P1 to P30, wherein $R^1$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P33. The compound of one of embodiments P1 to P30, wherein $R^1$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NO_2$, —SH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_4$ alkyl, or substituted or unsubstituted 2 to 4 membered heteroalkyl.

Embodiment P34. The compound of one of embodiments P1 to P30, wherein $R^1$ is independently halogen, —$CF_3$, —$NO_2$, or —$OCH_3$.

Embodiment P35. The compound of one of embodiments P1 to P34, wherein z1 is 1.

Embodiment P36. The compound of one of embodiments P1 to P34, wherein z1 is 2.

Embodiment P37. The compound of one of embodiments P1 to P36, wherein $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —NHC(O) $NR^{2A}R^{2B}$, —$N(O)_{m2}$, —$NR^{2A}R^{2B}$, —$C(O)R^{2C}$, —C(O)—$OR^{2C}$, —C(O) $NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P38. The compound of one of embodiments P1 to P36, wherein $R^2$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P39. The compound of one of embodiments P1 to P36, wherein $R^2$ is independently substituted or unsubstituted $C_1$-$C_6$ alkyl or substituted or unsubstituted 2 to 6 membered heteroalkyl.

Embodiment P40. The compound of one of embodiments P1 to P36, wherein $R^2$ is independently —$CH_3$ or —$COOCH_2CH_3$.

Embodiment P41. The compound of one of embodiments P1 to P40, wherein z2 is 1.

Embodiment P42. The compound of one of embodiments P1 to P41, wherein $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P43. The compound of one of embodiments P1 to P41, wherein $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P44. The compound of one of embodiments P1 to P41, wherein $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$NO_2$, or substituted or unsubstituted $C_1$-$C_6$ alkyl.

Embodiment P45. The compound of one of embodiments P1 to P41, wherein $R^3$ is independently halogen, —$CF_3$, —$NO_2$, or —$CH_3$.

Embodiment P46. A pharmaceutical composition comprising the compound of any one of embodiments P1 to P45 and a pharmaceutically acceptable excipient.

Embodiment P47. A method of decreasing the level of Aurora A kinase protein activity in a subject, said method comprising administering a compound of one of embodiments P1 to P45 to said subject.

Embodiment P48. A method of decreasing the level of Aurora A kinase protein activity in a cell, said method comprising contacting said cell with a compound of one of embodiments P1 to P45.

Embodiment P49. The method of one of embodiments P47 to P48, wherein the compound contacts an N-MYC protein or Aurora A kinase protein.

Embodiment P50. The method of one of embodiments P47 to P49, wherein the compound reduces the level of N-MYC activity.

Embodiment P51. The method of one of embodiments P47 to P50, wherein the compound modulates the protein conformation of the Aurora A kinase protein.

Embodiment P52. The method of one of embodiments P47 to P51, wherein the compound reduces the level of N-MYC protein.

Embodiment P53. The method of one of embodiments P47 to P52, wherein the compound reduces the level of N-MYC protein contacting an Aurora A kinase protein.

Embodiment P54. A method of decreasing the level of N-MYC protein activity in a subject, said method comprising administering a compound of one of embodiments P1 to P45 to said subject.

Embodiment P55. A method of decreasing the level of N-MYC protein activity in a cell, said method comprising contacting said cell with a compound of one of embodiments P1 to P45.

Embodiment P56. The method of one of embodiments P54 to P55, wherein the compound contacts an N-MYC protein or Aurora A kinase protein.

Embodiment P57. The method of one of embodiments P54 to P56, wherein the compound reduces the level of Aurora A kinase activity.

Embodiment P58. The method of one of embodiments P54 to P57, wherein the compound modulates the protein conformation of an Aurora A kinase protein.

Embodiment P59. The method of one of embodiments P54 to P58, wherein the compound reduces the level of Aurora A kinase protein.

Embodiment P60. The method of one of embodiments P54 to P59, wherein the compound reduces the level of N-MYC protein contacting an Aurora A kinase protein.

Embodiment P61. A method of inhibiting cancer growth in a subject in need thereof, said method comprising administering to the subject in need thereof an effective amount of a compound of one of embodiments P1 to P45, wherein the compound modulates the N-MYC activity level, Aurora A kinase activity level, N-MYC protein level, or Aurora A kinase protein level in the subject.

Embodiment P62. A method of inhibiting cancer cell growth, said method comprising contacting the cancer cell with an effective amount of a compound of one of embodiments P1 to P45, wherein the compound modulates the N-MYC activity level, Aurora A kinase activity level, N-MYC protein level, or Aurora A kinase protein level in the cancer cell.

Embodiment P63. A method of treating a cancer in a subject in need thereof, said method comprising administering to the subject in need thereof an effective amount of a compound of one of embodiments P1 to P45.

Embodiment P64. The method of embodiment P63, wherein the cancer is lung cancer, prostate cancer, ovarian cancer, lymphoma, acute lymphoblastic leukemia, acute myeloid leukemia, Ewing Sarcoma, multiple myeloma, Non-Hodgkin lymphoma, medulloblastoma, retinoblastoma, glioma, glioblastoma, pancreatic cancer, or neuroblastoma.

Embodiment P65. The method of one of embodiments P63 to P64, further comprising co-administering an anti-cancer agent to said subject in need.

VI. Additional Embodiments

Embodiment 1. A compound having the formula:

(I)

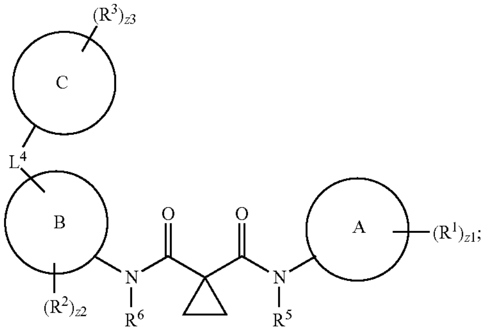

wherein,

Ring A is phenyl or 5 to 6 membered heteroaryl;

$R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —NHC(O) $NR^{1A}R^{1B}$, —$N(O)_{m1}$, —$NR^{1A}R^{1B}$, —$C(O)R^{1C}$, —C(O)—$OR^{1C}$, —C(O) $NR^{1A}R^{1B}$, —$OR^{1D}$, —$NR^{1A}SO_2R^{1D}$, —$NR^{1C}(O)R^{1C}$, —$NR^{1C}(O)OR^{1C}$, —$NR^{1A}OR^{1C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

Ring B is 5 membered heteroaryl;

$R^2$ is independently halogen, —$CX^2_3$, —$CHX^2_2$, —$CH_2X^2$, —$OCX^2_3$, —$OCH_2X^2$, —$OCHX^2$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —NHC(O) $NR^{2A}R^{2B}$, —$N(O)_{m2}$, —$NR^{2A}R^{2B}$, —$C(O)R^{2C}$, —C(O)—$OR^{2C}$, —C(O) $NR^{2A}R^{2B}$, —$OR^{2D}$, —$NR^{2A}SO_2R^{1D}$, —$NR^{2A}C(O)R^{2C}$, —$NR^{2A}C(O)$ $OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl z2 is an integer from 0 to 4;

Ring C is phenyl or 5 to 6 membered heteroaryl;

$R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —NHC(O) $NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)$ $OR^{3C}$, —$NR^{3A}OR^{3C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl z3 is an integer from 0 to 5;

$L^4$ is a bond, —$N(R^4)$—, —O—, —S—, —$SO_2$—, —C(O)—, —$C(O)N(R^4)$—, —$N(R^4)C(O)$—, —$N(R^4)C(O)$NH—, —$NHC(O)N(R^4)$—, —C(O)O—, —OC(O)—, —$SO_2N(R^4)$—, —$N(R^4)SO_2$—, substituted or unsubstituted alkylene, or substituted or unsubstituted heteroalkylene;

z4 is an integer from 1 to 5;

$R^4$, $R^5$, and $R^6$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2; or a pharmaceutically acceptable salt thereof.

Embodiment 2. The compound of embodiment 1, wherein Ring A is phenyl.

Embodiment 3. The compound of embodiment 1, wherein Ring A is a 5 to 6 membered heteroaryl.

Embodiment 4. The compound of one of embodiments 1 to 3, wherein Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl.

Embodiment 5. The compound of one of embodiments 1 to 4, wherein Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

Embodiment 6. The compound of one of embodiments 1 to 5, wherein $R^5$ and $R^6$ are independently hydrogen.

Embodiment 7. The compound of one of embodiments 1 to 6, wherein $L^4$ is a bond, —NH—, —O—, —S—, —$SO_2$—, —C(O)—, —C(O)NH—, —NHC(O)—, —NHC(O)NH—, —C(O)O—, —OC(O)—, —$SO_2$NH—, —$NHSO_2$—, substituted or unsubstituted $C_1$-$C_6$ alkylene, or substituted or unsubstituted 2 to 6 membered heteroalkylene.

Embodiment 8. The compound of one of embodiments 1 to 6, wherein $L^4$ is a bond, —$SO_2$—, —C(O)NH—, —NHC(O)—, —$SO_2$NH—, —$NHSO_2$—, substituted or unsubstituted $C_1$-$C_4$ alkylene, or substituted or unsubstituted 2 to 4 membered heteroalkylene.

Embodiment 9. The compound of one of embodiments 1 to 8, wherein z4 is 1.

Embodiment 10. The compound of one of embodiments 1 to 9, having the formula:

(Ia)

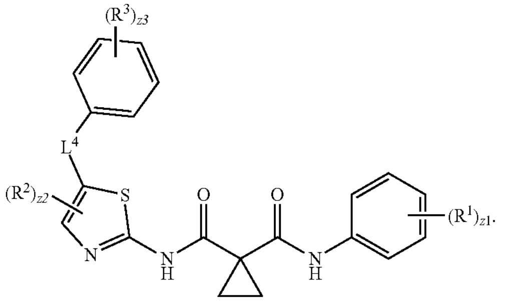

Embodiment 11. The compound of embodiment 10, wherein $L^4$ is a bond, —$SO_2$—, —C(O)NH—, —NHC(O)—, —$SO_2$NH—, or —$NHSO_2$—.

Embodiment 12. The compound of one of embodiments 1 to 9, having the formula:

(Ib)

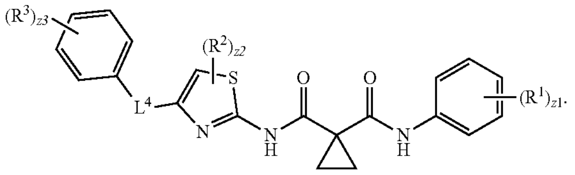

Embodiment 13. The compound of embodiment 12, wherein $L^4$ is —$SO_2$NH— or —$NHSO_2$—.

Embodiment 14. The compound of one of embodiments 1 to 9, having the formula:

(Ic)

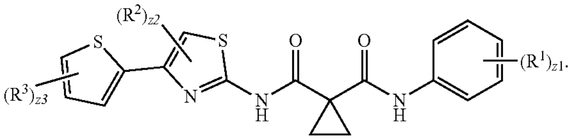

Embodiment 15. The compound of one of embodiments 1 to 9, having the formula:

(Ie)

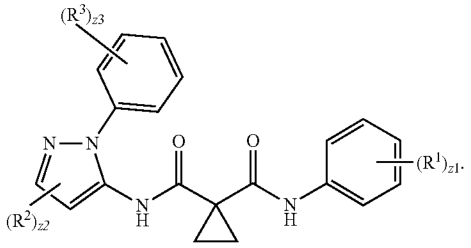

Embodiment 16. The compound of one of embodiments 1 to 9, having the formula:

(If)

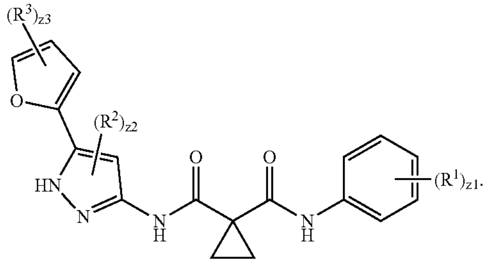

Embodiment 17. The compound of one of embodiments 1 to 3, having the formula:

(II)

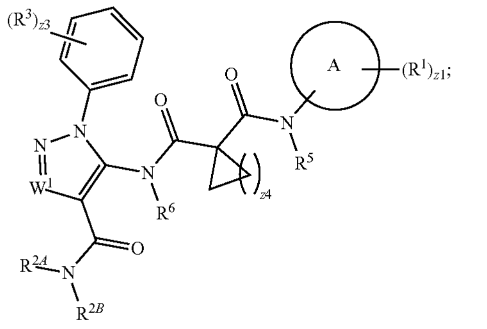

wherein $W^1$ is independently CH, N, or $C(R^2)$.

Embodiment 18. The compound of embodiment 17, having the formula:

(III)

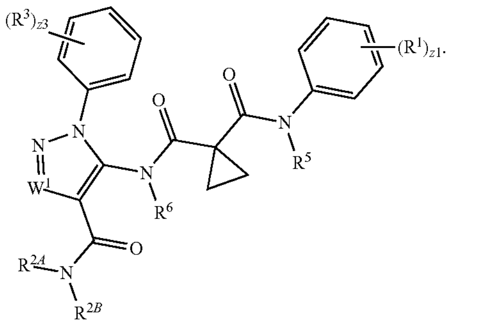

Embodiment 19. The compound of one of embodiments 17 to 18, wherein $R^5$ and $R^6$ are independently hydrogen.

Embodiment 20. The compound of one of embodiments 1 to 3, having the formula:

(IV)

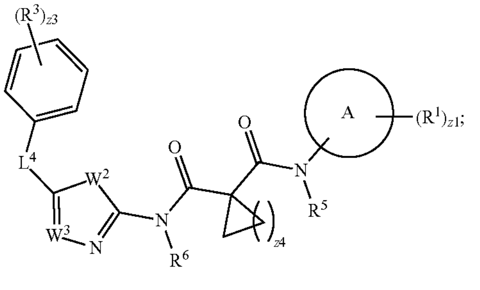

wherein $W^2$ is independently S or O; and $W^3$ is independently CH or $C(R^2)$.

Embodiment 21. The compound of embodiment 20, having the formula:

(V)

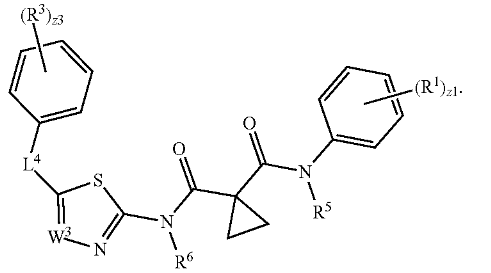

Embodiment 22. The compound of one of embodiments 20 to 21, wherein $L^4$ is $—C(O)N(R^4)—$, $—N(R^4)C(O)—$, $—SO_2N(R^4)—$, or $—N(R^4)SO_2—$.

Embodiment 23. The compound of one of embodiments 20 to 21, wherein $L^4$ is —C(O)NH—, —NHC(O)—, $—SO_2NH—$, or $—NHSO_2—$.

Embodiment 24. The compound of one of embodiments 20 to 23, wherein $R^5$ and $R^6$ are independently hydrogen.

Embodiment 25. A compound having the formula:

(Id)

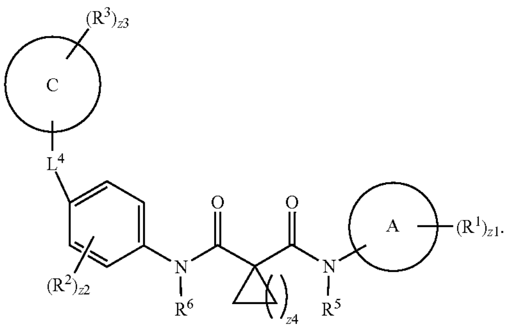

wherein,

Ring A is phenyl or 5 to 6 membered heteroaryl;

$R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—O—NR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O) NR^{1A}R^{1B}$, $—OR^{1D}$, $—NR^{1A}SO_2R^{1D}$, $—NR^{1C}(O)R^{1C}$, $—NR^{1C}(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

$R^2$ is independently halogen, $—CX^2_3$, $—CHX^{22}$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^2R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O) NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl z2 is an integer from 0 to 4;

Ring C is phenyl or 5 to 6 membered heteroaryl;

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl z3 is an integer from 0 to 5;

$L^4$ is $—SO_2N(R^4)CH_2CH_2—$, $—CH_2CH_2N(R^4)SO_2—$, $—SO_2N(R^4)CH_2—$, or $—CH_2N(R^4)SO_2—$;

z4 is an integer from 1 to 5;

$R^4$, $R^5$, and $R^6$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2;

or a pharmaceutically acceptable salt thereof.

Embodiment 26. The compound of embodiment 25, wherein Ring A is phenyl.

Embodiment 27. The compound of embodiment 25, wherein Ring A is a 5 to 6 membered heteroaryl.

Embodiment 28. The compound of one of embodiments 25 to 27, wherein Ring B is pyrrolyl, pyrazolyl, imidazolyl, triazolyl, tetrazolyl, furanyl, thienyl, oxazolyl, isoxazolyl, thiazolyl, isothiazolyl, oxadiazolyl, or thiadiazolyl.

Embodiment 29. The compound of one of embodiments 25 to 28 wherein Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

Embodiment 30. The compound of one of embodiments 25 to 29, wherein $R^5$ and $R^6$ are independently hydrogen.

Embodiment 31. The compound of one of embodiments 1 to 30, wherein $R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1C}(O)OR^{1C}$, $—NR^{1A}OR^{1C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 32. The compound of one of embodiments 1 to 30, wherein $R^1$ is independently halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 33. The compound of one of embodiments 1 to 30, wherein $R^1$ is independently halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NO_2$, —SH, $—OCCl_3$, $—OCF_3$, $—OCBr_3$, $—OCI_3$, $—OCHCl_2$, $—OCHBr_2$, $—OCHI_2$, $—OCHF_2$, —$OCH_2Cl$, —$OCH_2Br$, —$OCH_2I$, —$OCH_2F$, substituted or unsubstituted $C_1$-$C_4$ alkyl, or substituted or unsubstituted 2 to 4 membered heteroalkyl.

Embodiment 34. The compound of one of embodiments 1 to 30, wherein $R^1$ is independently halogen, —$CF_3$, —$NO_2$, or —$OCH_3$.

Embodiment 35. The compound of one of embodiments 1 to 34, wherein z1 is 1.

Embodiment 36. The compound of one of embodiments 1 to 34, wherein z1 is 2.

Embodiment 37. The compound of one of embodiments 1 to 36, wherein $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —C(O) $NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 38. The compound of one of embodiments 1 to 36, wherein $R^2$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 39. The compound of one of embodiments 1 to 36, wherein $R^2$ is independently substituted or unsubstituted $C_1$-$C_6$ alkyl or substituted or unsubstituted 2 to 6 membered heteroalkyl.

Embodiment 40. The compound of one of embodiments 1 to 36, wherein $R^2$ is independently —$CH_3$ or —$COOCH_2CH_3$.

Embodiment 41. The compound of one of embodiments 1 to 40, wherein z2 is 1.

Embodiment 42. The compound of one of embodiments 1 to 41, wherein $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 43. The compound of one of embodiments 1 to 41, wherein $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 44. The compound of one of embodiments 1 to 41, wherein $R^3$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$NO_2$, or substituted or unsubstituted $C_1$-$C_6$ alkyl.

Embodiment 45. The compound of one of embodiments 1 to 41, wherein $R^3$ is independently halogen, —$CF_3$, —$NO_2$, or —$CH_3$.

Embodiment 46. The compound embodiment 1, having the formula:

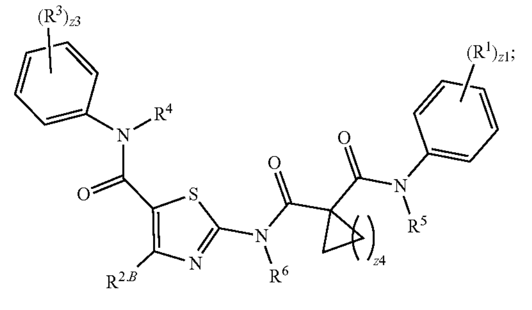

Wherein $R^{2.B}$ is independently hydrogen, substituted or unsubstituted $C_1$-$C_6$ alkyl, or substituted or unsubstituted $C_3$-$C_6$ cycloalkyl.

Embodiment 47. The compound of embodiment 46, having the formula:

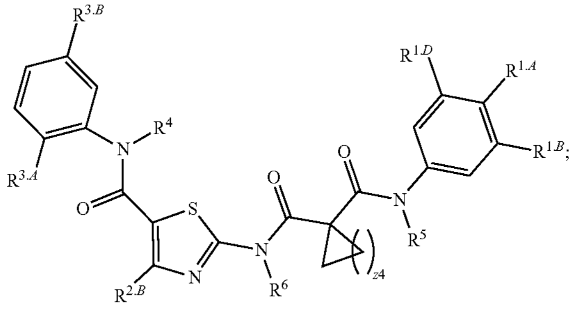

wherein $R^{1.A}$, $R^{1.B}$, and $R^{1.D}$, are independently hydrogen, halogen, —$CX^1_3$, —$CHX^1_2$, —$CH_2X'$, or substituted or unsubstituted alkyl;

$R^{3.A}$ and $R^{3.B}$ are independently hydrogen, halogen, —$CX^3_3$, —$CHX^3_2$, —$CH_2X^3$, or substituted or unsubstituted alkyl.

Embodiment 48. The compound of embodiment 47, having the formula:

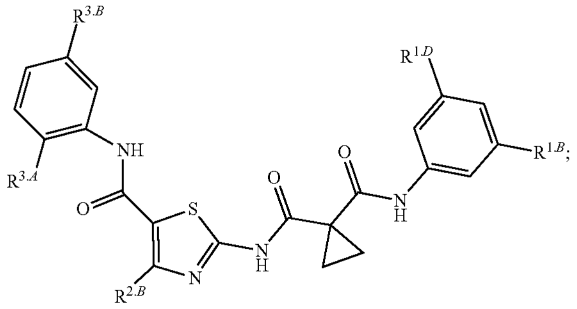

wherein $R^{1.B}$ and $R^{1.D}$, are independently halogen or —$CX^1_3$; and $R^{3.A}$ and $R^{3.B}$ are independently halogen or —$CX^3_3$.

Embodiment 49. The compound of embodiment 48, having the formula:

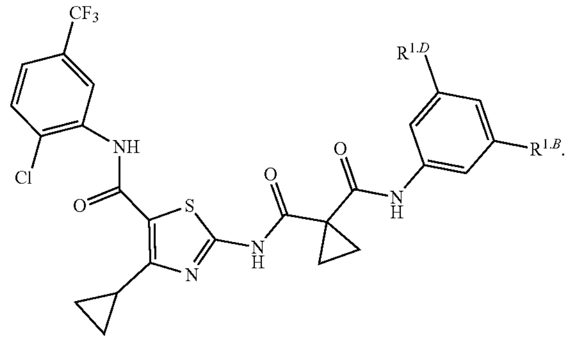

Embodiment 50. The compound of embodiment 47, having the formula:

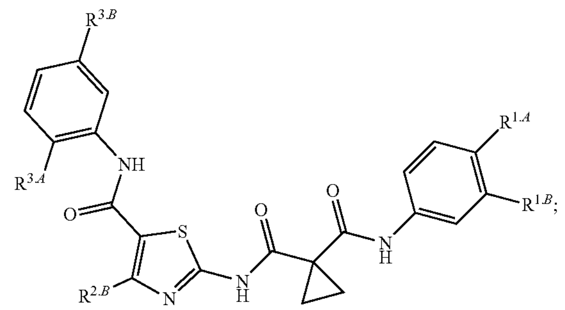

wherein $R^{1.A}$ and $R^{1.B}$, are independently halogen or —$CX^1_3$; and $R^{3.A}$ and $R^{3.B}$ are independently halogen or —$CX^3_3$.

Embodiment 51. The compound of embodiment 50, having the formula:

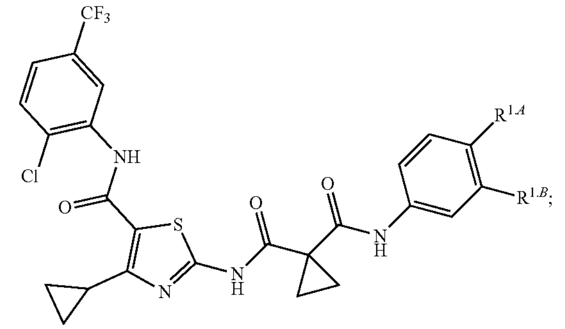

Embodiment 52. The compound of embodiment 1, having the formula:

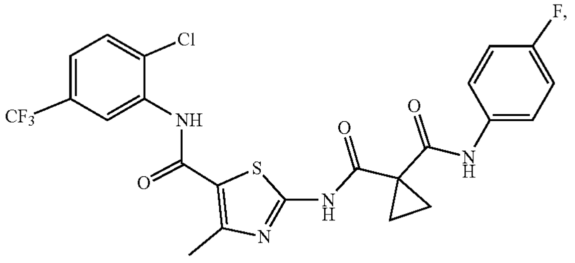

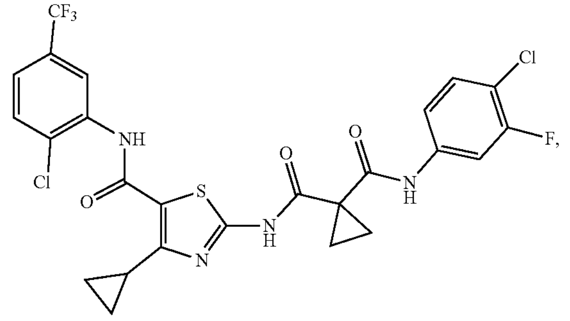

-continued

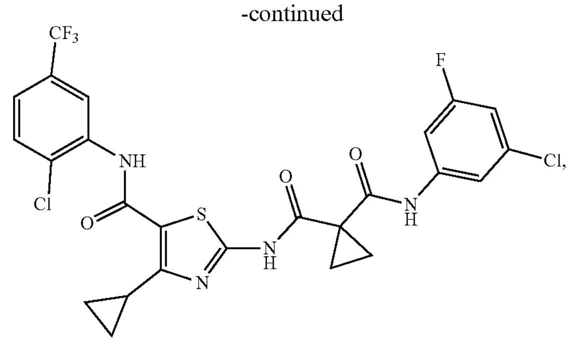

,

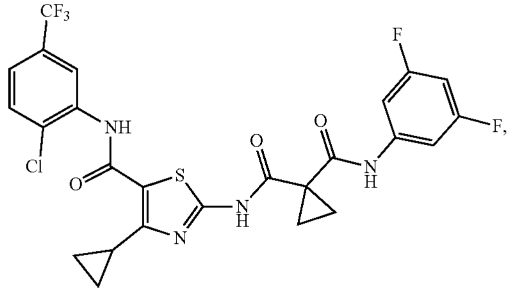

, or

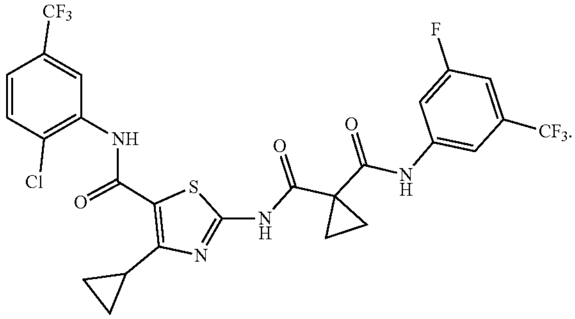

.

Embodiment 53. A pharmaceutical composition comprising the compound of any one of embodiments 1 to 52 and a pharmaceutically acceptable excipient.

Embodiment 54. A method of decreasing the level of Aurora A kinase protein activity in a subject, said method comprising administering a compound of one of embodiments 1 to 52 to said subject.

Embodiment 55. A method of decreasing the level of Aurora A kinase protein activity in a cell, said method comprising contacting said cell with a compound of one of embodiments 1 to 52.

Embodiment 56. The method of one of embodiments 54 to 55, wherein the compound contacts an N-MYC protein or Aurora A kinase protein.

Embodiment 57. The method of one of embodiments 54 to 56, wherein the compound reduces the level of N-MYC activity.

Embodiment 58. The method of one of embodiments 54 to 57, wherein the compound modulates the protein conformation of the Aurora A kinase protein.

Embodiment 59. The method of one of embodiments 54 to 58, wherein the compound reduces the level of N-MYC protein.

Embodiment 60. The method of one of embodiments 54 to 59, wherein the compound reduces the level of N-MYC protein contacting an Aurora A kinase protein.

Embodiment 61. A method of decreasing the level of N-MYC protein activity in a subject, said method comprising administering a compound of one of embodiments 1 to 52. to said subject.

Embodiment 62. A method of decreasing the level of N-MYC protein activity in a cell, said method comprising contacting said cell with a compound of one of embodiments 1 to 52.

Embodiment 63. The method of one of embodiments 61 to 62, wherein the compound contacts an N-MYC protein or Aurora A kinase protein.

Embodiment 64. The method of one of embodiments 61 to 63, wherein the compound reduces the level of Aurora A kinase activity.

Embodiment 65. The method of one of embodiments 61 to 64, wherein the compound modulates the protein conformation of an Aurora A kinase protein.

Embodiment 66. The method of one of embodiments 61 to 65, wherein the compound reduces the level of Aurora A kinase protein.

Embodiment 67. The method of one of embodiments 61 to 66, wherein the compound reduces the level of N-MYC protein contacting an Aurora A kinase protein.

Embodiment 68. A method of inhibiting cancer growth in a subject in need thereof, said method comprising administering to the subject in need thereof an effective amount of a compound of one of embodiments 1 to 52, wherein the compound modulates the N-MYC activity level, Aurora A kinase activity level, N-MYC protein level, or Aurora A kinase protein level in the subject.

Embodiment 69. A method of inhibiting cancer cell growth, said method comprising contacting the cancer cell with an effective amount of a compound of one of embodiments 1 to 52, wherein the compound modulates the N-MYC activity level, Aurora A kinase activity level, N-MYC protein level, or Aurora A kinase protein level in the cancer cell.

Embodiment 70. A method of treating a cancer in a subject in need thereof, said method comprising administering to the subject in need thereof an effective amount of a compound of one of embodiments 1 to 52.

Embodiment 71. The method of embodiment 70, wherein the cancer is lung cancer, prostate cancer, ovarian cancer, lymphoma, acute lymphoblastic leukemia, acute myeloid leukemia, Ewing Sarcoma, multiple myeloma, Non-Hodgkin lymphoma, medulloblastoma, retinoblastoma, glioma, glioblastoma, pancreatic cancer, or neuroblastoma.

Embodiment 72. The method of one of embodiments 70 to 71, further comprising co-administering an anti-cancer agent to said subject in need.

VII. Further Embodiments

Embodiment C1. A compound having the formula:

(I)

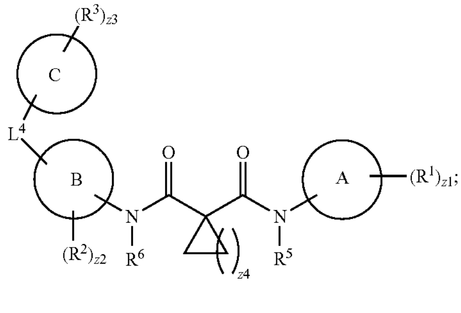

;

wherein, Ring A is phenyl or 5 to 6 membered heteroaryl; $R^1$ is independently halogen, $—CX^1_3$, $—CHX^1_2$, $—CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —NHC(O)$NR^{1C}NR^{1A}R^{1B}$, —NHC(O)$NR^{1A}R^{1B}$, —$N(O)_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1C}$(O)$R^{1C}$, —$NR^{1C}$(O)$OR^{1C}$, —$NR^{1A}OR^{1C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; z1 is an integer from 2, 1, 0, 3, 4, or 5; Ring B is 5 membered heteroaryl; $R^2$ is independently unsubstituted or substituted cycloalkyl, unsubstituted or substituted alkyl, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O) $NR^{2A}R^{2B}$, —$OR^{2D}$, —$NR^{2A}SO_2R^{1D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted heteroalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl z2 is an integer from 1, 0, 2, 3, or 4; Ring C is phenyl or 5 to 6 membered heteroaryl; $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —NHC(O)$NR^{3C}NR^{3A}R^{3B}$, —NHC(O)$NR^{3A}R^{3B}$, —$N(O)_{m3}$, —$NR^{3A}R^{3B}$, —C(O)$R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is an integer from 2, 0, 1, 3, 4, or 5; $L^4$ is —C(O)N($R^4$)—, —N($R^4$)C(O)—, a bond, —N($R^4$)—, —O—, —S—, —$SO_2$—, —C(O)—, —N($R^4$)C(O)NH—, —NHC(O)N($R^4$)—, —C(O)O—, —OC(O)—, —$SO_2$N($R^4$)—, —N($R^4$)$SO_2$—, substituted or unsubstituted alkylene, or substituted or unsubstituted heteroalkylene; z4 is an integer from 1, 2, 3, 4, or 5; $R^4$, $R^5$, and $R^6$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^1$, $X^2$, and $X^3$ are independently —F, —Cl, —Br, or —I; n1, n2, and n3 are independently an integer from 0 to 4; and m1, m2, m3, v1, v2, and v3 are independently 1 or 2; or a pharmaceutically acceptable salt thereof.

Embodiment C2. The compound of embodiment C1, wherein Ring A is phenyl.

Embodiment C3. The compound of embodiment C1, wherein Ring A is a 5 to 6 membered heteroaryl.

Embodiment C4. The compound of one of embodiments C1 to C3, wherein Ring B is thiazolyl, oxazolyl, pyrrolyl, pyrazolyl, imidazolyl, triazolyl, tetrazolyl, furanyl, thienyl, isoxazolyl, isothiazolyl, oxadiazolyl, thiadiazolyl.

Embodiment C5. The compound of one of embodiments C1 to C4, wherein Ring C is phenyl, pyrrolyl, pyrazolyl, imidazolyl, triazolyl, tetrazolyl, furanyl, thienyl, oxazolyl, isoxazolyl, thiazolyl, isothiazolyl, oxadiazolyl, thiadiazolyl, pyridyl, pyrimidinyl, pyridazinyl, pyrazinyl, or triazinyl.

Embodiment C6. The compound of one of embodiments C1 to C5, wherein $R^5$ and $R^6$ are independently hydrogen.

Embodiment C7. The compound of one of embodiments C1 to C6, wherein $L^4$ is —C(O)NH—, —NHC(O)—, a bond, —NH—, —O—, —S—, —$SO_2$—, —C(O)—, —NHC(O)NH—, —C(O)O—, —OC(O)—, —$SO_2$NH—, —$NHSO_2$—, substituted or unsubstituted $C_1$-$C_6$ alkylene, or substituted or unsubstituted 2 to 6 membered heteroalkylene.

Embodiment C8. The compound of one of embodiments C1 to C6, wherein $L^4$ is —C(O)NH—, —NHC(O)—, a bond, —$SO_2$—, —$SO_2$NH—, —$NHSO_2$—, substituted or unsubstituted $C_1$-$C_4$ alkylene, or substituted or unsubstituted 2 to 4 membered heteroalkylene.

Embodiment C9. The compound of one of embodiments C1 to C8, wherein z4 is 1.

Embodiment C10. The compound of one of embodiments C1 to C9, having the formula:

(Ia)

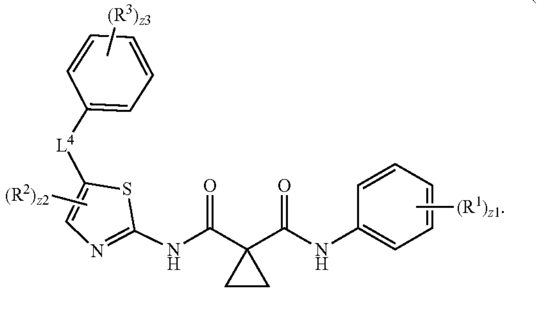

Embodiment C11. The compound of one of embodiments C1 to C10, wherein $L^4$ is —C(O)NH—, —NHC(O)—, a bond, —$SO_2$—, —$SO_2NH$—, or —$NHSO_2$—.

Embodiment C12. The compound of one of embodiments C1 to C9, having the formula:

(Ib)

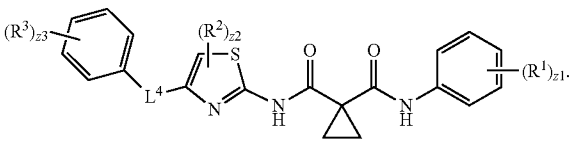

Embodiment C13. The compound of embodiment C12, wherein $L^4$ is —$SO_2NH$— or —$NHSO_2$—.

Embodiment C14. The compound of one of embodiments C1 to C9, having the formula:

(Ic)

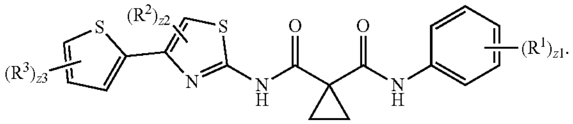

Embodiment C15. The compound of one of embodiments C1 to C3, having the formula:

(IV)

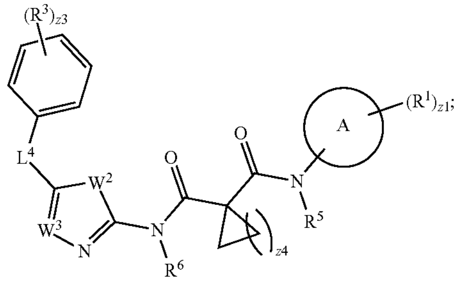

wherein $W^2$ is independently S or O; and $W^3$ is independently CH or $C(R^2)$.

Embodiment C16. The compound of embodiment C15, having the formula:

(V)

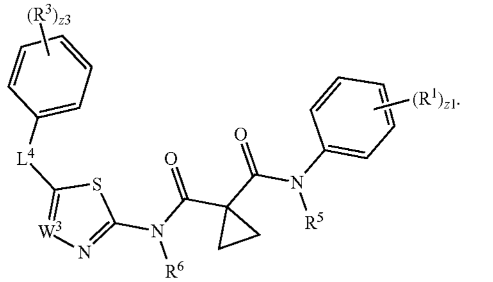

Embodiment C17. The compound of one of embodiments C15 to C16, wherein $L^4$ is —$C(O)N(R^4)$—, —$N(R^4)C(O)$—, —$SO_2N(R^4)$—, or —$N(R^4)SO_2$—.

Embodiment C18. The compound of one of embodiments C15 to C16, wherein $L^4$ is —C(O)NH—, —NHC(O)—, —$SO_2NH$—, or —$NHSO_2$—.

Embodiment C19. The compound of one of embodiments C15 to C16, wherein $R^5$ and $R^6$ are independently hydrogen.

Embodiment C20. The compound of one of embodiments C1 to C19, wherein $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, $C(O)R^{1C}$, —$C(O)$—$OR^{1C}$, —$C(O)$ $NR^{1A}R^{1B}$, —$OR^{1D}$, —$NR^{1A}SO_2R^{1D}$, —$NR^{1A}C(O)R^{1C}$, —$NR^{1C}(O)OR^{1C}$, —$NR^{1A}OR^{1C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C21. The compound of one of embodiments C1 to C19, wherein $R^1$ is independently halogen, —$CF_3$, —$CCl_3$, —$CBr_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C22. The compound of one of embodiments C1 to C19, wherein $R^1$ is independently halogen, —$CF_3$, —$CCl_3$, —$CBr_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NO_2$, —SH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted $C_1$-$C_4$ alkyl, or substituted or unsubstituted 2 to 4 membered heteroalkyl.

Embodiment C23. The compound of one of embodiments C1 to C19, wherein $R^1$ is independently halogen, —$CF_3$, —$NO_2$, or —$OCH_3$.

Embodiment C24. The compound of one of embodiments C1 to C23, wherein z1 is 2.

Embodiment C25. The compound of one of embodiments C1 to C23, wherein z1 is 1.

Embodiment C26. The compound of one of embodiments C1 to C25, wherein $R^2$ is independently unsubstituted or substituted $C_3$-$C_6$ cycloalkyl, unsubstituted or substituted $C_1$-$C_6$ alkyl, halogen, —$CX^2_3$, —$CHX^{22}$, —$CH_2X^2$, —$OCX^2_3$, —$OCH_2X^2$, —$OCHX^{22}$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted 2 to 6 membered heteroalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C27. The compound of one of embodiments C1 to C25, wherein $R^2$ is independently unsubstituted or substituted $C_3$-$C_6$ cycloalkyl, unsubstituted or substituted $C_1$-$C_6$ alkyl, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted 2 to 6 membered heteroalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C28. The compound of one of embodiments C1 to C25, wherein $R^2$ is independently unsubstituted or substituted $C_3$-$C_6$ cycloalkyl or unsubstituted or substituted $C_1$-$C_6$ alkyl, Embodiment C29. The compound of one of embodiments C1 to C25, wherein $R^2$ is independently unsubstituted cyclopropyl or —$CH_3$.

Embodiment C30. The compound of one of embodiments C1 to C29, wherein z2 is 1.

Embodiment C31. The compound of one of embodiments C1 to C30, wherein $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NR^{3C}NR^{3A}R^{3B}$, —$ONR^{3A}R^{3B}$, —NHC(O)$NR^{3C}NR^{3A}R^{3B}$, —NHC(O)$NR^{3A}R^{3B}$, —$N(O)_{m3}$, —$NR^{3A}R^{3B}$, —$C(O)R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C32. The compound of one of embodiments C1 to C30, wherein $R^3$ is independently halogen, —$CF_3$, —$CCl_3$, —$CBr_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^3$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment C33. The compound of one of embodiments C1 to C30, wherein $R^3$ is independently halogen, —$CF_3$, —$CCl_3$, —$CBr_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$NO_2$, or substituted or unsubstituted $C_1$-$C_6$ alkyl.

Embodiment C34. The compound of one of embodiments C1 to C30, wherein $R^3$ is independently halogen, —$CF_3$, —$NO_2$, or —$CH_3$.

Embodiment C35. The compound embodiment C1, having the formula:

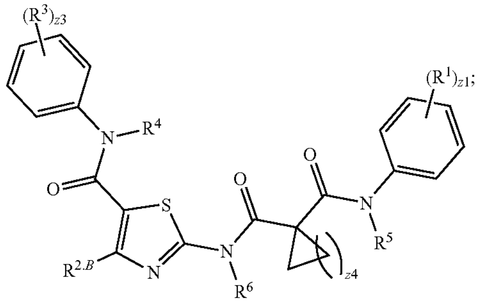

wherein $R^{2.B}$ is independently hydrogen, unsubstituted or substituted $C_3$-$C_6$ cycloalkyl, or unsubstituted or substituted $C_1$-$C_6$ alkyl.

Embodiment C36. The compound of embodiment C35, having the formula:

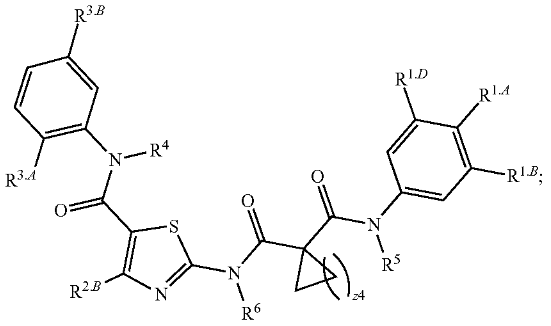

Wherein $R^{1.A}$, $R^{1.B}$, and $R^{1.D}$, are independently hydrogen, halogen, —$CX^1_3$, —$CHX^1_2$, —$CH_2X^1$, or substituted or unsubstituted alkyl; $R^{3.A}$ and $R^{3.B}$ are independently halogen, —$CX^3_3$, hydrogen, —$CHX^3_2$, —$CH_2X^3$, or substituted or unsubstituted alkyl.

Embodiment C37. The compound of one of embodiments C35 to C36, having the formula:

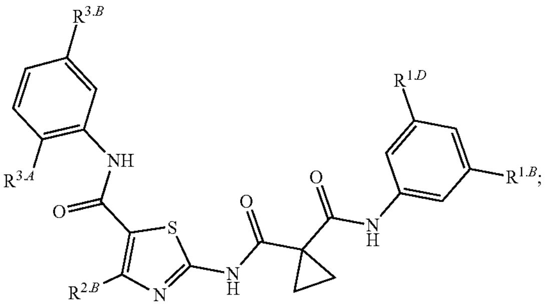

Wherein $R^{1.B}$ and $R^{1.D}$, are independently halogen or $—CX^1_3$; and $R^{3.A}$ and $R^{3.B}$ are independently halogen or $—CX^3_3$.

Embodiment C38. The compound of embodiment C37, having the formula:

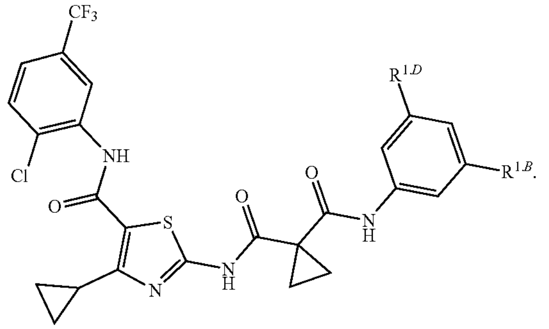

Embodiment C39. The compound of embodiment C36, having the formula:

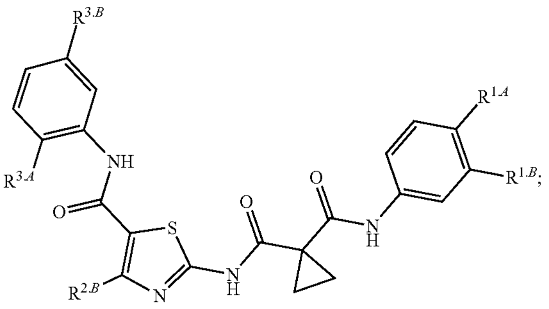

Wherein $R^{1.A}$ and $R^{1.B}$, are independently halogen or $—CX^1_3$; and $R^{3.A}$ and $R^{3.B}$ are independently halogen or $—CX^3_3$.

Embodiment C40. The compound of embodiment C39, having the formula:

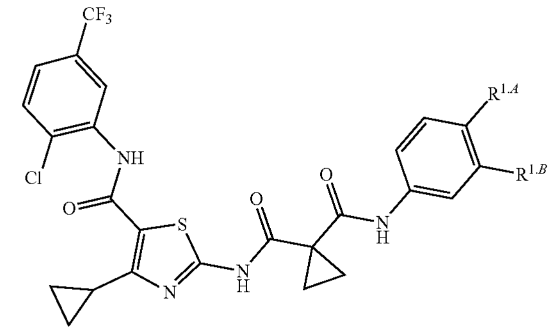

Embodiment C41. The compound of embodiment C1, having the formula:

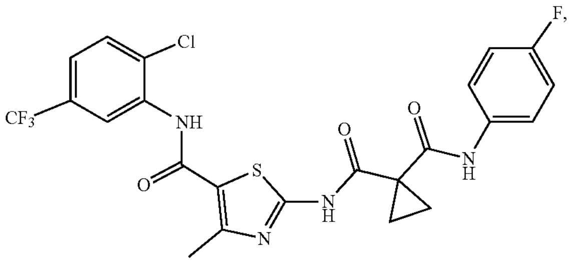

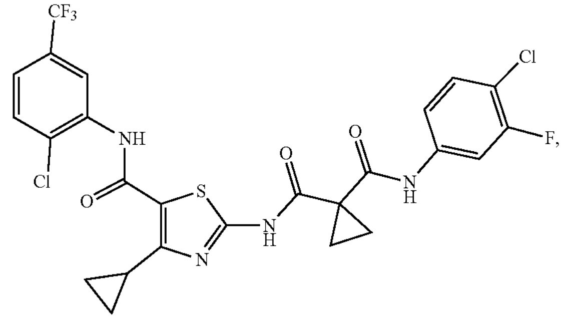

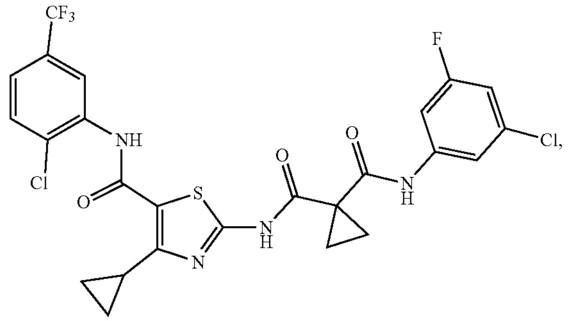

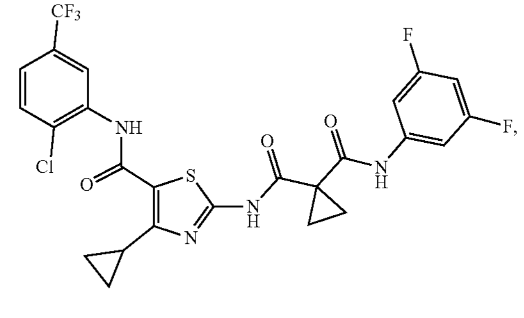

or

-continued

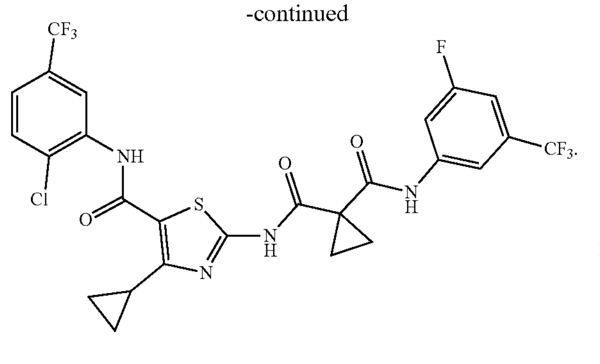

Embodiment C42. A pharmaceutical composition comprising the compound of any one of embodiments C1 to C41 and a pharmaceutically acceptable excipient.

Embodiment C43. A method of decreasing the level of Aurora A kinase protein activity in a subject, said method comprising administering a compound of one of embodiments C1 to C41 to said subject.

Embodiment C44. A method of decreasing the level of Aurora A kinase protein activity in a cell, said method comprising contacting said cell with a compound of one of embodiments C1 to C41.

Embodiment C45. The method of one of embodiments C43 to C45, wherein the compound contacts an N-MYC protein or Aurora A kinase protein.

Embodiment C46. The method of one of embodiments C43 to C46, wherein the compound reduces the level of N-MYC activity.

Embodiment C47. The method of one of embodiments C43 to C47, wherein the compound modulates the protein conformation of the Aurora A kinase protein.

Embodiment C48. The method of one of embodiments C43 to C47, wherein the compound reduces the level of N-MYC protein.

Embodiment C49. The method of one of embodiments C43 to C48, wherein the compound reduces the level of N-MYC protein contacting an Aurora A kinase protein.

Embodiment C50. A method of decreasing the level of N-MYC protein activity in a subject, said method comprising administering a compound of one of embodiments C1 to C41 to said subject.

Embodiment C51. A method of decreasing the level of N-MYC protein activity in a cell, said method comprising contacting said cell with a compound of one of embodiments C1 to C41.

Embodiment C52. The method of one of embodiments C50 to C51, wherein the compound contacts an N-MYC protein or Aurora A kinase protein.

Embodiment C53. The method of one of embodiments C50 to C52, wherein the compound reduces the level of Aurora A kinase activity.

Embodiment C54. The method of one of embodiments C50 to C53, wherein the compound modulates the protein conformation of an Aurora A kinase protein.

Embodiment C55. The method of one of embodiments C50 to C54, wherein the compound reduces the level of Aurora A kinase protein.

Embodiment C56. The method of one of embodiments C50 to C55, wherein the compound reduces the level of N-MYC protein contacting an Aurora A kinase protein.

Embodiment C57. A method of inhibiting cancer growth in a subject in need thereof, said method comprising administering to the subject in need thereof an effective amount of a compound of one of embodiments C1 to C41, wherein the compound modulates the N-MYC activity level, Aurora A kinase activity level, N-MYC protein level, or Aurora A kinase protein level in the subject.

Embodiment C58. A method of inhibiting cancer cell growth, said method comprising contacting the cancer cell with an effective amount of a compound of one of embodiments C1 to C41, wherein the compound modulates the N-MYC activity level, Aurora A kinase activity level, N-MYC protein level, or Aurora A kinase protein level in the cancer cell.

Embodiment C59. A method of treating a cancer in a subject in need thereof, said method comprising administering to the subject in need thereof an effective amount of a compound of one of embodiments C1 to C41.

Embodiment C60. The method of one of embodiments C57 to C59, wherein the cancer is lung cancer, prostate cancer, ovarian cancer, lymphoma, acute lymphoblastic leukemia, acute myeloid leukemia, Ewing Sarcoma, multiple myeloma, Non-Hodgkin lymphoma, medulloblastoma, retinoblastoma, glioma, glioblastoma, pancreatic cancer, or neuroblastoma.

Embodiment C61. The method of one of embodiments C57 to C59, further comprising co-administering an anti-cancer agent to said subject in need.

EXAMPLES

Example 1: Compound Characterization

Human neuroblastoma cell lines were obtained from either Millipore Sigma, St. Louis, MO (Kelly cells) or American Type Culture Collection, Manassas, VA (IMR32 and SK-N-BE(2) cells). Cells were cultured in RPMI1640 medium (Corning, New York, NY), supplemented with 10% fetal bovine serum, 100 unit/mL penicillin and 100 μg/mL streptomycin (Corning, New York, NY) at 37 degree Celsius with 5% $CO_2$ in air atmosphere. Cells cultured in flat clear bottom, black 96-well plates (Corning, New York, NY) were treated with different concentrations of a compound of the invention, which was dissolved in the culture media (200 μL/well), overnight or up to 3 days. Cells were fixed with 4% paraformaldehyde (in Phosphate-Buffered Saline or PBS, 100 μL/well) for 30 minutes at room temperature. Cells were briefly washed three times with PBS afterwards, and then treated with PBS containing 0.1% Triton X-100 (100 μL/well) for 30 minutes at room temperature. For N-myc staining, cells were further treated with PBS containing 0.01% IRDye 700DX NHS Ester (LI-COR Biosciences, Lincoln, NE. 100 μL/well) for 30 minutes at room temperature. Cells were again washed three times with PBS, and then treated with a Tris-buffered saline solution with 0.1% Tween 20 (TBST) and 5% non-fat milk (50 μL/well) for 1 hour at room temperature. Cells were then treated with TBST with 5% non-fat milk (50 μL/well) containing a mouse anti N-Myc antibody (Clone B8.4.B, 1:500 dilution, Santa Cruz Biotechnology, Santa Cruz, CA), or a combination of a rabbit anti-Histone H3 (phospho S10) antibody (Clone EPR17246, 1:10000 dilution, abcam, Cambridge, MA) and a mouse anti-Histone H3 antibody (Clone 1G1, 1:250 dilution, Santa Cruz Biotechnology, Santa Cruz, CA) overnight at 4 degree Celsius in the dark. Cells were washed three times with TBST, and then treated with TBST with 5% non-fat milk (50 μL/well) containing an IRDye 800CW donkey anti-mouse IgG antibody (1:1000 dilution, LI-COR Biosciences, Lincoln, NE) for N-myc staining, or IRDye® 800CW donkey anti-rabbit IgG and IRDye 680RD donkey anti-mouse IgG antibodies (1:1000 dilution, LI-COR Biosciences, Lincoln, NE) for Histone H3 (phospho S10) and Histone H3 staining, incubated for 1 hour at room temperature in the dark. Cells were then washed four times with TBST and the plate was scanned using an Odyssey 9120 Imaging System (LI-COR Biosciences, Lincoln, NE). Signals for N-myc, total protein, Histone H3 (phospho S10), and Histone H3 were obtained from the images using the ImageStudio software (Version 4.0.21, LI-COR Biosciences, Lincoln, NE). Normalized signals for N-myc (over total protein), and Histone H3 (phospho S10) (over Histone H3) were plotted in Prism 7 software (GraphPad Software, San Diego, CA). A four-parameter dose-response curve was fitted using a variable slope model and the $EC_{50}$ was calculated in Prism 7 software (GraphPad Software, San Diego, CA).

Table of Compound Activity (EC50+(greater than 1 μM), ++(250 nM-1 μM), +++(less than 250 nM)) measured using activity assay described immediately above wherein Activity is EC50 for decreasing N-myc protein level.

| Compound | Activity |
|---|---|
| SSTA-0152 | ++ |
| SSTA-0168 | + |
| SSTA-0169 | + |
| SSTA-0170 | + |
| SSTA-0171 | + |
| SSTA-0190 | + |
| SSTA-0191 | + |
| SSTA-0194 | + |
| SSTA-0195 | + |
| SSTA-0196 | + |
| SSTA-0200 | + |
| SSTA-0204 | ++ |
| SSTA-0217 | ++ |
| SSTA-0218 | ++ |
| SSTA-0229 | + |
| SSTA-0233 | ++ |
| SSTA-0234 | ++ |
| SSTA-0235 | ++ |
| SSTA-0236 | ++ |
| SSTA-0237 | ++ |
| SSTA-0238 | ++ |
| SSTA-0239 | + |
| SSTA-0240 | + |
| SSTA-0241 | ++ |
| SSTA-0242 | + |
| SSTA-0247 | + |
| SSTA-0248 | + |
| SSTA-0250 | ++ |
| SSTA-0251 | ++ |
| SSTA-0252 | + |
| SSTA-0258 | + |
| SSTA-0259 | +++ |
| SSTA-0260 | +++ |
| SSTA-0261 | ++ |
| SSTA-0262 | ++ |
| SSTA-0263 | +++ |
| SSTA-0264 | +++ |

Example 2: Compound Synthesis and Characterization

General Synthetic Route #1: Disconnection of the thiazole 5-position amide—Modification of Ring B and Ring C. Variables used in the scheme below are only intended as placeholder variables and do not necessarily correspond to variables recited in aspects, embodiments, claims, or elsewhere in the application and a person having ordinary skill will understand which variables outside the scheme below correspond to the variables used in the scheme below (e.g., X, $R_1$, and $R_2$ in the scheme below may correspond to $R^1$, $R^2$, and $R^3$ respectively, used elsewhere in the application).

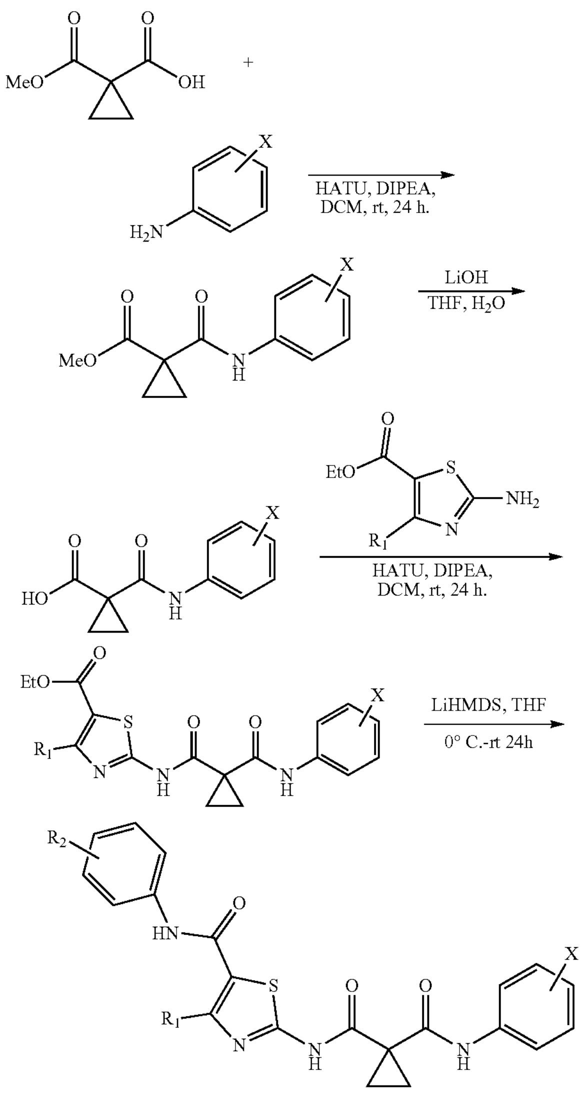

General Synthetic Route #2: Disconnection of the thiazole 5-position amide—Modification of Ring B and Ring C. Variables used in the scheme below are only intended as placeholder variables and do not necessarily correspond to variables recited in aspects, embodiments, claims, or elsewhere in the application and a person having ordinary skill will understand which variables outside the scheme below correspond to the variables used in the scheme below (e.g., X, $R_1$, and $R^2$ in the scheme below may correspond to $R^1$, $R^2$, and $R^3$ respectively, used elsewhere in the application).

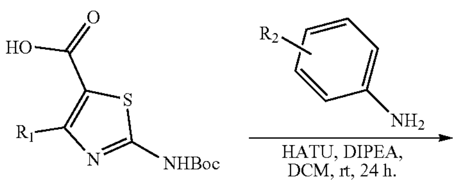

-continued

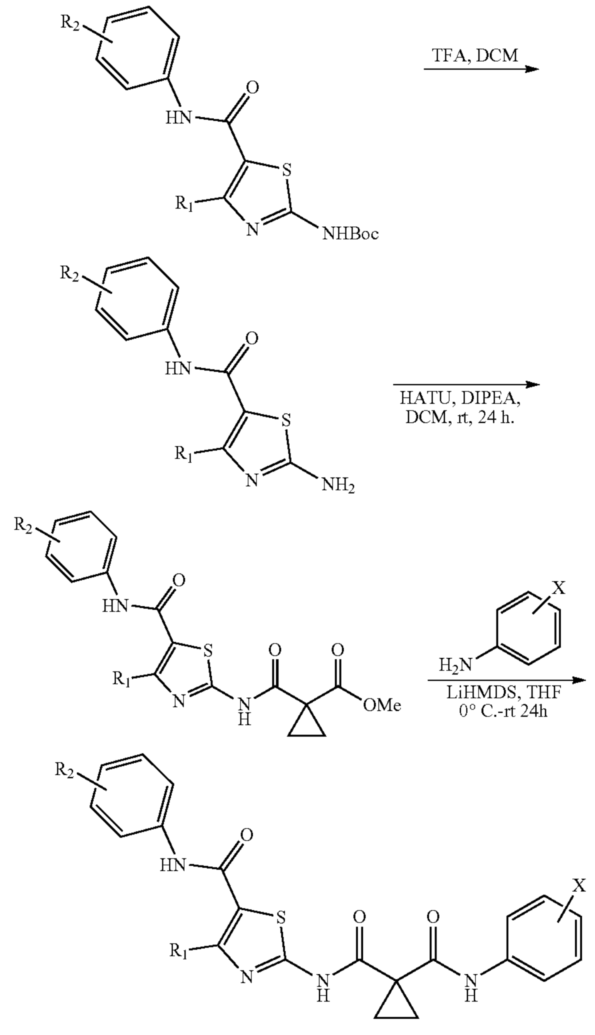

General Procedure for the Synthesis of Intermediate Substituted Cyclopropane Carboxylic Acids

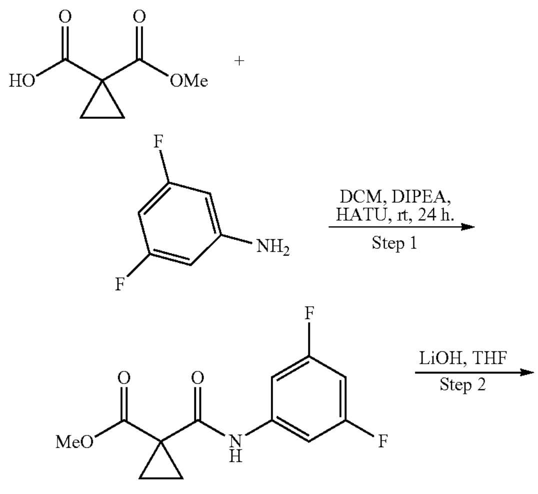

-continued

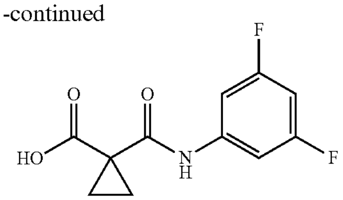

Step 1: Synthesis of methyl 1-((3,5-difluorophenyl)carbamoyl)cyclopropane-1-carboxylate: cyclopropane-1,1-dicarboxylic acid methyl ester (7 mmol, 1 eq), 3,5-difluoroaniline (14 mmol, 2 eq), was dissolved in DMF (30 mL) at room temperature. and DIPEA (28 mmol, 4.0 eq) was added followed by HATU (12 mmol, 1.7 eq). The reaction was stirred at 60° C. for 18 hours. The reaction was cooled to room temperature, diluted with EtOAc (40 mL), washed with water (30 mL), washed with 10% LiCl (20 mL), washed with brine (20 mL), dried over $Na_2SO_4$, and concentrated under reduced pressure. The product was purified by normal phase chromatography using hexanes/ethyl acetate (10-50%) to afford a pale yellow solid (850 mg, 48%). 1H NMR (400 MHz, DMSO-d6) δ 10.75 (s, 1H), 7.55 (dd, 2H), 6.98 (t, 1H), 3.69 (s, 3H), 1.3 (s, 4H). Calc. for $C_{12}$H11F2NO3, found 256.5 (MH+).

Step 2: Synthesis of 1-((3,5-difluorophenyl)carbamoyl)cyclopropane-1-carboxylic acid: methyl 1-((3,5-difluorophenyl)carbamoyl)cyclopropane-1-carboxylate (3.0 mmol, 1 eq) was stirred in THF at room temperature. 1 N LiOH (13 mmol, 4 eq) was added and the reaction was stirred for 2 hours monitored by LCMS. The reaction was cooled to 5° C. with an ice bath and acidified to pH 3 with 1 N HCl. The product was extracted with EtOAc (3×50 mL), dried over $Na_2SO_4$ and concentrated under reduced pressure to afford a white solid (750 mg, 94%). 1H NMR (400 MHz, DMSO-d6) δ 10.75 (s, 1H), 7.55 (dd, 2H), 6.98 (t, 1H), 1.3 (s, 4H). Calc. for C11H9F2NO3, found 242.1 (MH+).

Example #1: N-(5-((2-chloro-5-(trifluoromethyl)phenyl)carbamoyl)-4-methylthiazol-2-yl)-N-(4-fluorophenyl)cyclopropane-1,1-dicarboxamide (SSTA-0152)

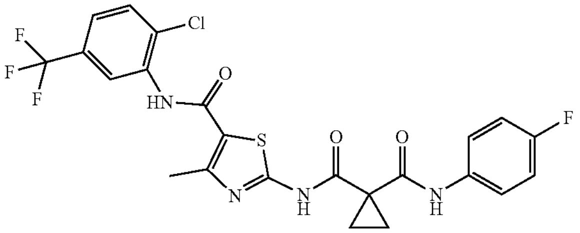 [SMILES: Cc1nc(NC(=O)C2(C(=O)Nc3ccc(F)cc3)CC2)sc1C(=O)Nc1cc(C(F)(F)F)ccc1Cl]

Final step: 1-((4-fluorophenyl)carbamoyl)cyclopropane-1-carboxylic acid (0.13 mmol, 1 eq), 2-amino-N-(2-chloro-5-(trifluoromethyl)phenyl)-4-methylthiazole-5-carboxamide (0.15 mmol, 1.1 eq), was dissolved in DMF (1 mL) at room temperature. and DIPEA (0.40 mmol, 3.0 eq) was added followed by HATU (0.18 mmol, 1.3 eq). The reaction was stirred at room temperature for 24 hours. The reaction was cooled to room temperature, diluted with EtOAc (40 mL), washed with water (10 mL), washed with brine (10 mL), dried over $Na_2SO_4$ and concentrated under reduced pressure. The product was purified by normal phase chromatography using hexanes/ethyl acetate (10-50%) to afford a pale yellow solid (20 mg, 28%). $^1$H NMR (400 MHz, DMSO-$d_6$) δ 9.95 (s, 1H), 9.78 (s, 1H), 8.09 (s, 1H), 7.80 (d, 1H), 7.70-7.52 (m, 3H), 7.22-7.07 (m, 2H), 2.57 (s, 3H), 1.54 (s, 4H). MS (EI) Calc. for $C_{23}H_{17}ClF_4N_4O_3S$, found 541.3 (MH+).

General Procedure #1 for the Synthesis of Final Compounds Using N-(5-((2-chloro-5-(trifluoromethyl)phenyl)carbamoyl)-4-methylthiazol-2-yl)-N-(4-fluorophenyl)cyclopropane-1,1-dicarboxamide (SSTA-0152) as an Example

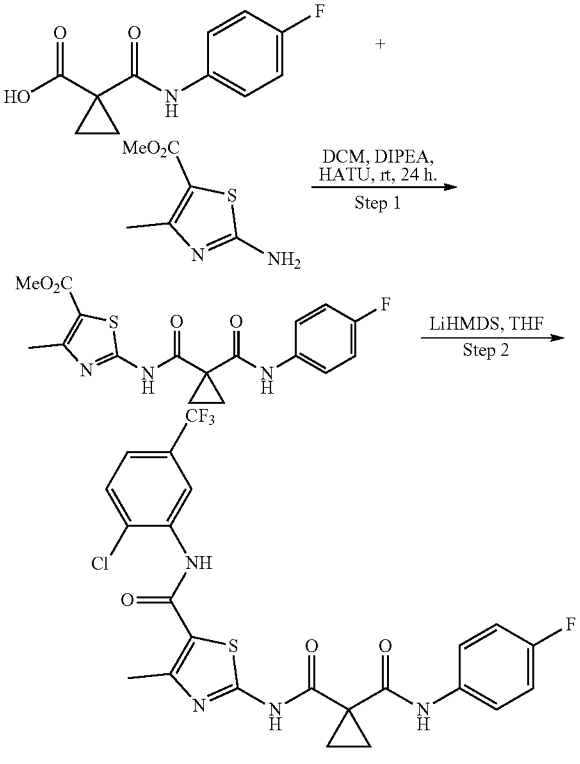

Step 1: Synthesis of methyl 2-(1-((4-fluorophenyl)carbamoyl)cyclopropane-J-carboxamido)-4-methylthiazole-5-carboxylate: 1-((4-fluorophenyl) carbamoyl)cyclopropane-1-carboxylic acid (22 mmol, 1 eq), methyl 2-amino-4-methylthiazole-5-carboxylate (34 mmol, 1.5 eq), was dissolved in DMF (100 mL) at room temperature. and DIPEA (67 mmol, 3.0 eq) was added followed by HATU (29 mmol, 1.3 eq). The reaction was stirred at room temperature for 36 hours. The reaction was diluted with EtOAc (200 mL), washed with water (100 mL), washed with brine (100 mL), dried over $Na_2SO_4$, and concentrated under reduced pressure. The product was purified by normal phase chromatography using hexanes/ethyl acetate (10-50%) to afford a pale yellow solid (4.2 g, 50%). 1H NMR (400 MHz, DMSO) δ 9.95 (s, 1H), 7.61 (dd, 2H), 7.20-7.06 (m, 2H), 3.77 (s, 3H), 2.53 (s, 3H), 1.52 (s, 4H). Calc. for $C_{17}H_{16}FN_3O_4S$, found 378.1 (MH+).

Step 2: To a stirred solution of ethyl 2-(1-((4-fluorophenyl)carbamoyl)cyclopropane-1-carboxamido)-4-methylthiazole-5-carboxylate (SSTA-0152): methyl 2-(1-((4-fluorophenyl)carbamoyl)cyclopropane-1-carboxamido)-4-methylthiazole-5-carboxylate (200 mg, 0.511 mmol, 1 eq) in THF (10 mL) at 0° C. was added 2-chloro-5-(trifluoromethyl)aniline (119 mg, 0.613 mmol, 1.2 eq) followed by LiHMDS (1M solution in THF, 2.55 mL, 2.557 mmol, 5 eq). The reaction mixture was allowed to attain room temperature and stirred for 1 h. The progress of the reaction was monitored by TLC (M.Ph: 50% EtOAc in n-hexane; $Rf_{SM1}$: 0.6, $Rf_{SM2}$: 0.8, $Rf_{RM}$: 0.4). After completion of reaction, the reaction mixture was quenched with ice cold water and extracted with ethyl acetate (2×25 mL). The combined organic layers was dried over anhydrous sodium sulfate, filtered and concentrated to dryness. The crude was purified by preparative HPLC to afford SSTA-0152 (20 mg, 14.4%) as an off-white solid. $^1$H NMR (400 MHz, DMSO-$d_6$) δ ppm 12.70 (br. s, 1H), 9.98 (br. s, 1H), 9.80 (br. s, 1H), 8.05-8.15 (m, 1H), 7.81 (d, J=8.80 Hz, 1H), 7.64 (d, J=8.31 Hz, 3H), 7.16 (t, J=8.80 Hz, 2H), 2.58 (s, 3H), 1.51-1.57 (m, 4H). LCMS: 541.05 $(M+H)^+$, $R_f$=2.331 min. HPLC: 97.71%; $R_f$=10.13 min.

Example #2: Synthesis N-(5-((2-chloro-5-(trifluoromethyl)phenyl)carbamoyl)-4-methylthiazol-2-yl)-N-(3-(trifluoromethyl)phenyl)cyclopropane-1,1-dicarboxamide (SSTA-0168)

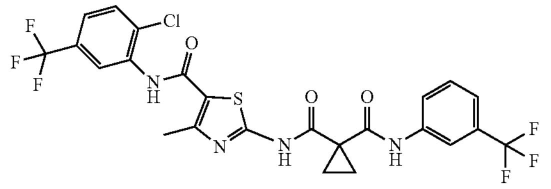 [SMILES: Cc1nc(NC(=O)C2(C(=O)Nc3cccc(C(F)(F)F)c3)CC2)sc1C(=O)Nc1cc(C(F)(F)F)ccc1Cl]

Synthesis was performed using general procedure #1. Analytical data: $^1$H NMR (400 MHz, DMSO-$d_6$) δ 10.26 (s, 1H), 9.74 (s, 1H), 8.10 (d, J=6.9 Hz, 2H), 7.77 (s, 2H), 7.62 (s, 1H), 7.55 (s, 1H), 7.41 (s, 1H), 2.57 (s, 3H), 1.52 (s, 4H). MS (EI) Calc. for $C_{24}H_{17}ClF_6N_4O_3S$, found 590.06 (MH+).

Example #3: Synthesis of N-(5-((2-chloro-5-(trifluoromethyl)phenyl)carbamoyl)-4-methylthiazol-2-yl)-N-(4-chlorophenyl)cyclopropane-1,1-dicarboxamide (SSTA-169)

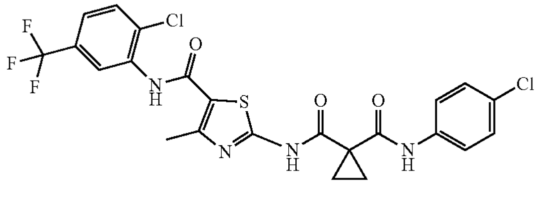 [SMILES: Cc1nc(NC(=O)C2(C(=O)Nc3ccc(Cl)cc3)CC2)sc1C(=O)Nc1cc(C(F)(F)F)ccc1Cl]

Synthesis was performed using general procedure #1. Analytical data: $^1$H NMR (400 MHz, DMSO) δ 12.65 (s, 1H), 10.06 (s, 1H), 9.78 (s, 1H), 8.09 (s, 1H), 7.80 (d, J=8.4 Hz, 1H), 7.73-7.56 (m, 3H), 7.42-7.30 (m, 2H), 2.57 (s, 3H), 1.54 (s, 4H). MS (EI) Calc. for $C_{23}H_{17}C_{12}F_3N_4O_3S$, found 558.1 (MH+).

Example #4: Synthesis N-(5-((2-chloro-5-(trifluoromethyl)phenyl)carbamoyl)-4-methylthiazol-2-yl)-N-(2-chlorophenyl)cyclopropane-1,1-dicarboxamide (SSTA-170)

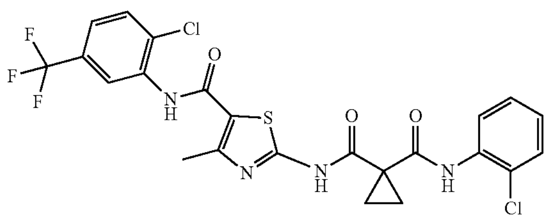 [SMILES: Cc1nc(NC(=O)C2(C(=O)Nc3ccccc3Cl)CC2)sc1C(=O)Nc1cc(C(F)(F)F)ccc1Cl]

Synthesis was performed using general procedure #1. Analytical data: $^{1}$H NMR (400 MHz, DMSO) δ 9.89 (s, 1H), 8.05 (s, 1H), 7.80 (d, 1H), 7.67-7.61 (m, 1H), 7.52 (dd, 1H), 7.35 (t, 1H), 7.19 (s, 1H), 2.57 (s, 3H), 1.79-1.60 (m, 4H). MS (EI) Calc. for $C_{23}H_{17}Cl_2F_3N_4O_3S$, found 558.1 (MH+).

Example #5: Synthesis of N-(5-((2-chloro-5-(trifluoromethyl)phenyl)carbamoyl)-4-methylthiazol-2-yl)-N-(3-fluorophenyl)cyclopropane-1,1-dicarboxamide (SSTA-171)

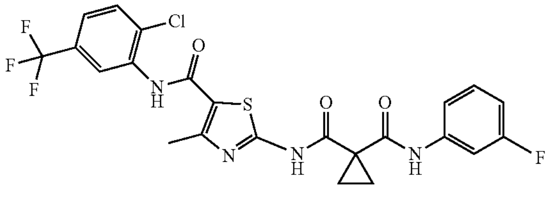 [SMILES: Cc1nc(NC(=O)C2(C(=O)Nc3cccc(F)c3)CC2)sc1C(=O)Nc1cc(C(F)(F)F)ccc1Cl]

Synthesis was performed using general procedure. Analytical data: $^{1}$H NMR (400 MHz, DMSO) δ 12.65 (s, 1H), 10.16 (s, 1H), 9.78 (s, 1H), 8.09 (s, 1H), 7.80 (d, 1H), 7.67-7.55 (m, 2H), 7.33 (q, 2H), 6.89 (ddt, 1H), 2.58 (s, 3H), 1.54 (s, 4H). MS (EI) Calc. for $C_{23}H_{17}ClF_4N_4O_3S$, found 541.5 (MH+).

Example #6: N-(4-fluorophenyl)-N-(4-methyl-5-((3-(trifluoromethyl)phenyl)carbamoyl)oxazol-2-yl)cyclopropane-1,1-dicarboxamide (SSTA-190)

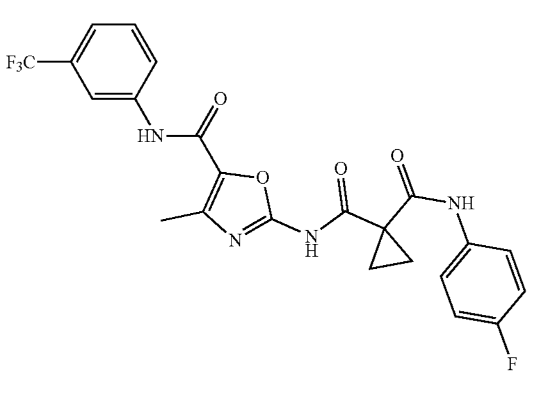 [SMILES: Cc1nc(NC(=O)C2(C(=O)Nc3ccc(F)cc3)CC2)oc1C(=O)Nc1cccc(C(F)(F)F)c1]

Synthesis was performed using general procedure #1. Final step: To a stirred solution of ethyl 2-(1-((4-fluorophenyl)carbamoyl)cyclopropane-1-carboxamido)-4-methyloxazole-5-carboxylate (96 mg, 0.255 mmol, 1 eq) in THF (10 mL) at 0° C. was added 3-(trifluoromethyl)aniline (49.4 mg, 0.306 mmol, 1.2 eq) followed by LiHMDS (1M solution in THF, 1.27 mL, 1.278 mmol, 5 eq). The reaction mixture was allowed to attain room temperature and stirred for 16 h. The progress of the reaction was monitored by TLC (M.Ph: 50% EtOAc in n-hexane; $Rf_{SM}$: 0.7, $Rf_{RM}$: 0.5). After completion of reaction, the reaction mixture was quenched with water and extracted with EtOAc (3×25 mL). The combined organic layer was dried over anhydrous sodium sulfate, filtered and concentrated to dryness. The crude was purified through silica gel column chromatography (elution: 0-50% EtOAc in n-hexane) to afford SSTA-190 (30 mg, 24%) as an off-white solid. $^{1}$H NMR (400 MHz, DMSO-$d_6$) δ ppm 10.30 (br. s, 1H), 9.93 (br. s, 1H), 8.20 (br. s, 1H), 7.98 (d, J=7.34 Hz, 1H), 7.53-7.66 (m, 4H), 7.45 (d, J=7.83 Hz, 1H), 7.15 (t, J=9.05 Hz, 2H), 2.41 (br. s, 3H), 1.49-1.55 (m, 4H). LCMS: 513.13 $(M+Na)^+$, $R_f$=2.083 min. HPLC: 95.07%; $R_f$=9.150 min.

Example #7. Synthesis N-(5-((3,4-dichlorophenyl)carbamoyl)-4-(trifluoromethyl)thiazol-2-yl)-N-(4-fluorophenyl)cyclopropane-1,1-dicarboxamide (SSTA-0194)

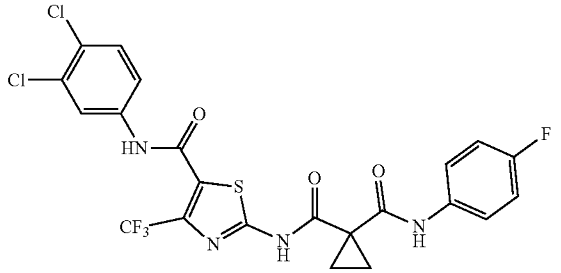 [SMILES: O=C(Nc1ccc(Cl)c(Cl)c1)c1sc(NC(=O)C2(C(=O)Nc3ccc(F)cc3)CC2)nc1C(F)(F)F]

Synthesis was performed using general procedure #1. Final step: To a stirred solution of ethyl 2-(1-((4-fluorophenyl)carbamoyl)cyclopropane-1-carboxamido)-4-(trifluoromethyl)thiazole-5-carboxylate (1) (120 mg, 0.269 mmol, 1 eq) in THF (10 mL) at 0° C. was added 3,4-dichloroaniline (43.6 mg, 0.269 mmol, 1 eq) followed by LiHMDS (1M solution in THF, 1.34 mL, 1.345 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with ice cold water and extracted with DCM (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0194 (50 mg, 33.1%) as an off-white solid. $^{1}$H NMR (400 MHz, DMSO-$d_6$) δ ppm 13.12 (s, 1H), 11.02 (s, 1H), 10.01 (br. s, 1H), 8.02 (d, J=1.96 Hz, 1H), 7.55-7.67 (m, 4H), 7.16 (t, J=8.80 Hz, 2H), 1.52-1.59 (m, 4H). LCMS: 560.95 $(M+H)^+$, $R_f$=2.320 min. HPLC: 99.80%; $R_f$=10.21 min.

Example #8: Synthesis of N-(5-((3,4-dichlorophenyl)carbamoyl)-4-methyloxazol-2-yl)-N-(4-fluorophenyl)cyclopropane-1,1-dicarboxamide (SSTA-191)

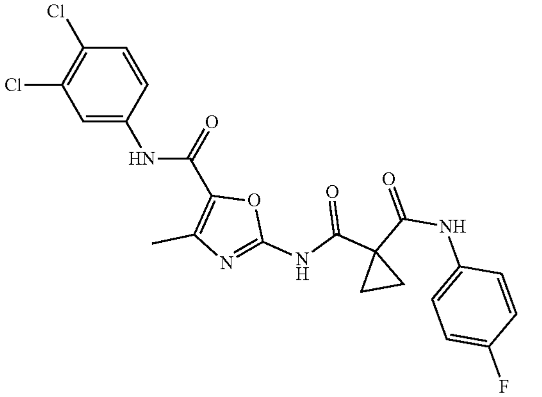 [SMILES: Cc1nc(NC(=O)C2(C(=O)Nc3ccc(F)cc3)CC2)oc1C(=O)Nc1ccc(Cl)c(Cl)c1]

Synthesis was performed using general procedure #1. Final step: To a stirred solution of ethyl 2-(1-((4-fluorophenyl)carbamoyl)cyclopropane-1-carboxamido)-4-methyloxazole-5-carboxylate (96 mg, 0.255 mmol, 1 eq) in DMF (10 mL) was added 3,4-dichloroaniline (49.7 mg, 0.306 mmol, 1.2 eq), HATU (0.146 mg, 0.383 mmol, 1.5 eq) followed by DIPEA (0.067 mL, 0.383 mmol, 1.5 eq) at room temperature and stirred for 16 h. The progress of the reaction was monitored by TLC (M.Ph: 50% EtOAc in n-hexane; $Rf_{SM}$: 0.7, $Rf_{RM}$: 0.3). After completion of reaction, the reaction mixture was quenched with water and extracted with EtOAc (3x25 mL). The combined organic layer was dried over anhydrous sodium sulfate, filtered and concentrated to dryness. The crude was purified through silica gel column chromatography (elution: 0-50% EtOAc in n-hexane) to afford SSTA-0191 (40 mg, 33.3%) as an off white solid. $^1$H NMR (400 MHz, DMSO-$d_6$) δ ppm 11.83 (br. s, 1H), 10.49 (br. s, 1H), 9.92 (br. s, 1H), 8.10 (br. s, 1H), 7.71 (d, J=7.83 Hz, 1H), 7.54-7.63 (m, 3H), 7.16 (t, J=8.80 Hz, 2H), 2.40 (br. s, 3H), 1.47-1.60 (m, 4H). LCMS: 490.95 $(M+H)^+$, $R_f$=2.156 min. HPLC: 95.43%; $R_f$=9.272 min.

Example #9: Synthesis of N-(4-fluorophenyl)-N-(4-phenyl-5-((3-(trifluoromethyl)phenyl)carbamoyl)thiazol-2-yl)cyclopropane-1,1-dicarboxamide (SSTA-195)

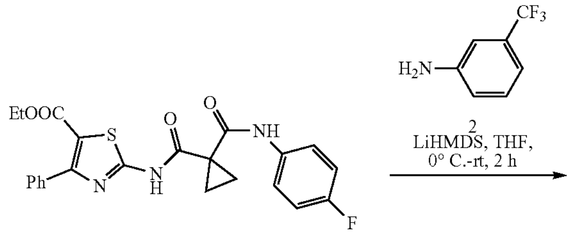

-continued

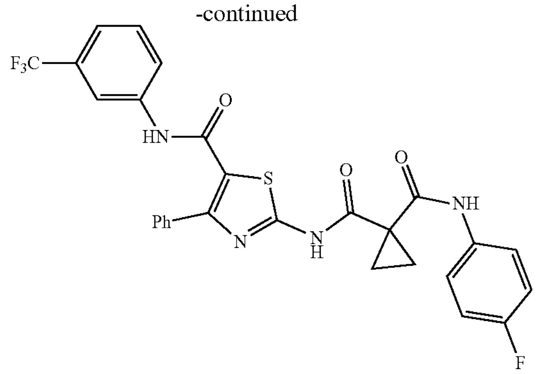

Synthesis was performed using general procedure #1. Final step: To a stirred solution of ethyl 2-(1-((4-fluorophenyl)carbamoyl)cyclopropane-1-carboxamido)-4-phenylthiazole-5-carboxylate (1) (100 mg, 0.220 mmol, 1 eq) in THF (10 mL) at 0° C. was added 3-(trifluoromethyl)aniline (35.4 mg, 0.220 mmol, 1.2 eq) followed by LiHMDS (1M solution in THF, 2.20 mL, 2.205 mmol, 10 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with ice cold water and extracted with DCM (2x25 mL). The combined organic layers was dried over anhydrous sodium sulfate, filtered and concentrated to dryness. The crude was purified through silica gel column chromatography (elution: 0-50% EtOAc in n-hexane) followed by preparative HPLC purification to afford SSTA-0195 (40 mg, 32%) as an off-white solid. $^1$H NMR (400 MHz, DMSO-$d_6$) δ ppm 12.84 (s, 1H), 10.52 (br. s, 1H), 9.98 (br. s, 1H), 8.03 (br. s, 1H), 7.76 (d, J=7.82 Hz, 1H), 7.68 (d, J=6.85 Hz, 2H), 7.63 (dd, J=5.14, 9.05 Hz, 2H), 7.56 (t, J=7.83 Hz, 1H), 7.34-7.48 (m, 4H), 7.16 (t, J=9.05 Hz, 2H), 1.54-1.60 (m, 4H). LCMS: 569.05 $(M+H)^+$, $R_f$=2.309 min. HPLC: 97.45%; $R_f$=9.820 min.

Example #10: Synthesis of N-(5-((3,4-dichlorophenyl)carbamoyl)-4-phenylthiazol-2-yl)-N-(4-fluorophenyl)cyclopropane-1,1-dicarboxamide (SSTA-0196)

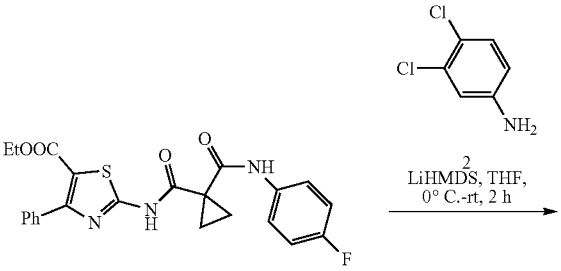

-continued

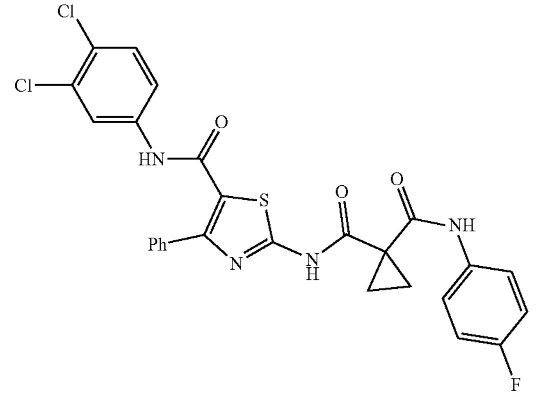

Synthesis was performed using general procedure #1. Final step: To a stirred solution of ethyl 2-(1-((4-fluorophenyl)carbamoyl)cyclopropane-1-carboxamido)-4-phenylthiazole-5-carboxylate (1) (100 mg, 0.220 mmol, 1 eq) in THF (10 mL) at 0° C. was added 3,4-dichloroaniline (42.8 mg, 0.264 mmol, 1.2 eq) followed by LiHMDS (1M solution in THF, 1.10 mL, 1.102 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with ice cold water and extracted with DCM (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0196 (14.1 mg, 11.2%) as an off-white solid. $^1$H NMR (400 MHz, DMSO-$d_6$) δ ppm 12.83 (s, 1H), 10.48 (br. s, 1H), 9.96 (br. s, 1H), 7.94 (s, 1H), 7.55-7.70 (m, 5H), 7.46 (d, J=8.80 Hz, 1H), 7.35-7.44 (m, 3H), 7.16 (t, J=8.56 Hz, 2H), 1.54-1.59 (m, 4H). LCMS: 569.10 $(M+H)^+$, $R_f$=2.382 min. HPLC: 99.27%; $R_f$=10.20 min.

Example #11: Synthesis of N-(4-cyclopropyl-5-((3,4-dichlorophenyl)carbamoyl)thiazol-2-yl)-N-(4-fluorophenyl)cyclopropane-1,1-dicarboxamide (SSTA-200)

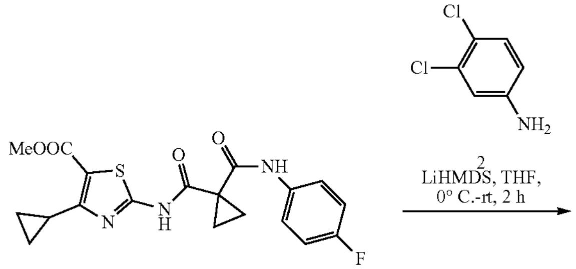

-continued

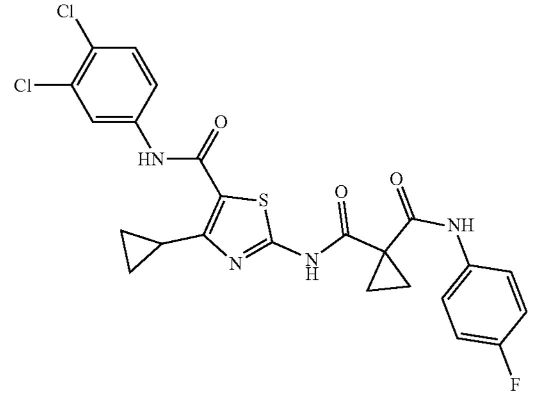

Synthesis was performed using general procedure #1. Final step: To a stirred solution of methyl 4-cyclopropyl-2-(1-((4-fluorophenyl)carbamoyl)cyclopropane-1-carboxamido)thiazole-5-carboxylate (1) (100 mg, 0.247 mmol, 1 eq) in THF (10 mL) at 0° C. was added 3,4-dichloroaniline (40.1 mg, 0.247 mmol, 1 eq) followed by LiHMDS (1M solution in THF, 1.23 mL, 1.235 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.3, $Rf_{RM}$: 0.2). After completion of reaction, the reaction mixture was quenched with ice cold water and extracted with DCM (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0200 (11.5 mg, 8.71%) as an off-white solid. $^1$H NMR (400 MHz, DMSO-$d_6$) δ ppm 12.62 (br. s, 1H), 10.19 (br. s, 1H), 9.87 (br. s, 1H), 8.07 (s, 1H), 7.65-7.71 (m, 1H), 7.56-7.64 (m, 3H), 7.16 (t, J=8.80 Hz, 2H), 2.80-2.89 (m, 1H), 1.46-1.57 (m, 4H), 0.89-1.02 (m, 4H). LCMS: 533.00 $(M+H)^+$, $R_f$=2.428 min. HPLC: 99.18%; $R_f$=10.29 min.

Example #12: Synthesis of N-(5-((2-chloro-5-(trifluoromethyl)phenyl)carbamoyl)-4-(trifluoromethyl)thiazol-2-yl)-N-(4-fluorophenyl)cyclopropane-1,1-dicarboxamide (SSTA-0217)

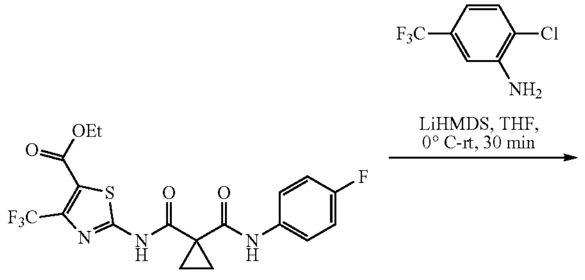

-continued

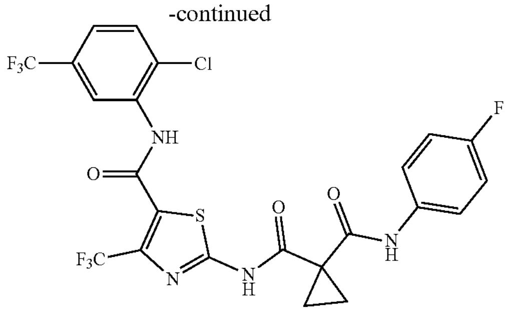

Synthesis was performed using general procedure #1. Final step: To a stirred solution of ethyl 2-(1-((4-fluorophenyl)carbamoyl)cyclopropane-1-carboxamido)-4-(trifluoromethyl)thiazole-5-carboxylate (1) (190 mg, 0.224 mmol, 1 eq) in THF (5 mL) at 0° C. was added 2-chloro-5-(trifluoromethyl)aniline (52.7 mg, 0.269 mmol, 1.2 eq) followed by LiHMDS (1M solution in THF, 1.10 mL, 1.122 mmol, 5 eq). The reaction mixture was allowed to attain room temperature and stirred for 30 min. The progress of the reaction was monitored by TLC (M.Ph: 15% EtOAc in n-hexane; $Rf_{SM}$: 0.4, $Rf_{RM}$: 0.3). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through preparative HPLC to afford SSTA-0217 (15 mg, 11.2%) as an off-white solid. $^1H$ NMR (400 MHz, DMSO-$d_6$) δ ppm $^1H$ NMR (400 MHz, DMSO-$d_6$) δ 13.11 (br. s, 1H), 10.71 (br. s, 1H), 10.02 (br. s, 1H), 8.08 (br. s, 1H), 7.83 (d, J=8.31 Hz, 1H), 7.69 (d, J=7.82 Hz, 1H), 7.62 (dd, J=4.89, 8.31 Hz, 2H), 7.16 (t, J=8.56 Hz, 2H), 1.51-1.60 (m, 4H). LCMS: 595.00 $(M+H)^+$, $R_f$=2.342 min. HPLC: 97.63%; $R_f$=9.890 min Example #13: Synthesis of N-(5-((2-chloro-5-(trifluoromethyl)phenyl)carbamoyl)-4-cyclopropylthiazol-2-yl)-N-(4-fluorophenyl)cyclopropane-1,1-dicarboxamide (SSTA-0218)

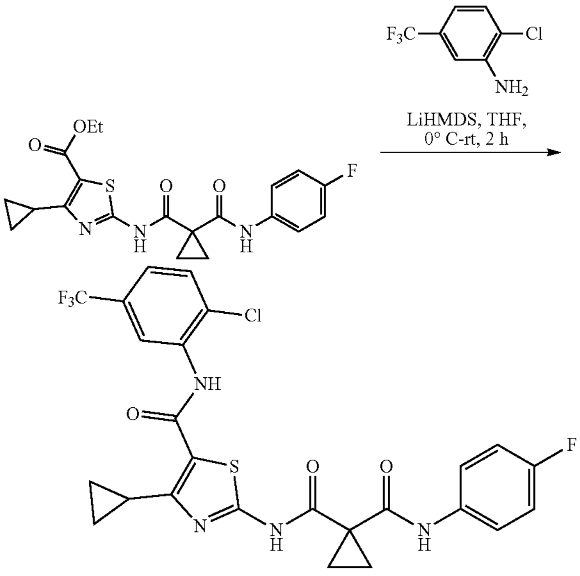

Synthesis was performed using general procedure #1. Final step: To a stirred solution of ethyl 4-cyclopropyl-2-(1-((4-fluorophenyl)carbamoyl)cyclopropane-1-carboxamido)thiazole-5-carboxylate (1) (100 mg, 0.248 mmol, 1 eq) in THF (5 mL) at 0° C. was added 2-chloro-5-(trifluoromethyl)aniline (72.7 mg, 0.372 mmol, 1.5 eq) followed by LiHMDS (1M in THF, 1.24 mL, 1.240 mmol, 5 eq). The reaction mixture was allowed to attain room temperature and stirred for 2 h. The progress of the reaction was monitored by TLC (M.Ph: 40% EtOAc in n-hexane; $Rf_{SM}$: 0.4, $Rf_{RM}$: 0.5). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through preparative HPLC to afford SSTA-0218 (0.010 g, 7.14%) as an off-white solid. $^1H$ NMR (400 MHz, DMSO-$d_6$) δ ppm 12.63 (br. s, 1H), 9.85 (br. s, 1H), 9.79 (br. s, 1H), 8.11 (br. s, 1H), 7.80 (d, J=7.82 Hz, 1H), 7.55-7.66 (m, 3H), 7.16 (t, J=8.80 Hz, 2H), 2.82-2.92 (m, 1H), 1.54 (d, J=7.83 Hz, 4H), 0.92-1.05 (m, 4H). LCMS: 566.90 $(M+H)^+$, $R_f$=2.449 min. HPLC: 98.55%; $R_f$=10.38 min.

Example #14: Synthesis of N-(5-((2-chloro-5-(trifluoromethyl)phenyl)carbamoyl)-4-methylthiazol-2-yl)-N-(4-(5-methyl-1,2,4-oxadiazol-3-yl)phenyl)cyclopropane-1,1-dicarboxamide (SSTA-0229)

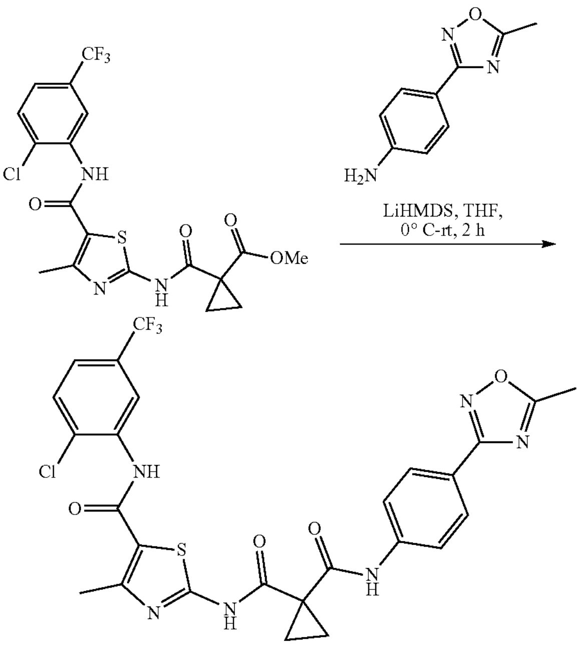

Synthesis was performed using general procedure #1. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 4-(5-methyl-1,2,4-oxadiazol-3-yl)aniline (49.1 mg, 0.280 mmol, 1.5 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 70% EtOAc in n-hexane; $Rf_{SM1}$: 0.5, $Rf_{RM}$: 0.4). After completion of reaction, the reaction mixture was quenched with saturated $NH_4Cl$ solution and extracted with ethyl acetate (2×25 mL). The combined organic layer was dried over anhydrous sodium sulfate, filtered and concentrated to dryness. The crude was purified through preparative HPLC to afford SSTA-0229 (17 mg, 13.4%) as an off white solid. $^1H$ NMR (400 MHz, DMSO-$d_6$) δ ppm 12.68 (br. s, 1H), 10.28 (br. s, 1H), 9.78 (br. s, 1H), 8.11 (br. s, 1H), 7.95 (d, J=7.63 Hz, 2H), 7.77-7.86 (m, 3H), 7.64 (d, J=6.61 Hz, 1H), 2.65 (br. s, 3H), 2.58 (br. s, 3H), 1.50-1.62 (m, 4H). LCMS: 605.15 $(M+H)^+$, $R_f$=2.225 min. HPLC: 96.09%; $R_f$=9.811 min.

Example #15: Synthesis of N-(5-((2-chloro-5-(trifluoromethyl)phenyl)carbamoyl)-4-methylthiazol-2-yl)-N-(4-chlorophenyl)cyclopropane-1,1-dicarboxamide (SSTA-0261)

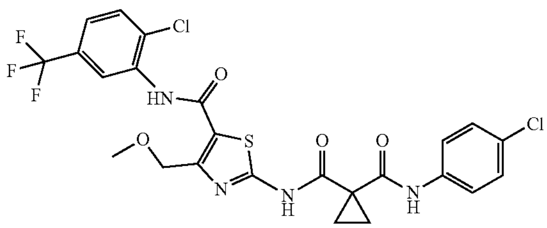 [SMILES: COCc1nc(NC(=O)C2(C(=O)Nc3ccc(Cl)cc3)CC2)sc1C(=O)Nc1cc(C(F)(F)F)ccc1Cl]

Synthesis was performed using general procedure #1. Final step: Methyl 2-((1-(4-fluorophenyl)carbamoyl) cyclopropane-1-carbonyl)oxy)-4-methyoxymethyl)thiazole-carboxylate (0.5 mmol, 1 eq), 2-chloro-5-(trifluoromethyl)aniline (0.74 mmol, 1.5 eq), was dissolved in THF (3 mL) at 0° C. and LHMDS (2.5 mmol, 5.0 eq) was added dropwise. The reaction was stirred at room temperature for 3 hours. The reaction was diluted with water (10 mL), extracted with ethyl acetate (30 mL), washed with saturated NaCl and dried over $Na_2SO_4$. Concentrated under reduced pressure. The product was purified by normal phase chromatography using hexanes/ethyl acetate (10-50%) to afford SSTA-0261 as a white solid (130 mg, 48%). $^1H$ NMR (400 MHz, DMSO-$d_6$) δ 8.34 (s, 1H), 7.80 (s, 1H), 7.64 (d, J=7.5 Hz, 1H), 7.61 (d, J=12.5 Hz, 2H), 4.73 (s, 2H), 1.54 (s, 4H). MS (EI) Calc. for $C_{24}H_{19}Cl_2F_3N_4O_4S$, found 586.05 (MH+).

Example #16: Synthesis of N-(4-chloro-3-fluorophenyl)-N-(5-((2-chloro-5-(trifluoromethyl)phenyl) carbamoyl)-4-(methoxymethyl)thiazol-2-yl)cyclopropane-1,1-dicarboxamide (SSTA-262)

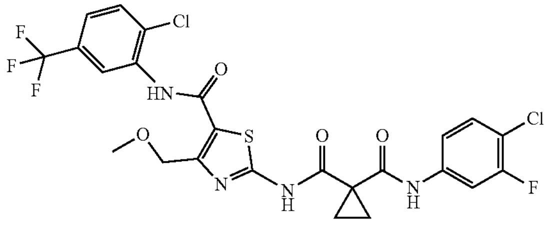 [SMILES: COCc1nc(NC(=O)C2(C(=O)Nc3ccc(Cl)c(F)c3)CC2)sc1C(=O)Nc1cc(C(F)(F)F)ccc1Cl]

Synthesis was performed using general procedure #1. Analytical data: $^1H$ NMR (400 MHz, DMSO-$d_6$) δ 10.29 (s, 2H), 8.34 (s, 1H), 7.80 (s, 2H), 7.57 (s, 1H), 7.52 (s, 1H), 7.34 (s, 1H), 4.71 (s, 2H), 3.35 (s, 3H), 1.53 (s, 4H). MS (EI) Calc. for $C_{24}H_{18}Cl_2F_4N_4O_4S$, found 604.04 (MH+).

Example #17. Synthesis of N-(5-((2-chloro-5-(trifluoromethyl)phenyl)carbamoyl)-4-cyclopropylthiazol-2-yl)-N-(3,5-difluorophenyl)cyclopropane-1,1-dicarboxamide (SSTA-263)

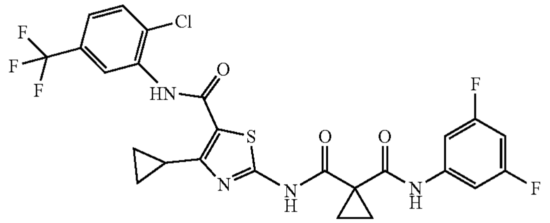 [SMILES: O=C(Nc1cc(C(F)(F)F)ccc1Cl)c1sc(NC(=O)C2(C(=O)Nc3cc(F)cc(F)c3)CC2)nc1C1CC1]

Synthesis was performed using general procedure #1. Analytical data: $^1H$ NMR (400 MHz, DMSO-$d_6$) δ 10.18 (s, 1H), 9.76 (s, 1H), 8.08 (s, 1H), 7.81 (s, 1H), 7.61 (s, 1H), 7.34 (s, 2H), 6.94 (s, 1H), 2.88 (s, 1H), 1.50 (s, 4H), 1.00 (s, 4H). MS (EI) Calc. for $C_{25}H_{18}ClF_5N_4O_3S$, found 584.07 (MH+).

Example #18: Synthesis of N-(5-((2-chloro-5-(trifluoromethyl)phenyl)carbamoyl)-4-cyclopropylthiazol-2-yl)-N-(3-fluoro-5-(trifluoromethyl)phenyl) cyclopropane-1,1-dicarboxamide (SSTA-264)

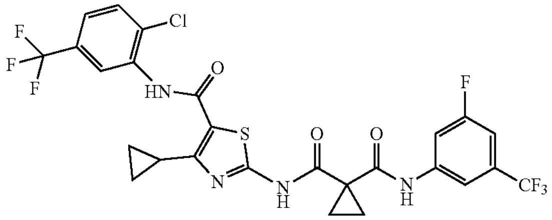 [SMILES: O=C(Nc1cc(C(F)(F)F)ccc1Cl)c1sc(NC(=O)C2(C(=O)Nc3cc(F)cc(C(F)(F)F)c3)CC2)nc1C1CC1]

Synthesis was performed using general procedure #1. Analytical data: $^1H$ NMR (400 MHz, DMSO-$d_6$) δ 10.36 (s, 1H), 9.78 (s, 1H), 8.07 (s, 1H), 7.85 (s, 3H), 7.61 (s, 1H), 7.34 (s, 1H), 2.86 (s, 1H), 1.52 (s, 4H), 0.98 (d, J=20.6 Hz, 4H). MS (EI) Calc. for $C_{26}H_{18}ClF_7N_4O_3S$, found 634.07 (MH+)

General Procedure #2 for the Synthesis of Final Compounds Using N-(5-((2-chloro-5-(trifluoromethyl)phenyl)carbamoyl)-4-methylthiazol-2-yl)-N-(3-fluoro-5-(trifluoromethyl)phenyl)cyclopropane-1,1-dicarboxamide (Example 19—SSTA-0233) as an Example

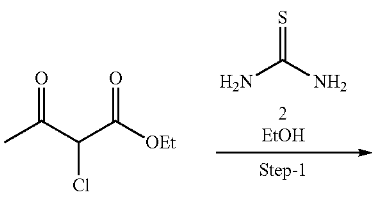

1

-continued

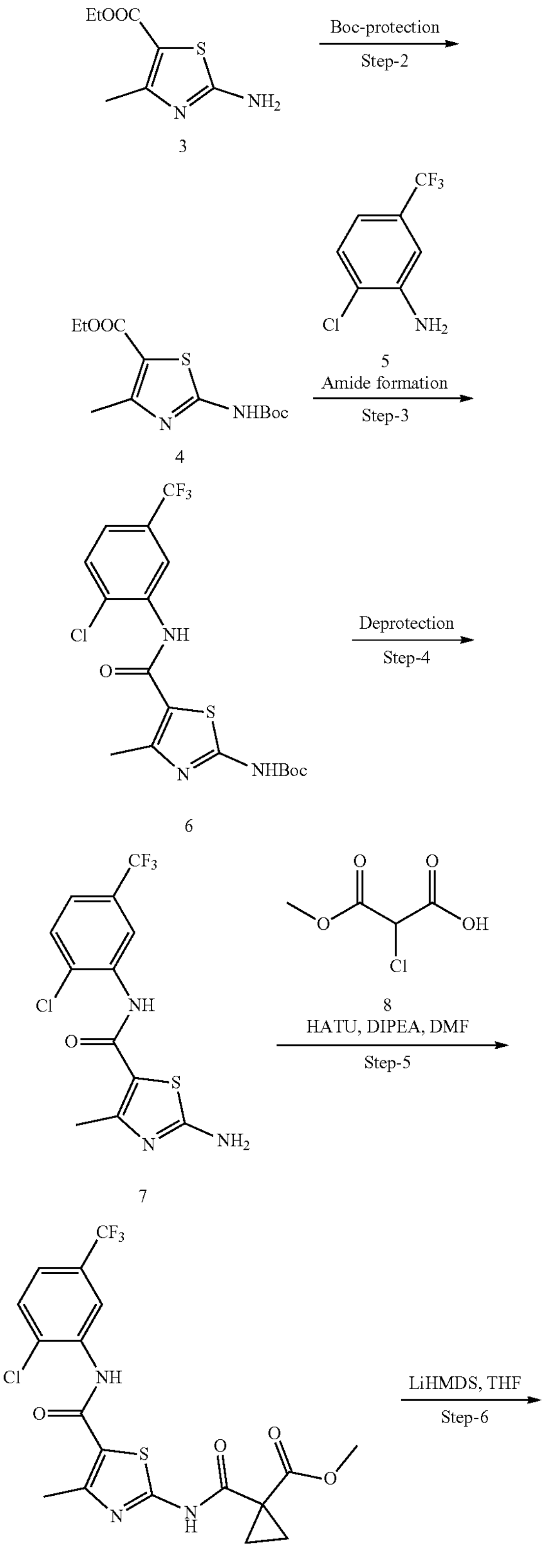

-continued

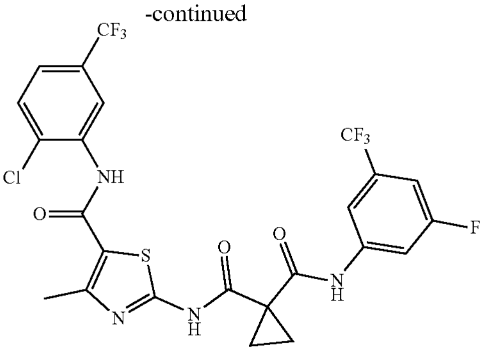

Step-1: Ethyl 2-amino-4-methylthiazole-5-carboxylate (3): To a stirred solution of ethyl 2-chloro-3-oxobutanoate (1) (20 g, 121.51 mmol, 1 eq) in EtOH (200 mL), thiourea (2) (46.24 g, 607.55 mmol, 5 eq) was added at RT. The reaction mixture was refluxed for 12 h. The progress of the reaction was monitored by TLC (M.Ph: 70% EtOAc in n-hexane; $Rf_{SM}$: 0.5, $Rf_{RM}$: 0.4). After completion of reaction, the reaction mixture was cooled to RT. The resulting precipitate so formed was filtered and dried to afford 3 (22 g, 97.34%) as a white solid. $^1$H NMR (400 MHz, DMSO-$d_6$) δ ppm 9.14 (br. s, 1H), 4.23 (q, J=6.8 Hz, 2H), 2.43 (s, 3H), 1.23 (t, J=7.6 Hz, 3H). LCMS: 187.20 $(M+H)^+$, $R_f$=1.25 min.

Step-2: Ethyl 2-((tert-butoxycarbonyl)amino)-4-methylthiazole-5-carboxylate (4): To a stirred solution of ethyl 2-amino-4-methylthiazole-5-carboxylate (3) (5.6 g, 30.07 mmol, 1 eq) in THF (50 mL), triethylamine (6.08 g, 60.14 mmol, 2 eq), DMAP (0.367 g, 0.03 mmol, 0.1 eq) and $Boc_2O$ (13.12 g, 30.07 mmol, 1 eq) were added at RT. The reaction mixture was stirred at RT for 12 h. The progress of the reaction was monitored by TLC (M.Ph: 10% EtOAc in n-hexane; $Rf_{SM}$: 0.5, $Rf_{RM}$: 0.65). After completion of reaction, the reaction mixture was diluted with water and extracted with ethyl acetate (2×500 mL). The combined organic layers was dried over anhydrous sodium sulfate, filtered and concentrated to dryness. The crude was purified through silica gel column chromatography (elution: 0-15% EtOAc in n-hexane) to afford 4 (2.3 g, 26.7%) as an off white solid. $^1$H NMR (400 MHz, DMSO-$d_6$) δ ppm 11.83 (br. s, 1H), 4.22 (q, J=6.0 Hz, 2H), 2.44 (s, 3H), 1.43 (s, 9H), 1.22 (t, J=7.6 Hz, 3H). LCMS: 287.13 $(M+H)^+$, R:=1.98 min.

Step-3: tert-Butyl (5-((2-chloro-5-(trifluoromethyl)phenyl)carbamoyl)-4-methylthiazol-2-yl)carbamate (6): To a stirred solution of ethyl 2-((tert-butoxycarbonyl)amino)-4-methylthiazole-5-carboxylate (4) (2.3 g, 8.04 mmol, 1 eq) in THF (23 mL) at 0° C. was added 3-chloro-5-fluoroaniline (5) (1.8 g, 9.65 mmol, 1.2 eq) followed by LiHMDS (1M solution in THF, 40.2 mL, 40.2 mmol, 5 eq). The reaction mixture was allowed to attain room temperature and stirred for 2 h. The progress of the reaction was monitored by TLC (M.Ph: 20% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×250 mL). The combined organic layers was dried over anhydrous sodium sulfate, filtered and concentrated to dryness to afford crude 6 (3.4 g, 58.8%) as an off-white solid. LCMS: 436.15 $(M+H)^+$, $R_f$=2.28 min.

Step-4: 2-Amino-N-(2-chloro-5-(trifluoromethyl)phenyl)-4-methylthiazole-5-carboxamide (7): To a stirred solution of tert-butyl (5-((2-chloro-5-(trifluoromethyl)phenyl) carbamoyl)-4-methylthiazol-2-yl)carbamate (6) (2.0 g, 4.60 mmol, 1 eq) in DCM (10 mL) at 0° C. was added trifluoroacetic acid (1 mL, 13.06 mmol, 2.84 eq). The reaction mixture was allowed to attain room temperature and stirred for 2 h. The progress of the reaction was monitored by TLC (M.Ph: 70% EtOAc in n-hexane; $Rf_{SM}$: 0.7, $Rf_{RM}$: 0.3). After completion of reaction, the reaction mixture was concentrated to dryness. The residue was diluted with ethyl acetate (250 mL) and washed with saturated $NaHCO_3$ solution. The organic layer was dried over anhydrous sodium sulfate, filtered and concentrated to dryness. The crude was purified through silica gel column chromatography (elution: 0-20% EtOAc in n-hexane) to afford 7 (1.1 g, 55%) as an off-white solid. $^1H$ NMR (400 MHz, DMSO-$d_6$) δ ppm 9.19 (br. s, 1H), 8.14 (br. s, 1H), 7.78-7.76 (m, 3H), 7.59-7.57 (m, 1H), 2.45 (s, 3H). LCMS: 335.90 $(M+H)^+$, $R_f$=1.76 min.

Step-5: Methyl 1-((5-((2-chloro-5-(trifluoromethyl)phenyl)carbamoyl)-4-methylthiazol-2-yl)carbamoyl)cyclopropane-1-carboxylate (9): To a stirred mixture of 2-amino-N-(2-chloro-5-(trifluoromethyl)phenyl)-4-methylthiazole-5-carboxamide (7) (2.5 g, 7.46 mmol, 1 eqv) in DMF (25 mL), HATU (4.2 g, 11.1 mmol, 1.5 eqv) and DIPEA (4.1 mL, 22.3 mmol, 3.0 eqv) were added at RT. The mixture was stirred at same temperature for 30 min. Then, 1-(methoxycarbonyl) cyclopropane-1-carboxylic acid (8) (1.2 g, 8.55 mmol, 1.2 eqv) was added into the reaction mixture at 0-5° C. and allowed to stirred at RT for 12 h. The progress of the reaction was monitored by TLC (M.Ph: 60% EtOAc in n-hexane). The reaction mixture was diluted with water and extracted with EtOAc (2×150 mL). The combined organic layers was washed with brine, dried over sodium sulfate, filtered and concentrated to dryness. The crude was purified through silica gel column chromatography (elution: 10-40% EtOAc in n-hexane) to afford 9 (1.3 g, 37.9%) as an off-white solid. $^1H$ NMR (400 MHz, DMSO-$d_6$) δ ppm 12.63 (br. s, 1H), 9.79 (br. s, 1H), 8.09 (s, 1H), 7.81 (d, J=8.4 Hz, 1H), 7.64 (d, J=7.6 Hz, 1H), 3.68 (s, 3H), 3.59 (s, 3H), 1.49-1.46 (m, 4H). LCMS: 461.9 $(M+H)^+$, $R_f$=2.31 min.

Step 6: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-fluoro-5-(trifluoromethyl)aniline (42.6 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.6). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0233 (32.8 mg, 24.4%) as an off-white solid. $^1H$ NMR (400 MHz, DMSO-$d_6$) δ ppm 12.69 (br. s, 1H), 10.46 (br. s, 1H), 9.61 (br. s, 1H), 8.05 (br. s, 1H), 7.79 (br. s, 1H), 7.72 (d, J=8.31 Hz, 2H), 7.54 (d, J=7.34 Hz, 1H), 7.28 (d, J=5.87 Hz, 1H), 2.50 (br. s, 3H), 1.39-1.54 (m, 4H). LCMS: 608.85 $(M+H)^+$, $R_f$=2.267 min. HPLC: 96.81%; $R_f$=10.42 min Example #20: Synthesis N-(5-((2-chloro-5-(trifluoromethyl)phenyl)carbamoyl)-4-methylthiazol-2-yl)-N-(3-methoxy-5-(trifluoromethyl)phenyl)cyclopropane-1,1-dicarboxamide (SSTA-0234)

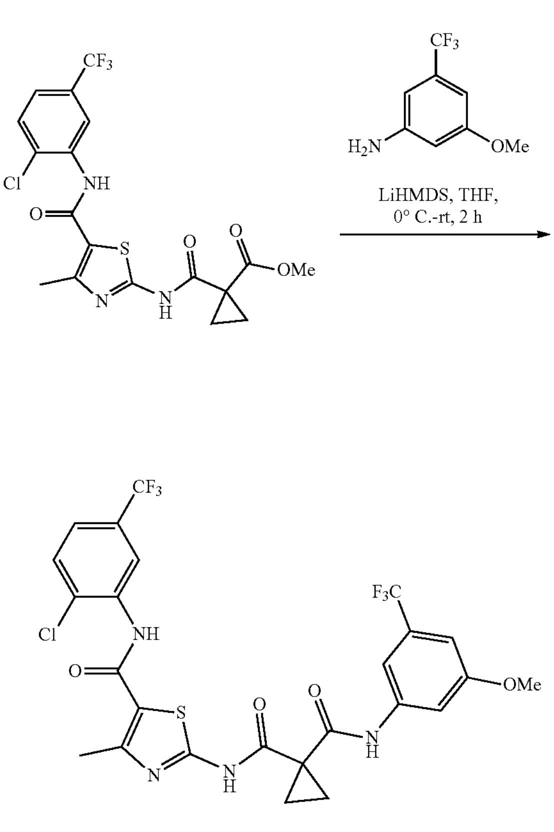

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-methoxy-5-(trifluoromethyl)aniline (45.4 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0234 (9.90 mg, 7.44%) as an off-white solid. $^1H$ NMR (400 MHz, DMSO-$d_6$) δ ppm 12.67 (br. s, 1H), 10.23 (br. s, 1H), 9.77 (br. s, 1H), 8.11 (br. s, 1H), 7.81 (d, J=8.31 Hz, 1H), 7.59-7.71 (m, 2H), 7.51 (br. s, 1H), 6.95 (s, 1H), 3.81 (s, 3H), 2.58 (s, 3H), 1.51-1.58 (m, 4H). LCMS: 620.90 $(M+H)^+$, $R_f$=2.353 min. HPLC: 98.12%; $R_f$=10.65 min.

Example #21: Synthesis of N-(4-chloro-3-fluorophenyl)-N-(5-((2-chloro-5-(trifluoromethyl)phenyl)carbamoyl)-4-methylthiazol-2-yl)cyclopropane-1,1-dicarboxamide (SSTA-236)

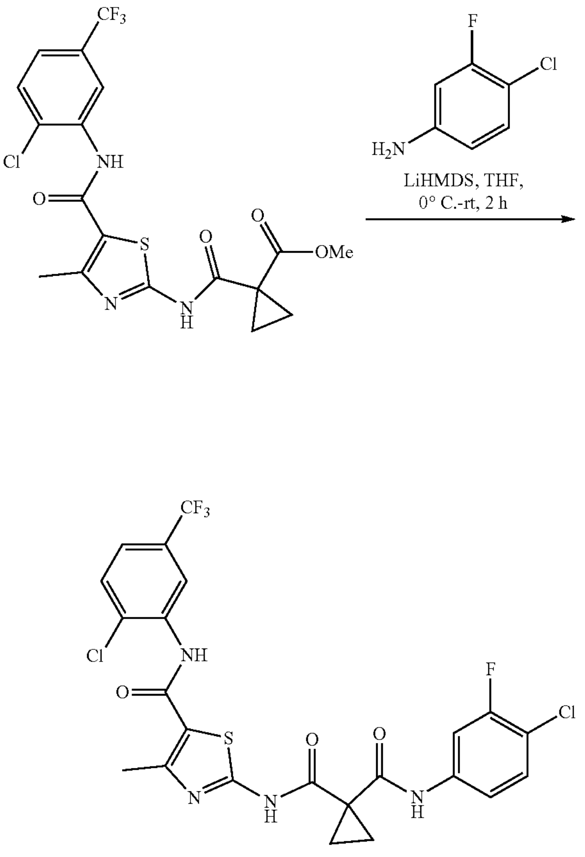

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 4-chloro-3-fluoroaniline (34.6 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0236 (52.3 mg, 42.1%) as an off-white solid. $^1H$ NMR (400 MHz, DMSO-$d_6$) δ ppm 12.65 (br. s, 1H), 10.29 (br. s, 1H), 9.77 (br. s, 1H), 8.11 (br. s, 1H), 7.81 (d, J=8.80 Hz, 2H), 7.64 (d, J=7.83 Hz, 1H), 7.53 (t, J=8.31 Hz, 1H), 7.41 (br. s, 1H), 2.59 (br. s, 3H), 1.44-1.64 (m, 4H). LCMS: 574.80 $(M+H)^+$, $R_f$=2.377 min. HPLC: 98.53%; $R_f$=10.30 min.

Example #22: Synthesis of N-(5-((2-chloro-5-(trifluoromethyl)phenyl)carbamoyl)-4-methylthiazol-2-yl)-N-(3-chloro-5-fluorophenyl)cyclopropane-1,1-dicarboxamide (SSTA-0237)

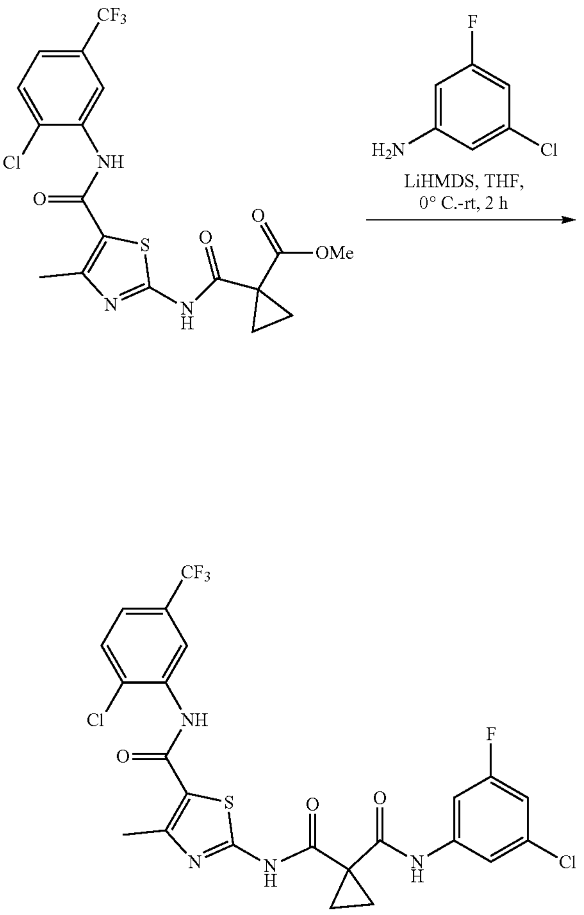 [SMILES: COC(=O)C1(C(=O)Nc2nc(C)c(C(=O)Nc3cc(C(F)(F)F)ccc3Cl)s2)CC1 ; Nc1cc(F)cc(Cl)c1 ; Cc1nc(NC(=O)C2(C(=O)Nc3cc(F)cc(Cl)c3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-chloro-5-fluoroaniline (34.6 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.6). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0237 (21.3 mg, 17.3%) as an off-white solid. $^1H$ NMR (400 MHz, DMSO-$d_6$) δ ppm 12.59 (br. s, 1H), 10.22 (br. s, 1H), 9.68 (br. s, 1H), 7.97-8.06 (m, 1H), 7.72 (d, 1=8.31 Hz, 1H), 7.46-7.61 (m, 2H), 7.36-7.45 (m, 1H), 7.04 (d, J=6.36 Hz, 1H), 2.50 (br. s, 3H), 1.41-1.49 (m, 4H). LCMS: 574.90 $(M+H)^+$, $R_f$=2.406 min. HPLC: 99.56%; $R_f$=10.43 min.

Example #23: Synthesis of N-(5-((2-chloro-5-(trifluoromethyl)phenyl)carbamoyl)-4-methylthiazol-2-yl)-N-(3,4-difluorophenyl)cyclopropane-1,1-dicarboxamide (SSTA-0238)

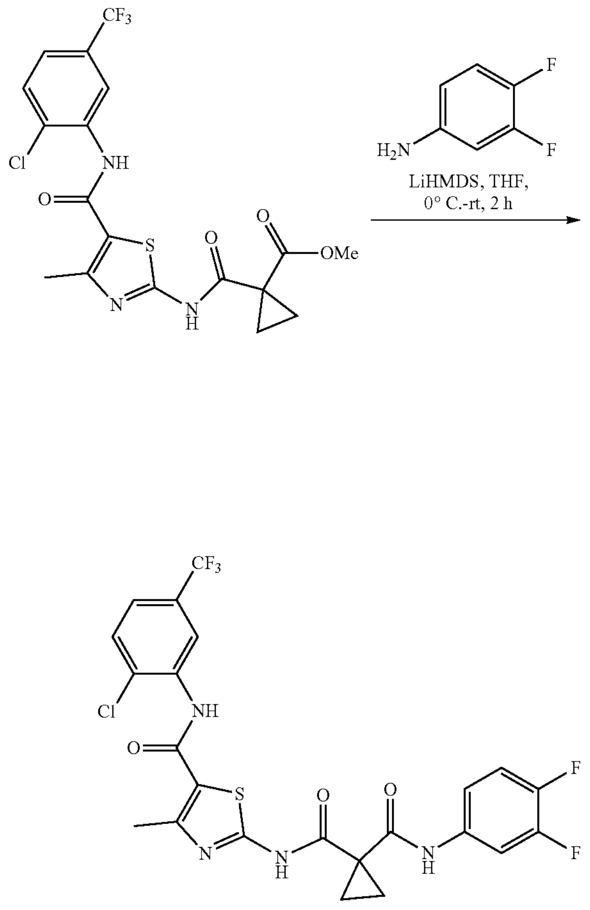 [SMILES: COC(=O)C1(C(=O)Nc2nc(C)c(C(=O)Nc3cc(C(F)(F)F)ccc3Cl)s2)CC1 ; Nc1ccc(F)c(F)c1 ; Cc1nc(NC(=O)C2(C(=O)Nc3ccc(F)c(F)c3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3,4-difluoroaniline (33.4 mg, 0.260 mmol, 1.2 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0238 (24.6 mg, 20.5%) as an off-white solid. $^1H$ NMR (400 MHz, DMSO-$d_6$) δ ppm 12.65 (br. s, 1H), 10.18 (br. s, 1H), 9.76 (br. s, 1H), 8.11 (br. s, 1H), 7.81 (d, J=6.85 Hz, 2H), 7.63 (d, J=7.82 Hz, 1H), 7.26-7.46 (m, 2H), 2.59 (br. s, 3H), 1.46-1.61 (m, 4H). LCMS: 558.90 $(M+H)^+$, $R_f$=2.224 min. HPLC: 98.17%; $R_f$=10.34 min.

Example #24: Synthesis of N-(5-((2-chloro-5-(trifluoromethyl)phenyl)carbamoyl)-4-methylthiazol-2-yl)-N-(2,5-difluorophenyl)cyclopropane-1,1-dicarboxamide (SSTA-0239)

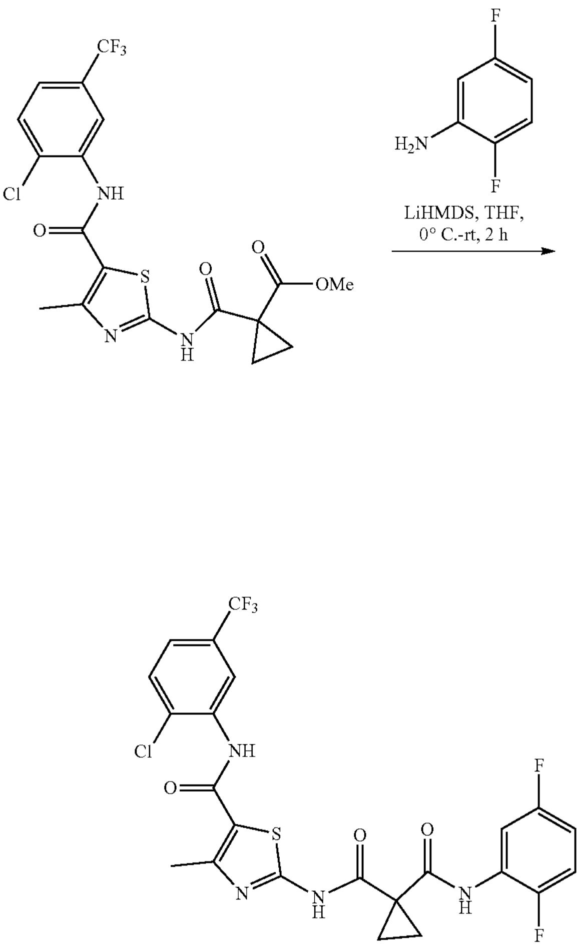 [SMILES: COC(=O)C1(C(=O)Nc2nc(C)c(C(=O)Nc3cc(C(F)(F)F)ccc3Cl)s2)CC1 ; Nc1cc(F)ccc1F ; Cc1nc(NC(=O)C2(C(=O)Nc3cc(F)ccc3F)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 2,5-difluoroaniline (30.7 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.4, $Rf_{RM}$: 0.3). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0239 (45.3 mg, 37.5%) as an off-white solid. $^1H$ NMR (400 MHz, DMSO-$d_6$) δ ppm 12.53 (br. s, 1H), 10.27 (br. s, 1H), 9.85 (br. s, 1H), 8.07 (br. s, 1H), 7.81 (d, J=7.82 Hz, 1H), 7.64 (d, J=6.85 Hz, 2H), 7.11-7.30 (m, 2H), 2.59 (br. s, 3H), 1.66 (d, J=17.61 Hz, 4H). LCMS: 588.90 $(M+H)^+$, $R_f$=2.303 min. HPLC: 97.62%; $R_f$=10.29 min.

Example #24: Synthesis of N-(5-((2-chloro-5-(trifluoromethyl)phenyl)carbamoyl)-4-methylthiazol-2-yl)-N-(3-fluoro-2-methoxyphenyl)cyclopropane-1,1-dicarboxamide (SSTA-0240)

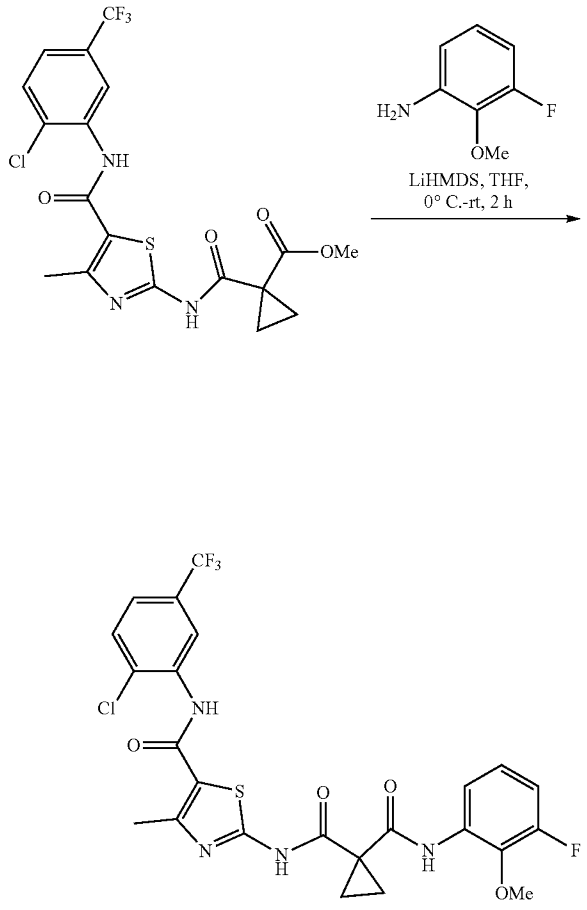 [SMILES: COC(=O)C1(C(=O)Nc2nc(C)c(C(=O)Nc3cc(C(F)(F)F)ccc3Cl)s2)CC1 ; COc1c(N)cccc1F ; COc1c(F)cccc1NC(=O)C1(C(=O)Nc2nc(C)c(C(=O)Nc3cc(C(F)(F)F)ccc3Cl)s2)CC1]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-fluoro-2-methoxyaniline (33.5 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.5, $Rf_{RM}$: 0.6). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0240 (65.1 mg, 52.8%) as an off-white solid. $^1H$ NMR (400 MHz, DMSO-$d_6$) δ ppm 12.37 (br. s, 1H), 10.60 (br. s, 1H), 9.87 (br. s, 1H), 8.09 (br. s, 1H), 7.86-8.01 (m, 1H), 7.81 (d, J=8.80 Hz, 1H), 7.65 (d, J=7.82 Hz, 1H), 6.94-7.15 (m, 2H), 3.93 (br. s, 3H), 2.59 (br. s, 3H), 1.60-1.81 (m, 4H). LCMS: 569.00 $(M-H)^+$, $R_f$=2.363 min. HPLC: 97.45%; $R_f$=10.45 min.

Example #25: Synthesis of N-(5-((2-chloro-5-(trifluoromethyl)phenyl)carbamoyl)-4-methylthiazol-2-yl)-N-(3-fluoro-5-methoxyphenyl)cyclopropane-1,1-dicarboxamide (SSTA-0241)

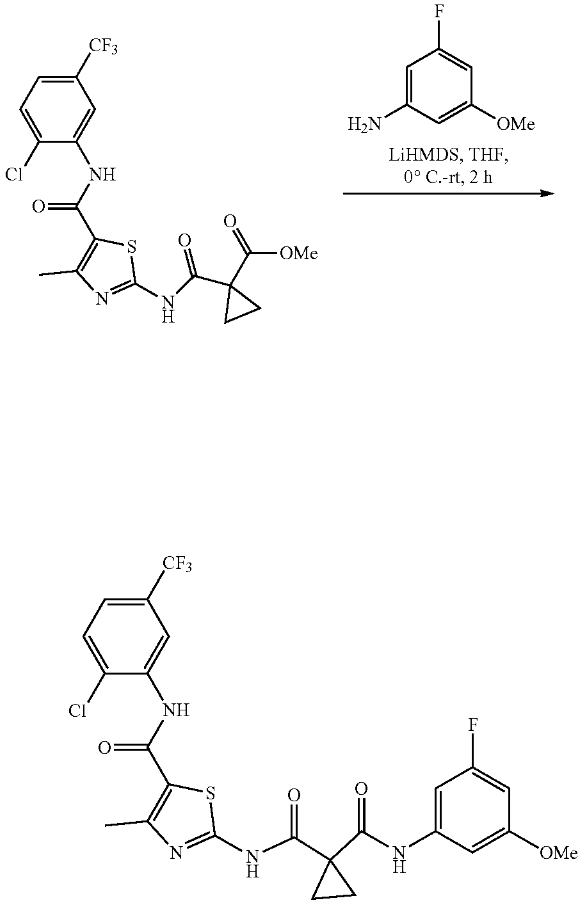 [SMILES: COC(=O)C1(C(=O)Nc2nc(C)c(C(=O)Nc3cc(C(F)(F)F)ccc3Cl)s2)CC1 ; COc1cc(N)cc(F)c1 ; COc1cc(F)cc(NC(=O)C2(C(=O)Nc3nc(C)c(C(=O)Nc4cc(C(F)(F)F)ccc4Cl)s3)CC2)c1]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-fluoro-5-methoxyaniline (33.5 mg, 0.237 mmol, 1.1 eq) followed by LiHMDS (1M solution in THF, 1.08 mL, 1.079 mmol, 5 eq). The reaction mixture was allowed to attain room temperature and stirred for 3 h. The progress of the reaction was monitored by TLC (M.Ph: 40% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-40% EtOAc in n-hexane) to afford SSTA-0241 (15.7 mg, 12.1%) as an off-white solid. $^1H$ NMR (400 MHz, DMSO-$d_6$) δ ppm 12.63 (br. s, 1H), 10.18 (br. s, 1H), 10.08 (br. s, 1H), 9.77 (br. s, 1H), 8.11 (br. s, 1H), 7.81 (d, J=7.34 Hz, 1H), 7.63 (d, J=7.34 Hz, 1H), 7.17 (d, J=11.25 Hz, 1H), 7.06 (br. s, 1H), 6.54 (d, J=10.76 Hz, 1H), 3.74 (br. s, 3H), 2.59 (br. s, 3H), 1.50-1.58 (m, 4H). LCMS: 570.95 $(M+H)^+$, $R_f$=2.332 min. HPLC: 97.81%; $R_f$=9.993 min.

Example #26: Synthesis of N-(5-((2-chloro-5-(trifluoromethyl)phenyl)carbamoyl)-4-methylthiazol-2-yl)-N-(4-fluoro-2-isopropoxyphenyl)cyclopropane-1,1-dicarboxamide (SSTA-0242)

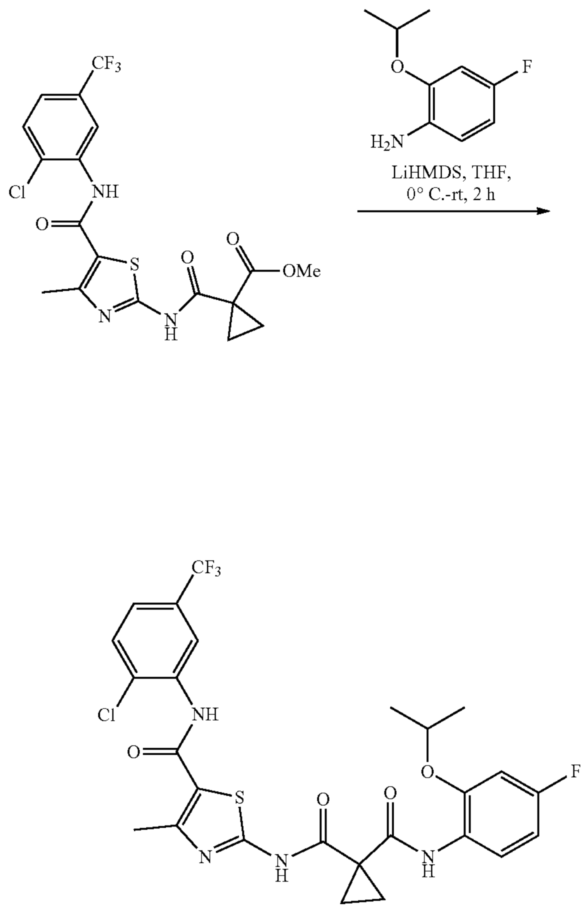 [SMILES: COC(=O)C1(C(=O)Nc2nc(C)c(C(=O)Nc3cc(C(F)(F)F)ccc3Cl)s2)CC1 ; CC(C)Oc1cc(F)ccc1N ; Cc1nc(NC(=O)C2(C(=O)Nc3ccc(F)cc3OC(C)C)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 4-fluoro-2-isopropoxyaniline (40 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.6). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0242 (9.50 mg, 7.36%) as an off-white solid. $^1H$ NMR (400 MHz, DMSO-$d_6$) δ ppm 12.44 (br. s, 1H), 10.61 (br. s, 1H), 9.76 (br. s, 1H), 8.19 (br. s, 1H), 8.12 (br. s, 1H), 7.82 (d, J=7.34 Hz, 1H), 7.63 (d, J=6.36 Hz, 1H), 7.04 (d, J=9.78 Hz, 1H), 6.72 (d, J=5.87 Hz, 1H), 4.65-4.76 (m, 1H), 2.59 (br. s, 3H), 1.57-1.78 (m, 4H), 1.34 (d, J=4.89 Hz, 6H). LCMS: 599.05 $(M+H)^+$, $R_f$=2.456 min. HPLC: 99.05%; $R_f$=10.61 min.

Example #27. Synthesis of N-(2-chloro-4-fluorophenyl)-N-(5-((2-chloro-5-(trifluoromethyl)phenyl)carbamoyl)-4-methylthiazol-2-yl)cyclopropane-1,1-dicarboxamide (SSTA-0247)

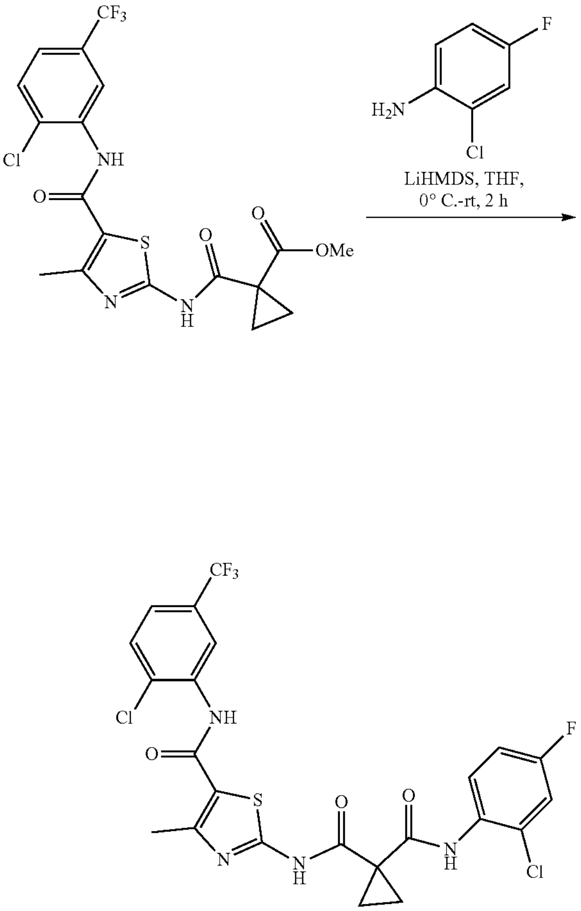 [SMILES: COC(=O)C1(C(=O)Nc2nc(C)c(C(=O)Nc3cc(C(F)(F)F)ccc3Cl)s2)CC1 ; Nc1ccc(F)cc1Cl ; Cc1nc(NC(=O)C2(C(=O)Nc3ccc(F)cc3Cl)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 2-chloro-4-fluoroaniline (34.7 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layer was dried over anhydrous sodium sulfate, filtered and concentrated to dryness. The crude was purified through silica gel column chromatography (elution: 0-50% EtOAc in n-hexane) to afford SSTA-0247 (72.2 mg, 58.2%) as an off white solid. $^1H$ NMR (400 MHz, DMSO-$d_6$) δ ppm 12.56 (br. s, 1H), 10.18 (br. s, 1H), 9.83 (br. s, 1H), 8.08 (br. s, 1H), 7.85-7.91 (m, 1H), 7.80 (d, J=7.34 Hz, 1H), 7.64 (d, J==6.85 Hz, 1H), 7.53 (d, J=5.87 Hz, 1H), 7.26 (d, J=7.34 Hz, 1H), 2.58 (br. s, 3H), 1.69 (d, J=12.72 Hz, 4H). LCMS: 572.90 $(M-H)^+$, $R_f$=2.256 min. HPLC: 96.58%; $R_f$=10.15 min.

Example #28: Synthesis of N-(5-((2-chloro-5-(trifluoromethyl)phenyl)carbamoyl)-4-methylthiazol-2-yl)-N-(2,4-difluorophenyl)cyclopropane-1,1-dicarboxamide (SSTA-0248)

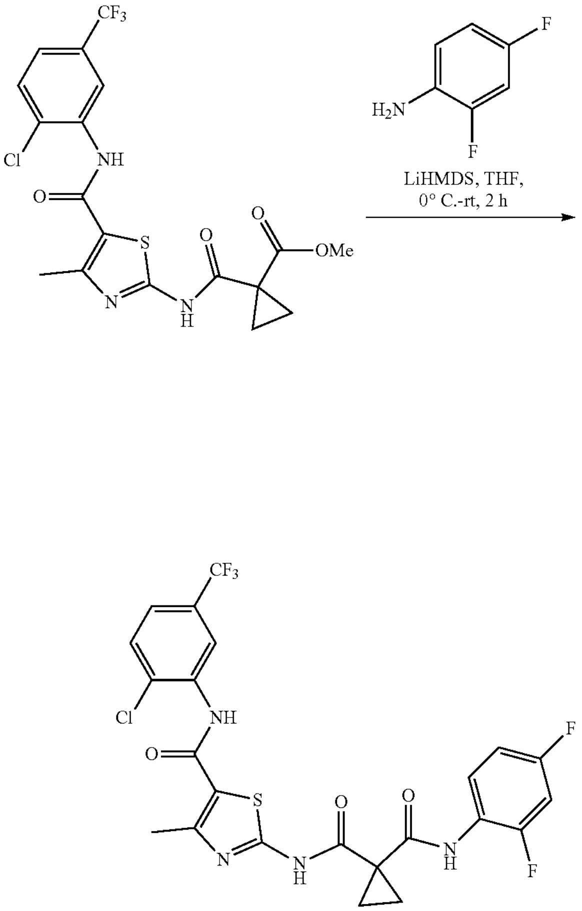 [SMILES: COC(=O)C1(C(=O)Nc2nc(C)c(C(=O)Nc3cc(C(F)(F)F)ccc3Cl)s2)CC1 ; Nc1ccc(F)cc1F ; Cc1nc(NC(=O)C2(C(=O)Nc3ccc(F)cc3F)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 2,4-difluoroaniline (30.7 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 50% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-50% EtOAc in n-hexane) to afford SSTA-0248 (51.3 mg, 42.5%) as an off-white solid. $^1$H NMR (400 MHz, DMSO-$d_6$) δ ppm 12.54 (br. s, 1H), 10.27 (br. s, 1H), 9.84 (br. s, 1H), 8.07 (br. s, 1H), 7.81 (d, J=7.34 Hz, 1H), 7.64 (d, J=7.34 Hz, 2H), 7.21 (d, J=5.38 Hz, 2H), 2.58 (br. s, 3H), 1.66 (d, J=17.61 Hz, 4H). LCMS: 558.90 $(M+H)^+$, $R_f$=2.287 min. HPLC: 95.02%; $R_f$=9.952 min.

Example #29: Synthesis of N-(2-chloro-5-(trifluoromethyl)phenyl)-N-(5-((2-chloro-5-(trifluoromethyl)phenyl)carbamoyl)-4-methylthiazol-2-yl)cyclopropane-1,1-dicarboxamide (SSTA-0250)

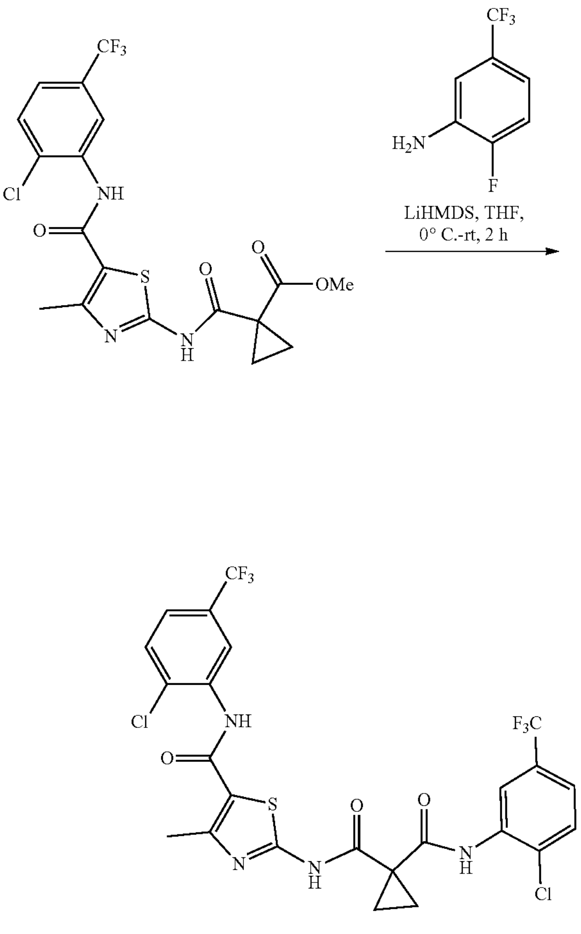 [SMILES: COC(=O)C1(C(=O)Nc2nc(C)c(C(=O)Nc3cc(C(F)(F)F)ccc3Cl)s2)CC1 ; Nc1cc(C(F)(F)F)ccc1F ; Cc1nc(NC(=O)C2(C(=O)Nc3cc(C(F)(F)F)ccc3Cl)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 2-chloro-5-(trifluoromethyl)aniline (46.5 mg, 0.238 mmol, 1.1 eq) followed by LiHMDS (1M in THF, 1.08 mL, 1.079 mmol, 5 eq). The reaction mixture was allowed to attain room temperature and stirred for 2 h. The progress of the reaction was monitored by TLC (M.Ph: 20% EtOAc in n-hexane; $Rf_{SM}$: 0.45, $Rf_{RM}$: 0.5). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-20% EtOAc in n-hexane) to afford SSTA-0250 (37.1 mg, 29.8%) as an off-white solid. $^1$H NMR (400 MHz, DMSO-$d_6$) δ ppm 12.48 (br. s, 1H), 10.73 (br. s, 1H), 9.90 (br. s, 1H), 8.47 (br. s, 1H), 8.07 (br. s, 1H), 7.76-7.85 (m, 2H), 7.65 (d, J=8.31 Hz, 1H), 7.55 (d, J=7.34 Hz, 1H), 2.58 (br. s, 3H), 1.65-1.82 (m, 4H). LCMS: 624.80 $(M+H)^+$, $R_f$=2.409 min. HPLC: 95.09%; $R_f$=10.65 min.

Example #30: Synthesis of N-(3-chloro-5-(trifluoromethyl)phenyl)-N-(5-((2-chloro-5-(trifluoromethyl)phenyl)carbamoyl)-4-methylthiazol-2-yl)cyclopropane-1,1-dicarboxamide (SSTA-0251)

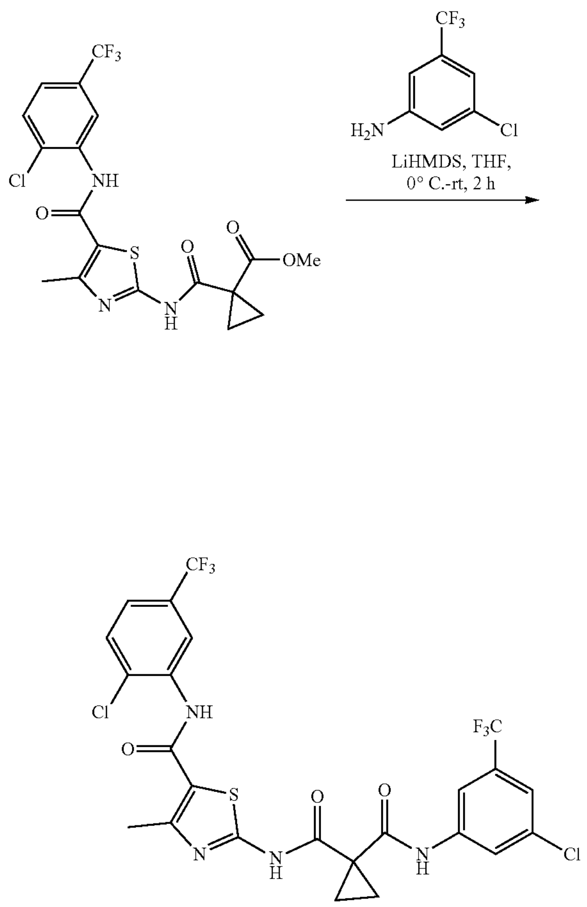 [SMILES: COC(=O)C1(C(=O)Nc2nc(C)c(C(=O)Nc3cc(C(F)(F)F)ccc3Cl)s2)CC1 ; Nc1cc(Cl)cc(C(F)(F)F)c1 ; Cc1nc(NC(=O)C2(C(=O)Nc3cc(Cl)cc(C(F)(F)F)c3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 3-chloro-5-(trifluoromethyl)aniline (46.5 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.4, $Rf_{RM}$: 0.5). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0251 (15.5 mg, 12.6%) as an off-white solid. $^1H$ NMR (400 MHz, DMSO-$d_6$) δ 12.73 (br. s, 1H), 10.47 (br. s, 1H), 9.78 (br. s, 1H), 8.11 (s, 1H), 8.01 (d, J=11.74 Hz, 2H), 7.81 (d, J=8.31 Hz, 1H), 7.64 (d, J=8.31 Hz, 1H), 7.56 (s, 1H), 2.58 (s, 3H), 1.52-1.58 (m, 4H). LCMS: 624.90 $(M+H)^+$, $R_f$=2.104 min. HPLC: 98.69%; $R_f$=10.75 min.

Example #31: Synthesis of N-(5-((2-chloro-5-(trifluoromethyl)phenyl)carbamoyl)-4-methylthiazol-2-yl)-N-(4-fluoropyridin-2-yl)cyclopropane-1,1-dicarboxamide (SSTA-0252)

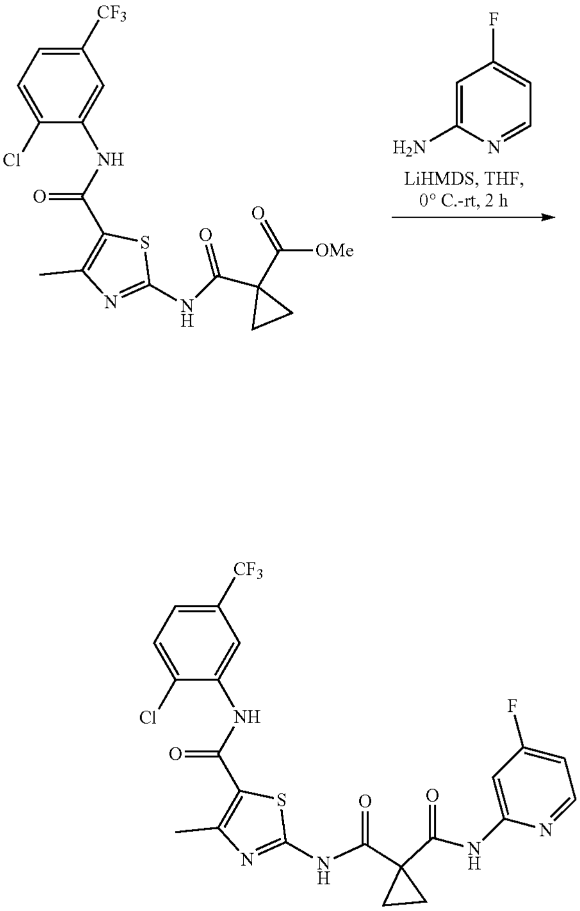 [SMILES: COC(=O)C1(C(=O)Nc2nc(C)c(C(=O)Nc3cc(C(F)(F)F)ccc3Cl)s2)CC1 ; Nc1cc(F)ccn1 ; Cc1nc(NC(=O)C2(C(=O)Nc3cc(F)ccn3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 4-fluoropyridin-2-amine (26.6 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0252 (25.2 mg, 21.5%) as an off-white solid. $^1H$ NMR (400 MHz, DMSO-$d_6$) δ ppm 12.43 (br. s, 1H), 11.25 (br. s, 1H), 9.80 (br. s, 1H), 8.37 (dd, J=5.87, 9.29 Hz, 1H), 8.09 (s, 1H), 7.87-7.95 (m, 1H), 7.81 (d, J=8.31 Hz, 1H), 7.64 (d, J=8.31 Hz, 1H), 7.01-7.13 (m, 1H), 2.58 (s, 3H), 1.62 (d, J=19.56 Hz, 4H). LCMS: 541.80 $(M+H)^+$, $R_f$=2.176 min. HPLC: 99.87%; $R_f$=10.47 min.

Example #32: Synthesis of N-(5-((2-chloro-5-(trifluoromethyl)phenyl)carbamoyl)-4-methylthiazol-2-yl)-N-(4-fluoropyridin-2-yl)cyclopropane-1,1-dicarboxamide (SSTA-0258)

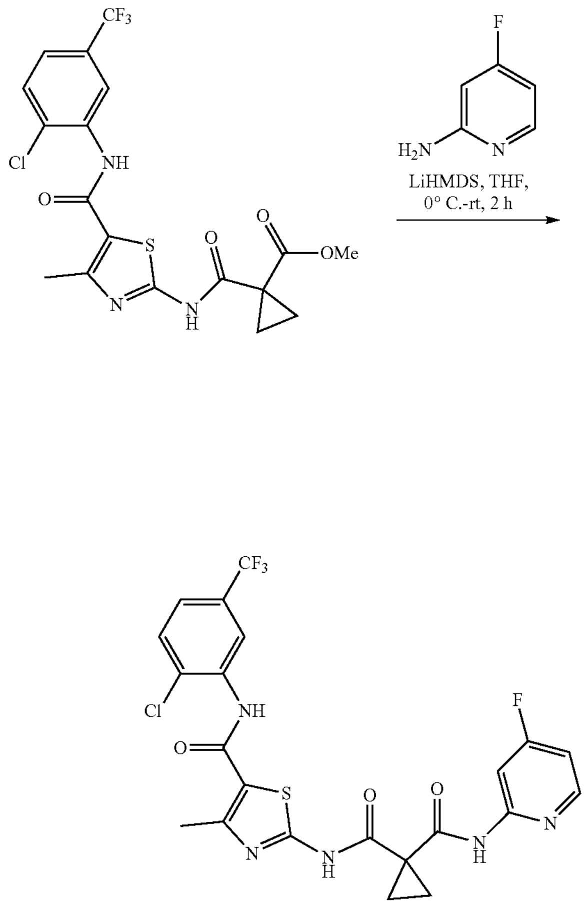 [SMILES: COC(=O)C1(C(=O)Nc2nc(C)c(C(=O)Nc3cc(C(F)(F)F)ccc3Cl)s2)CC1 ; Nc1cc(F)ccn1 ; Cc1nc(NC(=O)C2(C(=O)Nc3cc(F)ccn3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-methylthiazol-2-yl)carbamoyl)cyclopropane-1-carboxylate (100 mg, 0.216 mmol, 1 eq) in THF (1 mL) at 0° C. was added 4-fluoropyridin-2-amine (26.6 mg, 0.238 mmol, 1.1 eq) followed by LiHMDS (1M solution in THF, 1.08 mL, 1.079 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0258 (25.2 mg, 21.5%) as an off-white solid. $^1$H NMR (400 MHz, DMSO-$d_6$) δ ppm 12.43 (br. s, 1H), 11.25 (br. s, 1H), 9.80 (br. s, 1H), 8.37 (dd, J=5.87, 9.29 Hz, 1H), 8.09 (s, 1H), 7.87-7.95 (m, 1H), 7.81 (d, J=8.31 Hz, 1H), 7.64 (d, J=8.31 Hz, 1H), 7.01-7.13 (m, 1H), 2.58 (s, 3H), 1.62 (d, J=19.56 Hz, 4H). LCMS: 541.80 $(M+H)^+$, $R_f$=2.176 min. HPLC: 99.87%; $R_f$=10.47 min.

Example #33: Synthesis of N-(4-chloro-3-fluorophenyl)-N-(5-((2-chloro-5-(trifluoromethyl)phenyl)carbamoyl)-4-cyclopropylthiazol-2-yl)cyclopropane-1,1-dicarboxamide (SSTA-0259)

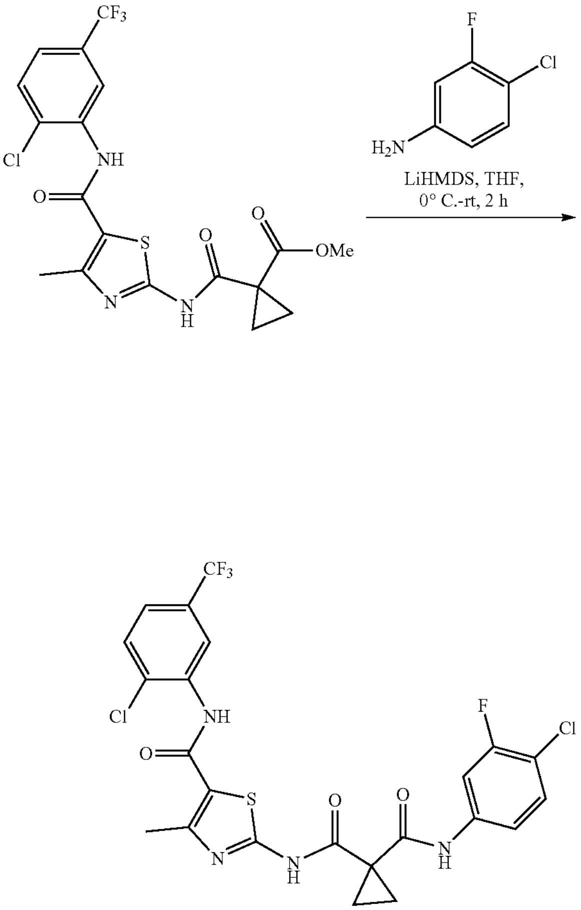 [SMILES: COC(=O)C1(C(=O)Nc2nc(C)c(C(=O)Nc3cc(C(F)(F)F)ccc3Cl)s2)CC1 ; Nc1ccc(Cl)c(F)c1 ; Cc1nc(NC(=O)C2(C(=O)Nc3ccc(Cl)c(F)c3)CC2)sc1C(=O)Nc1cc(C(F)(F)F)ccc1Cl]

Synthesis was performed using general procedure #2. Final step: To a stirred solution of methyl 1-((5-((2-chloro-5-(trifluoromethyl)phenyl)carbamoyl)-4-cyclopropylthiazol-2-yl)carbamoyl)cyclopropane-1-carboxylate (75 mg, 0.154 mmol, 1 eq) in THF (1 mL) at 0° C. was added 4-chloro-3-fluoroaniline (22.4 mg, 0.154 mmol, 1 eq) followed by LiHMDS (1M solution in THF, 0.77 mL, 0.770 mmol, 5 eq). The reaction mixture was allowed to attain room temperature and stirred for 2 h. The progress of the reaction was monitored by TLC (M.Ph: 30% EtOAc in n-hexane; $Rf_{SM}$: 0.4, $Rf_{RM}$: 0.5). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-30% EtOAc in n-hexane) to afford SSTA-0259 (16.7 mg, 18%) as an off-white solid. $^1$H NMR (400 MHz, DMSO-$d_6$) δ ppm 12.59 (br. s, 1H), 10.21 (br. s, 1H), 9.76 (br. s, 1H), 8.13 (br. s, 1H), 7.76-7.83 (m, 2H), 7.62 (d, J=7.83 Hz, 1H), 7.49-7.56 (m, 1H), 7.39 (d, J=7.83 Hz, 1H), 2.85-2.93 (m, 1H), 1.53 (s, 4H), 0.93-1.04 (m, 4H). LCMS: 601.60 $(M+H)^+$, $R_f$=2.479 min. HPLC: 97.53%; $R_f$=11.36 min.

Example #34: Synthesis of N-(5-((2-chloro-5-(trifluoromethyl)phenyl)carbamoyl)-4-cyclopropylthiazol-2-yl)-N-(3-chloro-5-fluorophenyl)cyclopropane-1,1-dicarboxamide (SSTA-0260)

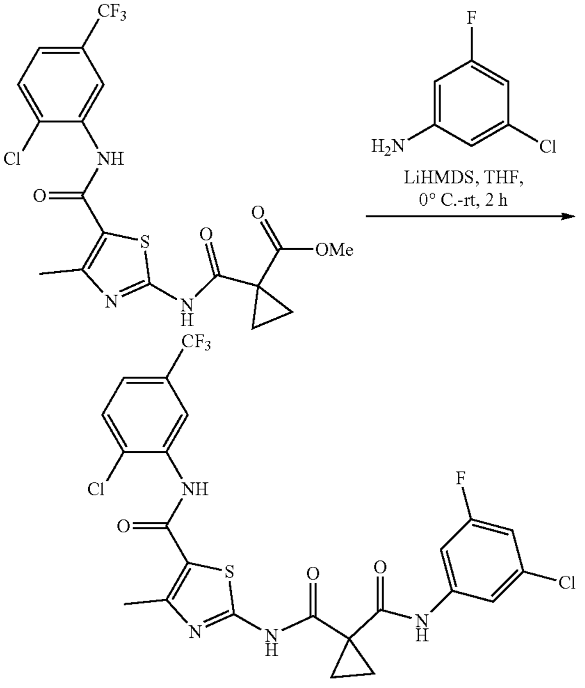

Synthesis was performed using general procedure #2. Final step: To a stirred solution of methyl 1-((5-((2-chloro-5-(trifluoromethyl)phenyl)carbamoyl)-4-cyclopropylthiazol-2-yl)carbamoyl)cyclopropane-1-carboxylate (70 mg, 0.144 mmol, 1 eq) in THF (1 mL) at 0° C. was added 3-chloro-5-fluoroaniline (20.9 mg, 0.144 mmol, 1 eq) followed by LiHMDS (1M solution in THF, 0.72 mL, 0.720 mmol, 5 eq). The reaction mixture was allowed to attain room temperature and stirred for 2 h. The progress of the reaction was monitored by TLC (M.Ph: 20% EtOAc in n-hexane; $Rf_{SM}$: 0.5, $Rf_{RM}$: 0.4). After completion of reaction, the reaction mixture was quenched with saturated $NH_4Cl$ solution and extracted with ethyl acetate (2×25 mL). The combined organic layers was dried over anhydrous sodium sulfate, filtered and concentrated to dryness. The crude was purified through silica gel column chromatography (elution: 0-20% EtOAc in n-hexane) to afford SSTA-0260 (20 mg, 23.2%) as an off-white solid. $^1H$ NMR (400 MHz, DMSO-$d_6$) δ ppm 12.63 (br. s, 1H), 10.23 (br. s, 1H), 9.77 (br. s, 1H), 8.12 (br. s, 1H), 7.80 (d, J=8.31 Hz, 1H), 7.63 (d, J=8.31 Hz, 1H), 7.57 (s, 1H), 7.49 (d, J=11.25 Hz, 1H), 7.13 (d, J=8.31 Hz, 1H), 2.83-2.92 (m, 1H), 1.50-1.55 (m, 4H), 0.93-1.06 (m, 4H). LCMS: 601.50 $(M+H)^+$, $R_f$=2.483 min. HPLC: 99.47%; $R_f$=10.90 min.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

(I)

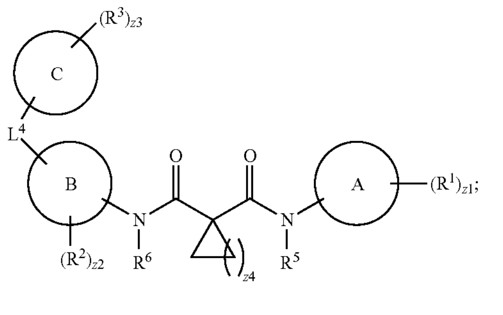

wherein,

Ring A is phenyl or 5 to 6 membered heteroaryl;

$R^1$ is independently halogen, $-CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

Ring B is thiazolyl;

$R^2$ is unsubstituted or substituted cycloalkyl, unsubstituted or substituted alkyl, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted heteroalkyl, substituted or unsubstituted heterocycloalkyl, substituted or unsubstituted aryl, or substituted or unsubstituted heteroaryl;

z2 is 1 or 0;

Ring C is phenyl or 5 to 6 membered heteroaryl;

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z3 is an integer from 0 to 5;

$L^4$ is $—C(O)N(R^4)—$, $—N(R^4)C(O)—$, a bond, $—N(R^4)—$, —O—, —S—, $—SO_2—$, —C(O)—, $—N(R^4)C(O)NH—$, $—NHC(O)N(R^4)—$, —C(O)O—, —OC(O)—, $—SO_2N(R^4)—$, $—N(R^4)SO_2—$, substituted or unsubstituted alkylene, or substituted or unsubstituted heteroalkylene;

z4 is an integer from 1 to 5;

$R^4$, $R^5$, and $R^6$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2;

or a pharmaceutically acceptable salt thereof.

2. The compound of claim 1, wherein $R^5$ and $R^6$ are hydrogen.

3. The compound of claim 1, wherein $L^4$ is —C(O)NH—, —NHC(O)—, a bond, —NH—, —O—, —S—, $—SO_2—$, —C(O)—, —NHC(O)NH—, —C(O)O—, —OC(O)—, $—SO_2NH—$, $—NHSO_2—$, substituted or unsubstituted $C_1$-$C_6$ alkylene, or substituted or unsubstituted 2 to 6 membered heteroalkylene.

4. The compound of claim 1, wherein z4 is 1.

5. The compound of claim 1, having the formula:

(Ia)

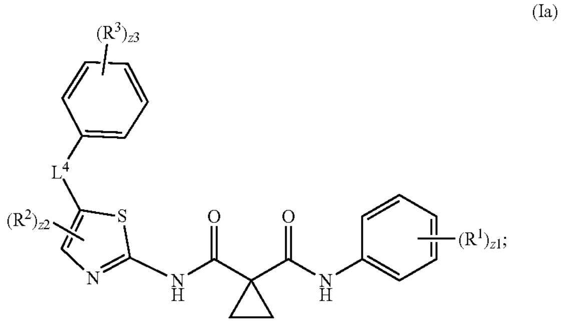

wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

$R^2$ is unsubstituted or substituted cycloalkyl, unsubstituted or substituted alkyl, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted heteroalkyl, substituted or unsubstituted heterocycloalkyl, substituted or unsubstituted aryl, or substituted or unsubstituted heteroaryl;

z2 is 1 or 0;

$R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NR^{3C}NR^{3A}R^{3B}$, $-ONR^{3A}R^{3B}$, $-NHC(O)NR^{3C}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z3 is an integer from 0 to 5;

$L^4$ is $-C(O)N(R^4)-$, $-N(R^4)C(O)-$, a bond, $-N(R^4)-$, $-O-$, $-S-$, $-SO_2-$, $-C(O)-$, $-N(R^4)C(O)NH-$, $-NHC(O)N(R^4)-$, $-C(O)O-$, $-OC(O)-$, $-SO_2N(R^4)-$, $-N(R^4)SO_2-$, substituted or unsubstituted alkylene, or substituted or unsubstituted heteroalkylene;

$R^4$ is hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently $-F$, $-Cl$, $-Br$, or $-I$;

n1, n2, and n3 are independently an integer from 0 to 4; and m1, m2, m3, v1, v2, and v3 are independently 1 or 2;

or a pharmaceutically acceptable salt thereof.

6. The compound of claim 1, having the formula:

(IV)

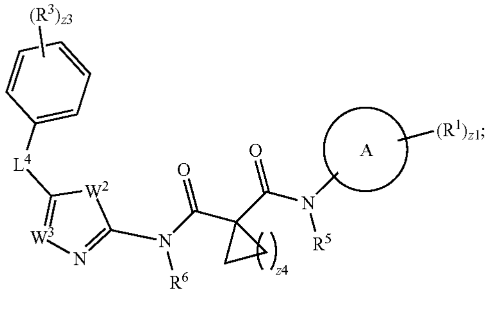

wherein $W^2$ is S; $W^3$ is CH or $C(R^2)$;

Ring A is phenyl or 5 to 6 membered heteroaryl;

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)$ $OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

$R^2$ is unsubstituted or substituted cycloalkyl, unsubstituted or substituted alkyl, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted heteroalkyl, substituted or unsubstituted heterocycloalkyl, substituted or unsubstituted aryl, or substituted or unsubstituted heteroaryl;

$R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z3 is an integer from 0 to 5;

$L^4$ is $—C(O)N(R^4)—$, $—N(R^4)C(O)—$, a bond, $—N(R^4)—$, —O—, —S—, $—SO_2—$, —C(O)—, $—N(R^4)C(O)NH—$, $—NHC(O)N(R^4)—$, —C(O)O—, —OC(O)—, $—SO_2N(R^4)—$, $—N(R^4)SO_2—$, substituted or unsubstituted alkylene, or substituted or unsubstituted heteroalkylene;

z4 is an integer from 1 to 5;

$R^4$, $R^5$, and $R^6$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^1$, $X^2$, and $X^3$ are independently —F, —Cl, —Br, or —I;

n1, n2, and n3 are independently an integer from 0 to 4; and m1, m2, m3, v1, v2, and v3 are independently 1 or 2;

or a pharmaceutically acceptable salt thereof.

7. The compound of claim 1, wherein $R^1$ is independently halogen, $—CF_3$, $—NO_2$, or $—OCH_3$.

8. The compound of claim 1, wherein z1 is 1 or 2.

9. The compound of claim 1, wherein $R^2$ is unsubstituted or substituted $C_3$-$C_6$ cycloalkyl or unsubstituted or substituted $C_1$-$C_6$ alkyl.

10. The compound of claim 1, wherein z2 is 1.

11. The compound of claim 1, having the formula:

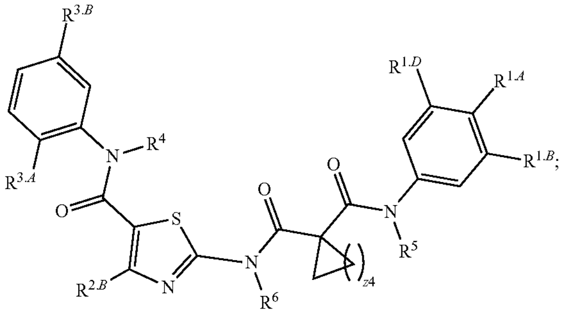

wherein $R^{1.A}$, $R^{1.B}$, and $R^{1.D}$ are independently hydrogen, halogen, $—CX^1_3$, $—CHX^1_2$, $—CH_2X^1$, or substituted or unsubstituted alkyl;

$R^{2.B}$ is hydrogen, unsubstituted or substituted $C_3$-$C_6$ cycloalkyl, or unsubstituted or substituted $C_1$-$C_6$ alkyl;

$R^{3.A}$ and $R^{3.B}$ are independently halogen, $—CX^3_3$, hydrogen, $—CHX^3_2$, $—CH_2X^3$, or substituted or unsubstituted alkyl;

$X^1$ and $X^3$ are independently —F, —CI, —Br, or —I; and $R^4$, $R^5$, and $R^6$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

12. The compound of claim 1, having the formula:

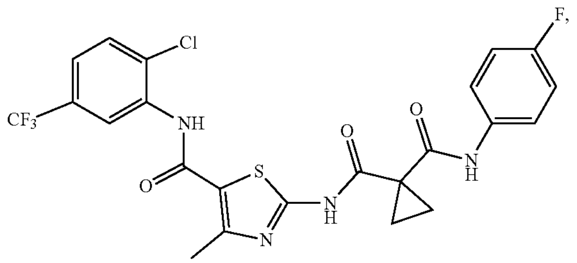

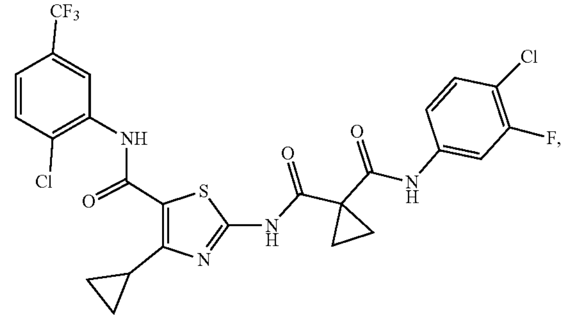

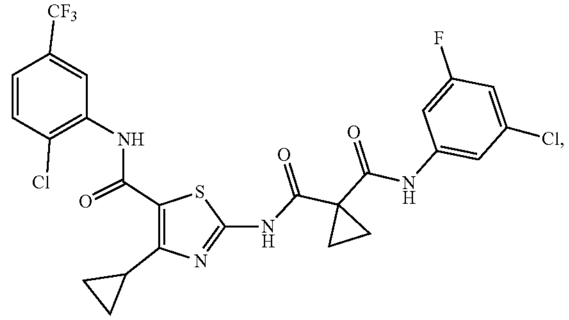

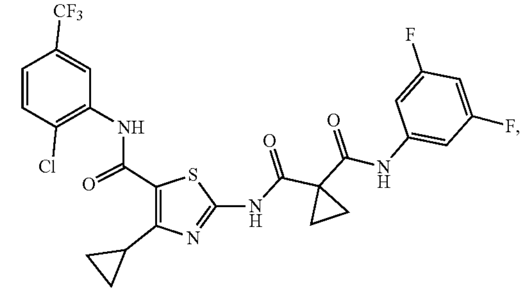

or

-continued

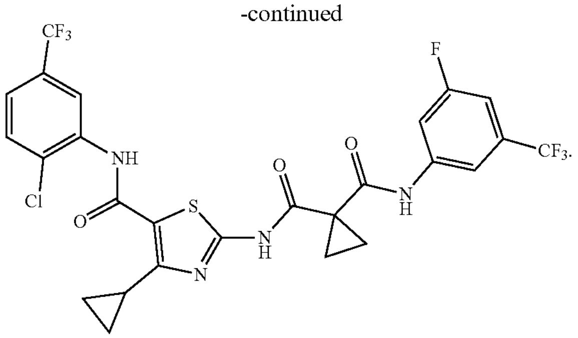

13. A pharmaceutical composition comprising the compound of claim 1 and a pharmaceutically acceptable excipient.

14. A method of decreasing the level of Aurora A kinase protein activity in a subject, said method comprising administering the compound of claim 1 to said subject.

15. A method of decreasing the level of Aurora A kinase protein activity in a cell, said method comprising contacting said cell with the compound of claim 1.

16. A method of decreasing the level of N-MYC protein activity in a subject, said method comprising administering the compound of claim 1 to said subject.

17. A method of decreasing the level of N-MYC protein activity in a cell, said method comprising contacting said cell with the compound of claim 1.

18. A method of inhibiting cancer growth in a subject in need thereof, said method comprising administering to the subject in need thereof an effective amount of the compound of claim 1, wherein the compound modulates the N-MYC activity level, Aurora A kinase activity level, N-MYC protein level, or Aurora A kinase protein level in the subject.

19. A method of inhibiting cancer cell growth, said method comprising contacting the cancer cell with an effective amount of the compound of claim 1, wherein the compound modulates the N-MYC activity level, Aurora A kinase activity level, N-MYC protein level, or Aurora A kinase protein level in the cancer cell.

20. A method of treating a cancer in a subject in need thereof, said method comprising administering to the subject in need thereof an effective amount of the compound of claim 1.

* * * * *

SEQUENCE LISTING

<160> NUMBER OF SEQ ID NOS: 2

<210> SEQ ID NO 1
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 1

Met Pro Ser Cys Ser Thr Ser Thr Met Pro Gly Met Ile Cys Lys Asn
1 5 10 15

Pro Asp Leu Glu Phe Asp Ser Leu Gln Pro Cys Phe Tyr Pro Asp Glu
20 25 30

Asp Asp Phe Tyr Phe Gly Gly Pro Asp Ser Thr Pro Pro Gly Glu Asp
35 40 45

Ile Trp Lys Lys Phe Glu Leu Leu Pro Thr Pro Pro Leu Ser Pro Ser
50 55 60

Arg Gly Phe Ala Glu His Ser Ser Glu Pro Pro Ser Trp Val Thr Glu
65 70 75 80

Met Leu Leu Glu Asn Glu Leu Trp Gly Ser Pro Ala Glu Glu Asp Ala
85 90 95

Phe Gly Leu Gly Gly Leu Gly Gly Leu Thr Pro Asn Pro Val Ile Leu
100 105 110

Gln Asp Cys Met Trp Ser Gly Phe Ser Ala Arg Glu Lys Leu Glu Arg
115 120 125

```
Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Asp Glu Glu Glu Asp
            260                 265                 270

Glu Glu Glu Glu Ile Asp Val Val Thr Val Glu Lys Arg Arg Ser Ser
        275                 280                 285

Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
    450                 455                 460
```

<210> SEQ ID NO 2
<211> LENGTH: 403
<212> TYPE: PRT
<213> ORGANISM: Artificial Sequence
<220> FEATURE:
<223> OTHER INFORMATION: Synthetic polypeptide

<400> SEQUENCE: 2

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30
```

```
Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser
```